US008557848B2

(12) United States Patent
Chen et al.

(10) Patent No.: US 8,557,848 B2
(45) Date of Patent: *Oct. 15, 2013

(54) 4,5-RING ANNULATED INDOLE DERIVATIVES FOR TREATING OR PREVENTING OF HCV AND RELATED VIRAL INFECTIONS

(75) Inventors: Kevin X. Chen, Edison, NJ (US); Srikanth Venkatraman, Edison, NJ (US); F. George Njoroge, Warren, NJ (US); Stuart B. Rosenblum, West Orange, NJ (US); Charles A. Lesburg, Short Hills, NJ (US); Jose S. Duca, Cranford, NJ (US); Neng-Yang Shih, Lexington, MA (US); Francisco Velazquez, Clinton, NJ (US); Gopinadhan N. Anilkumar, Edison, NJ (US); Qingbei Zeng, Edison, NJ (US); Joseph A. Kozlowski, Princeton, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 827 days.

This patent is subject to a terminal disclaimer.

(21) Appl. No.: 12/519,715

(22) PCT Filed: Dec. 17, 2007

(86) PCT No.: PCT/US2007/025754
§ 371 (c)(1),
(2), (4) Date: Nov. 9, 2009

(87) PCT Pub. No.: WO2008/082484
PCT Pub. Date: Jul. 10, 2008

(65) Prior Publication Data
US 2010/0098661 A1 Apr. 22, 2010

Related U.S. Application Data

(60) Provisional application No. 60/876,877, filed on Dec. 22, 2006.

(51) Int. Cl.
*A61K 31/497* (2006.01)
*A61K 31/4353* (2006.01)
*A61K 31/4439* (2006.01)
*A61K 31/444* (2006.01)
*A61K 31/4709* (2006.01)
*A61K 31/498* (2006.01)
*A61K 31/517* (2006.01)
*C07D 215/12* (2006.01)
*C07D 401/14* (2006.01)
*C07D 241/44* (2006.01)
*C07D 239/88* (2006.01)

(52) U.S. Cl.
USPC .............. 514/338; 514/255.05; 514/266.2; 514/303; 546/276.7; 546/256; 546/174; 546/119; 544/349; 544/284

(58) Field of Classification Search
USPC .............. 546/276.7, 256, 174, 119; 544/284, 544/349; 514/338, 255.05, 266.2, 303
See application file for complete search history.

(56) References Cited

U.S. PATENT DOCUMENTS

| 3,632,805 | A | 1/1972 | Yamamoto et al. |
|---|---|---|---|
| 4,634,697 | A | 1/1987 | Hamashima |
| 4,812,561 | A | 3/1989 | Hamashima et al. |
| 4,933,443 | A | 6/1990 | Hamashima et al. |
| 5,017,380 | A | 5/1991 | Hamashima et al. |
| 6,800,434 | B2 | 10/2004 | Saksena et al. |
| 6,838,475 | B2 | 1/2005 | Arasappan et al. |
| 6,846,802 | B2 | 1/2005 | Chen et al. |
| 6,911,428 | B2 | 6/2005 | Zhu et al. |
| 6,914,122 | B2 | 7/2005 | Venkatraman et al. |
| 7,012,066 | B2 | 3/2006 | Saksena et al. |
| 7,153,848 | B2 * | 12/2006 | Hudyma et al. ......... 514/214.01 |
| 2002/0160962 | A1 | 10/2002 | Saksena et al. |

(Continued)

FOREIGN PATENT DOCUMENTS

| AU | 2002313410 B2 | 7/2002 |
|---|---|---|
| DE | 648639 C | 8/1937 |

(Continued)

OTHER PUBLICATIONS

Morissette et al Advanced Drug Delivery Reviews 2004, 56, 275-300.*

(Continued)

*Primary Examiner* — Jason M Nolan
(74) *Attorney, Agent, or Firm* — Melissa B. Wenk; Sheldon O. Heber

(57) ABSTRACT

The present invention relates to 4,5-ring annulated indole derivatives, compositions comprising at least one 4,5-ring annulated indole derivatives, and methods of using the 4,5-ring annulated indole derivatives for treating or preventing a viral infection or a virus-related disorder in a patient. Wherein ring Z, of formula (I), is a cyclopentyl, cyclopentenyl, 5-membered heterocycloalkyl, 5-membered heterocycloalkenyl or 5-membered heteroaryl ring.

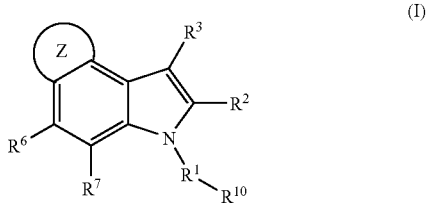

(I)

13 Claims, No Drawings

(56) References Cited

U.S. PATENT DOCUMENTS

| | | | |
|---|---|---|---|
| 2004/0077704 | A1 | 4/2004 | Beight et al. |
| 2005/0075331 | A1 | 4/2005 | Pratt et al. |
| 2005/0101770 | A1 | 5/2005 | Presta |
| 2005/0176648 | A1 | 8/2005 | Saksena et al. |
| 2005/0249702 | A1 | 11/2005 | Njoroge et al. |
| 2007/0274951 | A1 | 11/2007 | Tong et al. |
| 2010/0196319 | A1 | 8/2010 | Anilkumar et al. |
| 2010/0239527 | A1 | 9/2010 | Anilkumar et al. |
| 2010/0260711 | A1 | 10/2010 | Chen et al. |
| 2010/0322901 | A1 | 12/2010 | Bennett et al. |
| 2011/0033417 | A1 | 2/2011 | Anilkumar et al. |
| 2011/0104109 | A1 | 5/2011 | Bennett et al. |
| 2011/0104110 | A1 | 5/2011 | Anikumar et al. |
| 2011/0165118 | A1 | 7/2011 | Chan et al. |
| 2011/0189127 | A1 | 8/2011 | Venkatraman et al. |

FOREIGN PATENT DOCUMENTS

| | | | |
|---|---|---|---|
| EP | 0449196 | A2 | 10/1991 |
| FR | 2768146 | A1 | 3/1999 |
| JP | 4-149429 | | 5/2004 |
| WO | 96/37619 | A1 | 11/1996 |
| WO | 98/14181 | A1 | 4/1998 |
| WO | 98/17679 | A1 | 4/1998 |
| WO | 98/22496 | A2 | 5/1998 |
| WO | 99/07734 | A2 | 2/1999 |
| WO | 02/30895 | A1 | 4/2002 |
| WO | WO 0230895 | A1 * | 4/2002 |
| WO | 02/068412 | A1 | 9/2002 |
| WO | 2004/035571 | A1 | 4/2004 |
| WO | 2004/106328 | A1 | 12/2004 |
| WO | 2005/034941 | A1 | 4/2005 |
| WO | 2005/084315 | A2 | 9/2005 |
| WO | 2005/087731 | A1 | 9/2005 |
| WO | 2005/111018 | A1 | 11/2005 |
| WO | 2006/020082 | A1 | 2/2006 |
| WO | 2006/032541 | A1 | 3/2006 |
| WO | 2006/034337 | A2 | 3/2006 |
| WO | 2006/046030 | A2 | 5/2006 |
| WO | 2006/076529 | A1 | 7/2006 |
| WO | 2007/029029 | A2 | 3/2007 |
| WO | 2007/038209 | A2 | 4/2007 |
| WO | 2007/084413 | A2 | 7/2007 |
| WO | 2007/084435 | A2 | 7/2007 |
| WO | 2008/082484 | A1 | 7/2008 |

OTHER PUBLICATIONS

Hamdi et al., Solvates of indomethacin. Journal of Thermal Analysis and Calorimetry 2004, 76, 985-1001.*
Schafer et al. Drug Discovery Today 2008, 13 (21/22), 913-916.*
Beaulieu et al., "Inhibitors of the HCV NS5B polymerase. New hope for the treatment of hepatitis C infections", Current Opinion in Investigational Drugs, 2004, vol. 5, pp. 838-850, No. 8.
Behrens et al. "Identification and properties of the RNA-dependent RNA polymerase of hepatitis C virus". The EMBO Journal, 1996, vol. 15, pp. 12-22, No. 1.
Bioworld Today, 9 (217):4 Nov. 10, 1998, pp. 1-5.
Birnbock et al., "Sulfate Derivatives of 2-Phenylindols as Novel Steroid Sulfatase Inhibitors", Biochemical Pharmacology, 1990, vol. 39, pp. 1709-1713, No. 11.
Bunker et al., "1,3-Diaryl-2-Carboxyindoles as Potent Non-Peptide Endolhelin Antagonists", Bioorganic & Medicinal Chemistry Letters, 1996, vol. 6, pp. 1061-1066, No. 9.
Chemical and Pharmaceutical Bulletin, vol. 19, 1971, p. 263-270.
Denmark et al., "Palladium-Catalyzed Cross-Coupling Reactions of Silanolates: A Paradigm Shift in Silicon-Based Cross-Coupling Reactions", Chem Eur. J., 2006, vol. 12, pp. 4954-4963.
Dimasi et al., "Characterization of Engineered Hepatitis C Virus NS3 Protease Inhibitors Affinity Selected from Human Pancreatic Secretory Trypsin Inhibitor and Minibody Repertoires", Journal of Virology, 1997, vol. 71, pp. 7461-7469, No. 10.
Elzouki et al., "Senne protease inhibitors in patients with chronic viral hepatitis", Journal of Hepatology, 1997, vol. 27, pp. 42-48.
Ferrari et al., "Characterization of Soluble Hepatitis C Virus RNA-Dependent RNA Polymerase Expressed in *Escherchia coli*", Journal of Virology, 1999, vol. 73, pp. 1649-1654, No. 2.
Fonseca et al., "Synthesis and antiviral evaluation of benzimidazoles, quinoxalines and indoles from dehydroabietic acid", Bioorganic & Medicianl Chemistry, 2004, vol. 12, pp. 103-112.
Forbes et a., "Synthesis Biological Activity and Molecular Modeling Studies of Selective 5-HT2C/2B Receptor Antagonists", J Med. Chem., 1996, vol. 39, pp. 4966-4977, No. 25.
Goldsmith et al , "Studies in the Benzindole Series", J. Org. Chem. 1952, vol. 18, pp. 507-514.
Gopalsamy et al., "Design and synthesis of 2,3,4,9-tetrahydro-1H-carbazole and 1,2,3,4-tetrahydro-cyclopenta[b] indole derivatives as non-nucleoside inhibitors of hepatitis C virus NS5B RNA-dependent RNA polymerase", Bioorganic & Medicinal Chemistry Letters, 2006, vol. 16, pp. 2532-2534.
Humphrey et al., "Practical Methodologies for the Synthesis of Indoles", Chem. Rev., 2006, vol. 105, pp. 2875-2911.
International Search Report for International Application No. PCT/US2007/025754, mailed May 13, 2008, (4 pages).
Written Opinion for PCT/US2007/025754, filed Dec. 17, 2007, (7 pages).
International Search Report for International Application No. PCT/US2007/025765, maiiled May 13, 2008, (6 pages).
Written Opinion for PCT/US2007/025765, filed Dec. 17, 2007, (8 pages).
International Search Report for International Application No. PCT/US2007/025757, mailed Mar. 6, 2009, (8 pages).
Written Opinion for PCT/US2007/025757, Dec. 17, 2007 (12 pages).
International Search Report for International Application No. PCT/US2008/010130, mailed Jan. 22, (5 pages).
Written Opinion for PCT/US2008/010130, filed Aug. 27, 2008 (9 pages).
International Search Report for International Application No. PCT/US2008/010149, mailed Feb. 2, 2009, (5 pages).
Written Opinion for PCT/US2008/010149, filed Aug. 27, 2008 (6 pages).
International Search Report for International Application No. PCT/US2008/083351, mailed Feb. 17, 2009, (3 pages).
Written Opinion for PCT/US2008/083351, filed Nov. 13, 2008 (5 pages).
International Search Report for International Application No. PCT/US2008/010147, mailed May 4, 2009. (3 pages).
Written Opinion for PCT/US2008/010148, filed Aug. 27, 2008 (6 pages).
International Search Report for International Application No. PCT/US2008/083358, mailed Mar. 6, 2009, (2 pages).
Written Opinion for PCT/US2008/083358, filed Nov. 13, 2008 (5 pages).
International Search Report for International Application No. PCT/US2008/010148, mailed Dec. 9, 2009, (3 pages).
Written Opinion for PCT/US2008/010148, filed Aug. 27, 2008 (7 pages).
International Search Report for International Application No. PCT/US2009/046822, mailed Oct. 7, 2009, (5 pages).
Written Opinion for PCT/US2009/046822, filed Jun. 10, 2009 (8 pages).
Ingallinella et al., "Potent Peptide Inhibitors of Human Hepatitis C Virus NS3 Protease are Obtained by Optimizing the Cleavage Products", Biochemistry, 1998, Vol, 37, pp. 8906-8914.
Journal of Heterocyclic Chemistry, vol. 12, 1975, pp. 351-358.
Journal of Medicinal Chemistry, Vol, 23, No. 7, 1980, pp. 784-773.
Journal of Organic Chemistry, vol. 27, 1962, pp, 3782-3786.
Landro et al , "Mechanistic Role of an NS4A Peptide Cofactor with the Truncated NS3 Protease of Hepatitis C Virus: Elucidation of the NS4A Stimulatory Effect via Kinetic Analysis and Inhibitor Mapping", Biochemistry, 1957, vol. 36, pp. 9340-9348.
Lindsay et al., "Sml2-Promoted Radical Addition Reactions with N-(2-Indolylacyl)oxazolidinones, Synthesis of Bisindole Compounds". Journal of Organic Chemistry, 2007, vol. 72, pp. 4181-4188, No. 11.

(56) References Cited

OTHER PUBLICATIONS

Llina-Brunet et al., "Peptide-Based Inhibitors of the Hepatitis C Virus Serine Protease", Bioorganic & Medicinal Chemistry Letters, 1998. vol. 8, pp. 1713-1718.

Malcolm et al., "SCH 503034, a Mechanisim-Based Inhibitor of Hepatitis C Virus NS3 Protease, Suppresses Polyprotein Maturation and Enhances the Antiviral Activity of Alpha Interferon in Replicon Cells", Antimicrobial Agents and Chemotherapy, 2006, vol. 50, pp. 1013-1020, No. 3.

Martin, et al., "Affinity selection of a camelized VH domain antibody inhibitor of hepatitis C virus NS3 protease", Protein Engineering, 1997, vol. 10, pp. 607-614, No. 5.

Martin et al., "Design of Selective EgiIn Inhibitors of HCV NS3 Proteinase", Biochemistry, 1998, vol. 37, pp. 11459-11468.

Muratake et al., "Synthesis of Duocarmycin SA by Way of Methyl 4-(Methoxycarbonyl)oxy-3H-pyrrolo[3,2-l]quinoline-2-carboxylate as a Tricyclic Heteroaromatic Intermediate". Chem. Pharm. Bulletin, 1998, vol. 46, pp. 400-412, No. 3.

Ni et al., "Progress and development of small molecule HCV antivirals". Current Opinion in Drug Discovery & Development, 2004, vol. 7, pp. 446-459, No. 4.

Rawal et al., "Photocyclization of Pyrrole Analogues of Stilbene an Expedient Approach to Anti-tumor Agent CC-1065", Journal Chem. Soc., Chem. Commun., 1984, pp. 1526-1527.

Sechi et al., "Design and Synthesis of Novel Indole β-Dikelo Acid Derivatives as HIV-1 Integrase Inhibitors", J Med. Chem., 2004, vol. 47, pp. 5298-5310, No. 21.

Silvestri et al., "Synthesis and biological evaluation of 5H-indolo [3,2-b][1,5]benzothiazepine derivatives, designed as conformationally constrained analogues of the human immunodeficiency virus type 1 reverse transcriptase inhibitor L-737,126", Antiviral Chemistry & Chemotherapy, 1998, vol. 9, pp. 139-148.

Tan et al., "Hepatitis C Therapeutics: Current Status and Emerging Strategies", Nature Reviews, 2002, vol. 1, pp. 867-881.

* cited by examiner

4,5-RING ANNULATED INDOLE DERIVATIVES FOR TREATING OR PREVENTING OF HCV AND RELATED VIRAL INFECTIONS

RELATED APPLICATIONS

This application is the national stage application under 35 U.S.C. 371 of International Patent Application No. PCT/US2007/025754, filed Dec. 17, 2007, which claims priority to U.S. Provisional Application No. 60/876,596, filed Dec. 22, 2006. Each of the aforementioned PCT and priority applications is incorporated by reference in its entirety.

FIELD OF THE INVENTION

The present invention relates to 4,5-ring annulated indole derivatives, compositions comprising at least one 4,5-ring annulated indole derivatives, and methods of using the 4,5-ring annulated indole derivatives for treating or preventing a viral infection or a virus-related disorder in a patient.

BACKGROUND OF THE INVENTION

HCV is a (+)-sense single-stranded RNA virus that has been implicated as the major causative agent in non-A, non-B hepatitis (NANBH). NANBH is distinguished from other types of viral-induced liver disease, such as hepatitis A virus (HAV), hepatitis B virus (HBV), hepatitis delta virus (HDV), as well as from other forms of liver disease such as alcoholism and primary biliary cirrhosis.

Hepatitis C virus is a member of the hepacivirus genus in the family Flaviviridae. It is the major causative agent of non-A, non-B viral hepatitis and is the major cause of transfusion-associated hepatitis and accounts for a significant proportion of hepatitis cases worldwide. Although acute HCV infection is often asymptomatic, nearly 80% of cases resolve to chronic hepatitis. About 60% of patients develop liver disease with various clinical outcomes ranging from an asymptomatic carrier state to chronic active hepatitis and liver cirrhosis (occurring in about 20% of patients), which is strongly associated with the development of hepatocellular carcinoma (occurring in about 1-5% of patients). The World Health Organization estimates that 170 million people are chronically infected with HCV, with an estimated 4 million living in the United States.

HCV has been implicated in cirrhosis of the liver and in induction of hepatocellular carcinoma. The prognosis for patients suffering from HCV infection remains poor as HCV infection is more difficult to treat than other forms of hepatitis. Current data indicates a four-year survival rate of below 50% for patients suffering from cirrhosis and a five-year survival rate of below 30% for patients diagnosed with localized resectable hepatocellular carcinoma. Patients diagnosed with localized unresectable hepatocellular carcinoma fare even worse, having a five-year survival rate of less than 1%.

HCV is an enveloped RNA virus containing a single-stranded positive-sense RNA genome approximately 9.5 kb in length. The RNA genome contains a 5'-nontranslated region (5' NTR) of 341 nucleotides, a large open reading frame (ORF) encoding a single polypeptide of 3,010 to 3,040 amino acids, and a 3'-nontranslated region (3'-NTR) of variable length of about 230 nucleotides. HCV is similar in amino acid sequence and genome organization to flaviviruses and pestiviruses, and therefore HCV has been classified as a third genus of the family Flaviviridae.

The 5' NTR, one of the most conserved regions of the viral genome, contains an internal ribosome entry site (IRES) which plays a pivotal role in the initiation of translation of the viral polyprotein. A single long open reading frame encodes a polyprotein, which is co- or post-translationally processed into structural (core, E1, E2 and p7) and nonstructural (NS2, NS3, NS4A, NS4B, NS5A, and NS5B) viral proteins by either cellular or viral proteinases. The 3' NTR consists of three distinct regions: a variable region of about 38 nucleotides following the stop codon of the polyprotein, a polyuridine tract of variable length with interspersed substitutions of cytidines, and 98 nucleotides (nt) at the very 3' end which are highly conserved among various HCV isolates. By analogy to other plus-strand RNA viruses, the 3'-NTR is thought to play an important role in viral RNA synthesis. The order of the genes within the genome is: $NH_2$-C-E1-E2-p7-NS2-NS3-NS4A-NS4B-NS5A-NS5B-COOH.

Processing of the structural proteins core (C), envelope protein 1 and (E1, E2), and the p7 region is mediated by host signal peptidases. In contrast, maturation of the nonstructural (NS) region is accomplished by two viral enzymes. The HCV polyprotein is first cleaved by a host signal peptidase generating the structural proteins C/E1, E1/E2, E2/p7, and p7/NS2. The NS2-3 proteinase, which is a metalloprotease, then cleaves at the NS2/NS3 junction. The NS3/4A proteinase complex (NS3 being a serine protease and NS4A acting as a cofactor of the NS3 protease), is then responsible for processing all the remaining cleavage junctions. RNA helicase and NTPase activities have also been identified in the NS3 protein. One-third of the NS3 protein functions as a protease, and the remaining two-thirds of the molecule acts as the helicase/ATPase that is thought to be involved in HCV replication. NS5A may be phosphorylated and acts as a putative cofactor of NS5B. The fourth viral enzyme, NS5B, is a membrane-associated RNA-dependent RNA polymerase (RdRp) and a key component responsible for replication of the viral RNA genome. NS5B contains the "GDD" sequence motif, which is highly conserved among all RdRps characterized to date.

Replication of HCV is thought to occur in membrane-associated replication complexes. Within these, the genomic plus-strand RNA is transcribed into minus-strand RNA, which in turn can be used as a template for synthesis of progeny genomic plus-strands. At least two viral enzymes appear to be involved in this reaction: the NS3 helicase/NTPase, and the NS5B RNA-dependent RNA polymerase. While the role of NS3 in RNA replication is less clear, NS5B is the key enzyme responsible for synthesis of progeny RNA strands. Using recombinant baculoviruses to express NS5B in insect cells and a synthetic nonviral RNA as a substrate, two enzymatic activities have been identified as being associated with it: a primer-dependent RdRp and a terminal transferase (TNTase) activity. It was subsequently confirmed and further characterized through the use of the HCV RNA genome as a substrate. Other studies have shown that NS5B with a C-terminal 21 amino-acid truncation expressed in *Escherichia coli* is also active for in vitro RNA synthesis. On certain RNA templates, NS5B has been shown to catalyze RNA synthesis via a de novo initiation mechanism, which has been postulated to be the mode of viral replication in vivo. Templates with single-stranded 3' termini, especially those containing a 3'-terminal cytidylate moiety, have been found to direct de novo synthesis efficiently. There has also been evidence for NS5B to utilize di- or tri-nucleotides as short primers to initiate replication.

It is well-established that persistent infection of HCV is related to chronic hepatitis, and as such, inhibition of HCV replication is a viable strategy for the prevention of hepatocellular carcinoma. Present treatment approaches for HCV infection suffer from poor efficacy and unfavorable side-effects and there is currently a strong effort directed to the discovery of HCV replication inhibitors that are useful for the treatment and prevention of HCV related disorders. New approaches currently under investigation include the development of prophylactic and therapeutic vaccines, the identification of interferons with improved pharmacokinetic characteristics, and the discovery of agents designed to inhibit the function of three major viral proteins: protease, helicase and polymerase. In addition, the HCV RNA genome itself, particularly the IRES element, is being actively exploited as an antiviral target using antisense molecules and catalytic ribozymes.

Particular therapies for HCV infection include α-interferon monotherapy and combination therapy comprising α-interferon and ribavirin. These therapies have been shown to be effective in some patients with chronic HCV infection. The use of antisense oligonucleotides for treatment of HCV infection has also been proposed as has the use of free bile acids, such as ursodeoxycholic acid and chenodeoxycholic acid, and conjugated bile acids, such as tauroursodeoxycholic acid. Phosphonoformic acid esters have also been proposed as potentially for the treatment of various viral infections including HCV. Vaccine development, however, has been hampered by the high degree of viral strain heterogeneity and immune evasion and the lack of protection against reinfection, even with the same inoculum.

The development of small-molecule inhibitors directed against specific viral targets has become a major focus of anti-HCV research. The determination of crystal structures for NS3 protease, NS3 RNA helicase, and NS5B polymerase, with and without bound ligands, has provided important structural insights useful for the rational design of specific inhibitors.

NS5B, the RNA-dependent RNA polymerase, is an important and attractive target for small-molecule inhibitors. Studies with pestiviruses have shown that the small molecule compound VP32947 (3-[((2-dipropylamino)ethyl)thio]-5H-1,2,4-triazino[5,6-b]indole) is a potent inhibitor of pestivirus replication and most likely inhibits the NS5B enzyme since resistant strains are mutated in this gene. Inhibition of RdRp activity by (−)β-L-2',3'-dideoxy-3'-thiacytidine 5'-triphosphate (3TC; lamivudine triphosphate) and phosphonoacetic acid also has been observed.

Despite the intensive effort directed at the treatment and prevention of HCV and related viral infections, there exists a need in the art for non-peptide, small-molecule compounds having desirable or improved physicochemical properties that are useful for inhibiting viruses and treating viral infections and virus-related disorders.

SUMMARY OF THE INVENTION

In one aspect, the present invention provides 4,5-ring annulated indole deriviatives (herein referred to as the "Compounds of Formula (I)"):

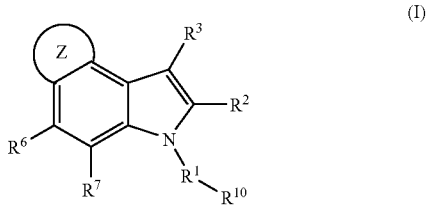

and pharmaceutically acceptable salts and solvates thereof, wherein ring Z, of formula (I), is a cyclopentyl, cyclopentenyl, 5-membered heterocycloalkyl, 5-membered heterocycloalkenyl or 5-membered heteroaryl ring, wherein ring Z may be: (i) optionally substituted on one or more ring carbon atoms with substituents, which are the same or different, and which are selected from alkyl, aryl, heteroaryl, halo, haloalkyl, hydroxyalkyl, —OH, —CN, —C(O)R$^8$, —C(O)OR$^9$, —C(O)N(R$^9$)$_2$, —[C(R$^{12}$)$_2$]$_q$—OR$^9$, —[C(R$^{12}$)$_2$]$_q$—N(R$^9$)$_2$, —NHC(O)R$^8$, —NHSO$_2$R$^{11}$, —S(O)$_p$R$^{11}$ or —SO$_2$N(R$^9$)$_2$; and/or (ii) optionally substituted on a ring nitrogen atom with substituents, which are the same or different, and which are selected from alkyl, aryl, haloalkyl, heteroaryl, hydroxyalkyl, —C(O)R$^8$, —C(O)OR$^9$, —C(O)N(R$^9$)$_2$, —[C(R$^{12}$)$_2$]$_r$—OR$^9$, —[C(R$^{12}$)$_2$]$_r$—N(R$^9$)$_2$, —NHC(O)R$^8$, —NHSO$_2$R$^{11}$, —S(O)$_p$R$^{11}$ or —SO$_2$N(R$^9$)$_2$;

R$^1$ is a bond, —[C(R$^{12}$)$_2$]$_r$—, —[C(R$^{12}$)$_2$]$_r$—O—[C(R$^{12}$)$_2$]$_q$—, —[C(R$^{12}$)$_2$]$_r$—N(R$^9$)—[C(R$^{12}$)$_2$]$_q$—, —[C(R$^{12}$)$_2$]$_q$—CH=CH—[C(R$^{12}$)$_2$]$_q$—, —[C(R$^{12}$)$_2$]$_q$—C≡C—[C(R$^{12}$)$_2$]$_q$—, or —[C(R$^{12}$)$_2$]$_q$—SO$_2$—[C(R$^{12}$)$_2$]$_q$—;

R$^2$ is —C(O)R$^9$, —C(O)OR$^9$, —C(O)OCH$_2$OR$^9$, —C(O)N(R$^9$)$_2$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—C(O)N(R$^9$)C=N(R$^9$)$_2$, —[C(R$^{12}$)$_2$]$_q$-aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heteroaryl, —[C(R$^{12}$)$_2$]$_q$-heterocycloalkenyl, —[C(R$^{12}$)$_2$]$_q$—C(O)N(R$^9$)SOR$^{11}$, —[C(R$^{12}$)$_2$]$_q$—C(O)N(R$^9$)SO$_2$R$^{11}$, —[C(R$^{12}$)$_2$]$_q$—C(O)N(R$^9$)SO$_2$N(R$^9$)$_2$, alkyl,

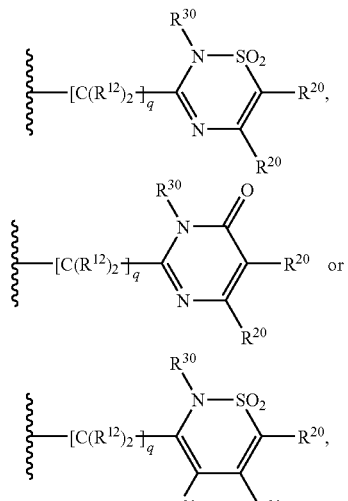

wherein an aryl, cycloalkyl, cycloalkenyl, heterocycloalkyl, heterocycloalkenyl or heteroaryl, group can be optionally substituted with up to 4 substituents, which are each independently selected from alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, —OH, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ and —SO$_2$N(R$^9$)C(O)N(R$^9$)$_2$;

R$^3$ is —H, —[C(R$^{12}$)$_2$]$_q$-alkyl, —[C(R$^{12}$)$_2$]$_q$-aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heteroaryl or —[C(R$^{12}$)$_2$]$_q$-heterocycloalkenyl,

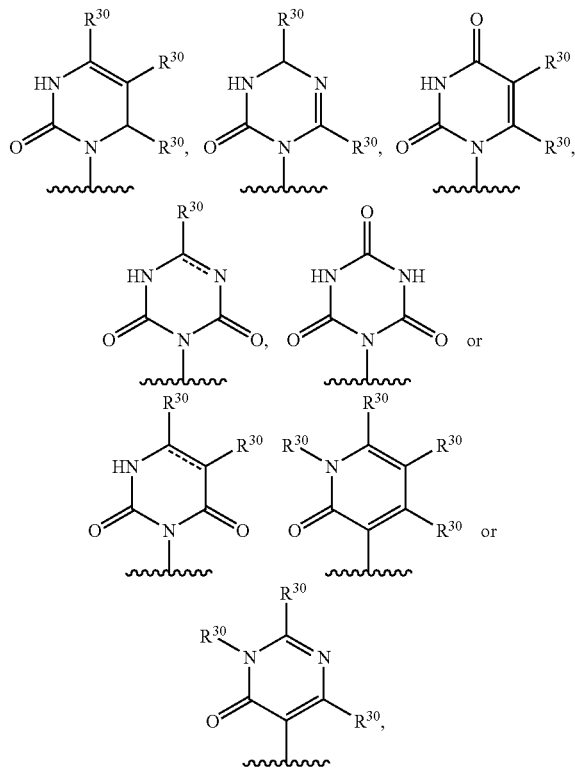

wherein an aryl, cycloalkyl, cycloalkenyl, heterocycloalkyl, heterocycloalkenyl or heteroaryl group can be optionally substituted with up to 3 substituents, which are the same or different, and are selected from alkyl, aryl, cycloalkyl, heteroaryl, heterocycloalkyl, halo, haloalkyl, hydroxyalkyl, —OH, —CN, —C(O)R$^8$, —C(O)OR$^9$, —C(O)N(R$^9$)$_2$, —[C(R$^{12}$)$_2$]$_q$—OR$^9$, —[C(R$^{12}$)$_2$]$_q$—N(R$^9$)$_2$, —NHC(O)R$^8$, —NHSO$_2$R$^{11}$, —S(O)$_p$R$^{11}$ or —SO$_2$N(R$^9$)$_2$;

R$^6$ and R$^7$ are each, independently, H, alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, —OH, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ or —SO$_2$N(R$^9$)C(O)N(R$^9$)$_2$;

each occurrence of R$^8$ is independently H, alkyl, alkenyl, alkynyl, —[C(R$^{12}$)$_2$]$_q$-aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, haloalkyl or hydroxyalkyl;

each occurrence of R$^9$ is independently H, alkyl, alkenyl, alkynyl, —[C(R$^{12}$)$_2$]$_q$-aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, [C(R$^{12}$)$_2$]$_q$-heteroaryl, haloalkyl or hydroxyalkyl, or two R$^9$ groups that are attached to a common nitrogen atom, together with the nitrogen atom to which they are attached, combine to form a heterocycloalkyl, heterocycloalkenyl or heteroaryl group;

R$^{10}$ is H, cycloalkyl, cycloalkenyl, heterocycloalkyl, heterocycloalkenyl, aryl, heteroaryl, wherein a cycloalkyl, cycloalkenyl, heterocycloalkyl, heterocycloalkenyl, aryl or heteroaryl group can be optionally substituted with up to 4 substituents, which are each independently selected from H, alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, —OH, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ and —SO$_2$N(R$^9$)C(O)N(R$^9$)$_2$, such that when R$^1$ is a bond, R$^{10}$ is not H;

each occurrence of R$^{11}$ is independently alkyl, aryl, cycloalkyl, cycloalkenyl, heterocycloalkyl, heterocycloalkenyl, heteroaryl, haloalkyl, hydroxy or hydroxyalkyl, wherein a cycloalkyl, cycloalkenyl, heterocycloalkyl, heterocycloalkenyl, aryl or heteroaryl group can be optionally substituted with up to 4 substituents, which are each independently selected from —H, alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, —OH, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$alkyl, —[C(R$^{12}$)$_2$]$_q$—NHSO$_2$cycloalkyl, —[C(R$^{12}$)$_2$]$_q$—NHSO$_2$aryl, —[C(R$^{12}$)$_2$]$_q$—SO$_2$—N(R$^9$)$_2$ and —SO$_2$N(R$^9$)C(O)N(R$^9$)$_2$;

each occurrence of R$^{12}$ is independently H, halo, —N(R$^9$)$_2$, —OR$^9$, alkyl, cycloalkyl, cycloalkenyl, heterocycloalkyl or heterocycloalkenyl, wherein a cycloalkyl, cycloalkenyl, heterocycloalkyl or heterocycloalkenyl group can be optionally substituted with up to 4 substituents, which are each independently selected from alkyl, halo, haloalkyl, hydroxyalkyl, —OH, —CN, —C(O)alkyl, —C(O)Oalkyl, —C(O)NHalkyl, —C(O)N(alkyl)$_2$, —O-alkyl, —NH$_2$, —NH(alkyl), —N(alkyl)$_2$, —NHC(O)alkyl, —NHSO$_2$alkyl, —SO$_2$alkyl or —SO$_2$NH-alkyl, or two R$^{12}$ groups, together with the carbon atoms to which they are attached, join to form a cycloalkyl, heterocycloalkyl or C=O group;

each occurrence of R$^{20}$ is independently H, alkyl, aryl, cycloalkyl, heterocycloalkyl or heteroaryl, or both R$^{20}$ groups and the carbon atoms to which they are attached, join to form a cycloalkyl, cycloheteroalkyl, aryl or heteroaryl group wherein a cycloalkyl, cycloheteroalkyl, aryl or heteroaryl group can be substituted with up to 4 groups, which are each independently selected from alkyl, alkenyl, alkynyl, halo, —OH, —OR$^9$, —CN, —[C(R$^{12}$)$_2$]$_q$-cycloalkyl, —[C $(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$-haloalkyl, $-[C(R^{12})_2]_q$-hydroxyalkyl, $-[C(R^{12})_2]_q-C(O)R^8$, $-[C(R^{12})_2]_q-C(O)OR^9$, $-[C(R^{12})_2]_q-C(O)N(R^9)_2$, $-[C(R^{12})_2]_q-OR^9$, $-[C(R^{12})_2]_q-N(R^9)_2$, $-[C(R^{12})_2]_q-NHC(O)R^8$, $-[C(R^{12})_2]_q-NR^8C(O)N(R^9)_2$, $-[C(R^{12})_2]_q-NHSO_2R^{11}$, $-[C(R^{12})_2]_q-S(O)_pR^{11}$, $-[C(R^{12})_2]_q-SO_2N(R^9)_2$ and $-SO_2N(R^9)C(O)N(R^9)_2$;

each occurrence of $R^{30}$ is independently H, alkyl, alkenyl, alkynyl, aryl, $-[C(R^{12})_2]_q$-cycloalkyl, $-[C(R^{12})_2]_q$-cycloalkenyl, $-[C(R^{12})_2]_q$-heterocycloalkyl, $-[C(R^{12})_2]_q$-heterocycloalkenyl, $-[C(R^{12})_2]_q$-heteroaryl, $-[C(R^{12})_2]_q$-haloalkyl, $-[C(R^{12})_2]_q$-hydroxyalkyl, halo, $-OH$, $-OR^9$, $-CN$, $-[C(R^{12})_2]_q-C(O)R^8$, $-[C(R^{12})_2]_q-C(O)OR^9$, $-[C(R^{12})_2]_q-C(O)N(R^9)_2$, $-[C(R^{12})_2]_q-OR^9$, $-[C(R^{12})_2]_q-N(R^9)_2$, $-[C(R^{12})_2]_q-NHC(O)R^8$, $-[C(R^{12})_2]_q-NR^8C(O)N(R^9)_2$, $-[C(R^{12})_2]_q-NHSO_2R^{11}$, $-[C(R^{12})_2]_q-S(O)_pR^{11}$, $-[C(R^{12})_2]_q-SO_2N(R^9)_2$ or $-SO_2N(R^9)C(O)N(R^9)_2$, or two adjacent $R^{30}$ groups, together with the carbon atoms to which they are attached, join to form a –3- to 7-membered ring selected from aryl, cycloalkyl, heteroaryl and heterocycloalkyl;

each occurrence of p is independently 0, 1 or 2;

each occurrence of q is independently an integer ranging from 0 to 4; and each occurrence of r is independently an integer ranging from 1 to 4.

The Compounds of Formula (I) or pharmaceutically acceptable salts, solvates, prodrugs or esters thereof can be useful for treating or preventing a viral infection in a patient.

The Compounds of Formula (I) or pharmaceutically acceptable salts, solvates, prodrugs or esters thereof can be useful for treating or preventing a virus-related disorder in a patient.

Also provided by the invention are methods for treating or preventing a viral infection or a virus-related disorder in a patient, comprising administering to the patient an effective amount of at least one Compound of Formula (I).

The present invention further provides pharmaceutical compositions comprising an effective amount of at least one Compound of Formula (I) or a pharmaceutically acceptable salt, solvate thereof, and a pharmaceutically acceptable carrier. The compositions can be useful for treating or preventing a viral infection or a virus-related disorder in a patient.

The details of the invention are set forth in the accompanying detailed description below.

Although any methods and materials similar to those described herein can be used in the practice or testing of the present invention, illustrative methods and materials are now described. Other features, objects, and advantages of the invention will be apparent from the description and the claims. All patents and publications cited in this specification are incorporated herein by reference.

DETAILED DESCRIPTION OF THE INVENTION

The present invention provides Compounds of Formula (I), pharmaceutical compositions comprising at least one Compound of Formula (I), and methods of using the Compounds of Formula (I) for treating or preventing a viral infection or a virus-related disorder in a patient.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc. . . .

As used herein, and throughout this disclosure, the following terms, unless otherwise indicated, shall be understood to have the following meanings:

A "patient" is a human or non-human mammal. In one embodiment, a patient is a human. In another embodiment, a patient is a non-human mammal, including, but not limited to, a monkey, dog, baboon, rhesus, mouse, rat, horse, cat or rabbit. In another embodiment, a patient is a companion animal, including but not limited to a dog, cat, rabbit, horse or ferret. In one embodiment, a patient is a dog. In another embodiment, a patient is a cat.

The term "alkyl" as used herein, refers to an aliphatic hydrocarbon group, wherein one of the aliphatic hydrocarbon group's hydrogen atoms is replaced with a single bond. An alkyl group can be straight or branched and can contain from about 1 to about 20 carbon atoms. In one embodiment, an alkyl group contains from about 1 to about 12 carbon atoms. In another embodiment, an alkyl group contains from about 1 to about 6 carbon atoms. Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or optionally substituted by one or more substituents which may be the same or different, each substituent being independently selected from the group consisting of halo, alkenyl, alkynyl, —O-aryl, aryl, heteroaryl, cycloalkyl, cycloalkenyl, cyano, —OH, —O-alkyl, —O-haloalkyl, -alkylene-O-alkyl, alkylthio, —NH₂, —NH(alkyl), —N(alkyl)₂, —NH-aryl, —NH-heteroaryl, —NHC(O)-alkyl, —NHC(O)NH-alkyl, —NHSO₂-alkyl, —NHSO₂-aryl, —NHSO₂-heteroaryl, —NH(cycloalkyl), —OC(O)-alkyl, —OC(O)-aryl, —OC(O)-cycloalkyl, —C(O)alkyl, —C(O)NH₂, —C(O)NH-alkyl, —C(O)OH and —C(O)O-alkyl. In one embodiment, an alkyl group is unsubstituted. In another embodiment, an alkyl group is a straight chain alkyl group. In another embodiment, an alkyl group is a branched alkyl group.

The term "alkenyl" as used herein, refers to an aliphatic hydrocarbon group having at least one carbon-carbon double bond, wherein one of the aliphatic hydrocarbon group's hydrogen atoms is replaced with a single bond. An alkenyl group can be straight or branched and can contain from about 2 to about 15 carbon atoms. In one embodiment, an alkenyl group contains from about 2 to about 10 carbon atoms. In another embodiment, an alkenyl group contains from about 2 to about 6 carbon atoms. Non-limiting examples of illustrative alkenyl groups include ethenyl, propenyl, n-butenyl, 3-methylbut-2-enyl, n-pentenyl, octenyl and decenyl. An alkenyl group may be unsubstituted or optionally substituted by one or more substituents which may be the same or different, each substituent being independently selected from the group consisting of halo, alkyl, alkynyl, —O-aryl, aryl, cycloalkyl, cycloalkenyl, cyano, —OH, —O-alkyl, —O-haloalkyl, -alkylene-O-alkyl, alkylthio, —NH₂, —NH(alkyl), —N(alkyl)₂, —NH-aryl, —NH-heteroaryl, —NHC(O)-alkyl, —NHC(O)NH-alkyl, —NHSO₂-alkyl, —NHSO₂-heteroaryl, —NH(cycloalkyl), —OC(O)-alkyl, —OC(O)-aryl, —OC(O)-cycloalkyl, —C(O)alkyl, —C(O)NH₂, —C(O)NH-alkyl, —C(O)OH and —C(O)O-alkyl. In one embodiment, an alkenyl group is unsubstituted. In another embodiment, an alkenyl group is a straight chain alkenyl group. In another embodiment, an alkyl group is a branched alkenyl group.

The term "alkynyl" as used herein, refers to an aliphatic hydrocarbon group having at least one carbon-carbon triple bond, wherein one of the aliphatic hydrocarbon group's hydrogen atoms is replaced with a single bond. An alkynyl group can be straight or branched and can contain from about 2 to about 15 carbon atoms. In one embodiment, an alkynyl group contains from about 2 to about 10 carbon atoms. In another embodiment, an alkynyl group contains from about 2 to about 6 carbon atoms. Non-limiting examples of illustrative alkynyl groups include ethynyl, propynyl, 2-butynyl and 3-methylbutynyl. An alkynyl group may be unsubstituted or optionally substituted by one or more substituents which may be the same or different, each substituent being independently selected from the group consisting of halo, alkyl, alkenyl, —O-aryl, aryl, cycloalkyl, cycloalkenyl, cyano, —OH, —O-alkyl, -alkylene-O-alkyl, —O-haloalkyl, -alkylthio, —NH$_2$, —NH(alkyl), —N(alkyl)$_2$, —NH-aryl, —NH-heteroaryl, —NHC(O)-alkyl, —NHC(O)NH-alkyl, —NHSO$_2$-alkyl, —NHSO$_2$-aryl, —NHSO$_2$-heteroaryl, —NH(cycloalkyl), —OC(O)-alkyl, —OC(O)-aryl, —OC(O)-cycloalkyl, —C(O)alkyl, —C(O)NH$_2$, —C(O)NH-alkyl, —C(O)OH and —C(O)O-alkyl. In one embodiment, an alkynyl group is unsubstituted. In another embodiment, an alkynyl group is a straight chain alkynyl group. In another embodiment, an alkynyl group is a branched alkynyl group.

The term "alkylene" as used herein, refers to an alkyl group, as defined above, wherein one of the alkyl group's hydrogen atoms is replaced with a bond. Illustrative examples of alkylene include, but are not limited to, —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH$_2$CH(CH$_3$)CH$_2$— and —CH$_2$CH$_2$CH(CH$_3$)—. In one embodiment, an alkylene group is a straight chain alkylene group. In another embodiment, an alkylene group is a branched alkylene group.

"Aryl" means an aromatic monocyclic or multicyclic ring system having from about 6 to about 14 ring carbon atoms. In one embodiment, an aryl group has from about 6 to about 10 ring carbon atoms. An aryl group can be optionally substituted with one or more "ring system substituents" which may be the same or different, and are as defined herein below. Non-limiting examples of illustrative aryl groups include phenyl and naphthyl. In one embodiment, an aryl group is unsubstituted. In another embodiment, an aryl group is a phenyl group.

The term "cycloalkyl" as used herein, refers to a non-aromatic mono- or multicyclic ring system having from about 3 to about 10 ring carbon atoms. In one embodiment, a cycloalkyl has from about 5 to about 10 ring carbon atoms. In another embodiment, a cycloalkyl has from about 5 to about 7 ring carbon atoms. Non-limiting examples of illustrative monocyclic cycloalkyls include cyclopropyl, cyclopentyl, cyclohexyl, cycloheptyl and the like. Non-limiting examples of illustrative multicyclic cycloalkyls include 1-decalinyl, norbornyl, adamantyl and the like. A cycloalkyl group can be optionally substituted with one or more "ring system substituents" which may be the same or different, and are as defined herein below. In one embodiment, a cycloalkyl group is unsubstituted.

The term "cycloalkenyl" as used herein, refers to a non-aromatic mono- or multicyclic ring system comprising from about 3 to about 10 ring carbon atoms and containing at least one endocyclic double bond. In one embodiment, a cycloalkenyl contains from about 5 to about 10 ring carbon atoms. In another embodiment, a cycloalkenyl contains 5 or 6 ring carbon atoms. Non-limiting examples of illustrative monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein below. In one embodiment, a cycloalkenyl group is unsubstituted.

The term "5-membered cycloalkenyl" as used herein, refers to a cycloalkenyl group, as defined above, which has 5 ring carbon atoms.

The term "halo" as used herein, means —F, —Cl, —Br or —I. In one embodiment, halo refers to —Cl or —F.

The term "haloalkyl" as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3F atoms. Non-limiting examples of illustrative haloalkyl groups include —CH$_2$F, —CHF$_2$, —CF$_3$, —CH$_2$Cl and —CCl$_3$.

The term "hydroxyalkyl" as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of illustrative hydroxyalkyl groups include hydroxymethyl, 2-hydroxyethyl, 3-hydroxypropyl, 4-hydroxybutyl and —CH(OH)CH$_2$CH$_3$.

The term "heteroaryl" as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is monocyclic and has 5 or 6 ring atoms and at least one nitrogen ring atom. A heteroaryl group can be optionally substituted by one or more "ring system substituents" which may be the same or different, and are as defined herein below. A heteroaryl group is joined via a ring carbon atom and any nitrogen atom of a heteroaryl can be optionally oxidized to the corresponding N-oxide. The term "heteroaryl" also encompasses a heteroaryl group, as defined above, which has been fused to a benzene ring. Non-limiting examples of illustrative heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. In one embodiment, a heteroaryl group is a 6-membered heteroaryl group. In another embodiment, a heteroaryl group is a 5-membered heteroaryl group.

The term "5-membered heteroaryl" as used herein, refers to a heteroaryl group, as defined above, which has 5 ring atoms.

The term "heterocycloalkyl" as used herein, refers to a non-aromatic saturated monocyclic or multicyclic ring system comprising 3 to about 10 ring atoms, wherein from 1 to 4 of the ring atoms are independently O, S or N and the remainder of the ring atoms are carbon atoms. In one embodiment, a heterocycloalkyl group has from about 5 to about 10 ring atoms. In another embodiment, a heterocycloalkyl group has 5 or 6 ring atoms. There are no adjacent oxygen and/or sulfur atoms present in the ring system. Any —NH group in a heterocycloalkyl ring may exist protected such as, for example, as an —N(Boc), —N(CBz), —N(Tos) group and the like; such protected heterocycloalkyl groups are considered part of this invention. A heterocycloalkyl group can be optionally substituted by one or more "ring system substituents" which may be the same or different, and are as defined herein below. The nitrogen or sulfur atom of the heterocyclyl can be optionally oxidized to the corresponding N-oxide, S-oxide or S,S-dioxide. Non-limiting examples of illustrative monocyclic heterocycloalkyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. A ring carbon atom of a heterocycloalkyl group may be functionalized as a carbonyl group. An illustrative example of such a heterocycloalkyl group is pyrrolidonyl:

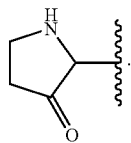 [SMILES: *C1NCCC1=O]

In one embodiment, a heterocycloalkyl group is a 6-membered heterocycloalkyl group. In another embodiment, a heterocycloalkyl group is a 5-membered heterocycloalkyl group.

The term "5-membered heterocycloalkyl" as used herein, refers to a heterocycloalkyl group, as defined above, which has 5 ring atoms.

The term "heterocycloalkenyl" as used herein, refers to a heterocycloalkyl group, as defined above, wherein the heterocycloalkyl group contains from 3 to 10 ring atoms, and at least one endocyclic carbon-carbon or carbon-nitrogen double bond. In one embodiment, a heterocycloalkenyl group has from 5 to 10 ring atoms. In another embodiment, a heterocycloalkenyl group is monocyclic and has 5 or 6 ring atoms. A heterocycloalkenyl group can optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. Non-limiting examples of illustrative heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, pyridone, 2-pyridone, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, pyridone, 2-pyridone, dihydrothiophenyl, dihydrothiopyranyl, and the like. A ring carbon atom of a heterocyclenyl group may be functionalized as a carbonyl group. An illustrative example of such a heterocyclenyl group is:

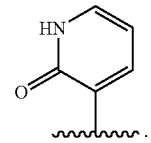 [SMILES: *c1ccc[nH]c1=O]

In one embodiment, a heterocycloalkenyl group is a 6-membered heterocycloalkenyl group. In another embodiment, a heterocycloalkenyl group is a 5-membered heterocycloalkenyl group.

The term "5-membered heterocycloalkenyl" as used herein, refers to a heterocycloalkenyl group, as defined above, which has 5 ring atoms.

The term "ring system substituent" as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, —OH, hydroxyalkyl, —O-alkyl, -alkylene-O-alkyl, —O-aryl, aralkoxy, acyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —OC(O)-alkyl, —OC(O)-aryl, —OC(O)-cycloalkyl, —C(=N—CN)—NH$_2$, —C(=NH)—NH$_2$, —C(=NH)—NH(alkyl), Y$_1$Y$_2$N—, Y$_1$Y$_2$N-alkylene-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

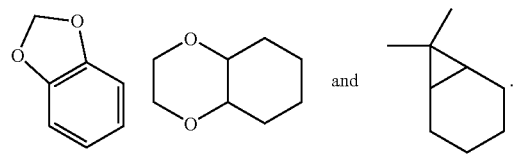

The term "substituted," as used herein, means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" as used herein, means optional substitution with the specified groups, radicals or moieties.

The terms "purified", "in purified form" or "in isolated and purified form" as used herein, for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^{11}$, etc.) occurs more than one time in any constituent or in Formula (I) or (II), its definition on each occurrence is independent of its definition at every other occurrence, unless otherwise noted.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" as used herein, refers to a compound (e.g, a drug precursor) that is transformed in vivo to provide a Compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a Compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl, and the like.

Similarly, if a Compound of Formula (I) contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate), and the like.

If a Compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl, —$C(OH)C(O)OY^1$ wherein $Y^1$ is H, $(C_1-C_6)$alkyl or benzyl, —$C(OY^2)Y^3$ wherein $Y^2$ is $(C_1-C_4)$ alkyl and $Y^3$ is $(C_1-C_6)$alkyl, carboxy$(C_1-C_6)$alkyl, amino$(C_1-C_4)$alkyl or mono-N— or di-N,N—$(C_1-C_6)$alkylaminoalkyl, —$C(Y^4)Y^5$ wherein $Y^4$ is H or methyl and $Y^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of illustrative solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The term "effective amount" or "therapeutically effective amount" is meant to describe an amount of compound or a composition of the present invention that is effective to treat or prevent a viral infection or a virus-related disorder.

Metabolic conjugates, such as glucuronides and sulfates which can undergo reversible conversion to the Compounds of Formula (I) are contemplated in the present invention.

The Compounds of Formula (I) may form salts, and all such salts are contemplated within the scope of this invention. Reference to a Compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a Compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

The Compounds of Formula (I) may contain asymmetric or chiral centers, and, therefore, exist in different stereoisomeric forms. It is intended that all stereoisomeric forms of the Compounds of Formula (I) as well as mixtures thereof, including racemic mixtures, form part of the present invention. In addition, the present invention embraces all geometric and positional isomers. For example, if a Compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the Compounds of Formula (I) may be atropisomers (e.g., substituted biaryls) and are considered as part of this invention. Enantiomers can also be separated by use of chiral HPLC column.

The straight line ____ as a bond generally indicates a mixture of, or either of, the possible isomers, non-limiting example(s) include, containing (R)- and (S)-stereochemistry. For example,

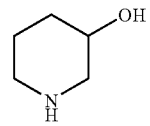

means containing both

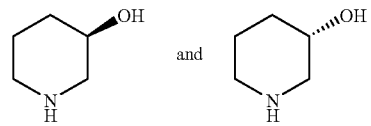 [SMILES: O[C@@H]1CCCNC1 ; O[C@H]1CCCNC1]

A dashed line (-----) represents an optional bond.

Lines drawn into the ring systems, such as, for example:

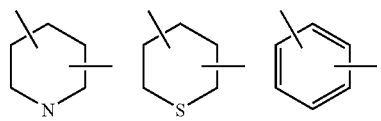

indicate that the indicated line (bond) may be attached to any of the substitutable ring atoms, non limiting examples include carbon, nitrogen and sulfur ring atoms.

As well known in the art, a bond drawn from a particular atom wherein no moiety is depicted at the terminal end of the bond indicates a methyl group bound through that bond to the atom, unless stated otherwise. For example:

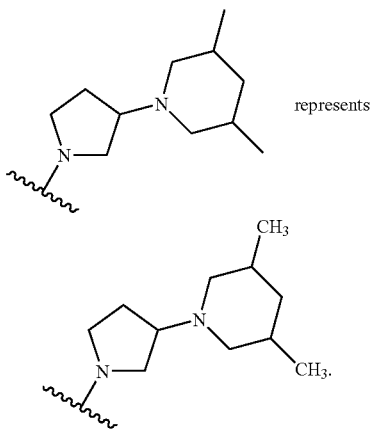 represents

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). For example, if a Compound of Formula (I) incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Such compounds are useful as therapeutic, diagnostic or research reagents. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled Compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled Compounds of Formula (I) can generally be prepared by following procedures analogous to those disclosed in the Schemes and/or in the Examples herein below, by substituting an appropriate isotopically labelled reagent for a non-isotopically labelled reagent.

Polymorphic forms of the Compounds of Formula (I), and of the salts, solvates, hydrates, esters and prodrugs of the Compounds of Formula (I), are intended to be included in the present invention.

The following abbreviations are used below and have the following meanings: BINAP is racemic-2,2'-bis(diphenylphosphino)-1,1'-binaphthyl; CSA is camphorsulfonic acid; DBPD is 2-(Di-t-butylphosphino)biphenyl, DBU is 1,8-diazabicyclo[5.4.0]undec-7-ene, DBN is 1,5-diazabicyclo[4.3.0]non-5-ene; DCC is dicyclohexylcarbodiimide; DCM is dichloromethane; Dibal-H is diisobutylaluminum hydride; DMF is dimethylformamide; EDCI is 1-(3-dimethylaminopropyl)-3-ethylcarbodiimide; HATU is N-(diethylamino)-1H-1,2,3-triazolo[4,5-b]pyridine-1-ylmethylene]-N-methylmethanaminium Hexafluorophosphate N-oxide; HOBT is 1-hydroxybenzotriazole; LAH is lithium aluminum hydride; LDA is lithium diisopropylamide; m-CPBA is m-chloroperbenzoic acid; NaBH(OAc)$_3$ is sodium triacetoxyborohydride; NaBH$_4$ is sodium borohydride; NaBH$_3$CN is sodium cyanoborohydride; NaHMDS is sodium hexamethyl disilylazide; p-TsOH is p-toluenesulfonic acid; p-TsCl is p-toluenesulfonyl chloride; PPTS is pyridinium p-toluenesulfonate; TMAD is N,N,N',N'-tetramethylazodicarboxamide; HRMS is high resolution mass spectrometry; HPLC is high performance liquid chromatography; LRMS is low resolution mass spectrometry; Tr is triphenylmethyl; Tris is tris(hydroxymethyl)aminomethane; THF is tetrahydrofuran; TFA is trifluoroacetic acid; Ci/mmol is Curie/mmol (a measure of specific activity); and Ki represents the dissociation constant for a substrate/receptor complex.

The Compounds of Formula (I)

The present invention provides Compounds of Formula (I):

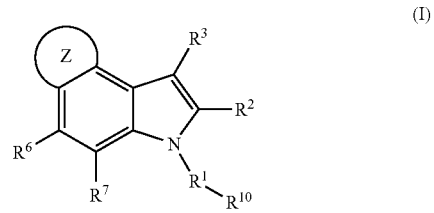

(I)

and pharmaceutically acceptable salts and solvates thereof, wherein $R^1$, $R^2$, $R^3$, $R^6$, $R^7$, $R^{10}$ and Z are defined above for the Compounds of Formula (I).

In one embodiment, when $R^1$ is a bond, $R^{10}$ is not H.
In another embodiment, $R^1$ is a bond or $-[C(R^{12})_2]_r-$.
In another embodiment, $R^1$ is a bond.
In another embodiment, $R^1$ is $-CH_2-$.
In still another embodiment, $R^1$ is $-[C(R^{12})_2]_r-$.
In another embodiment, $R^1$ is $-[C(R^{12})_2]_r-O-[C(R^{12})_2]_q-$.
In still another embodiment, $R^1$ is $-[C(R^{12})_2]_r-NR^9-[C(R^{12})_2]_q-$.
In yet another embodiment, $R^1$ is $-[C(R^{12})_2]_q-C\!\!=\!\!C-[C(R^{12})_2]_q-$.
In a further embodiment, $R^1$ is $-[C(R^{12})_2]_q-C\!\!\equiv\!\!C-[C(R^{12})_2]_q-$.

In another embodiment, $R^1$ is —$[C(R^{12})_2]_q$—$SO_2$—$[C(R^{12})_2]_q$—.

In one embodiment, $R^{10}$ is —H.
In another embodiment, $R^{10}$ is aryl.
In still another embodiment, $R^{10}$ is cycloalkyl.
In yet another embodiment, $R^{10}$ is cycloalkenyl.
In a further embodiment, $R^{10}$ is heterocycloalkyl.
In another embodiment, $R^{10}$ is heterocycloalkenyl.
In another embodiment, $R^{10}$ is heteroaryl.
In another embodiment, $R^{10}$ is bicyclic heteroaryl.
In one embodiment, $R^{10}$ is aryl or heteroaryl.
In another embodiment, $R^{10}$ is phenyl, pyridyl, benzimidazole, benzimidazolone, quinoline, quinolinone, quinoxaline, quinoxalinone, quinazoline, quinazolinone, naphthyridine, naphthyridinone, pteridine, pteridinone, each of which can be optionally substituted with up to 3 substituents, which are the same or different, and are selected from alkyl, cycloalkyl, heterocycloalkyl, heterocycloalkenyl, halo, haloalkyl, —O-haloalkyl, —OH, —CN, —$NH_2$, —NH-alkyl, —N(alkyl)$_2$ or —$NHSO_2$-alkyl.

In another embodiment, $R^{10}$ is phenyl, pyridyl, benzimidazole, benzimidazolone, quinoline, quinolinone, quinoxaline, quinoxalinone, quinazoline, quinazolinone, naphthyridine, naphthyridinone, pteridine, pteridinone, each of which can be optionally substituted with up to 3 substituents, which are the same or different, and are selected from methyl, cyclopropyl, halo, —OH, —$NH_2$, —$NHCH_3$ and —$N(CH_3)_2$.

In another embodiment, $R^{10}$ is quinoline, quinolinone, pteridine or pteridinone, each of which can be optionally substituted with up to 3 substituents, which are the same or different, and are selected from alkyl, cycloalkyl, heterocycloalkyl, heterocycloalkenyl, halo, haloalkyl, —O-haloalkyl, —OH, —CN, —$NH_2$, —NH-alkyl, —N(alkyl)$_2$ or —$NHSO_2$-alkyl.

In still another embodiment, $R^{10}$ is pteridine or pteridinone, either of which can be optionally substituted with up to 3 substituents, which are the same or different, and are selected from alkyl, cycloalkyl, heterocycloalkyl, heterocycloalkenyl, halo, haloalkyl, —O-haloalkyl, —OH, —CN, —$NH_2$, —NH-alkyl, —N(alkyl)$_2$ or —$NHSO_2$-alkyl.

In one embodiment, $R^{10}$ is quinoline or quinolinone, either of which can be optionally substituted with up to 3 substituents, which are the same or different, and are selected from alkyl, cycloalkyl, heterocycloalkyl, heterocycloalkenyl, halo, haloalkyl, —O-haloalkyl, —OH, —CN, —$NH_2$, —NH-alkyl, —N(alkyl)$_2$ or —$NHSO_2$-alkyl.

In another embodiment, $R^{10}$ is phenyl, pyridyl or pyrimidinyl, each of which is unsubstituted or optionally substituted with up to 3 substituents, which are the same or different, and are selected from alkyl, aryl, heteroaryl, heterocycloalkyl, heterocycloalkenyl, halo, haloalkyl, —OH, hydroxyalkyl, —CN, —C(O)alkyl, —C(O)Oalkyl, —C(O)N($R^9$)$_2$, -alkylene-O$R^9$, —O$R^9$, —N($R^9$)$_2$, —NHC(O)$R^8$, —$NHSO_2R^{11}$, —$S(O)_pR^{11}$ or —$SO_2N(R^9)_2$.

In one embodiment, $R^{10}$ is phenyl.
In another embodiment, $R^{10}$ is pyridyl.
In one embodiment, $R^{10}$ is:

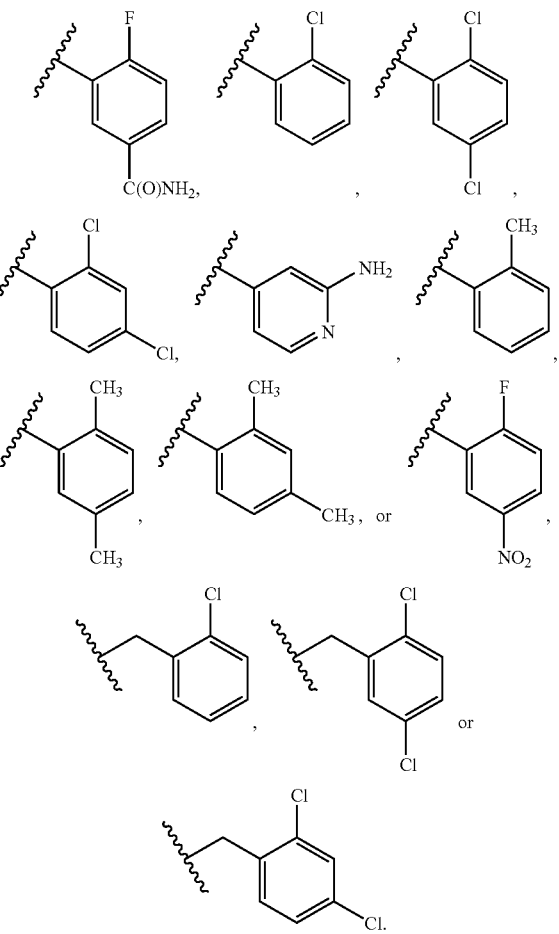

In another embodiment, $R^{10}$ is:

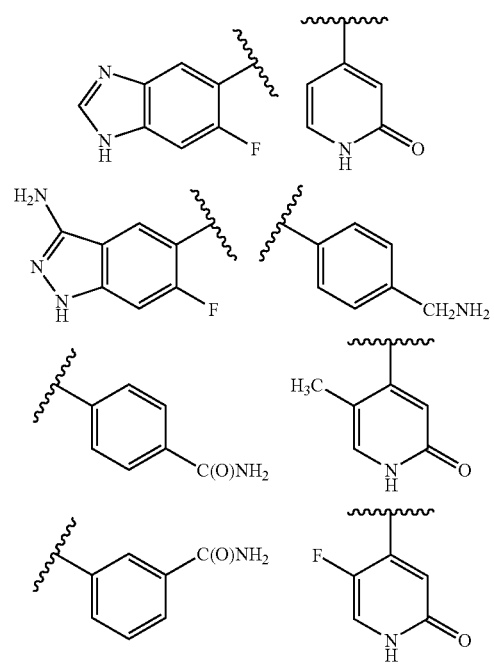

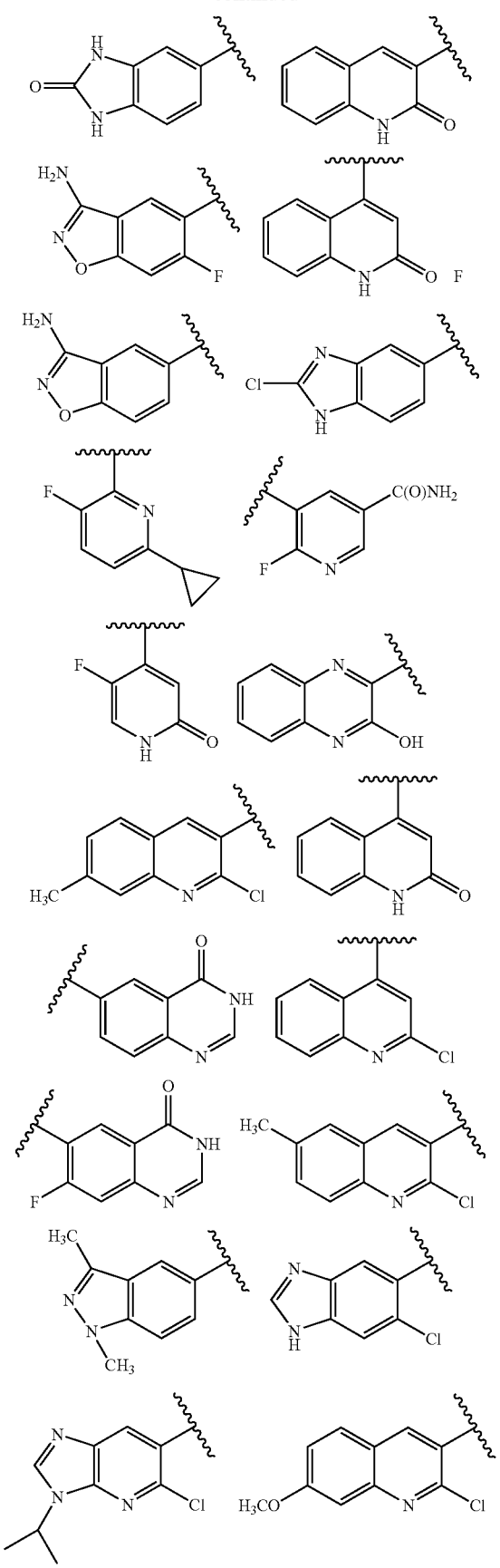
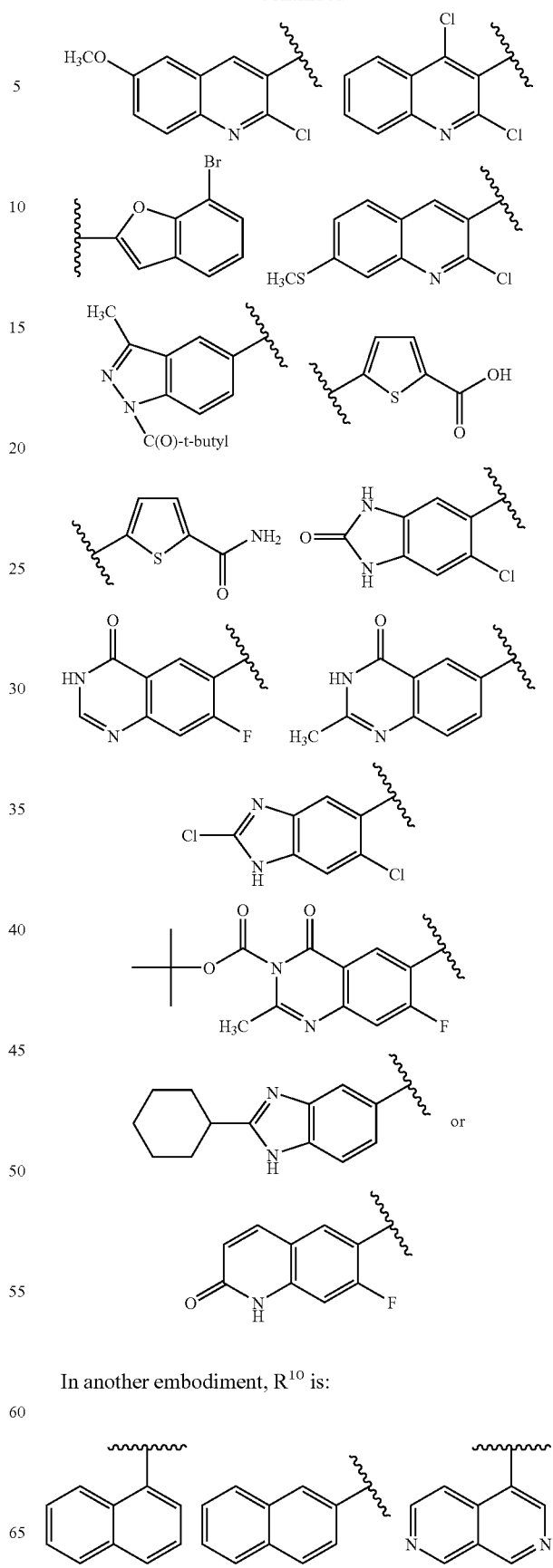
In another embodiment, $R^{10}$ is:

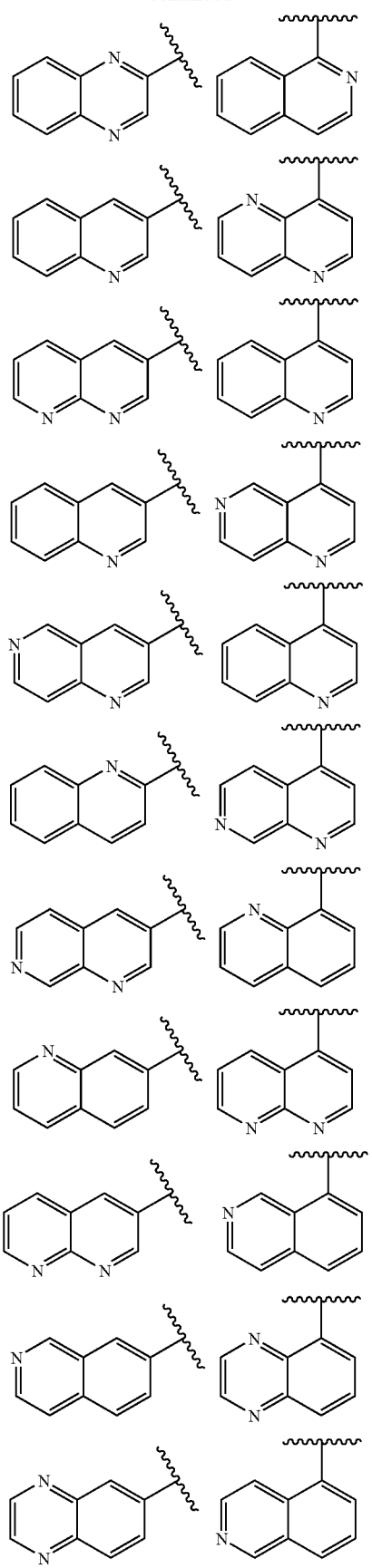
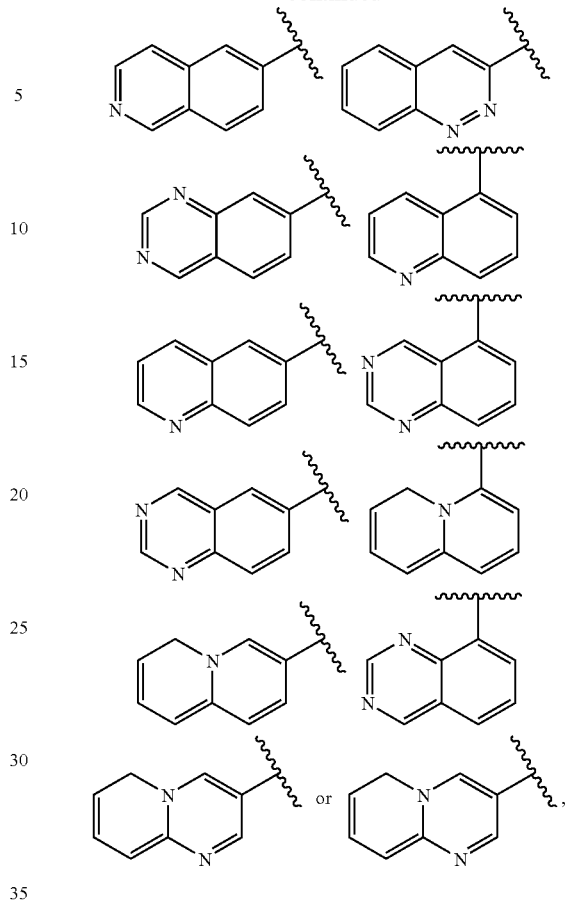
each of which can be optionally substituted with up to 3 substituents, which are the same or different, and are selected from alkyl, cycloalkyl, heterocycloalkyl, heterocycloalkenyl, halo, haloalkyl, —O-haloalkyl, —OH, —CN, —NH₂, —NH-alkyl, —N(alkyl)₂ or —NHSO₂-alkyl.
In another embodiment, R¹⁰ is:
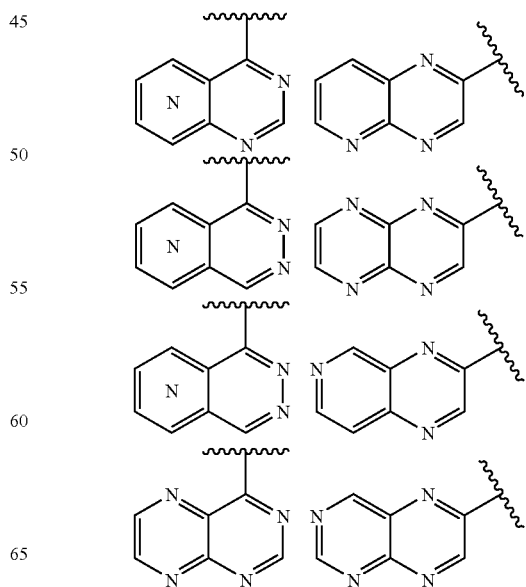

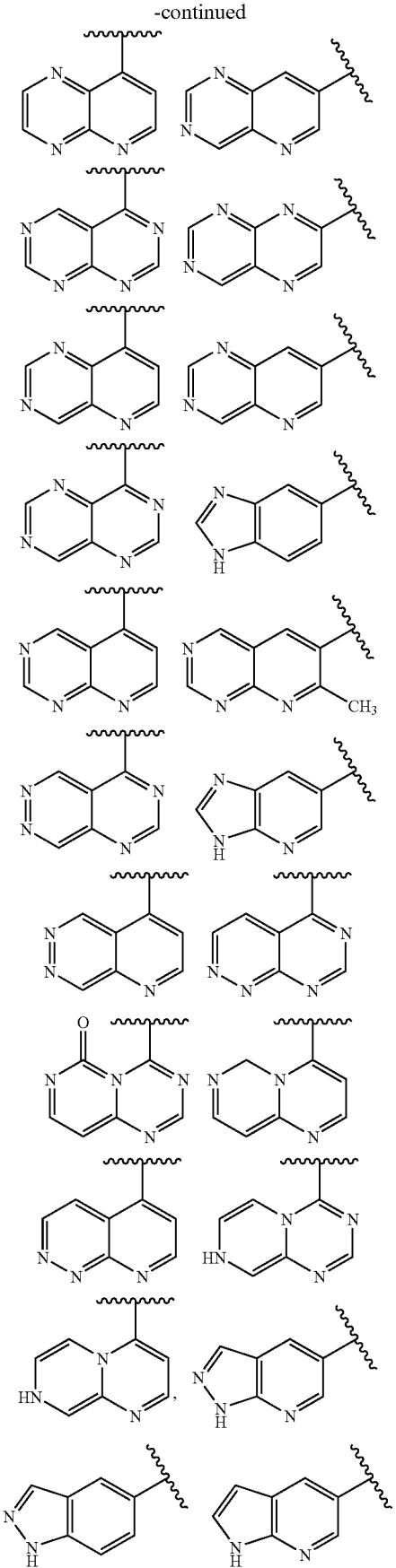

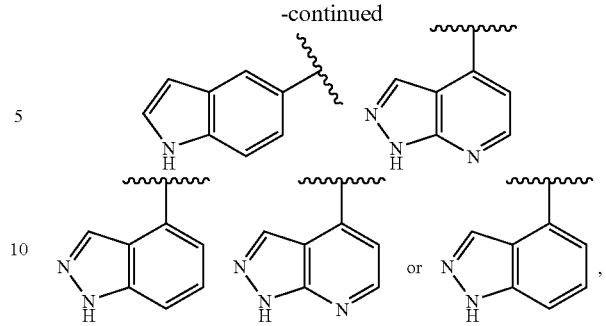

each of which can be optionally substituted with up to 3 substituents, which are the same or different, and are selected from alkyl, cycloalkyl, heterocycloalkyl, heterocycloalkenyl, halo, haloalkyl, —O-haloalkyl, —OH, —CN, —NH₂, —NH-alkyl, —N(alkyl)₂ or —NHSO₂-alkyl; wherein the letter "N" inside a ring indicates that the ring has 1 or 2 ring nitrogen atoms.

In one embodiment, $R^1$ is —[C($R^{12}$)₂]$_r$—, each occurrence of $R^{12}$ is H, and $R^{10}$ is —H.

In another embodiment, $R^1$ is —[C($R^{12}$)₂]$_r$—, each occurrence of $R^{12}$ is H, and $R^{10}$ is alkyl.

In another embodiment, $R^1$ is —[C($R^{12}$)₂]$_r$—, each occurrence of $R^{12}$ is H, and $R^{10}$ is aryl.

In still another embodiment, $R^1$ is —[C($R^{12}$)₂]$_r$—, each occurrence of $R^{12}$ is H, and $R^{10}$ is cycloalkyl.

In yet another embodiment, $R^1$ is —[C($R^{12}$)₂]$_r$—, each occurrence of $R^{12}$ is H, and $R^{10}$ is cycloalkylene.

In a further embodiment, $R^1$ is —[C($R^{12}$)₂]$_r$—, each occurrence of $R^{12}$ is H, and $R^{10}$ is heterocycloalkyl.

In another embodiment, $R^1$ is —[C($R^{12}$)₂]$_r$—, each occurrence of $R^{12}$ is H, and $R^{12}$ is heterocycloalkylene.

In another embodiment, $R^1$ is —[C($R^{12}$)₂]$_r$—, each occurrence of $R^{12}$ is H, and $R^{10}$ is heteroaryl.

In still another embodiment, $R^1$ is a bond or —[C($R^{12}$)₂]$_r$—, and $R^{10}$ is phenyl, pyridyl, benzimidazole, benzimidazolone, quinoline, quinolinone, quinoxaline, quinoxalinone, quinazoline, quinazolinone, naphthyridine, naphthyridinone, pteridine, pteridinone, each of which can be optionally substituted with up to 3 substituents, which are the same or different, and are selected from alkyl, cycloalkyl, heterocycloalkyl, heterocycloalkenyl, halo, haloalkyl, —O-haloalkyl, —OH, —CN, —NH₂, —NH-alkyl, —N(alkyl)₂ or —NHSO₂-alkyl.

In a further embodiment, $R^1$ is a bond or —[C($R^{12}$)₂]$_r$—, and $R^{10}$ is phenyl, pyridyl, benzimidazole, benzimidazolone, quinoline, quinolinone, quinoxaline, quinoxalinone, quinazoline, quinazolinone, naphthyridine, naphthyridinone, pteridine, pteridinone, each of which can be optionally substituted with up to 3 substituents, which are the same or different, and are selected from methyl, cyclopropyl, halo, —OH, —NH₂, —NHCH₃ and —N(CH₃)₂.

In one embodiment, $R^1$ is —CH₂— and $R^{10}$ is:

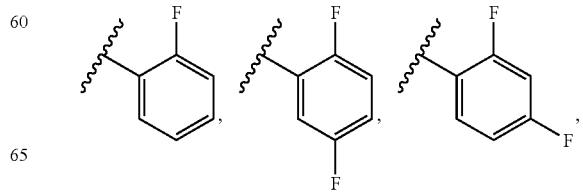

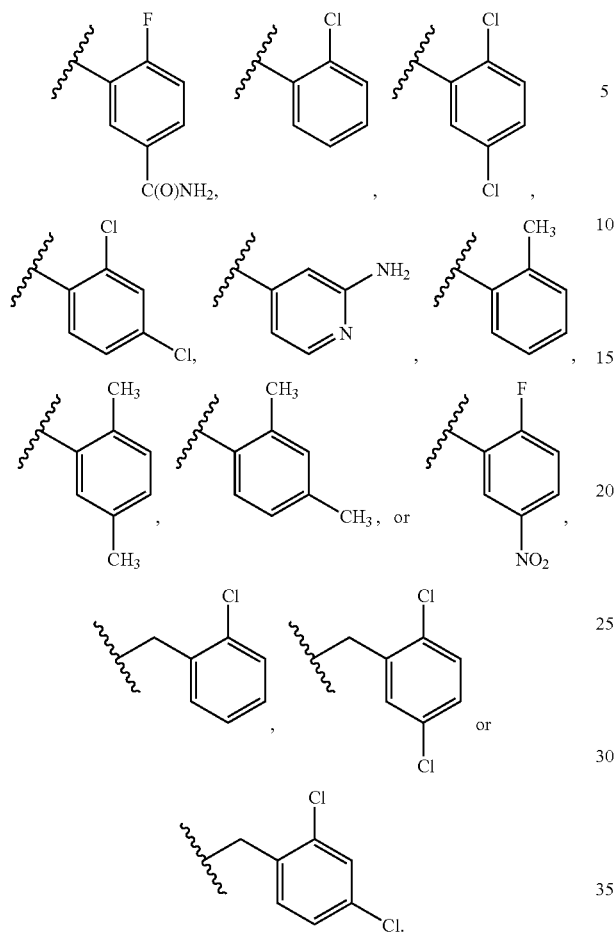
In another embodiment, $R^1$ is —$CH_2$— and $R^{10}$ is:
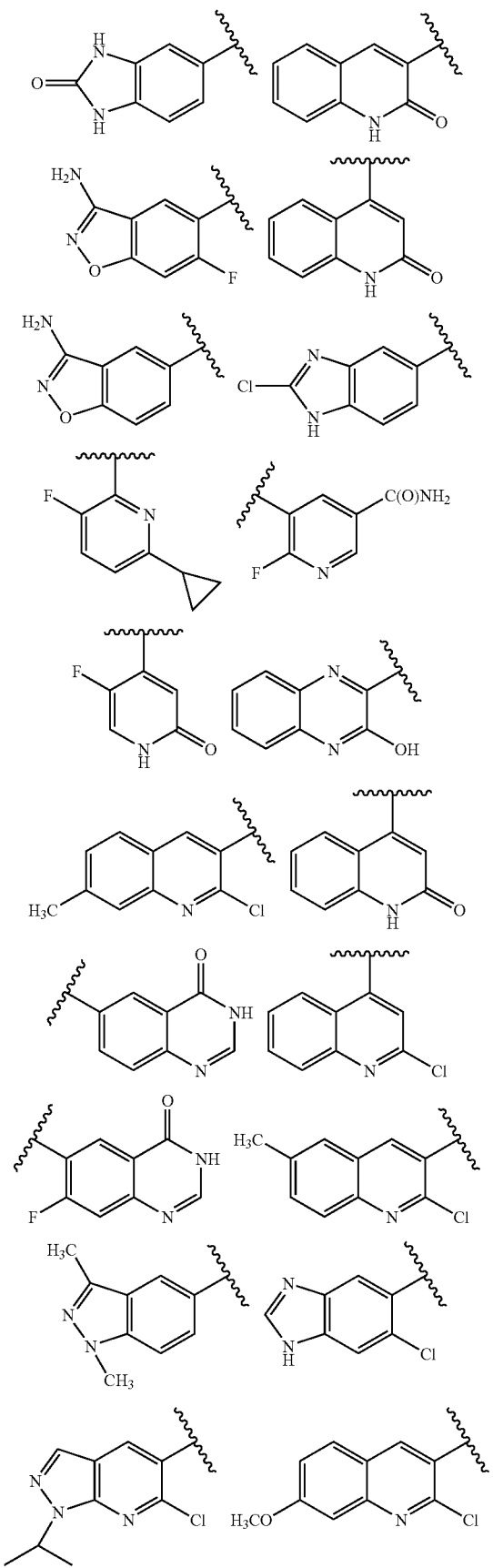

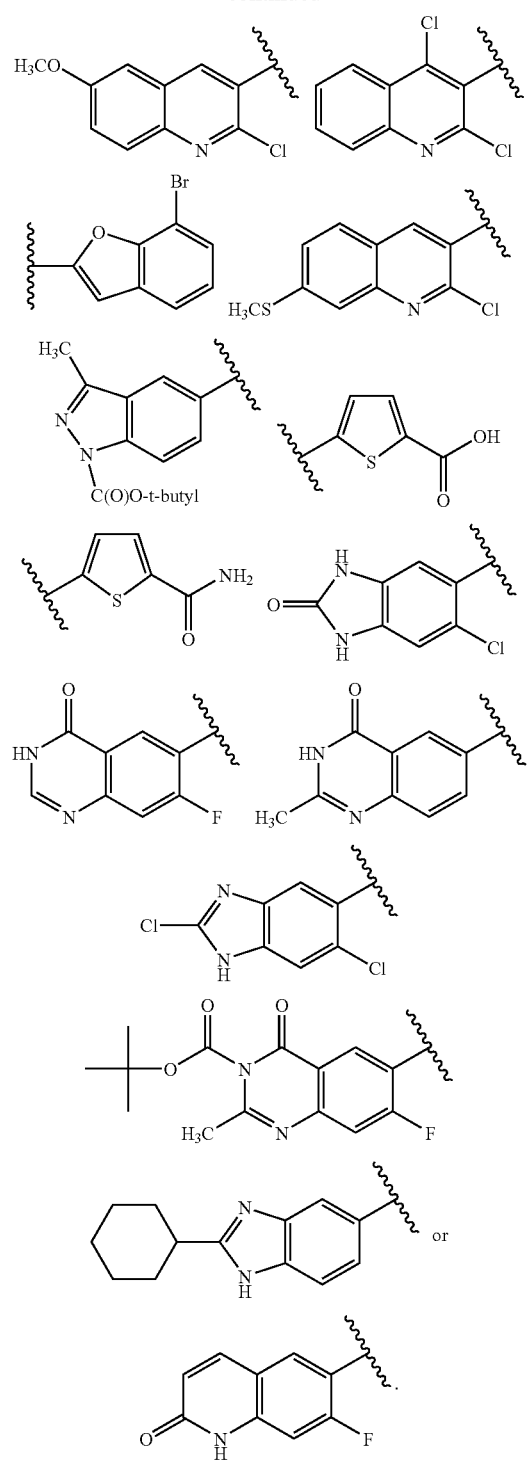
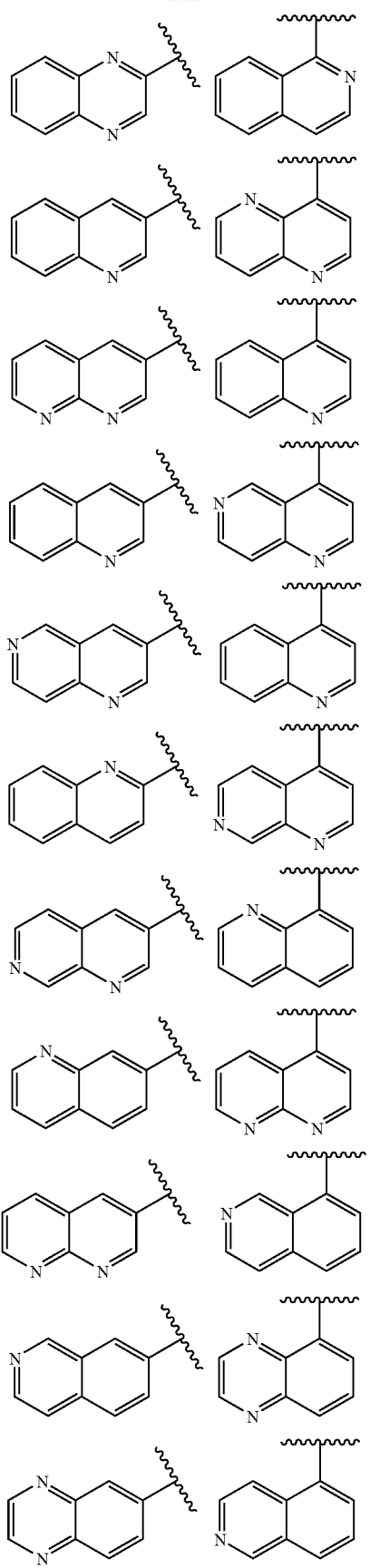
In another embodiment, $R^1$ is —CH$_2$— and $R^{10}$ is:
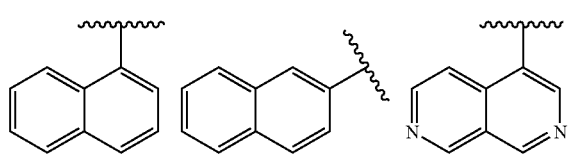

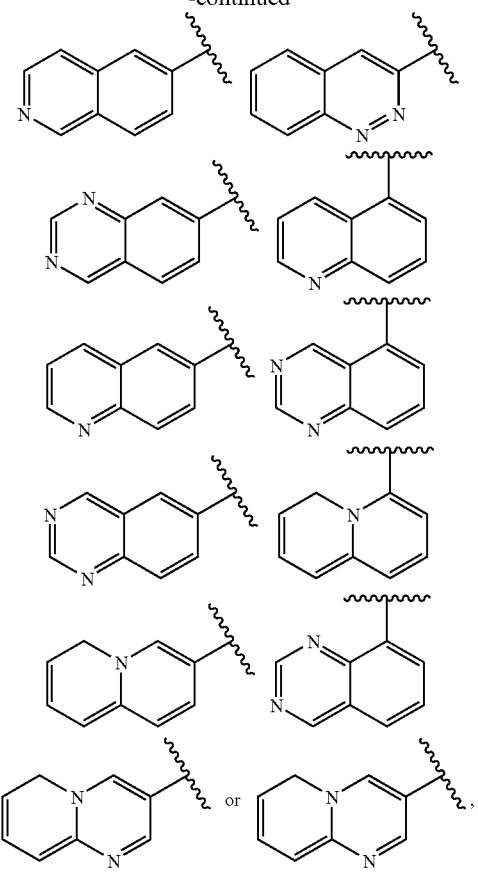
each of which can be optionally substituted with up to 3 substituents, which are the same or different, and are selected from alkyl, cycloalkyl, heterocycloalkyl, heterocycloalkenyl, halo, haloalkyl, —O-haloalkyl, —OH, —CN, —NH$_2$, —NH-alkyl, —N(alkyl)$_2$ or —NHSO$_2$-alkyl.
In still another embodiment, R$^1$ is —CH$_2$— and R$^{10}$ is:
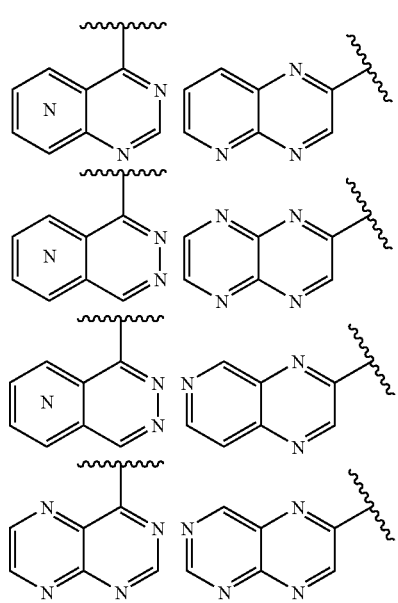
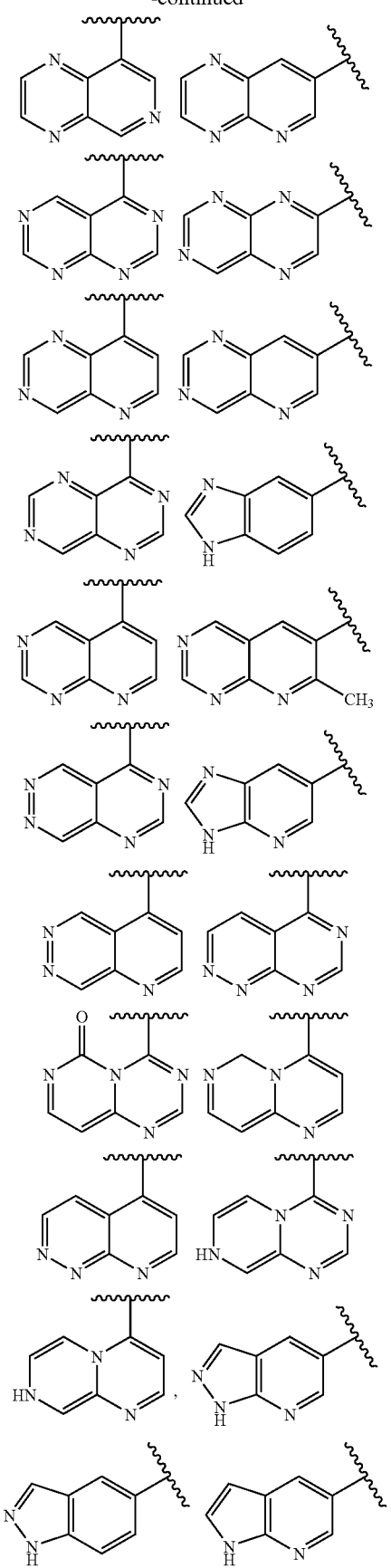

-continued

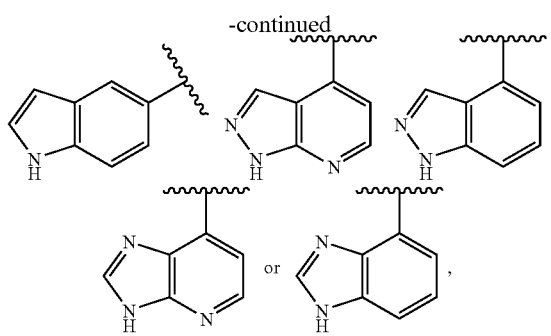

each of which can be optionally substituted with up to 3 substituents, which are the same or different, and are selected from alkyl, cycloalkyl, heterocycloalkyl, heterocycloalkenyl, halo, haloalkyl, —O-haloalkyl, —OH, —CN, —NH$_2$, —NH-alkyl, —N(alkyl)$_2$ or —NHSO$_2$-alkyl; wherein the letter "N" inside a ring indicates that the ring has 1 or 2 ring nitrogen atoms.

In one embodiment, —R$^1$-R$^{10}$ is methyl.
In another embodiment, —R$^1$-R$^{10}$ is benzyl.
In another embodiment, —R$^1$-R$^{10}$ is:

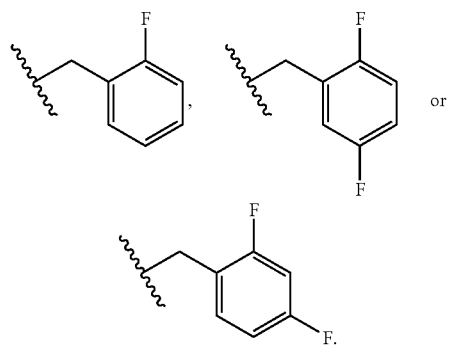

In still another embodiment, —R$^1$-R$^{10}$ is:

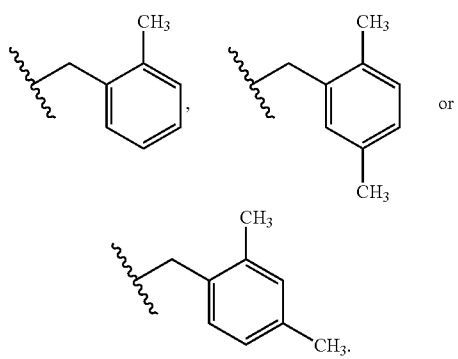

In yet another embodiment, —R$^1$-R$^{10}$ is:

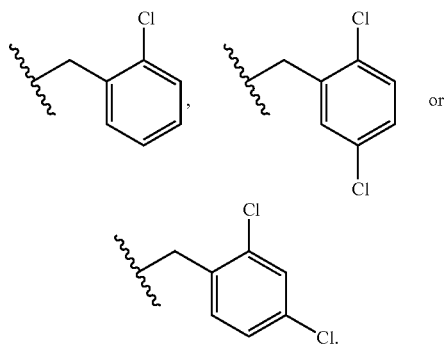

In a further embodiment, —R$^1$-R$^{10}$ is:

In another embodiment, —R$^1$-R$^{10}$ is:

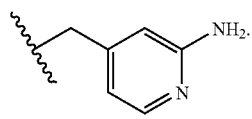 [SMILES: *Cc1ccnc(N)c1]

In one embodiment, R$^2$ is —C(O)OR$^9$.
In another embodiment, R$^2$ is —C(O)N(R$^9$)$_2$.
In another embodiment, R$^2$ is —C(O)N(R$^9$)SO$_2$R$^{11}$.
In still another embodiment, R$^2$ is —C(O)NHSO$_2$R$^{11}$.
In another embodiment, R$^2$ is —[C(R$^{12}$)$_2$]$_r$—C(O)OR$^9$.
In another embodiment, R$^2$ is —[C(R$^{12}$)$_2$]$_r$—C(O)N(R$^9$)$_2$.
In another embodiment, R$^2$ is —[C(R$^{12}$)$_2$]$_r$—C(O)N(R$^9$)SO$_2$R$^{11}$.
In yet another embodiment, R$^2$ is alkyl.
In a further embodiment, R$^2$ is —[C(R$^{12}$)$_2$]$_q$-aryl.
In another embodiment, R$^2$ is —[C(R$^{12}$)$_2$]$_q$-cycloalkyl.
In another embodiment, R$^2$ is —[C(R$^{12}$)$_2$]$_q$-cycloalkenyl.
In another embodiment, R$^2$ is —[C(R$^{12}$)$_2$]$_q$-heterocycloalkyl.
In still another embodiment, —[C(R$^{12}$)$_2$]$_q$-heteroaryl-.
In yet another embodiment, R$^2$ is —[C(R$^{12}$)$_2$]$_q$-heterocycloalkenyl.
In a further embodiment, R$^2$ is -arylthiazin-yl.
In another embodiment, R$^2$ is arylthiadiazol-yl-.
In one embodiment, R$^2$ is —C(O)OH.
In another embodiment, R$^2$ is —C(O)OCH$_3$
In another embodiment, R$^2$ is —C(O)OCH$_2$CH$_3$.
In still another embodiment, R$^2$ is —C(O)NHSO$_2$CH$_3$.
In yet another embodiment, R$^2$ is —C(O)NHSO$_2$CH$_2$CH$_3$.
In another embodiment, R$^2$ is —C(O)NHSO$_2$-isopropyl.
In another embodiment, R$^2$ is —C(O)NHSO$_2$-cyclopropyl.

In a further embodiment, R² is:

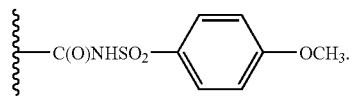

In yet another embodiment, R² is:

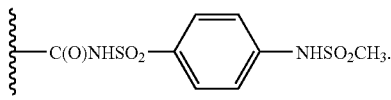

In a further embodiment, R² is:

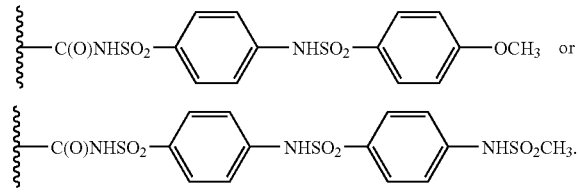

In one embodiment, R² is:

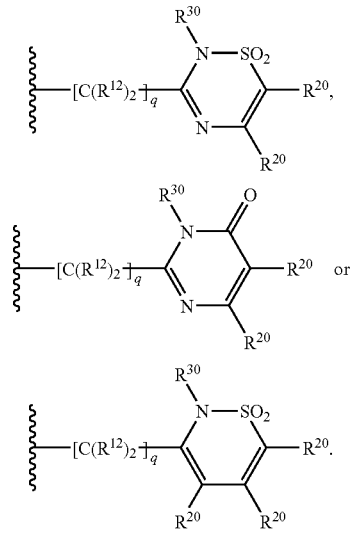

In another embodiment, R² is:

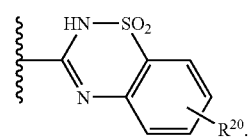

In another embodiment, R² is:

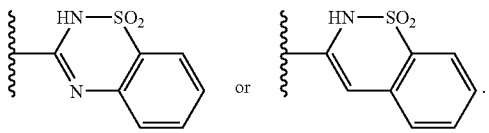 [SMILES: *C1=Nc2ccccc2S(=O)(=O)N1 ; *C1=Cc2ccccc2S(=O)(=O)N1]

In still another embodiment, R² is —C(O)OH, —C(O)Oalkyl, —C(O)NH₂, —C(O)NH-alkyl, —C(O)NH-cycloalkyl, —C(O)NHSO₂R¹¹, heteroaryl,

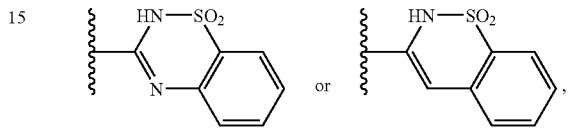

wherein a heteroaryl, arylthiazin-yl- or arylthiadiazol-yl-group can be optionally substituted with up to 3 substituents, which are the same or different, and are selected from alkyl, aryl, heteroaryl, halo, haloalkyl, hydroxyalkyl, —OH, —CN, —C(O)R⁸, —C(O)OR⁹, —C(O)N(R⁹)₂, —[C(R¹²)₂]_q—OR⁹, —[C(R¹²)₂]_q—N(R⁹)₂, —NHC(O)R⁸, —NHSO₂R¹¹, —S(O)_pR¹¹ or —SO₂N(R⁹)₂.

In one embodiment, R² is —C(O)OH, —C(O)NHSO₂-alkyl, —C(O)NHSO₂-aryl, —C(O)NHSO₂-cycloalkyl or —C(O)NHSO₂-alkylene-cycloalkyl.

In another embodiment, R² is —C(O)OH, —C(O)NHSO₂CH₃ or —C(O)NHSO₂-cyclopropyl.

In another embodiment, R² is —C(O)OH, —C(O)Oalkyl, —C(O)NH₂, —C(O)NH-alkyl, —C(O)NH-cycloalkyl, —C(O)NHSO₂R¹¹, heteroaryl,

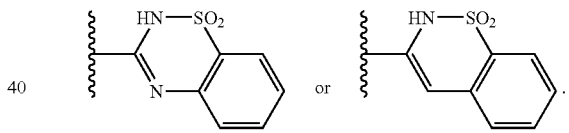

wherein the heteroaryl, arylthiazin-yl- or arylthiadiazol-yl-group can be optionally substituted with up to 3 substituents, which are the same or different, and are selected from alkyl, aryl, heteroaryl, halo, haloalkyl, hydroxyalkyl, —OH, —CN, —C(O)R⁸, —C(O)OR⁹, —C(O)N(R⁹)₂, —[C(R¹²)₂]_q—OR⁹, —[C(R¹²)₂]_q—N(R⁹)₂, —NHC(O)R⁸, —NHSO₂R¹¹, —S(O)_pR¹¹ or —SO₂N(R⁹)₂; such that if Z is thiophene-yl, R² is other than —C(O)O-alkyl.

In still another embodiment, R² is —C(O)NHSO₂-alkyl, —C(O)NHSO₂-aryl, —C(O)NHSO₂-cycloalkyl or —C(O)NHSO₂-alkylene-cycloalkyl.

In one embodiment, R³ is —H.

In another embodiment, R³ is —[C(R¹²)₂]_q-alkyl.

In another embodiment, R³ is —[C(R¹²)₂]_q-aryl.

In still another embodiment, R³ is —[C(R¹²)₂]_q-cycloalkyl.

In yet another embodiment, R³ is —[C(R¹²)₂]_q-cycloalkylene.

In a further embodiment, R³ is —[C(R¹²)₂]_q-heterocycloalkyl.

In another embodiment, R³ is —[C(R¹²)₂]_q-heterocycloalkylene.

In one embodiment, R³ is —[C(R¹²)₂]_q-heteroaryl.

In one embodiment, R³ is aryl, heteroaryl or heterocycloalkenyl, each of which is unsubstituted or optionally substituted with up to 3 substituents, which are the same or different, and are selected from alkyl, aryl, cycloalkyl, heterocycloalkyl, heteroaryl, halo, haloalkyl, hydroxyalkyl, —OH, —CN, —C(O)alkyl, —C(O)N(R$^9$)$_2$, —N(R$^9$)$_2$, —O-haloalkyl, —NHC(O)NH$_2$, —NHC(O)NH-alkyl, —NHSO$_2$R$^{11}$, —S(O)$_2$R$^{11}$ or —SO$_2$NHR$^{11}$.

In another embodiment, R$^3$ is pyridyl or phenyl which is unsubstituted or optionally substituted with 1 to 3 substituents, which are the same or different, and are selected from alkyl, aryl, heteroaryl, halo, haloalkyl, hydroxyalkyl, —OH, —CN, —C(O)R$^8$, —C(O)N(R$^9$)$_2$, —[C(R$^{12}$)$_2$]$_q$—OR$^9$, —[C(R$^{12}$)$_2$]$_q$—N(R$^9$)$_2$, or —NHC(O)R$^8$.

In another embodiment, R$^3$ is:

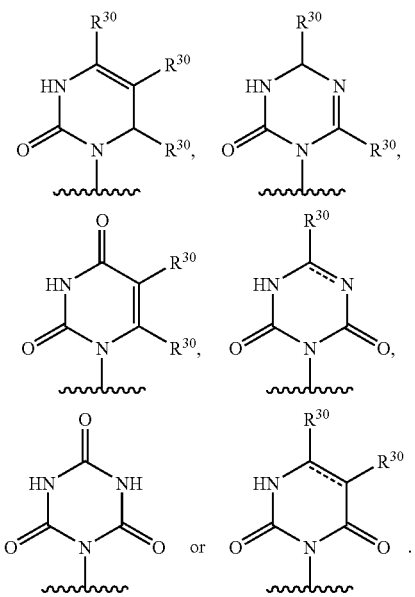

In another embodiment, R$^3$ is:

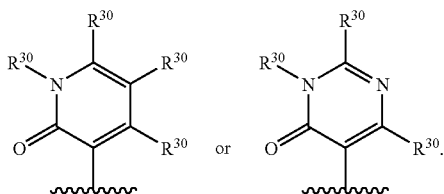

In still another embodiment, R$^3$ is:

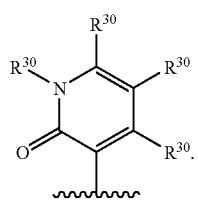

In one embodiment, R$^3$ is:

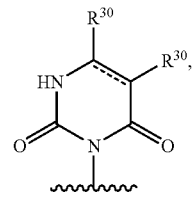

wherein both R$^{30}$ groups, together with the carbon atoms to which they are attached, join to form a –3- to 7-membered ring selected from aryl, cycloalkyl, heteroaryl and heterocycloalkyl.

In another embodiment, R$^3$ is aryl.
In another embodiment, R$^3$ is phenyl.
In still another embodiment, R$^3$ is benzyl.
In yet another embodiment, R$^3$ is:

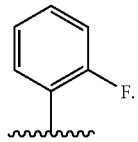 [SMILES: *c1ccccc1F]

In another embodiment, R$^3$ is:

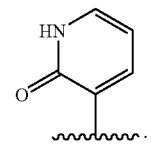 [SMILES: *c1ccc[nH]c1=O]

In one embodiment, R$^6$ is —H.
In another embodiment, R$^6$ is alkyl.
In another embodiment, R$^6$ is haloalkyl.
In another embodiment, R$^6$ is hydroxyalkyl.
In still another embodiment, R$^6$ is aryl.
In yet another embodiment, R$^6$ is halo.
In a further embodiment, R$^6$ is —OH.
In another embodiment, R$^6$ is —O-haloalkyl.
In one embodiment, R$^6$ is -alkoxy.
In another embodiment, R$^6$ is —CN.
In another embodiment, R$^6$ is —[C(R$^{12}$)$_2$]$_q$—OR$^9$.
In another embodiment, R$^6$ is —[C(R$^{12}$)$_2$]$_q$—N(R$^9$)$_2$.
In still another embodiment, R$^6$ is —C(O)R$^8$.
In another embodiment, R$^6$ is —C(O)OR$^9$.
In yet another embodiment, R$^6$ is —C(O)N(R$^9$)$_2$.
In a further embodiment, R$^6$ is —NHC(O)R$^8$.
In another embodiment, R$^6$ is —NHSO$_2$R$^{11}$.
In another embodiment, R$^6$ is —S(O)$_p$R$^{11}$
In another embodiment, R$^6$ is —SO$_2$N(R$^9$)$_2$.
In one embodiment, R$^7$ is —H.
In another embodiment, R$^7$ is alkyl.
In another embodiment, R$^7$ is haloalkyl.
In another embodiment, R$^7$ is hydroxyalkyl.
In still another embodiment, R$^7$ is aryl.
In yet another embodiment, R$^7$ is halo.
In a further embodiment, R$^7$ is —OH.
In another embodiment, R$^7$ is —O-haloalkyl.
In one embodiment, R$^7$ is -alkoxy.
In another embodiment, R$^7$ is —CN.
In another embodiment, R$^7$ is —[C(R$^{12}$)$_2$]$_q$—OR$^9$.
In another embodiment, R$^7$ is —[C(R$^{12}$)$_2$]$_q$—N(R$^9$)$_2$.

In still another embodiment, $R^7$ is —C(O)$R^8$.

In another embodiment, $R^7$ is —C(O)O$R^9$.

In yet another embodiment, $R^7$ is —C(O)N($R^9$)$_2$.

In a further embodiment, $R^7$ is —NHC(O)$R^8$.

In another embodiment, $R^7$ is —NHSO$_2$$R^{11}$.

In another embodiment, $R^7$ is —S(O)$_p$$R^{11}$

In another embodiment, $R^7$ is —SO$_2$N($R^9$)$_2$.

In one embodiment, $R^6$ and $R^7$ are each —H.

In another embodiment, one, but not both, of $R^6$ and $R^7$ is —H.

In another embodiment, each of $R^6$ and $R^7$ are other than —H.

In a further embodiment, $R^6$ and $R^7$ are each independently selected from H, alkyl, F, Cl, —CF$_3$, —OH, —O-alkyl, —OCF$_3$, —NH$_2$ or —NHSO$_2$-alkyl.

In one embodiment, ring Z is cyclopentenyl.

In another embodiment, the invention provides compounds of formula (I), wherein ring Z is a 5-membered heterocycloalkenyl or 5-membered heteroaryl.

In another embodiment, ring Z is a 5-membered heterocycloalkyl.

In still another embodiment, ring Z is a 5-membered heterocycloalkenyl.

In yet another embodiment, ring Z is a 5-membered heteroaryl.

In another embodiment, ring Z is a cyclopentyl.

In one embodiment, ring Z is:

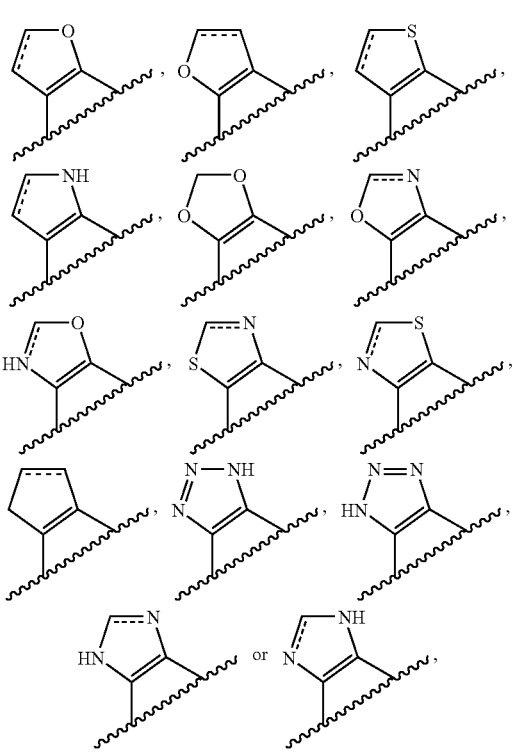

wherein a dotted line represents an optional and additional bond, and wherein the above ring Z groups can be optionally substituted as set forth above for the compounds of formula (I).

In another embodiment, ring Z is:

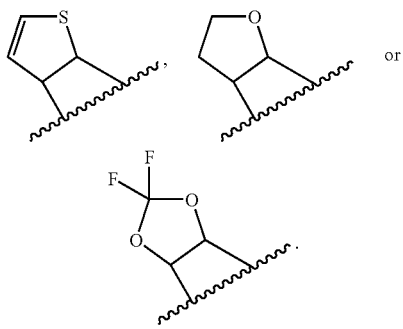

In another embodiment, ring Z is:

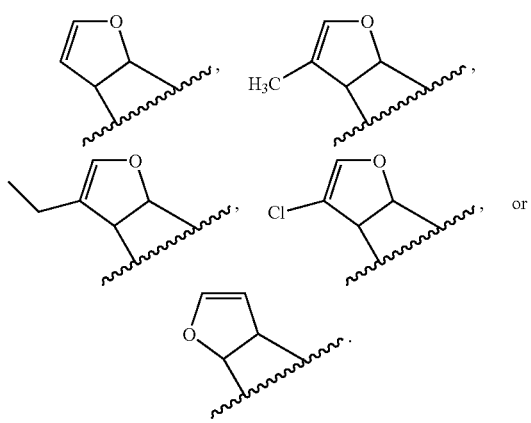

In another embodiment, ring Z is:

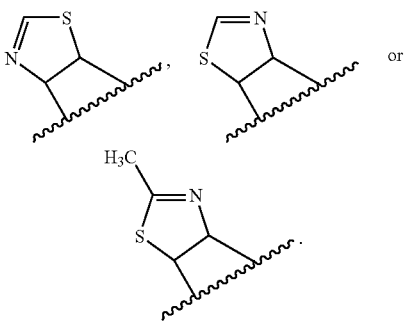

In another embodiment, ring Z is:

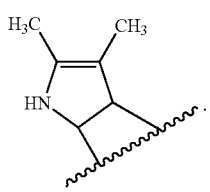

In one embodiment, ring Z is a 5-membered heterocycloalkyl, —$R^1$-$R^{10}$ is alkyl, -alkylene-aryl or -alkylene-heteroaryl, $R^2$ is —C(O)O$R^8$ or —C(O)NHSO$_2$$R^{11}$, and $R^3$ is aryl or heterocycloalkenyl.

In another embodiment, ring Z is a 5-membered heterocycloalkenyl or a 5-membered heteroaryl, —R¹-R¹⁰ is alkyl, -(alkylene)$_q$-aryl or -(alkylene)$_q$-heteroaryl, R² is —C(O)OR⁸ or —C(O)NHSO₂R¹¹, and R³ is aryl or heterocycloalkenyl.

In another embodiment, ring Z is

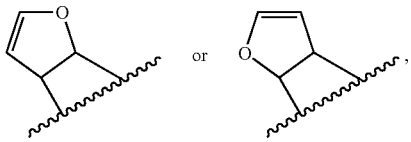

—R¹-R¹⁰ is alkyl, -(alkylene)$_q$-aryl or -(alkylene)$_q$-heteroaryl, R² is —C(O)OR⁸ or —C(O)NHSO₂R¹¹, and R³ is aryl or heterocycloalkenyl.

In another embodiment, ring Z is

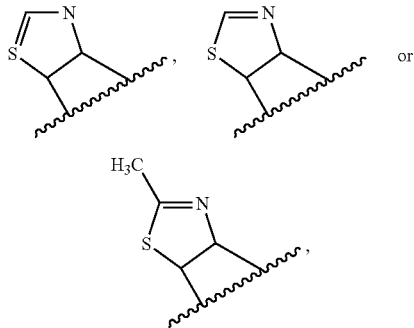

—R¹-R¹⁰ is alkyl, -(alkylene)$_q$-aryl or -(alkylene)$_q$-heteroaryl, R² is —C(O)OR⁸ or —C(O)NHSO₂R¹¹, and R³ is aryl or heterocycloalkenyl.

In still another embodiment, ring Z is

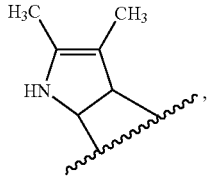

—R¹-R¹⁰ is alkyl, -(alkylene)$_q$-aryl or -(alkylene)$_q$-heteroaryl, R² is —C(O)OR⁸ or —C(O)NHSO₂R¹¹, and R³ is aryl or heterocycloalkenyl.

In one embodiment, ring Z is a cyclopentyl or cyclopentenyl group, —R¹-R¹⁰ is:

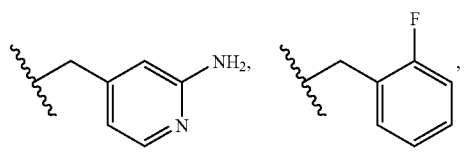

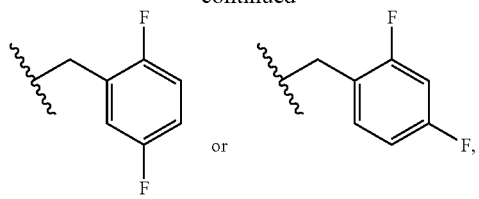

R² is —C(O)OR⁸ or —C(O)NHSO₂R¹¹, and R³ is aryl or heterocycloalkenyl.

In another embodiment, ring Z is a 5-membered heterocycloalkyl group, —R¹-R¹⁰ is:

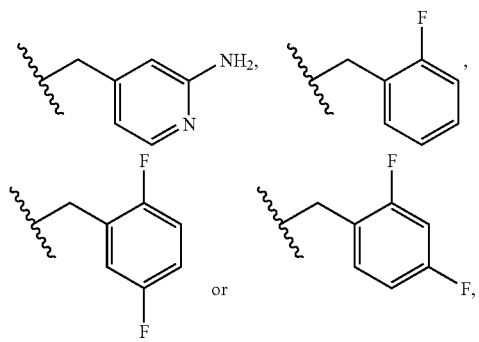

R² is —C(O)OR⁸ or —C(O)NHSO₂R¹¹, and R³ is aryl or heterocycloalkenyl.

In another embodiment, ring Z is a 5-membered heterocycloalkenyl or 5-membered heteroaryl group, —R¹-R¹⁰ is:

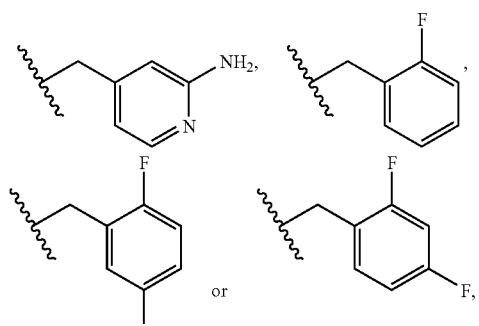

R² is —C(O)OR⁸ or —C(O)NHSO₂R¹¹, and R³ is aryl or heterocycloalkenyl.

In another embodiment, ring Z is a cyclopentyl or cyclopentenyl group, —R¹-R¹⁰ is alkyl, -(alkylene)$_q$-aryl or -(alkylene)$_q$-heteroaryl, R² is —C(O)OH, —C(O)NSO₂CH₃,

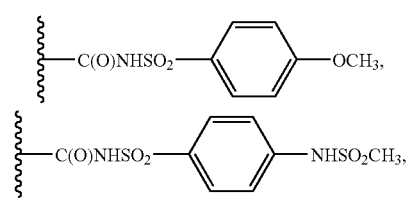

-continued

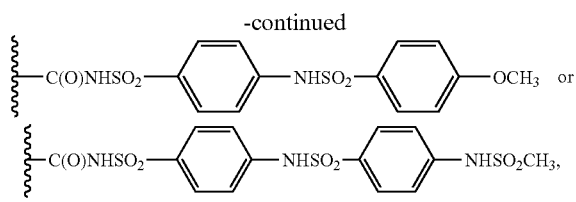

and R³ is aryl or heterocycloalkenyl.

In another embodiment, ring Z is a 5-membered heterocycloalkyl group, —R¹-R¹⁰ is alkyl, -(alkylene)$_q$-aryl or -(alkylene)$_q$-heteroaryl, R² is —C(O)OH, —C(O)NSO₂CH₃,

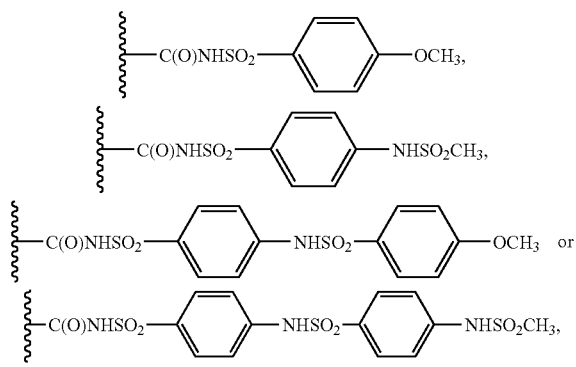

and R³ is aryl or heterocycloalkenyl.

In another embodiment, ring Z is a 5-membered heterocycloalkenyl or 5-membered heteroaryl group, —R¹-R¹⁰ is alkyl, -(alkylene)$_q$-aryl or -(alkylene)$_q$-heteroaryl, R² is —C(O)OH, —C(O)NSO₂CH₃,

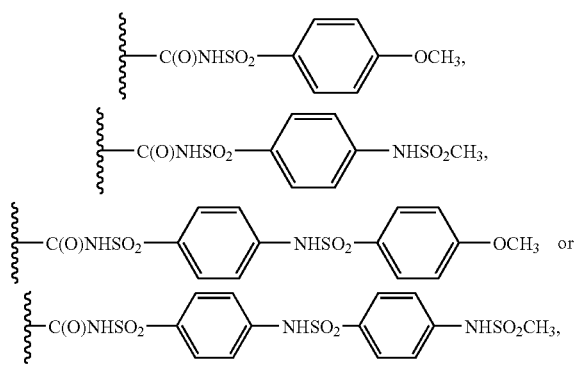

and R³ is aryl or heterocycloalkenyl.

In still another embodiment, ring Z is a cyclopentyl or cyclopentenyl group, —R¹-R¹⁰ is alkyl, -(alkylene)$_q$-aryl or -(alkylene)$_q$-heteroaryl, R² is R² is —C(O)OR⁸ or —C(O)NHSO₂R¹¹, and R³ is

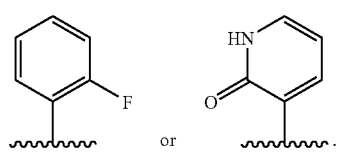 [SMILES: *c1ccccc1F ; *c1ccc[nH]c1=O]

In yet another embodiment, ring Z is a 5-membered heterocycloalkyl group, —R¹-R¹⁰ is alkyl, -(alkylene)$_q$-aryl or -(alkylene)$_q$-heteroaryl, R² is —C(O)OR⁸ or —C(O)NHSO₂R¹¹, and R³ is

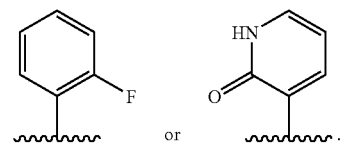 [SMILES: *c1ccccc1F ; *c1ccc[nH]c1=O]

In yet another embodiment, ring Z is a 5-membered heterocycloalkenyl or 5-membered heteroaryl group, —R¹-R¹⁰ is alkyl, -(alkylene)$_q$-aryl or -(alkylene)$_q$-heteroaryl, R² is —C(O)OR⁸ or —C(O)NHSO₂R¹¹, and R³ is

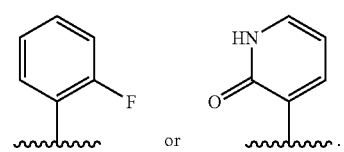

In another embodiment, ring Z is

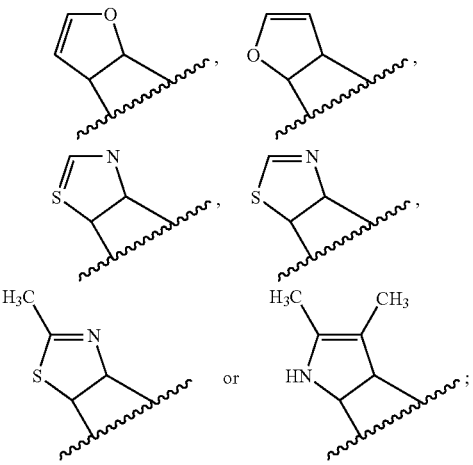

—R¹-R¹⁰ is:

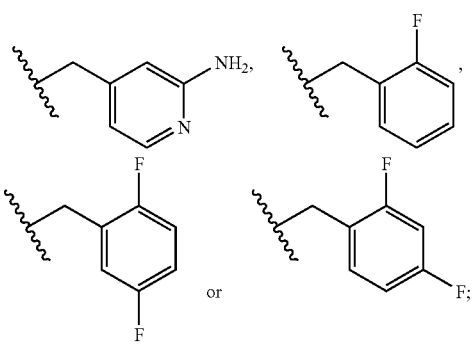

$R^2$ is —C(O)OH, —C(O)NSO$_2$CH$_3$,
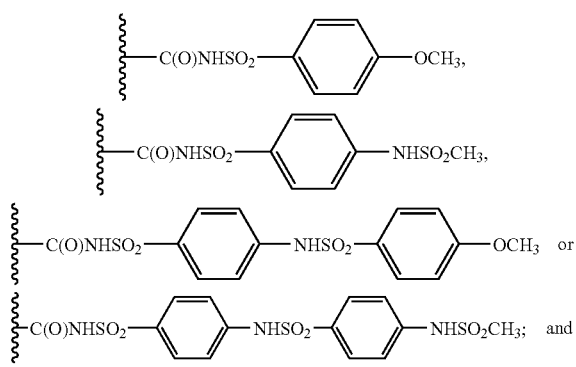
and
$R^3$ is:
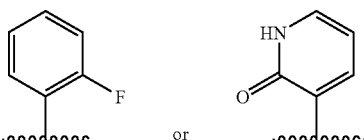 [SMILES: *c1ccccc1F ; *c1ccc[nH]c1=O]
In another embodiment, ring Z is
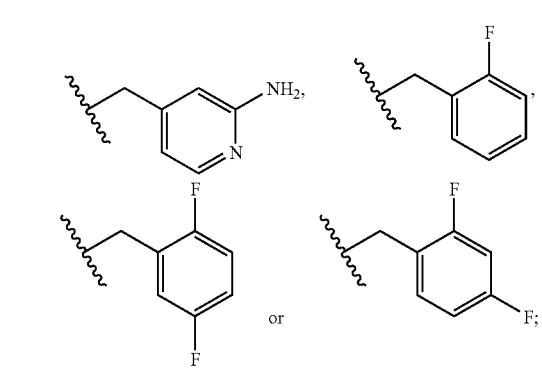
$R^{10}$ is bicyclic heteroaryl;
$R^2$ is —C(O)OH, —C(O)NSO$_2$CH$_3$,
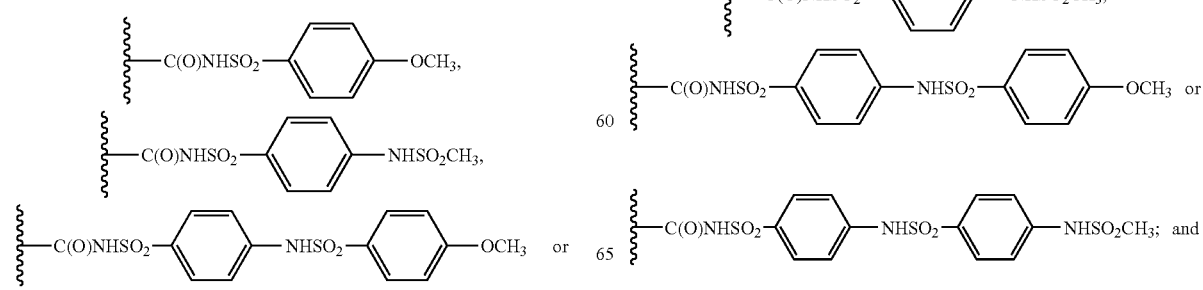
or
-continued
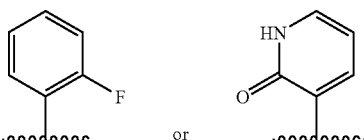 [SMILES: *c1ccccc1F ; *c1ccc[nH]c1=O]
$R^3$ is:
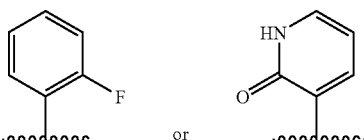 [SMILES: *c1ccccc1F ; *c1ccc[nH]c1=O]
In a further embodiment, ring Z is
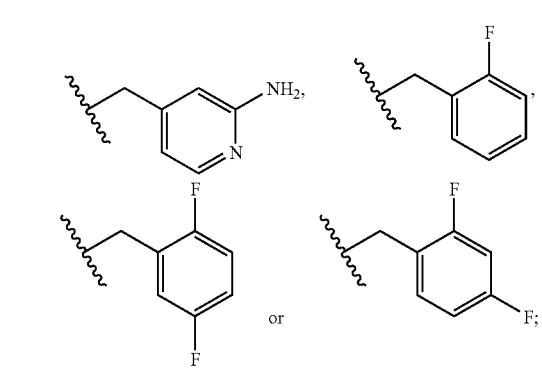
—$R^1$-$R^{10}$ is:
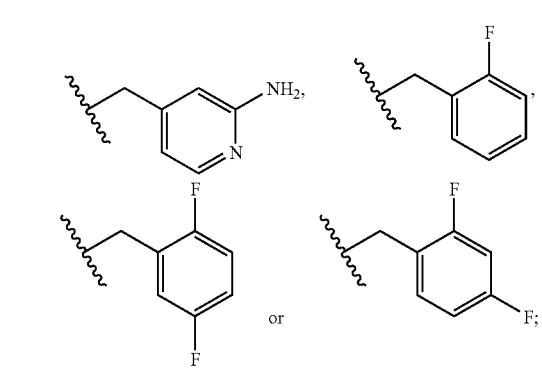
$R^2$ is —C(O)OH, —C(O)NSO$_2$CH$_3$,
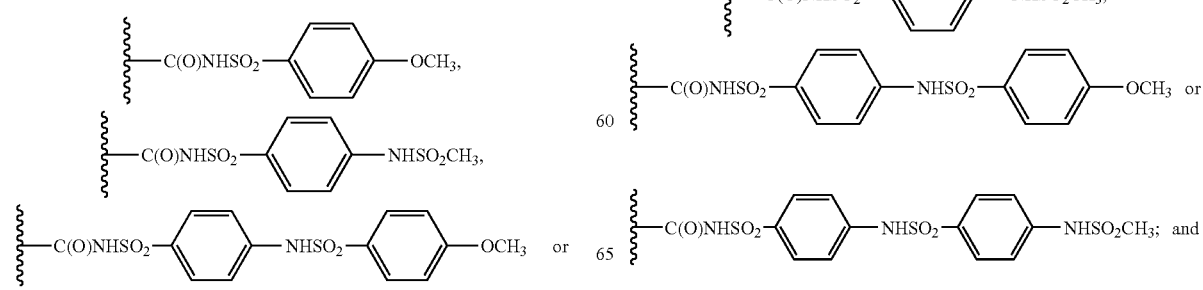

$R^3$ is:

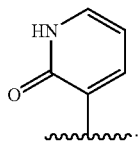 [SMILES: *c1ccc[nH]c1=O]

In one embodiment, $R^1$ is a bond or —$[C(R^{12})_2)]_r$—, and $R^{10}$ is phenyl, pyridyl or pyrimidinyl, each of which is unsubstituted or optionally substituted with up to 3 substituents, which are the same or different, and are selected from alkyl, aryl, heteroaryl, heterocycloalkyl, heterocycloalkenyl, halo, haloalkyl, —OH, hydroxyalkyl, —CN, —C(O)alkyl, —C(O)Oalkyl, —C(O)N($R^9$)$_2$, -alkylene-O$R^9$, —O$R^9$, —N($R^9$)$_2$, —NHC(O)$R^8$, —NHSO$_2R^{11}$, —S(O)$_pR^{11}$ or —SO$_2$N($R^9$)$_2$.

In another embodiment, $R^1$ is a bond or —$[C(R^{12})_2)]_r$—, and $R^2$ is —C(O)OH, —C(O)Oalkyl, —C(O)NH$_2$, —C(O)NH-alkyl, —C(O)NH-cycloalkyl, —C(O)NHSO$_2R^{11}$,

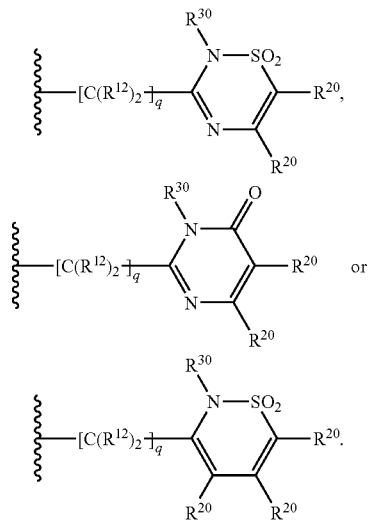

In another embodiment, $R^1$ is a bond or —$[C(R^{12})_2)]_r$—, and $R^2$ is —C(O)NHSO$_2$-alkyl, —C(O)NHSO$_2$-aryl, —C(O)NHSO$_2$-cycloalkyl or —C(O)NHSO$_2$-(alkylene)$_q$-cycloalkyl.

In another embodiment, $R^1$ is a bond or —$[C(R^{12})_2)]_r$—, and $R^3$ is aryl, heteroaryl or heterocycloalkenyl, each of which is unsubstituted or optionally substituted with up to 3 substituents, which are the same or different, and are selected from alkyl, aryl, cycloalkyl, heterocycloalkyl, heteroaryl, halo, haloalkyl, hydroxyalkyl, —OH, —CN, —C(O)alkyl, —C(O)N($R^9$)$_2$, —N($R^9$)$_2$, —O-haloalkyl, —NHC(O)NH$_2$, —NHC(O)NH-alkyl, —NHSO$_2R^{11}$, —S(O)$_2R^{11}$ or —SO$_2$NH$R^{11}$.

In still another embodiment, $R^1$ is a bond or —$[C(R^{12})_2)]_r$—, and $R^3$ is pyridyl, wherein the pyridyl group can be unsubstituted or optionally substituted with up to 3 substituents, which are the same or different, and are selected from alkyl, haloalkyl, hydroxyalkyl, halo, —OH, —CN, —C(O)CH$_3$, —C(O)NH$_2$, —C(O)NHalkyl, —O-hydroxyalkyl, —NH$_2$, —NHalkyl, —NHC(O)NH$_2$, —NHC(O)NH-alkyl, —NHSO$_2$alkyl, —S(O)$_2$alkyl or —SO$_2$NHalkyl.

In yet another embodiment, $R^1$ is a bond or —$[C(R^{12})_2)]_r$—, and ring Z is a 5-membered heterocycloalkenyl or 5-membered heteroaryl group.

In a further embodiment, $R^1$ is a bond or —$[C(R^{12})_2)]_r$—, and ring Z is one of the following:

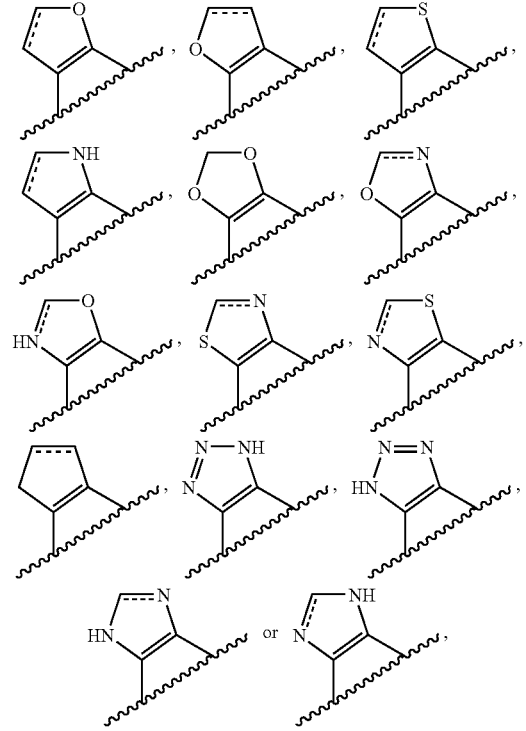

wherein a dotted line represents an optional and additional bond, and wherein the above ring Z groups can be optionally substituted as set forth above for the compounds of formula (I).

In another embodiment, $R^1$ is a bond, or an alkyl group having from 1-6 carbon atoms;

$R^2$ is —C(O)OH, —C(O)NH$_2$, —C(O)NH-alkyl, —C(O)NHSO$_2R^{11}$,

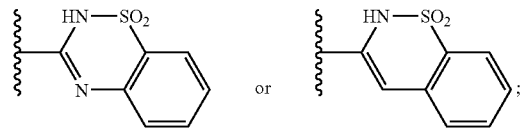

$R^3$ is aryl, heteroaryl or heterocycloalkenyl, each of which is unsubstituted or optionally substituted with up to 3 substituents, which are the same or different, and are selected from alkyl, aryl, cycloalkyl, heterocycloalkyl, heteroaryl, halo, haloalkyl, hydroxyalkyl, —OH, —CN, —C(O)alkyl, —C(O)N($R^9$)$_2$, —N($R^9$)$_2$, —O-haloalkyl, —NHC(O)NH$_2$, —NHC(O)NH-alkyl, —NHSO$_2R^{11}$, —S(O)$_2R^{11}$ or —SO$_2$NH$R^{11}$; ring Z is a 5-membered heterocycloalkenyl or 5-membered heteroaryl;

$R^6$ and $R^7$ are each independently selected from —H, alkyl, —F, —Cl, —OH, —O-alkyl, —OCF$_3$, —NH$_2$ or —NHSO$_2$-alkyl; and $R^{10}$ is phenyl, pyridyl or pyrimidinyl, each of which is unsubstituted or optionally substituted with up to 3 substituents, which are the same or different, and are selected from alkyl, aryl, heteroaryl, heterocycloalkyl, heterocycloalkenyl, halo, haloalkyl, —OH, hydroxyalkyl, —CN, —C(O)alkyl, —C(O)Oalkyl, —C(O)N(R⁹)₂, -alkylene-OR⁹, —OR⁹, —N(R⁹)₂, —NHC(O)R⁸, —NHSO₂R¹¹, —S(O)_pR¹¹ or —SO₂N(R⁹)₂. In another embodiment, R¹ is a bond, or an alkyl group having from 1-6 carbon atoms;

R² is —C(O)OH, —C(O)O-alkyl, —C(O)NH₂, —C(O)NH-alkyl, —C(O)NHSO₂R¹¹,

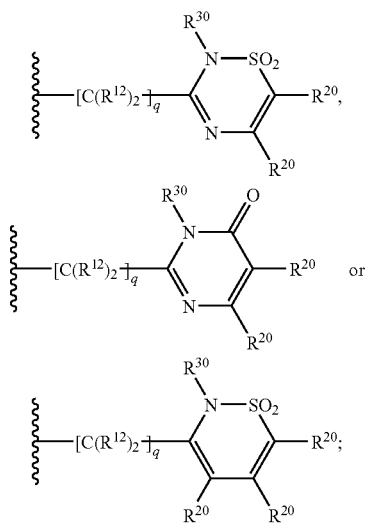

R³ is aryl, heteroaryl or heterocycloalkenyl, each of which is unsubstituted or optionally substituted with up to 3 substituents, which are the same or different, and are selected from alkyl, aryl, cycloalkyl, heterocycloalkyl, heteroaryl, halo, haloalkyl, hydroxyalkyl, —OH, —CN, —C(O)alkyl, —C(O)N(R⁹)₂, —N(R⁹)₂, —O-haloalkyl, —NHC(O)NH₂, —NHC(O)NH-alkyl, —NHSO₂R¹¹, —S(O)₂R¹¹ or —SO₂NHR¹¹;

ring Z is a 5-membered heterocycloalkenyl or 5-membered heteroaryl;

R⁶ and R⁷ are each independently selected from —H, alkyl, —F, —Cl, —OH, —O-alkyl, —OCF₃, —NH₂ or —NHSO₂-alkyl; and R¹⁰ is phenyl, pyridyl or pyrimidinyl, each of which is unsubstituted or optionally substituted with up to 3 substituents, which are the same or different, and are selected from alkyl, aryl, heteroaryl, heterocycloalkyl, heterocycloalkenyl, halo, haloalkyl, —OH, hydroxyalkyl, —CN, —C(O)alkyl, —C(O)Oalkyl, —C(O)N(R⁹)₂, -alkylene-OR⁹, —OR⁹, —N(R⁹)₂, —NHC(O)R⁸, —NHSO₂R¹¹, —S(O)_pR¹¹ or —SO₂N(R⁹)₂.

In still another embodiment, R¹ is a bond, or an alkyl group having from 1-6 carbon atoms;

R² is —C(O)OH, —C(O)O-alkyl, —C(O)NH₂, —C(O)NH-alkyl, —C(O)NHSO₂R¹¹,

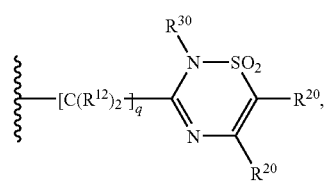

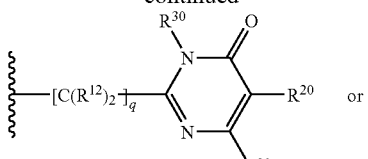

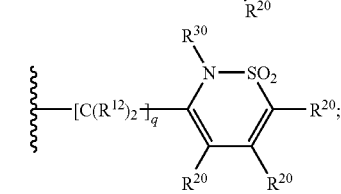

R³ is aryl, heteroaryl or heterocycloalkenyl, each of which is unsubstituted or optionally substituted with up to 3 substituents, which are the same or different, and are selected from alkyl, aryl, cycloalkyl, heterocycloalkyl, heteroaryl, halo, haloalkyl, hydroxyalkyl, —OH, —CN, —C(O)alkyl, —C(O)N(R⁹)₂, —N(R⁹)₂, —O-haloalkyl, —NHC(O)NH₂, —NHC(O)NH-alkyl, —NHSO₂R¹¹, —S(O)₂R¹¹ or —SO₂NHR¹¹;

ring Z is a 5-membered heterocycloalkenyl or 5-membered heteroaryl;

R⁶ and R⁷ are each independently selected from —H, alkyl, —F, —Cl, —OH, —O-alkyl, —OCF₃, —NH₂ or —NHSO₂-alkyl; and R¹⁰ is bicyclic aryl or bicyclic heteroaryl, each of which can be unsubstituted or optionally substituted with up to 3 substituents, which are the same or different, and are selected from alkyl, aryl, heteroaryl, halo, haloalkyl, heterocycloalkyl, heterocycloalkenyl, hydroxyalkyl, —CN, —C(O)alkyl, —C(O)Oalkyl, —C(O)N(R⁹)₂, -alkylene-OR⁹, —OR⁹, —N(R⁹)₂, —NHC(O)R⁸, —NHSO₂R¹¹, —S(O)_pR¹¹ or —SO₂N(R⁹)₂.

In another embodiment, R¹ is a bond, or an alkyl group having from 1-6 carbon atoms;

R² is —C(O)OH, —C(O)NH₂, —C(O)NH-alkyl, —C(O)NHSO₂R¹¹,

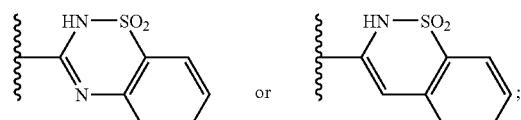

R³ is:

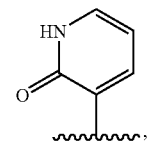

which is unsubstituted or optionally substituted with up to 3 substituents, which are the same or different, and are selected from alkyl, CN, —CF₃, —C(O)CH₃, —C(O)NH₂, —C(O)NHalkyl, —F, —Cl, —OH, —OCF₃, —NH₂, —NHalkyl, —NHC(O)NH₂, —NHC(O)NH-alkyl, —NHSO₂alkyl, —S(O)₂-alkyl or —SO₂NHalkyl;

ring Z is a 5-membered heterocycloalkenyl or 5-membered heteroaryl;

$R^6$ and $R^7$ are each independently selected from —H, alkyl, —F, —Cl, —OH, —O-alkyl, —OCF$_3$, —NH$_2$ or —NHSO$_2$-alkyl; and $R^{10}$ is phenyl, pyridyl or pyrimidinyl, each of which is unsubstituted or optionally substituted with up to 3 substituents, which are the same or different, and are selected from alkyl, aryl, heteroaryl, heterocycloalkyl, heterocycloalkenyl, halo, haloalkyl, —OH, hydroxyalkyl, —CN, —C(O)alkyl, —C(O)Oalkyl, —C(O)N(R$^9$)$_2$, -alkylene-OR$^9$, —OR$^9$, —N(R$^9$)$_2$, —NHC(O)R$^8$, —NHSO$_2$R$^{11}$, —S(O)$_p$R$^{11}$ or —SO$_2$N(R$^9$)$_2$.

In another embodiment, $R^1$ is a bond, or an alkyl group having from 1-6 carbon atoms;

$R^2$ is —C(O)OH, —C(O)NH$_2$, —C(O)NH-alkyl, —C(O)NHSO$_2$R$^{11}$,

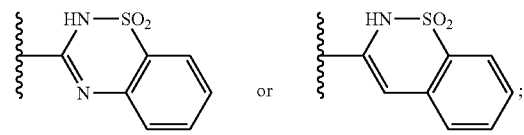

$R^3$ is:

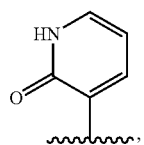

which is unsubstituted or optionally substituted with up to 3 substituents, which are the same or different, and are selected from alkyl, CN, —CF$_3$, —C(O)CH$_3$, —C(O)NH$_2$, —C(O)NHalkyl, —F, —Cl, —OH, —OCF$_3$, —NH$_2$, —NHalkyl, —NHC(O)NH$_2$, —NHC(O)NH-alkyl, —NHSO$_2$alkyl, —S(O)$_2$-alkyl or —SO$_2$NHalkyl;

ring Z is:

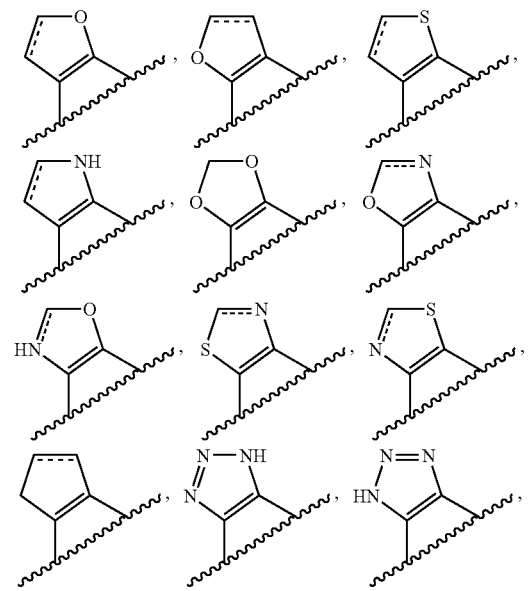

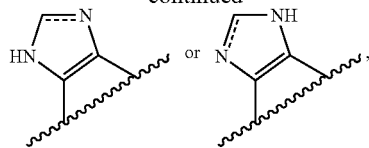

wherein a dotted line represents an optional and additional bond, and wherein the above ring Z groups can be optionally substituted as set forth above for the compounds of formula (I);

$R^6$ and $R^7$ are each independently selected from —H, alkyl, —F, —Cl, —OH, —O-alkyl, —OCF$_3$, —NH$_2$ or —NHSO$_2$-alkyl; and $R^{10}$ is phenyl, pyridyl or pyrimidinyl, each of which is unsubstituted or optionally substituted with up to 3 substituents, which are the same or different, and are selected from alkyl, aryl, heteroaryl, heterocycloalkyl, heterocycloalkenyl, halo, haloalkyl, —OH, hydroxyalkyl, —CN, —C(O)alkyl, —C(O)Oalkyl, —C(O)N(R$^9$)$_2$, -alkylene-OR$^9$, —OR$^9$, —N(R$^9$)$_2$, —NHC(O)R$^8$, —NHSO$_2$R$^{11}$, —S(O)$_p$R$^{11}$ or —SO$_2$N(R$^9$)$_2$.

In another embodiment, $R^1$ is a bond, or an alkyl group having from 1-6 carbon atoms;

$R^2$ is —C(O)OH, —C(O)NH$_2$, —C(O)NH-alkyl, —C(O)NHSO$_2$R$^{11}$,

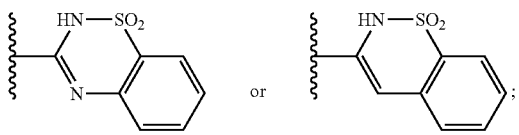 [SMILES: *C1=Nc2ccccc2S(=O)(=O)N1 ; *C1=Cc2ccccc2S(=O)(=O)N1]

$R^3$ is:

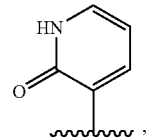

which is unsubstituted or optionally substituted with up to 3 substituents, which are the same or different, and are selected from alkyl, CN, —CF$_3$, —C(O)CH$_3$, —C(O)NH$_2$, —C(O)NHalkyl, —F, —Cl, —OH, —OCF$_3$, —NH$_2$, —NHalkyl, —NHC(O)NH$_2$, —NHC(O)NH-alkyl, —NHSO$_2$alkyl, —S(O)$_2$-alkyl or —SO$_2$NHalkyl;

ring Z is:

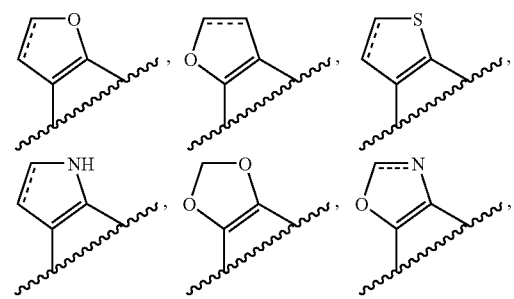

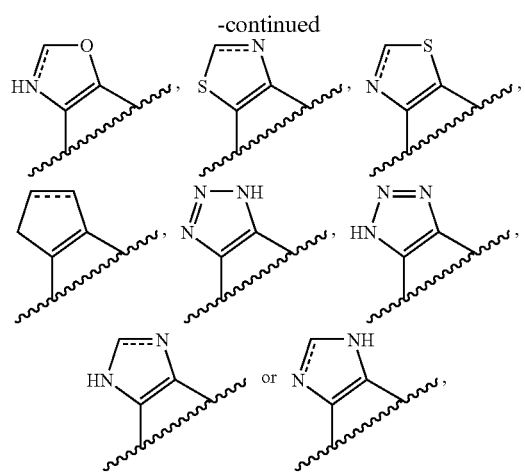
wherein a dotted line represents an optional and additional bond, and wherein the above ring Z groups can be optionally substituted as set forth above for the compounds of formula (I);
R$^6$ and R$^7$ are each independently selected from —H, alkyl, —F, —OH, —O-alkyl, —OCF$_3$, —NH$_2$ or —NHSO$_2$-alkyl; and R$^{10}$ is:
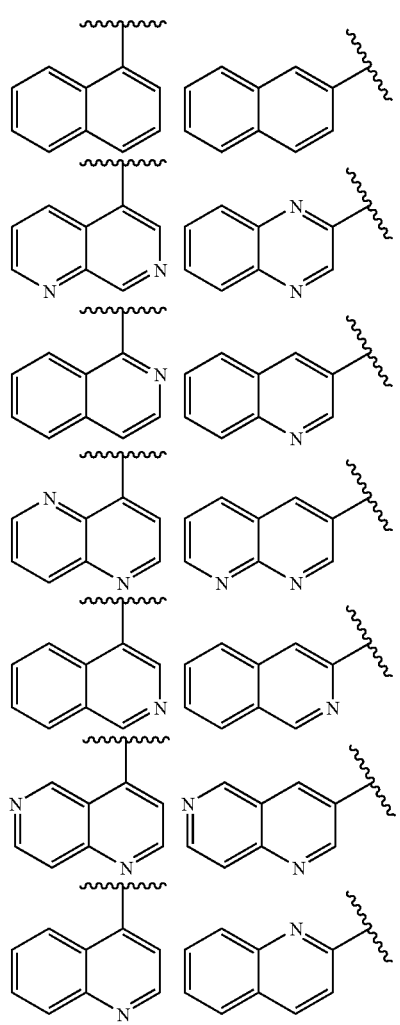
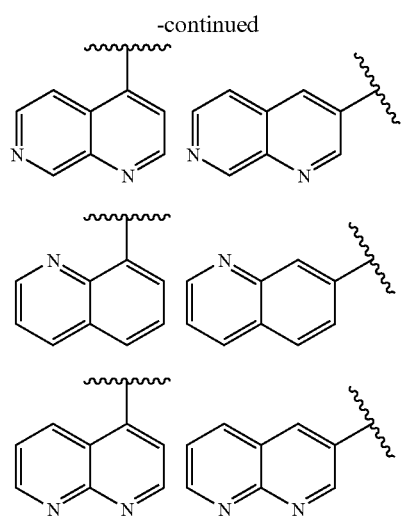
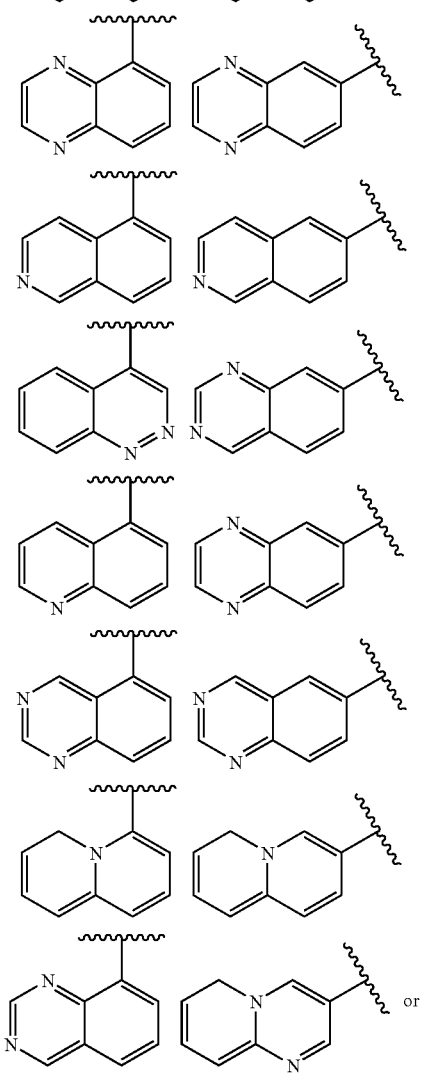

-continued

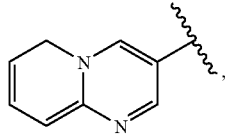

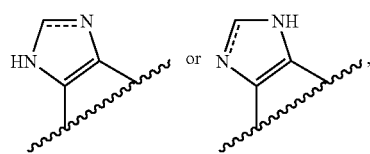

each of which can be optionally substituted with up to 3 substituents, which are the same or different, and are selected from alkyl, cycloalkyl, heterocycloalkyl, heterocycloalkenyl, halo, haloalkyl, —O-haloalkyl, —OH, —CN, —NH$_2$, —NH-alkyl, —N(alkyl)$_2$ or —NHSO$_2$-alkyl;

In one embodiment, R$^1$ is a bond, or an alkyl group having from 1-6 carbon atoms;

R$^2$ is —C(O)OH, —C(O)NH$_2$, —C(O)NH-alkyl, —C(O)NHSO$_2$R$^{11}$, wherein a dotted line represents an optional and additional bond, and wherein the above ring Z groups can be optionally substituted as set forth above for the compounds of formula (I);

R$^6$ and R$^7$ are each independently selected from —H, alkyl, —F, —Cl, —OH, —O-alkyl, —OCF$_3$, —NH$_2$ or —NHSO$_2$-alkyl; and R$^{10}$ is:

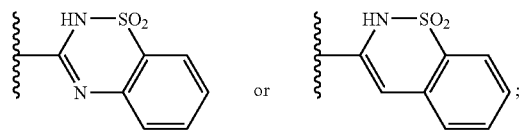 [SMILES: *C1=Nc2ccccc2S(=O)(=O)N1 ; *C1=Cc2ccccc2S(=O)(=O)N1]

R$^3$ is:

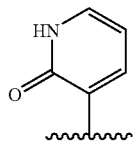

which is unsubstituted or optionally substituted with up to 3 substituents, which are the same or different, and are selected from alkyl, CN, —CF$_3$, —C(O)CH$_3$, —C(O)NH$_2$, —C(O)NHalkyl, —F, —Cl, —OH, —OCF$_3$, —NH$_2$, —NHalkyl, —NHC(O)NH$_2$, —NHC(O)NH-alkyl, —NHSO$_2$alkyl, —S(O)$_2$-alkyl or —SO$_2$NHalkyl;

ring Z is:

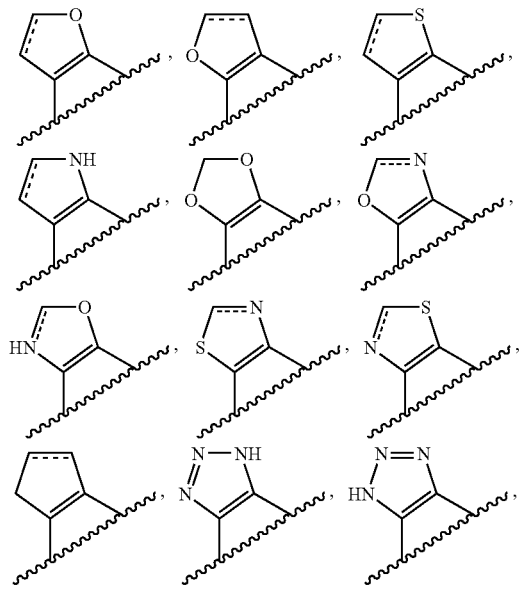

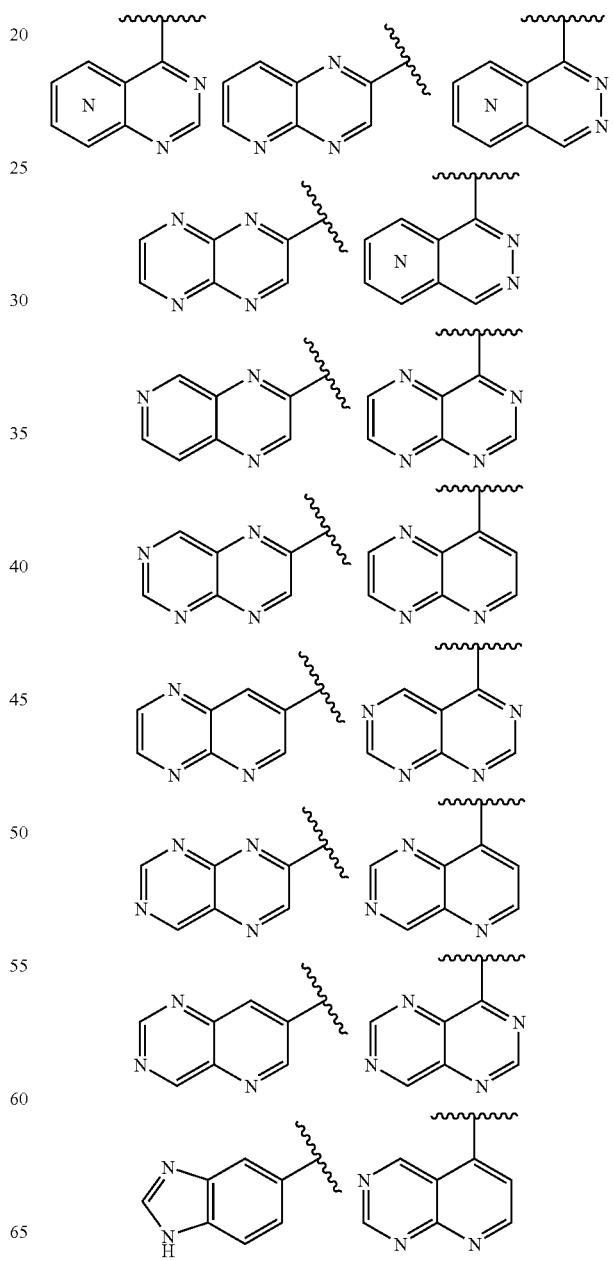

-continued

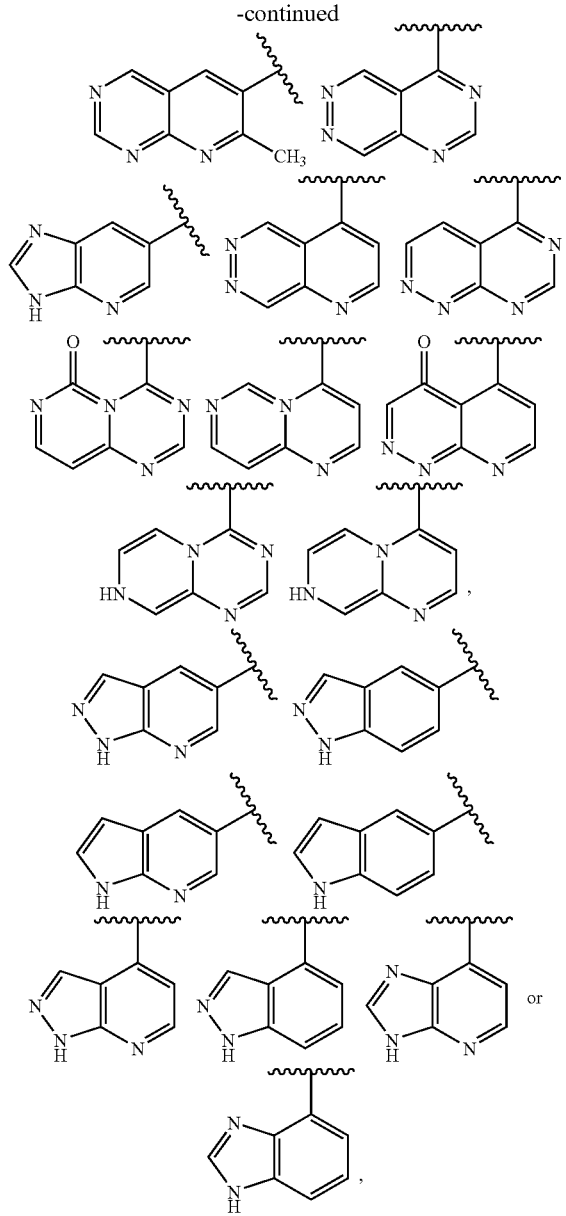

each of which can be optionally substituted with up to 3 substituents, which are the same or different, and are selected from alkyl, cycloalkyl, heterocycloalkyl, heterocycloalkenyl, halo, haloalkyl, —O-haloalkyl, —OH, —CN, —NH$_2$, —NH-alkyl, —N(alkyl)$_2$ or —NHSO$_2$-alkyl; wherein the letter "N" inside a ring indicates that the ring has 1 or 2 ring nitrogen atoms.

In one embodiment, $R^1$ is a bond, or an alkyl group having from 1-6 carbon atoms;

$R^2$ is —C(O)OH, —C(O)NH$_2$, —C(O)NH-alkyl, —C(O)NHSO$_2R^{11}$,

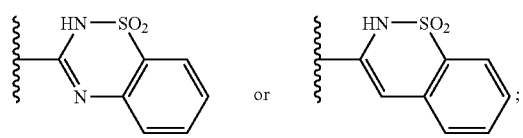 [SMILES: *C1=Nc2ccccc2S(=O)(=O)N1 ; *C1=Cc2ccccc2S(=O)(=O)N1]

$R^3$ is:

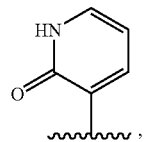

which is unsubstituted or optionally substituted with up to 3 substituents, which are the same or different, and are selected from alkyl, CN, —CF$_3$, —C(O)CH$_3$, —C(O)NH$_2$, —C(O)NHalkyl, —F, —Cl, —OH, —OCF$_3$, —NH$_2$, —NHalkyl, —NHC(O)NH$_2$, —NHC(O)NH-alkyl, —NHSO$_2$alkyl, —S(O)$_2$-alkyl or —SO$_2$NHalkyl;

ring Z is:

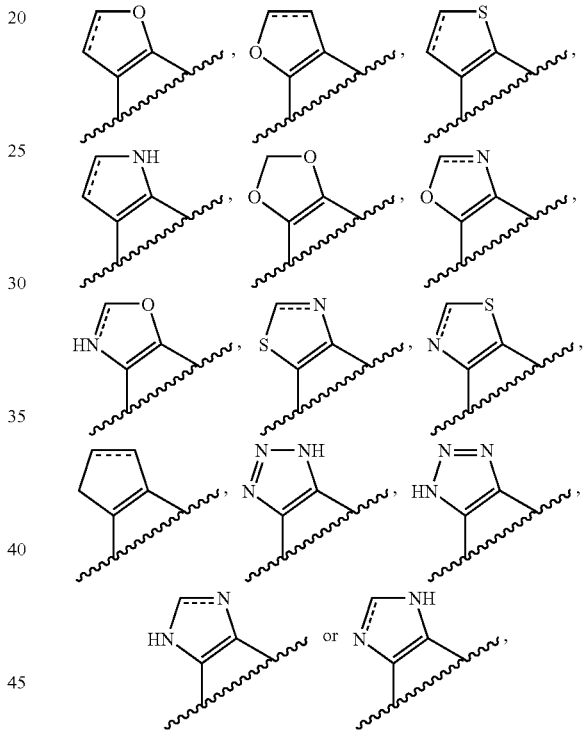

wherein a dotted line represents an optional and additional bond, and wherein the above ring Z groups can be optionally substituted as set forth above for the compounds of formula (I);

$R^6$ and $R^7$ are each independently selected from —H, alkyl, —F, —Cl, —OH, —O-alkyl, —OCF$_3$, —NH$_2$ or —NHSO$_2$-alkyl; and $R^{10}$ is:

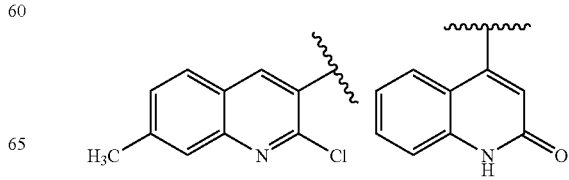

-continued

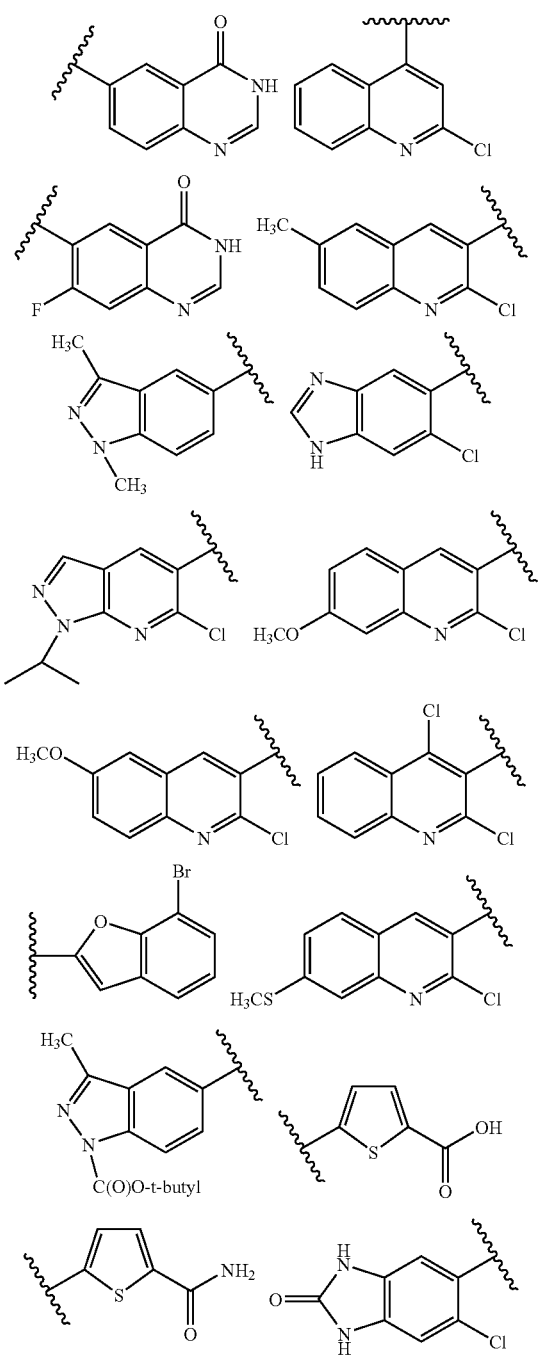

In another embodiment, $R^1$ is a bond, or an alkyl group having from 1-6 carbon atoms;

$R^2$ is —C(O)OH, —C(O)NH$_2$, —C(O)NH-alkyl, —C(O)NHSO$_2$R$^{11}$,

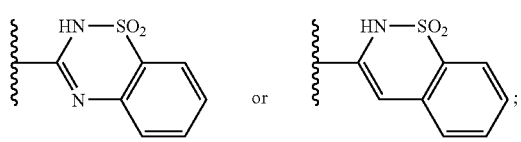

$R^3$ is:

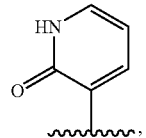 [SMILES: *c1ccc[nH]c1=O]

which is unsubstituted or optionally substituted with up to 3 substituents, which are the same or different, and are selected from alkyl, CN, —CF$_3$, —C(O)CH$_3$, —C(O)NH$_2$, —C(O)NHalkyl, —F, —Cl, —OH, —OCF$_3$, —NH$_2$, —NHalkyl, —NHC(O)NH$_2$, —NHC(O)NH-alkyl, —NHSO$_2$alkyl, —S(O)$_2$-alkyl or —SO$_2$NHalkyl;

ring Z is:

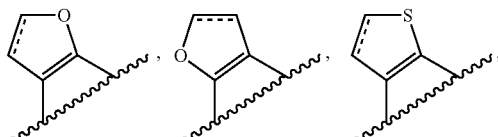

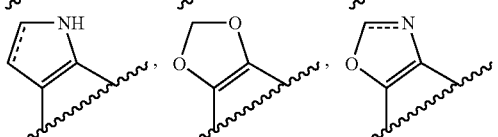

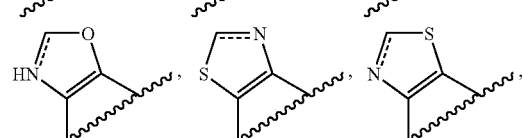

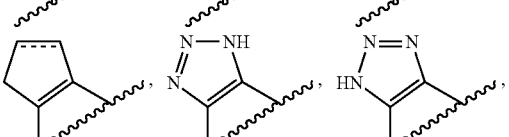

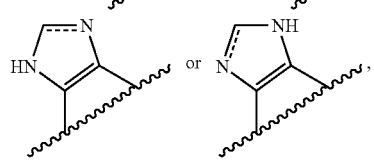

wherein a dotted line represents an optional and additional bond, and wherein the above ring Z groups can be optionally substituted as set forth above for the compounds of formula (I);

$R^6$ and $R^7$ are each independently selected from —H, alkyl, —F, —Cl, —OH, —O-alkyl, —OCF$_3$, —NH$_2$ or —NHSO$_2$-alkyl; and $R^{10}$ is phenyl, pyridyl or pyrimidinyl, each of which is unsubstituted or optionally substituted with up to 3 substituents, which are the same or different, and are selected from alkyl, aryl, heteroaryl, heterocycloalkyl, heterocycloalkenyl, halo, haloalkyl, —OH, hydroxyalkyl, —CN, —C(O)alkyl, —C(O)Oalkyl, —C(O)N(R$^9$)$_2$, -alkylene-OR$^9$, —OR$^9$, —N(R$^9$)$_2$, —NHC(O)R$^8$, —NHSO$_2$R$^{11}$, —S(O)$_p$R$^{11}$ or —SO$_2$N(R$^9$)$_2$.

In another embodiment, $R^1$ is a bond, or an alkyl group having from 1-6 carbon atoms, $R^2$ is —C(O)OH, —C(O)NH$_2$, —C(O)NH-alkyl, —C(O)NHSO$_2$R$^{11}$,

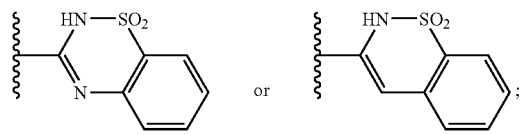

R³ is:

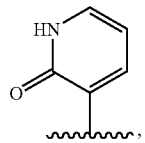 [SMILES: *c1ccc[nH]c1=O]

which is unsubstituted or optionally substituted with up to 3 substituents, which are the same or different, and are selected from alkyl, CN, —CF₃, —C(O)CH₃, —C(O)NH₂, —C(O)NHalkyl, —F, —Cl, —OH, —OCF₃, —NH₂, —NHalkyl, —NHC(O)NH₂, —NHC(O)NH-alkyl, —NHSO₂alkyl, —S(O)₂-alkyl or —SO₂NHalkyl;

ring Z is:

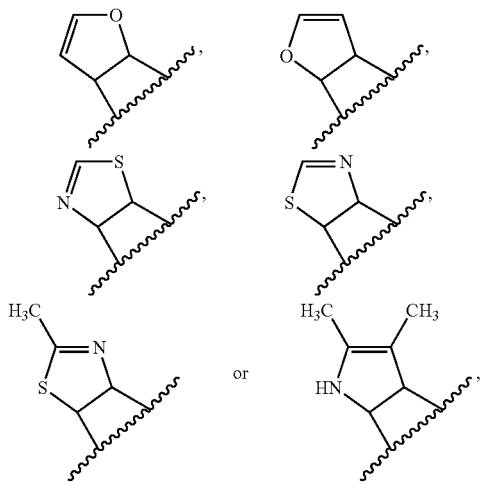

wherein ring Z can be optionally substituted on one or more ring carbon atoms with alkyl, —OH, —F, —Cl, —O-alkyl, —CF₃, cycloalkylalkyl, aryl or cycloalkyl.

R⁶ and R⁷ are each independently selected from —H, alkyl, —F, —Cl, —OH, —O-alkyl, —OCF₃, —NH₂ or —NHSO₂-alkyl; and R¹⁰ is phenyl, pyridyl or pyrimidinyl, each of which is unsubstituted or optionally substituted with up to 3 substituents, which are the same or different, and are selected from alkyl, aryl, heteroaryl, heterocycloalkyl, heterocycloalkenyl, halo, haloalkyl, —OH, hydroxyalkyl, —CN, —C(O)alkyl, —C(O)Oalkyl, —C(O)N(R⁹)₂, -alkylene-OR⁹, —OR⁹, —N(R⁹)₂, —NHC(O)R⁸, —NHSO₂R¹¹, —S(O)ₚR¹¹ or —SO₂N(R⁹)₂.

In a further embodiment, R¹ is a bond, or an alkyl group having from 1-6 carbon atoms, R² is —C(O)OH, —C(O)NH₂, —C(O)NH-alkyl, —C(O)NHSO₂R¹¹,

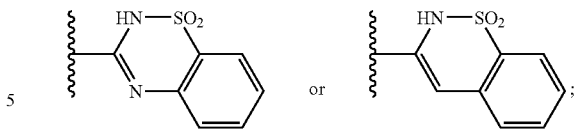

R³ is:

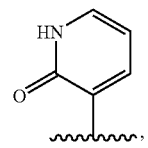 [SMILES: *c1ccc[nH]c1=O]

which is unsubstituted or optionally substituted with up to 3 substituents, which are the same or different, and are selected from alkyl, CN, —CF₃, —C(O)CH₃, —C(O)NH₂, —C(O)NHalkyl, —F, —Cl, —OH, —OCF₃, —NH₂, —NHalkyl, —NHC(O)NH₂, —NHC(O)NH-alkyl, —NHSO₂alkyl, —S(O)₂-alkyl or —SO₂NHalkyl;

ring Z is:

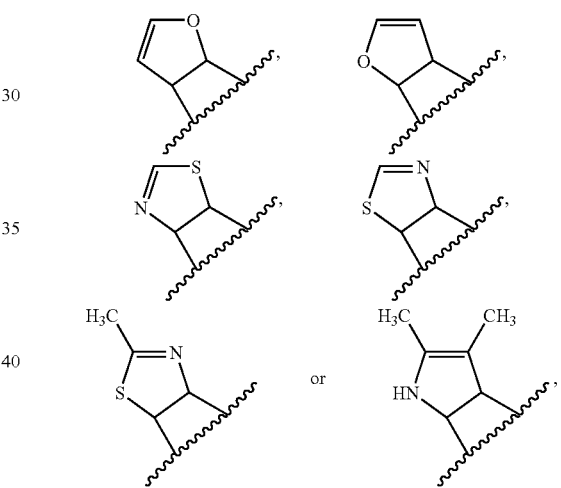

wherein ring Z can be optionally substituted on one or more ring carbon atoms with alkyl, —OH, —F, —Cl, —O-alkyl, —CF₃, cycloalkylalkyl, aryl or cycloalkyl.

R⁶ and R⁷ are each independently selected from —H, alkyl, —F, —Cl, —OH, —O-alkyl, —OCF₃, —NH₂ or —NHSO₂-alkyl; and R¹⁰ is bicyclic aryl or bicyclic heteroaryl, each of which can be unsubstituted or optionally substituted with up to 3 substituents, which are the same or different, and are selected from alkyl, aryl, heteroaryl, halo, haloalkyl, heterocycloalkyl, heterocycloalkenyl, hydroxyalkyl, —CN, —C(O)alkyl, —C(O)Oalkyl, —C(O)N(R⁹)₂, -alkylene-OR⁹, —OR⁹, —N(R⁹)₂, —NHC(O)R⁸, —NHSO₂R¹¹, —S(O)ₚR¹¹ or —SO₂N(R⁹)₂.

In another embodiment, the invention provides compounds of formula (I), wherein R¹ is a bond or —[C(R¹²)₂]ᵣ—; and R¹⁰ is phenyl, pyridyl or pyrimidinyl, each of which is unsubstituted or optionally substituted with up to 3 substituents, which are the same or different, and are selected from alkyl, aryl, heteroaryl, heterocycloalkyl, heterocycloalkenyl, halo, haloalkyl, —OH, hydroxyalkyl, —CN, —C(O)alkyl, —C(O)

Oalkyl, —C(O)N(R⁹)₂, -alkylene-OR⁹, —OR⁹, —N(R⁹)₂, —NHC(O)R⁸, —NHSO₂R¹¹, —S(O)ₚR¹¹ or —SO₂N(R⁹)₂.

In another embodiment, the invention provides compounds of formula (I), wherein
  ring Z is a 5-membered heterocycloalkenyl or 5-membered heteroaryl;
  R¹ is a bond or —[C(R¹²)₂]ᵣ—;
  R² is —C(O)OH, heteroaryl, or —C(O)NHSO₂R¹¹;
  R³ is aryl, heteroaryl or heterocycloalkenyl, each of which is unsubstituted or optionally substituted with up to 3 substituents, which are the same or different, and are selected from alkyl, aryl, cycloalkyl, heterocycloalkyl, heteroaryl, halo, haloalkyl, hydroxyalkyl, —OH, —CN, —C(O)alkyl, —C(O)N(R⁹)₂, —N(R⁹)₂, —O-haloalkyl, —NHC(O)NH₂, —NHC(O)NH-alkyl, —NHSO₂R¹¹, —S(O)₂R¹¹ or —SO₂NHR¹¹;
  R⁶ and R⁷ are each independently selected from H, alkyl, F, Cl, —CF₃, —OH, —O-alkyl, —OCF₃, —NH₂ or —NHSO₂-alkyl; and
  R¹⁰ is phenyl, pyridyl or pyrimidinyl, each of which can be optionally substituted with up to 3 substituents, which are the same or different, and are selected from alkyl, aryl, heteroaryl, halo, haloalkyl, hydroxyalkyl, —CN, —C(O)alkyl, —C(O)Oalkyl, —C(O)N(R⁹)₂, -(alkylene)-OR⁹, —OR⁹, —N(R⁹)₂, —NHC(O)R⁸, —NHSO₂R¹¹, —S(O)ₚR¹¹ or —SO₂N(R⁹)₂.

In still another embodiment, the invention provides compounds of formula (I), wherein
  ring Z is a 5-membered heterocycloalkenyl or 5-membered heteroaryl;
  R¹ is a bond or —[C(R¹²)₂]ᵣ—;
  R² is —C(O)OH, —C(O)NH₂, —C(O)NH-alkyl, —C(O)NHSO₂R¹¹;

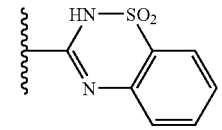 or 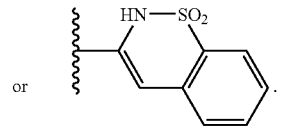.

wherein the heteroaryl, arylthiazin-yl- or arylthiadiazol-yl-group can be optionally substituted with up to 3 substituents, which are the same or different, and are selected from alkyl, heteroaryl, halo, haloalkyl, hydroxyalkyl, —OH, —CN, —C(O)N(R⁹)₂, —[C(R¹²)₂]_q—OR⁹, —[C(R¹²)₂]_q—N(R⁹)₂, —NHC(O)R⁸, —NHSO₂R¹¹, —S(O)ₚR¹¹ or —SO₂N(R⁹)₂;
  R³ is aryl, heteroaryl or heterocycloalkenyl, each of which is unsubstituted or optionally substituted with up to 3 substituents, which are the same or different, and are selected from alkyl, aryl, cycloalkyl, heterocycloalkyl, heteroaryl, halo, haloalkyl, hydroxyalkyl, —OH, —CN, —C(O)alkyl, —C(O)N(R⁹)₂, —N(R⁹)₂, —O-haloalkyl, —NHC(O)NH₂, —NHC(O)NH-alkyl, —NHSO₂R¹¹, —S(O)₂R¹¹ or —SO₂NHR¹¹;
  R⁶ and R⁷ are each independently selected from H, alkyl, F, Cl, —CF₃, —OH, —O-alkyl, —OCF₃, —NH₂ or —NHSO₂-alkyl; and
  R¹⁰ is phenyl, pyridyl or pyrimidinyl, each of which is unsubstituted or optionally substituted with up to 3 substituents, which are the same or different, and are selected from alkyl, aryl, heteroaryl, heterocycloalkyl, heterocycloalkenyl, halo, haloalkyl, —OH, hydroxyalkyl, —CN, —C(O)alkyl, —C(O)Oalkyl, —C(O)N(R⁹)₂, -alkylene-OR⁹, —OR⁹, —N(R⁹)₂, —NHC(O)R⁸, —NHSO₂R¹¹, —S(O)ₚR¹¹ or —SO₂N(R⁹)₂.

In yet another embodiment, the invention provides compounds of formula (I), wherein
  ring Z is a 5-membered heterocycloalkenyl or 5-membered heteroaryl;
  R¹ is a bond or —[C(R¹²)₂]ᵣ—;
  R² is —C(O)OH, heteroaryl, or —C(O)NHSO₂R¹¹;
  R³ is phenyl, pyridyl or

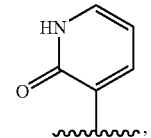

each of which can be optionally substituted with one to 3 substituents, which are the same or different, and are selected from alkyl, —CF₃, —CN, —C(O)alkyl, —C(O)NH₂, —C(O)NHalkyl, F, Cl, —OH, —OCF₃, —NH₂, —NHalkyl, —NHC(O)NH₂, —NHC(O)NH-alkyl, —NHSO₂alkyl, —S(O)₂-alkyl or —SO₂NHalkyl;
  R⁶ and R⁷ are each independently selected from H, alkyl, F, Cl, —CF₃, —OH, —O-alkyl, —OCF₃, —NH₂ or —NHSO₂-alkyl; and
  R¹⁰ is phenyl, pyridyl or pyrimidinyl, each of which is unsubstituted or optionally substituted with up to 3 substituents, which are the same or different, and are selected from alkyl, aryl, heteroaryl, heterocycloalkyl, heterocycloalkenyl, halo, haloalkyl, —OH, hydroxyalkyl, —CN, —C(O)alkyl, —C(O)Oalkyl, —C(O)N(R⁹)₂, -alkylene-OR⁹, —OR⁹, —N(R⁹)₂, —NHC(O)R⁸, —NHSO₂R¹¹, —S(O)ₚR¹¹ or —SO₂N(R⁹)₂.

In a further embodiment, the invention provides compounds of formula (I), wherein ring Z is:

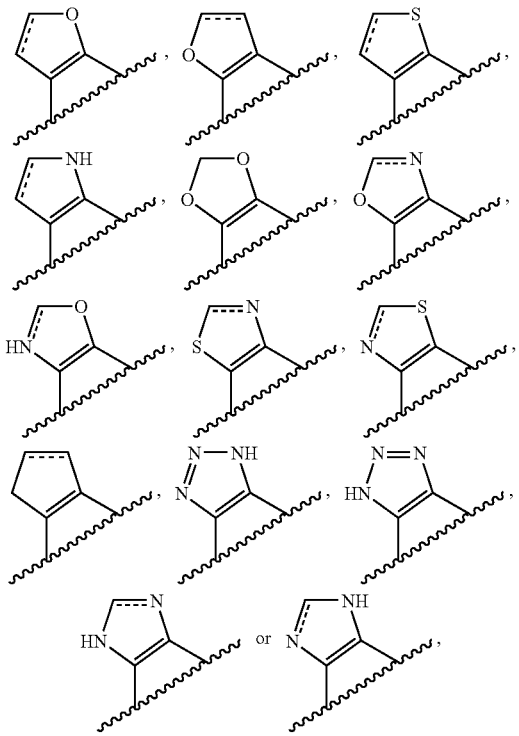

wherein a dotted line represents an optional and additional bond, and wherein the above ring Z groups can be optionally substituted as set forth above for the compounds of formula (I);

$R^1$ is a bond or —[C($R^{12}$)$_2$]$_r$—;

$R^2$ is —C(O)OH, heteroaryl, or —C(O)NHSO$_2$$R^{11}$;

$R^3$ is aryl, heteroaryl or heterocycloalkenyl, each of which is unsubstituted or optionally substituted with up to 3 substituents, which are the same or different, and are selected from alkyl, aryl, cycloalkyl, heterocycloalkyl, heteroaryl, halo, haloalkyl, hydroxyalkyl, —OH, —CN, —C(O)alkyl, —C(O)N($R^9$)$_2$, —N($R^9$)$_2$, —O-haloalkyl, —NHC(O)NH$_2$, —NHC(O)NH-alkyl, —NHSO$_2$$R^{11}$, —S(O)$_2$$R^{11}$ or —SO$_2$NH$R^{11}$;

$R^6$ and $R^7$ are each independently selected from H, alkyl, F, Cl, —CF$_3$, —OH, —O-alkyl, —OCF$_3$, —NH$_2$ or —NHSO$_2$-alkyl; and $R^{10}$ phenyl, pyridyl or pyrimidinyl, each of which is unsubstituted or optionally substituted with up to 3 substituents, which are the same or different, and are selected from alkyl, aryl, heteroaryl, heterocycloalkyl, heterocycloalkenyl, halo, haloalkyl, —OH, hydroxyalkyl, —CN, —C(O)alkyl, —C(O)Oalkyl, —C(O)N($R^9$)$_2$, -alkylene-O$R^9$, —O$R^9$, —N($R^9$)$_2$, —NHC(O)$R^8$, —NHSO$_2$$R^{11}$, —S(O)$_p$$R^{11}$ or —SO$_2$N($R^9$)$_2$.

In one embodiment, the invention provides compounds of formula (I), wherein ring Z is:

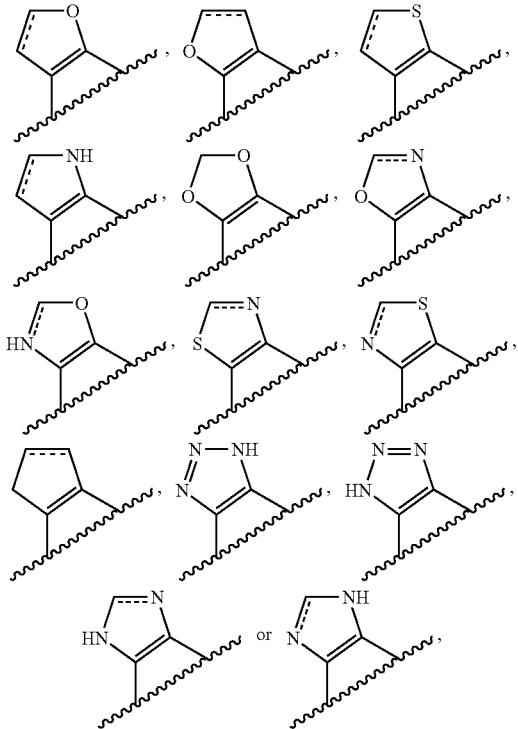

wherein ring Z can be substituted with up to 3 optional ring carbon substituents, which are the same or different, and which are selected from H, alkyl, —OH, F, Cl, —O-alkyl, —CF$_3$, —OCF$_3$ and cycloalkyl;

$R^1$ is a bond or —[C($R^{12}$)$_2$]$_r$—;

$R^2$ is —C(O)OH, heteroaryl, or —C(O)NHSO$_2$$R^{11}$;

$R^3$ is:

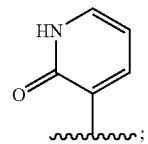

$R^6$ and $R^7$ are each independently selected from H, alkyl, F, Cl, —CF$_3$, —OH, —O-alkyl, —OCF$_3$, —NH$_2$ or —NHSO$_2$-alkyl; and $R^{10}$ is phenyl, pyridyl or pyrimidinyl, each of which is unsubstituted or optionally substituted with up to 3 substituents, which are the same or different, and are selected from alkyl, aryl, heteroaryl, heterocycloalkyl, heterocycloalkenyl, halo, haloalkyl, —OH, hydroxyalkyl, —CN, —C(O)alkyl, —C(O)Oalkyl, —C(O)N($R^9$)$_2$, -alkylene-O$R^9$, —O$R^9$, —N($R^9$)$_2$, —NHC(O)$R^8$, —NHSO$_2$$R^{11}$, —S(O)$_p$$R^{11}$ or —SO$_2$N($R^9$)$_2$.

In another embodiment, the invention provides compounds of formula (I), wherein ring Z is:

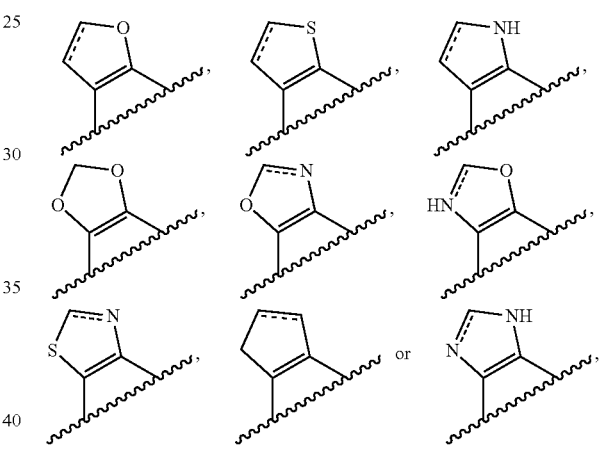

wherein ring Z can be substituted with up to 3 optional ring carbon substituents, which are the same or different, and which are selected from H, alkyl, —OH, F, Cl, —O-alkyl, —CF$_3$, —OCF$_3$ and cycloalkyl;

$R^1$ is a bond or —[C($R^{12}$)$_2$]$_r$—;

$R^2$ is —C(O)OH, heteroaryl, or —C(O)NHSO$_2$$R^{11}$;

$R^3$ is aryl, heteroaryl or heterocycloalkenyl, each of which is unsubstituted or optionally substituted with up to 3 substituents, which are the same or different, and are selected from alkyl, aryl, cycloalkyl, heterocycloalkyl, heteroaryl, halo, haloalkyl, hydroxyalkyl, —OH, —CN, —C(O)alkyl, —C(O)N($R^9$)$_2$, —N($R^9$)$_2$, —O-haloalkyl, —NHC(O)NH$_2$, —NHC(O)NH-alkyl, —NHSO$_2$$R^{11}$, —S(O)$_2$$R^{11}$ or —SO$_2$NH$R^{11}$;

$R^6$ and $R^7$ are each independently selected from H, alkyl, F, Cl, —CF$_3$, —OH, —O-alkyl, —OCF$_3$, —NH$_2$ or —NHSO$_2$-alkyl; and $R^{10}$ is phenyl, pyridyl or pyrimidinyl, each of which is unsubstituted or optionally substituted with up to 3 substituents, which are the same or different, and are selected from alkyl, aryl, heteroaryl, heterocycloalkyl, heterocycloalkenyl, halo, haloalkyl, —OH, hydroxyalkyl, —CN, —C(O)alkyl, —C(O)Oalkyl, —C(O)N($R^9$)$_2$, -alkylene-O$R^9$, —O$R^9$, —N($R^9$)$_2$, —NHC(O)$R^8$, —NHSO$_2$$R^{11}$, —S(O)$_p$$R^{11}$ or —SO$_2$N($R^9$)$_2$.

In another embodiment, the invention provides compounds of formula (I), wherein ring Z is

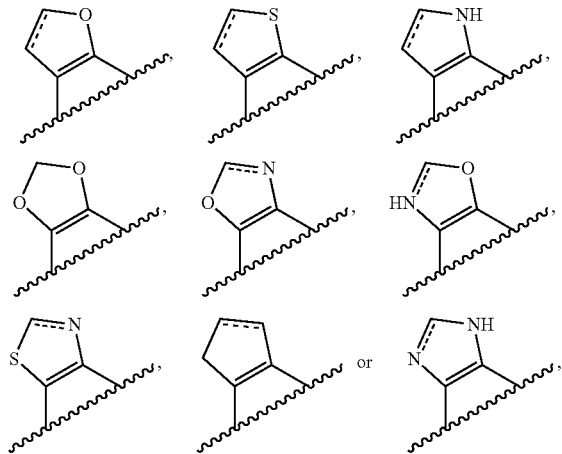

wherein a dotted line represents an optional and additional bond, and wherein the above ring Z groups can be optionally substituted as set forth above in claim 1;

$R^1$ is a bond or —[C($R^{12}$)$_2$]$_r$—;

$R^2$ is —C(O)OH or —C(O)NHSO$_2$$R^{11}$;

$R^3$ is phenyl, pyridyl or

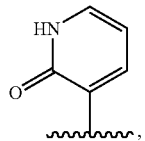 [SMILES: *c1ccc[nH]c1=O]

each of which can be optionally substituted with up to 3 substituents, which are the same or different, and are selected from alkyl, —CF$_3$, —CN, —C(O)CH$_3$, —C(O)NH$_2$, —C(O)NHalkyl, F, Cl, —OH, —OCF$_3$, —NH$_2$, —NHalkyl, —NHC(O)NH$_2$, —NHC(O)NH-alkyl, —NHSO$_2$alkyl, —S(O)$_2$-alkyl or —SO$_2$NHalkyl;

$R^3$ is aryl, heteroaryl or heterocycloalkenyl, each of which is unsubstituted or optionally substituted with up to 3 substituents, which are the same or different, and are selected from alkyl, aryl, cycloalkyl, heterocycloalkyl, heteroaryl, halo, haloalkyl, hydroxyalkyl, —OH, —CN, —C(O)alkyl, —C(O)N($R^9$)$_2$, —N($R^9$)$_2$, —O-haloalkyl, —NHC(O)NH$_2$, —NHC(O)NH-alkyl, —NHSO$_2$$R^{11}$, —S(O)$_2$$R^{11}$ or —SO$_2$NH$R^{11}$;

$R^6$ and $R^7$ are each independently selected from H, methyl, F, Cl, —CF$_3$, —OH, methoxy, —OCF$_3$, —NH$_2$ or —NHSO$_2$CH$_3$; and $R^{10}$ is phenyl, pyridyl or pyrimidinyl, each of which can be optionally substituted with up to 3 substituents, which are the same or different, and are selected from alkyl, F, Cl, —CF$_3$, —CN, —C(O)alkyl, —C(O)NH$_2$, —OR$^9$, —NH$_2$, —NHCH$_3$, —NHC(O)$R^8$, —NHSO$_2$CH$_3$, —SO$_2$CH$_3$ or —SO$_2$NH$_2$.

In one embodiment, the invention provides compounds of formula (I), wherein ring Z is

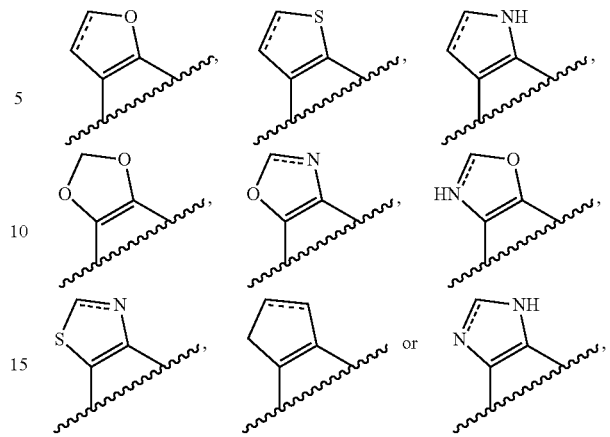

wherein a dotted line represents an optional and additional bond, and wherein the above ring Z groups can be optionally substituted as set forth above in claim 1;

$R^1$ is a bond or —CH$_2$—;

$R^2$ is —C(O)OH or —C(O)NHSO$_2$$R^{11}$;

$R^3$ is aryl, heteroaryl or heterocycloalkenyl, each of which is unsubstituted or optionally substituted with up to 3 substituents, which are the same or different, and are selected from alkyl, aryl, cycloalkyl, heterocycloalkyl, heteroaryl, halo, haloalkyl, hydroxyalkyl, —OH, —CN, —C(O)alkyl, —C(O)N($R^9$)$_2$, —N($R^9$)$_2$, —O-haloalkyl, —NHC(O)NH$_2$, —NHC(O)NH-alkyl, —NHSO$_2$$R^{11}$, —S(O)$_2$$R^{11}$ or —SO$_2$NH$R^{11}$;

$R^6$ and $R^7$ are each independently selected from H, methyl, F, Cl, —CF$_3$, —OH, methoxy, —OCF$_3$, —NH$_2$ or —NHSO$_2$CH$_3$; and $R^{10}$ is phenyl, pyridyl or pyrimidinyl, each of which can be optionally substituted with up to 3 substituents, which are the same or different, and are selected from alkyl, F, Cl, —CF$_3$, —CN, —C(O)alkyl, —C(O)NH$_2$, —OR$^9$, —NH$_2$, —NHCH$_3$, —NHC(O)$R^8$, —NHSO$_2$CH$_3$, —SO$_2$CH$_3$ or —SO$_2$NH$_2$.

In another embodiment, the invention provides compounds of formula (I), wherein ring Z is

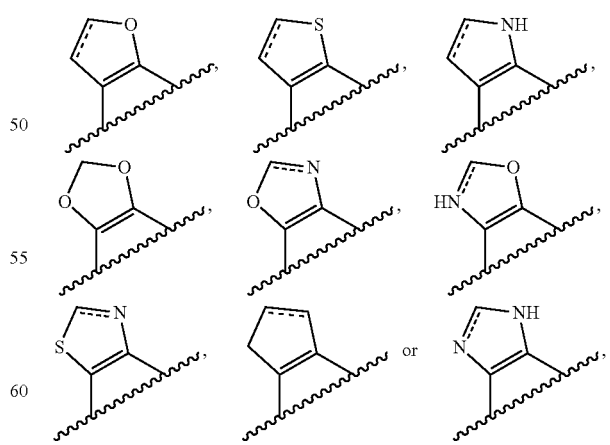

wherein a dotted line represents an optional and additional bond, and wherein the above ring Z groups can be optionally substituted as set forth above in claim 1;

$R^1$ is a bond or —CH$_2$—;

$R^2$ is —C(O)OH or —C(O)NHSO$_2$R$^{11}$;
$R^3$ is phenyl, pyridyl or

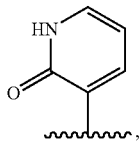

each of which can be optionally substituted with up to 3 substituents, which are the same or different, and are selected from alkyl, —CF$_3$, —CN, —C(O)CH$_3$, —C(O)NH$_2$, —C(O)NHalkyl, F, Cl, —OH, —OCF$_3$, —NH$_2$, —NHalkyl, —NHC(O)NH$_2$, —NHC(O)NH-alkyl, —NHSO$_2$alkyl, —S(O)$_2$-alkyl or —SO$_2$NHalkyl;

$R^6$ and $R^7$ are each independently selected from H, methyl, F, Cl, —CF$_3$, —OH, methoxy, —OCF$_3$, —NH$_2$ or —NHSO$_2$CH$_3$; and $R^{10}$ is phenyl, pyridyl or pyrimidinyl, each of which can be optionally substituted with up to 3 substituents, which are the same or different, and are selected from alkyl, F, Cl, —CF$_3$, —CN, —C(O)alkyl, —C(O)NH$_2$, —OR$^9$, —NH$_2$, —NHCH$_3$, —NHC(O)R$^8$, —NHSO$_2$CH$_3$, —SO$_2$CH$_3$ or —SO$_2$NH$_2$.

In still another embodiment, the invention provides compounds of formula (I), wherein ring Z is

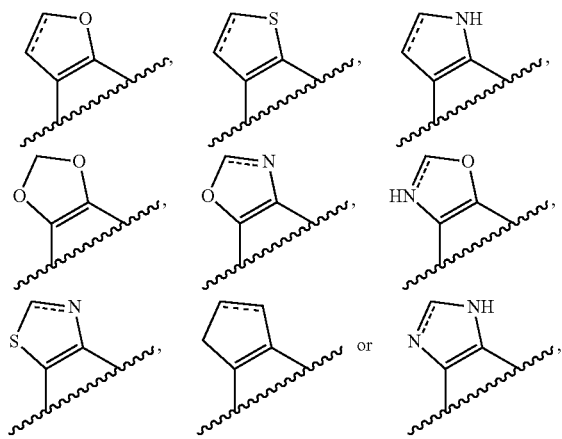

wherein a dotted line represents an optional and additional bond, and wherein the above ring Z groups can be optionally substituted as set forth above in claim 1;

$R^1$ is a bond or —CH$_2$—;
$R^2$ is —C(O)OH or —C(O)NHSO$_2$R$^{11}$;
$R^3$ is

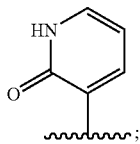 [SMILES: *c1ccc[nH]c1=O]

$R^6$ and $R^7$ are each independently selected from H, methyl, F, Cl, —CF$_3$, —OH, methoxy, —OCF$_3$, —NH$_2$ or —NHSO$_2$CH$_3$; and $R^{10}$ is phenyl, pyridyl or pyrimidinyl, each of which can be optionally substituted with up to 3 substituents, which are the same or different, and are selected from alkyl, F, Cl, —CF$_3$, —CN, —C(O)alkyl, —C(O)NH$_2$, —OR$^9$, —NH$_2$, —NHCH$_3$, —NHC(O)R$^8$, —NHSO$_2$CH$_3$, —SO$_2$CH$_3$ or —SO$_2$NH$_2$.

In one embodiment, the invention provides compounds of formula (I), wherein ring Z is

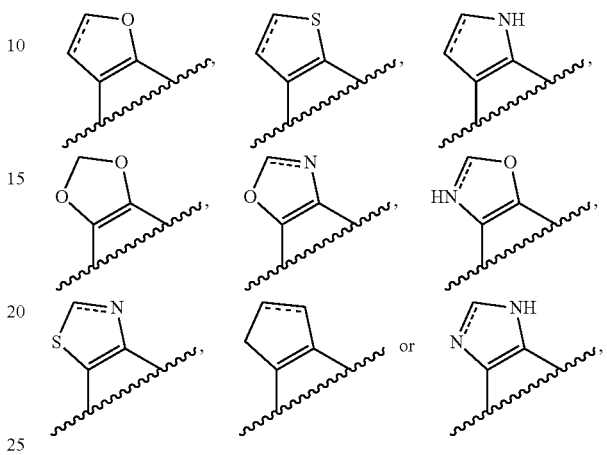

wherein a dotted line represents an optional and additional bond, and wherein the above ring Z groups can be optionally substituted as set forth above in claim 1;

$R^1$ is a bond or —CH$_2$—;
$R^2$ is —C(O)OH or —C(O)NHSO$_2$R$^{11}$;
$R^3$ is aryl, heteroaryl or heterocycloalkenyl, each of which is unsubstituted or optionally substituted with up to 3 substituents, which are the same or different, and are selected from alkyl, aryl, cycloalkyl, heterocycloalkyl, heteroaryl, halo, haloalkyl, hydroxyalkyl, —OH, —CN, —C(O)alkyl, —C(O)N(R$^9$)$_2$, —N(R$^9$)$_2$, —O-haloalkyl, —NHC(O)NH$_2$, —NHC(O)NH-alkyl, —NHSO$_2$R$^{11}$, —S(O)$_2$R$^{11}$ or —SO$_2$NHR$^{11}$;

$R^6$ and $R^7$ are each independently selected from H, methyl, F, Cl, —CF$_3$, —OH, methoxy, —OCF$_3$, —NH$_2$ or —NHSO$_2$CH$_3$; and $R^{10}$ is bicyclic aryl or bicyclic heteroaryl, each of which can be unsubstituted or optionally substituted with up to 3 substituents, which are the same or different, and are selected from alkyl, aryl, heteroaryl, halo, haloalkyl, heterocycloalkyl, heterocycloalkenyl, hydroxyalkyl, —CN, —C(O)alkyl, —C(O)Oalkyl, —C(O)N(R$^9$)$_2$, -alkylene-OR$^9$, —OR$^9$, —N(R$^9$)$_2$, —NHC(O)R$^8$, —NHSO$_2$R$^{11}$, —S(O)$_p$R$^{11}$ or —SO$_2$N(R$^9$)$_2$.

In another embodiment, the invention provides compounds of formula (I), wherein ring Z is

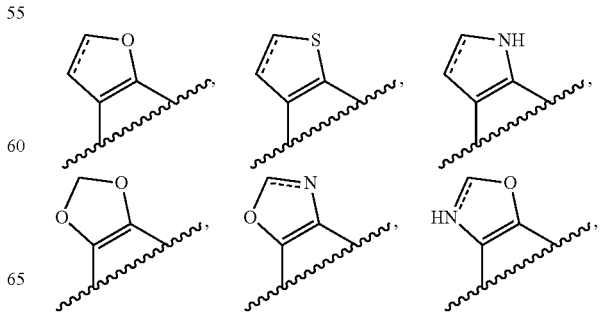

-continued

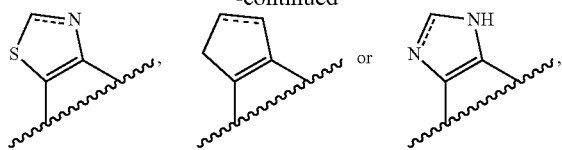

wherein a dotted line represents an optional and additional bond, and wherein the above ring Z groups can be optionally substituted as set forth above in claim 1;

$R^1$ is a bond or —CH$_2$—;
$R^2$ is —C(O)OH or —C(O)NHSO$_2R^{11}$;
$R^3$ is phenyl, pyridyl or

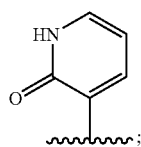

each of which can be optionally substituted with up to 3 substituents, which are the same or different, and are selected from alkyl, —CF$_3$, —CN, —C(O)CH$_3$, —C(O)NH$_2$, —C(O)NHalkyl, F, Cl, —OH, —OCF$_3$, —NH$_2$, —NHalkyl, —NHC(O)NH$_2$, —NHC(O)NH-alkyl, —NHSO$_2$alkyl, —S(O)$_2$-alkyl or —SO$_2$NHalkyl;

$R^6$ and $R^7$ are each independently selected from H, methyl, F, Cl, —CF$_3$, —OH, methoxy, —OCF$_3$, —NH$_2$ or —NHSO$_2$CH$_3$; and $R^{10}$ is bicyclic aryl or bicyclic heteroaryl, each of which can be unsubstituted or optionally substituted with up to 3 substituents, which are the same or different, and are selected from alkyl, aryl, heteroaryl, halo, haloalkyl, heterocycloalkyl, heterocycloalkenyl, hydroxyalkyl, —CN, —C(O)alkyl, —C(O)Oalkyl, —C(O)N(R$^9$)$_2$, -alkylene-OR$^9$, —OR$^9$, —N(R$^9$)$_2$, —NHC(O)R$^8$, —NHSO$_2R^{11}$, —S(O)$_pR^{11}$ or —SO$_2$N(R$^9$)$_2$.

In still another embodiment, the invention provides compounds of formula (I), wherein ring Z is

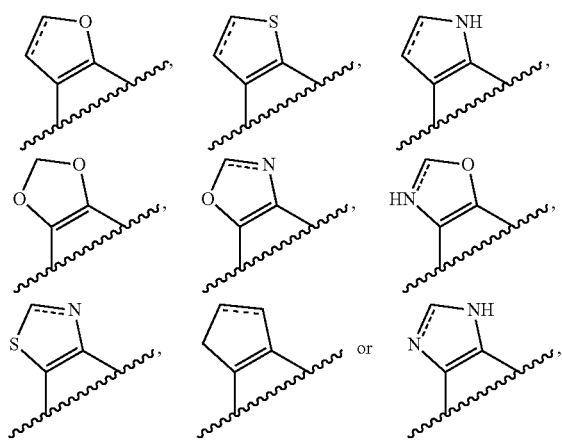

wherein a dotted line represents an optional and additional bond, and wherein the above ring Z groups can be optionally substituted as set forth above in claim 1;

$R^1$ is a bond or —CH$_2$—;
$R^2$ is —C(O)OH or —C(O)NHSO$_2R^{11}$;

$R^3$ is

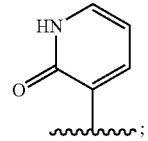 [SMILES: *c1ccc[nH]c1=O]

$R^6$ and $R^7$ are each independently selected from H, methyl, F, Cl, —CF$_3$, —OH, methoxy, —OCF$_3$, —NH$_2$ or —NHSO$_2$CH$_3$; and $R^{10}$ is:

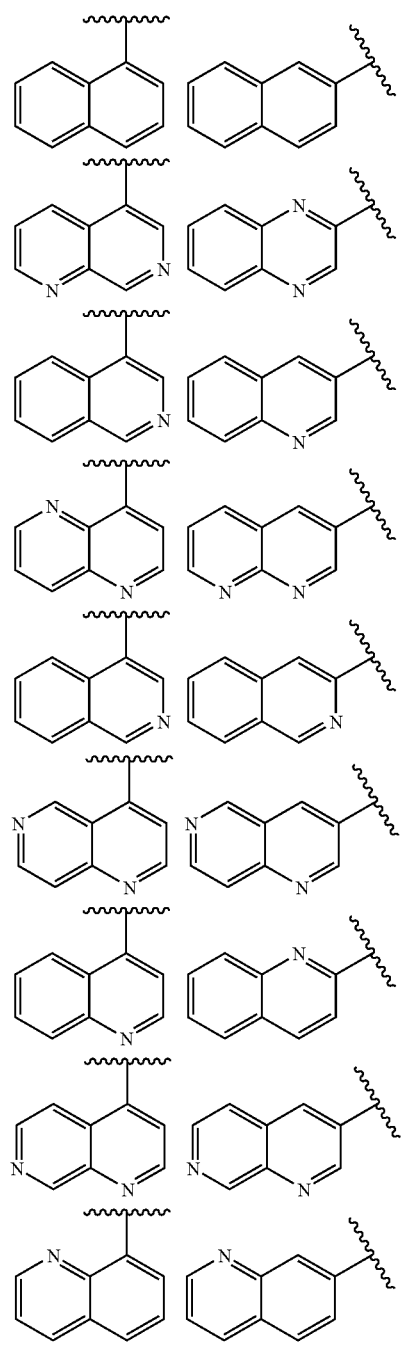

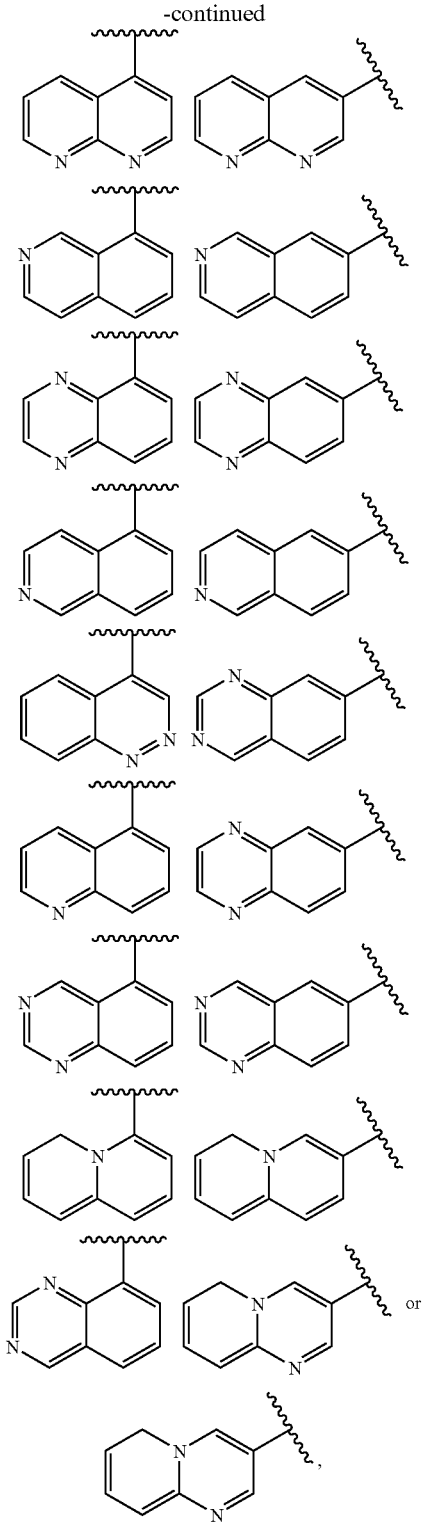

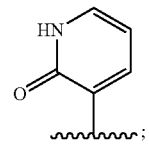 [SMILES: *c1ccc[nH]c1=O]

wherein a dotted line represents an optional and additional bond, and wherein the above ring Z groups can be optionally substituted as set forth above in claim 1;

$R^1$ is a bond or —CH$_2$—;
$R^2$ is —C(O)OH or —C(O)NHSO$_2$R$^{11}$;
$R^3$ is

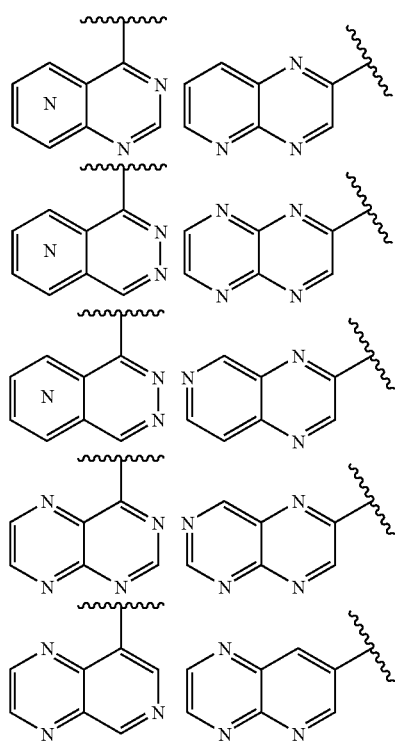

$R^6$ and $R^7$ are each independently selected from H, methyl, F, Cl, —CF$_3$, —OH, methoxy, —OCF$_3$, —NH$_2$ or —NHSO$_2$CH$_3$; and $R^{10}$ is:

each of which can be optionally substituted with up to 3 substituents, which are the same or different, and are selected from alkyl, cycloalkyl, heterocycloalkyl, heterocycloalkenyl, halo, haloalkyl, —O-haloalkyl, —OH, —CN, —NH$_2$, —NH-alkyl, —N(alkyl)$_2$ or —NHSO$_2$-alkyl;

In a further embodiment, the invention provides compounds of formula (I), wherein ring Z is

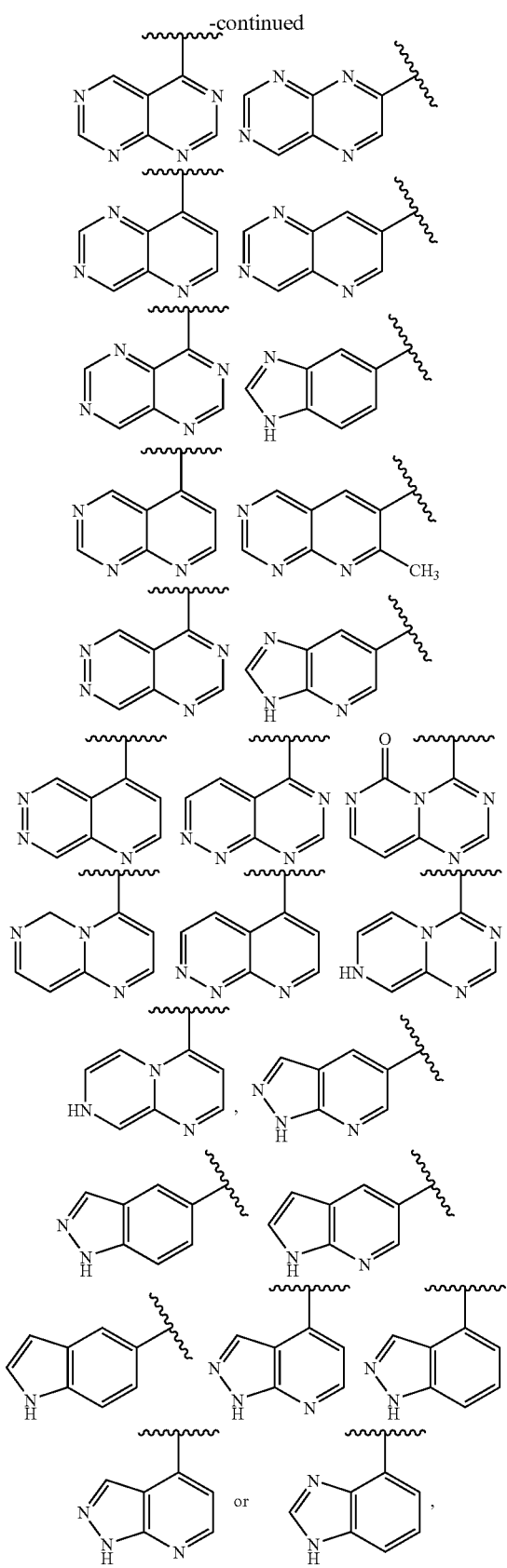

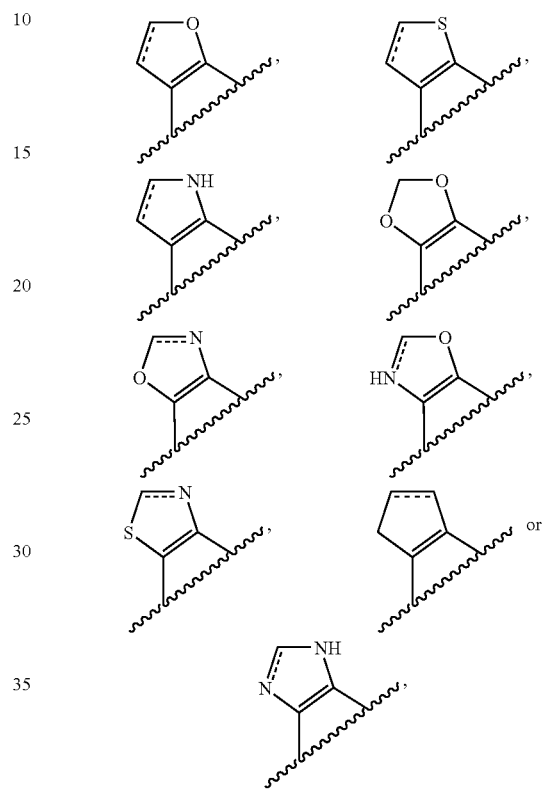

from alkyl, cycloalkyl, heterocycloalkyl, heterocycloalkenyl, halo, haloalkyl, —O-haloalkyl, —OH, —CN, —NH$_2$, —NH-alkyl, —N(alkyl)$_2$ or —NHSO$_2$-alkyl; wherein the letter "N" inside a ring indicates that the ring has 1 or 2 ring nitrogen atoms.

In still another embodiment, the invention provides compounds of formula (I), wherein ring Z is wherein a dotted line represents an optional and additional bond, and wherein the above ring Z groups can be optionally substituted as set forth above in claim 1;
R$^1$ is a bond or —CH$_2$—;
R$^2$ is —C(O)OH or —C(O)NHSO$_2$R$^{11}$;
R$^3$ is

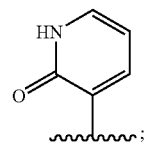

R$^6$ and R$^7$ are each independently selected from H, methyl, F, Cl, —CF$_3$, —OH, methoxy, —OCF$_3$, —NH$_2$ or —NHSO$_2$CH$_3$; and R$^{10}$ is:

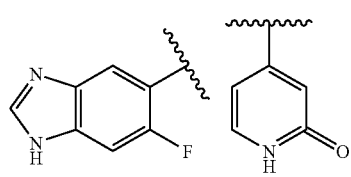

each of which can be optionally substituted with up to 3 substituents, which are the same or different, and are selected

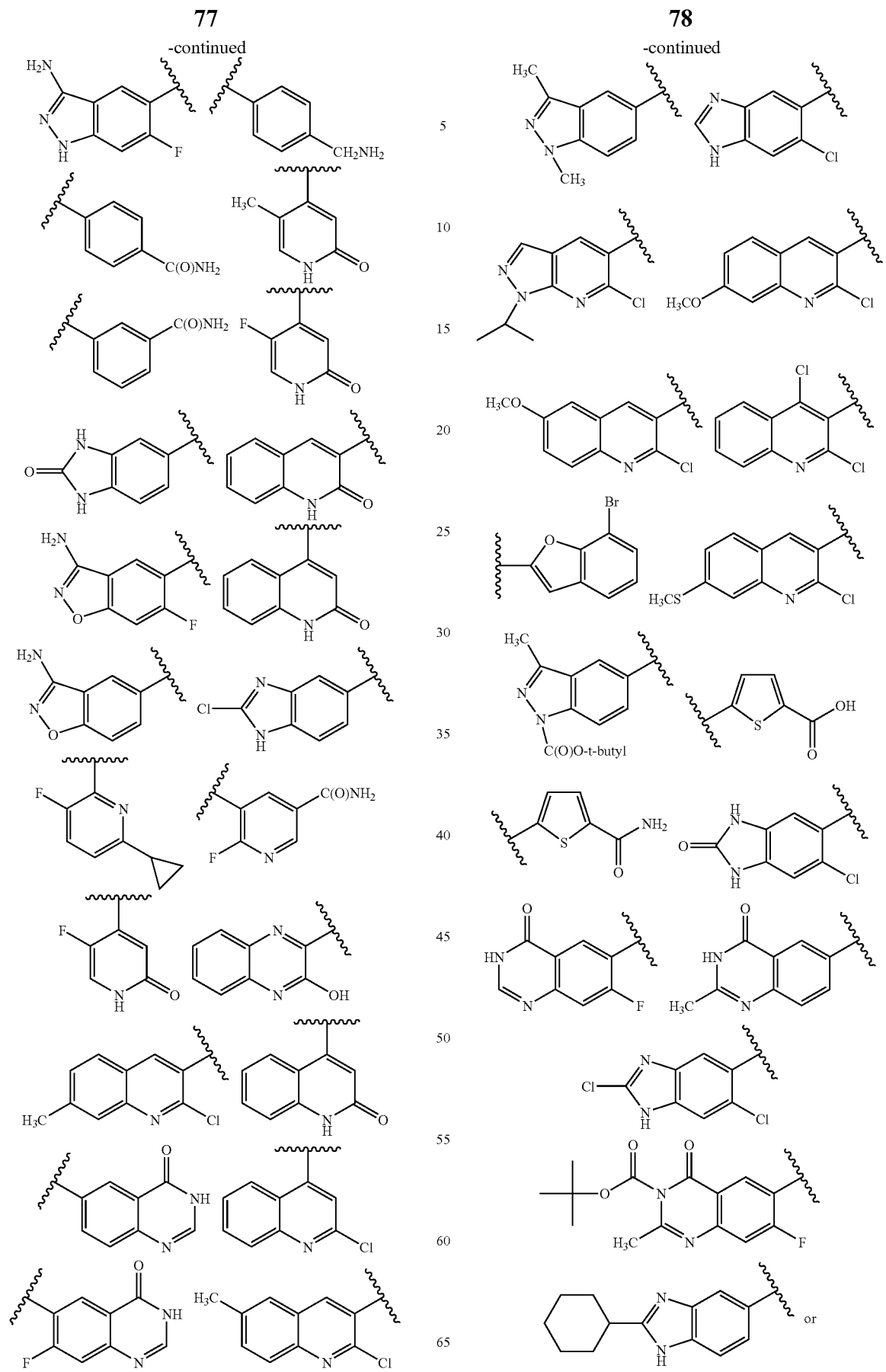

-continued

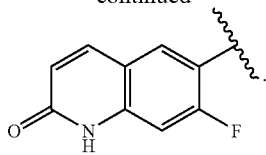

In one embodiment, the invention provides compounds of formula (I), wherein ring Z is:

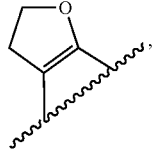

which can be substituted with up to 3 optional ring carbon substituents, which are the same or different, and which are selected from H, alkyl, —OH, F, Cl, —O-alkyl, —$CF_3$, —$OCF_3$ and cycloalkyl;

$R^1$ is a bond or —$[C(R^{12})_2]_r$—;

$R^2$ is —C(O)OH or —C(O)$NHSO_2R^{11}$;

$R^3$ is aryl, heteroaryl or heterocycloalkenyl, each of which is unsubstituted or optionally substituted with up to 3 substituents, which are the same or different, and are selected from alkyl, aryl, cycloalkyl, heterocycloalkyl, heteroaryl, halo, haloalkyl, hydroxyalkyl, —OH, —CN, —C(O)alkyl, —C(O)N($R^9$)$_2$, —N($R^9$)$_2$, —O-haloalkyl, —NHC(O)$NH_2$, —NHC(O)NH-alkyl, —$NHSO_2R^{11}$, —S(O)$_2R^{11}$ or —$SO_2NHR^{11}$;

$R^6$ and $R^7$ are each independently selected from H, alkyl, F, Cl, —$CF_3$, —OH, —O-alkyl, —$OCF_3$, —$NH_2$ or —$NHSO_2$-alkyl; and $R^{10}$ is phenyl, pyridyl or pyrimidinyl, each of which is unsubstituted or optionally substituted with up to 3 substituents, which are the same or different, and are selected from alkyl, aryl, heteroaryl, heterocycloalkyl, heterocycloalkenyl, halo, haloalkyl, —OH, hydroxyalkyl, —CN, —C(O)alkyl, —C(O)Oalkyl, —C(O)N($R^9$)$_2$, -alkylene-$OR^9$, —$OR^9$, —N($R^9$)$_2$, —NHC(O)$R^8$, —$NHSO_2R^{11}$, —S(O)$_pR^{11}$ or —$SO_2N(R^9)_2$.

In one embodiment, the compounds of formula (I) have the formula (Ia):

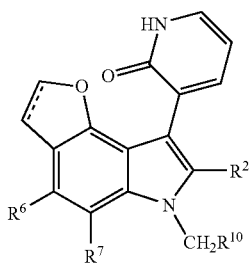

wherein the dotted line indicates an optional and additional bond;

$R^2$ is —C(O)$OR^9$ or —C(O)$NHSO_2R^{11}$;

$R^6$ and $R^7$ are each independently selected from H, alkyl, F, Cl, —$CF_3$, —OH, —O-alkyl, —$OCF_3$, —$NH_2$ and —$NHSO_2$-alkyl;

$R^9$ is H or alkyl;

$R^{10}$ is H, cycloalkyl, cycloalkenyl, heterocycloalkyl, heterocycloalkenyl, aryl or heteroaryl, wherein a cycloalkyl, cycloalkenyl, heterocycloalkyl, heterocycloalkenyl, aryl or heteroaryl group can be optionally substituted with up to 4 substituents, which are each independently selected from H, alkyl, alkenyl, alkynyl, aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, —[C($R^{12}$)$_2$]$_q$-haloalkyl, —[C($R^{12}$)$_2$]$_q$-hydroxyalkyl, halo, —OH, —$OR^9$, —CN, —[C($R^{12}$)$_2$]$_q$—C(O)$R^8$, —[C($R^{12}$)$_2$]$_q$—C(O)$OR^9$, —[C($R^{12}$)$_2$]$_q$—C(O)N($R^9$)$_2$, —[C($R^{12}$)$_2$]$_q$—$OR^9$, —[C($R^{12}$)$_2$]$_q$—N($R^9$)$_2$, —[C($R^{12}$)$_2$]$_q$—NHC(O)$R^8$, —[C($R^{12}$)$_2$]$_q$—$NR^8C(O)N(R^9)_2$, —[C($R^{12}$)$_2$]$_q$—$NHSO_2R^{11}$, —[C($R^{12}$)$_2$]$_q$—S(O)$_pR^{11}$, —[C($R^{12}$)$_2$]$_q$—$SO_2N(R^9)_2$ and —$SO_2N(R^9)C(O)N(R^9)_2$; and $R^{11}$ is alkyl, aryl or cycloalkyl.

In one embodiment, ring Z is:

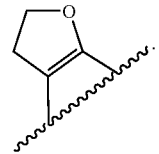

In another embodiment, $R^2$ is —C(O)OH.

In another embodiment, $R^2$ is —C(O)$NHSO_2R^{11}$.

In still another embodiment, $R^2$ is —C(O)$NHSO_2R^{11}$, wherein $R^{11}$ is alkyl, aryl or cycloalkyl.

In yet another embodiment, $R^2$ is —C(O)$NHSO_2R^{11}$, wherein $R^{11}$ is methyl, ethyl, isopropyl, t-butyl, phenyl or cyclopropyl.

In another embodiment, $R^6$ and $R^7$ are each H.

In a further embodiment, $R^6$ is other than H and $R^7$ is H.

In one embodiment, $R^{10}$ is phenyl, pyridyl or pyrimidinyl, each of which is unsubstituted or optionally substituted with up to 3 substituents, which are the same or different, and are selected from alkyl, aryl, heteroaryl, heterocycloalkyl, heterocycloalkenyl, halo, haloalkyl, —OH, hydroxyalkyl, —CN, —C(O)alkyl, —C(O)Oalkyl, —C(O)N($R^9$)$_2$, -alkylene-$OR^9$, —$OR^9$, —N($R^9$)$_2$, —NHC(O)$R^8$, —$NHSO_2R^{11}$, —S(O)$_pR^{11}$ or —$SO_2N(R^9)_2$.

In another embodiment, $R^{10}$ is bicyclic aryl or bicyclic heteroaryl, each of which can be unsubstituted or optionally substituted with up to 3 substituents, which are the same or different, and are selected from alkyl, aryl, heteroaryl, halo, haloalkyl, heterocycloalkyl, heterocycloalkenyl, hydroxyalkyl, —CN, —C(O)alkyl, —C(O)Oalkyl, —C(O)N($R^9$)$_2$, -alkylene-$OR^9$, —$OR^9$, —N($R^9$)$_2$, —NHC(O)$R^8$, —$NHSO_2R^{11}$, —S(O)$_pR^{11}$ or —$SO_2N(R^9)_2$.

In still another embodiment, $R^{10}$ is bicyclic heteroaryl, which can be optionally substituted with up to 3 substituents, which are the same or different, and are selected from alkyl, aryl, heteroaryl, halo, haloalkyl, hydroxyalkyl, —CN, —C(O)alkyl, —C(O)Oalkyl, —C(O)N($R^9$)$_2$, -(alkylene)-$OR^9$, —$OR^9$, —N($R^9$)$_2$, —NHC(O)$R^8$, —$NHSO_2R^{11}$, —S(O)$_pR^{11}$ or —$SO_2N(R^9)_2$.

In another embodiment, $R^{10}$ is quinoline, quinolinone, pteridine or pteridinone, each of which can be optionally substituted with up to 3 substituents, which are the same or different, and are selected from alkyl, cycloalkyl, heterocycloalkyl, heterocycloalkenyl, halo, haloalkyl, —O-haloalkyl, —OH, —CN, —$NH_2$, —NH-alkyl, —N(alkyl)$_2$ or —$NHSO_2$-alkyl.

In one embodiment, $R^{10}$ is quinoline or quinolinone, either of which can be optionally substituted with up to 3 substituents, which are the same or different, and are selected from alkyl, cycloalkyl, heterocycloalkyl, heterocycloalkenyl, halo, haloalkyl, —O-haloalkyl, —OH, —CN, —NH$_2$, —NH-alkyl, —N(alkyl)$_2$ or —NHSO$_2$-alkyl.

In one embodiment, $R^{10}$ is:

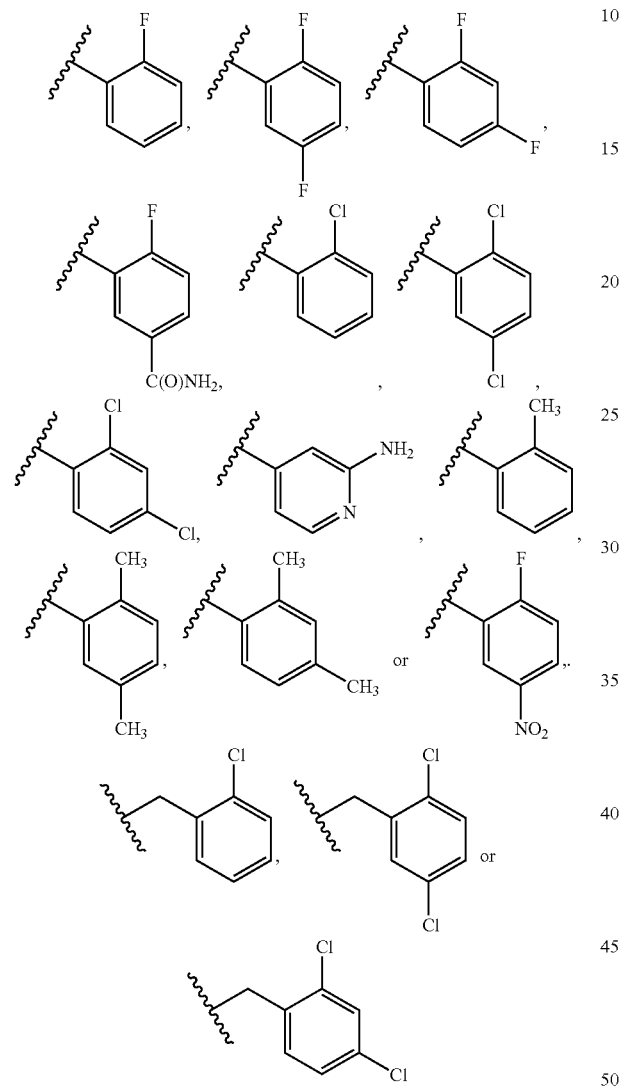

In another embodiment, $R^{10}$ is:

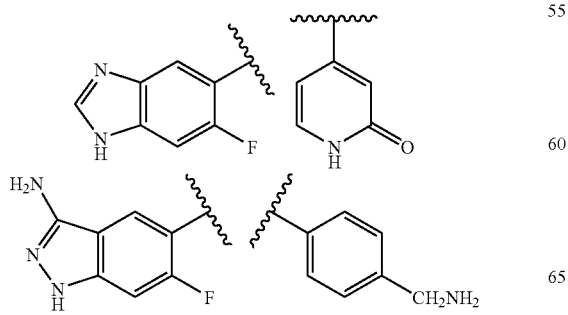

-continued

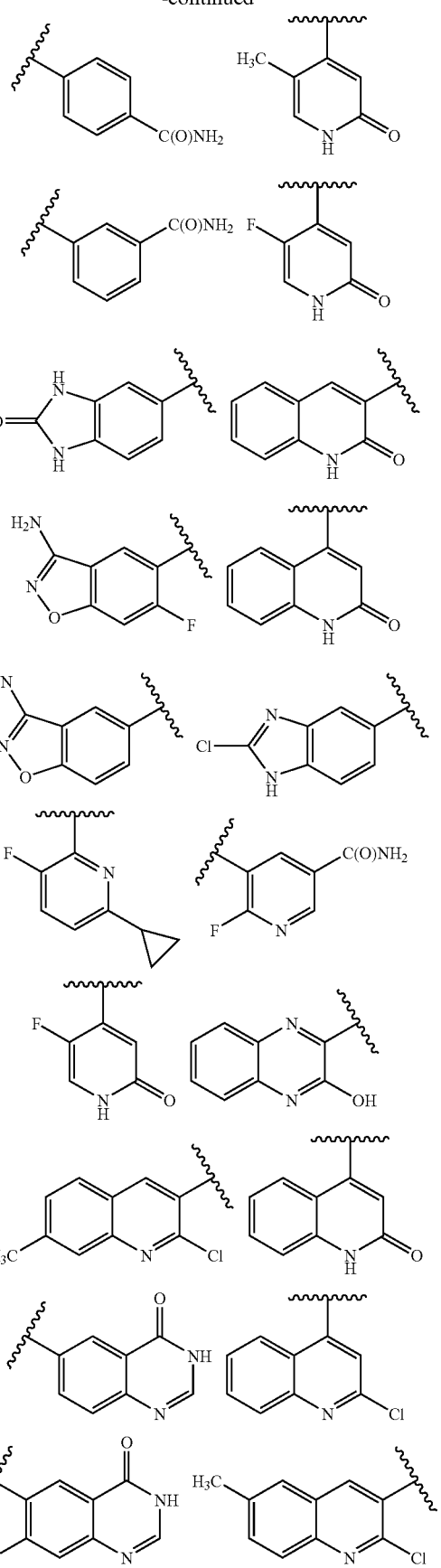

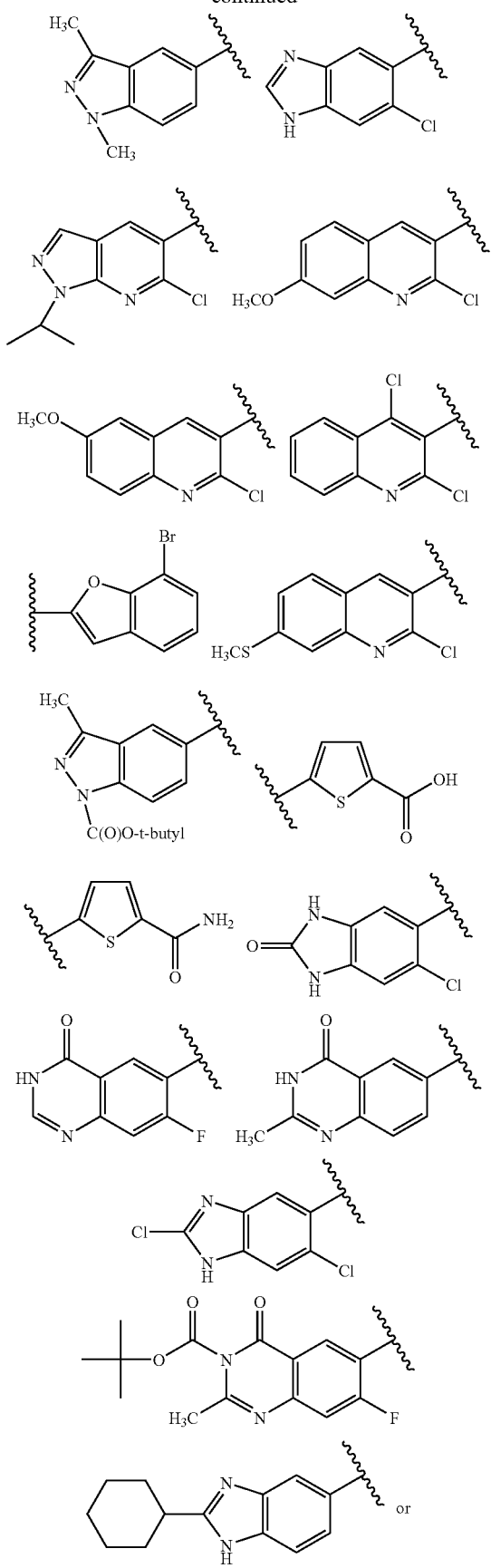
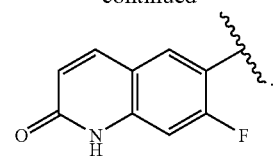
In another embodiment, $R^{10}$ is:
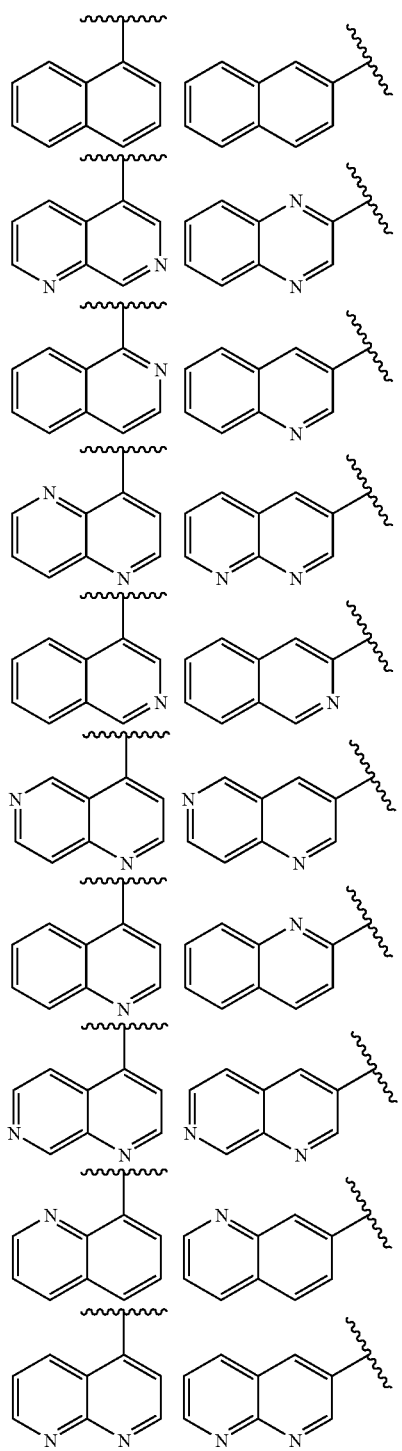

-continued
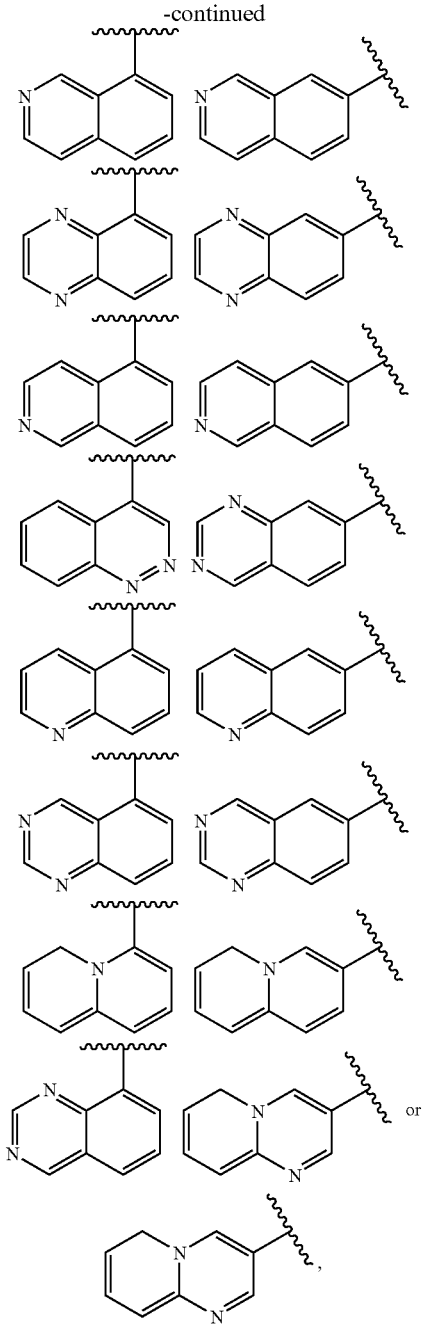
each of which can be optionally substituted with up to 3 substituents, which are the same or different, and are selected from alkyl, cycloalkyl, heterocycloalkyl, heterocycloalkenyl, halo, haloalkyl, —O-haloalkyl, —OH, —CN, —NH$_2$, —NH-alkyl, —N(alkyl)$_2$ or —NHSO$_2$-alkyl.
In still another embodiment, R$^{10}$ is:
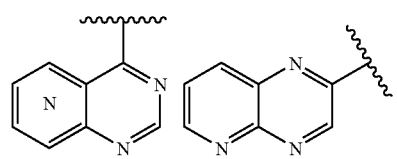
-continued
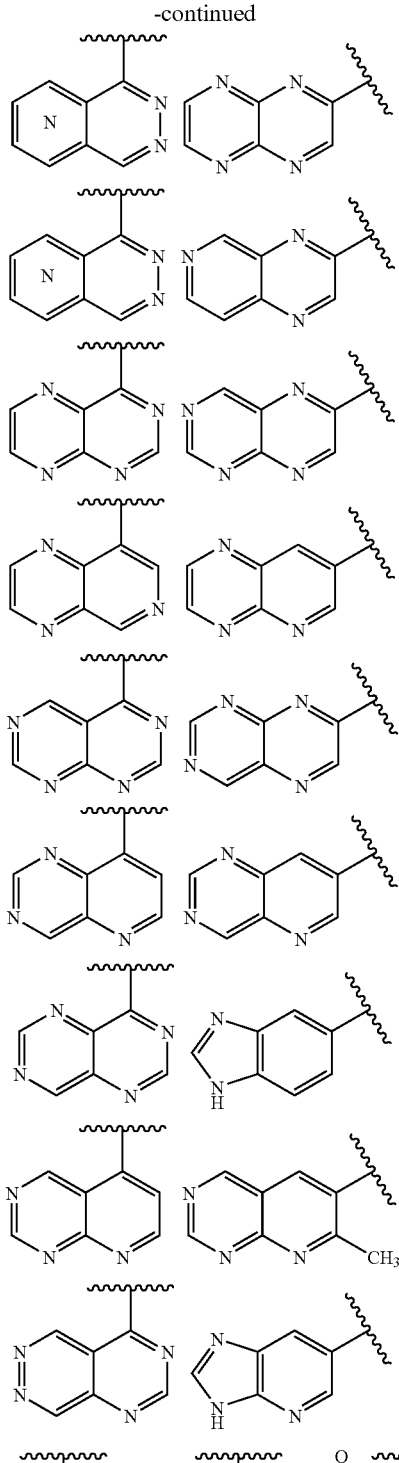
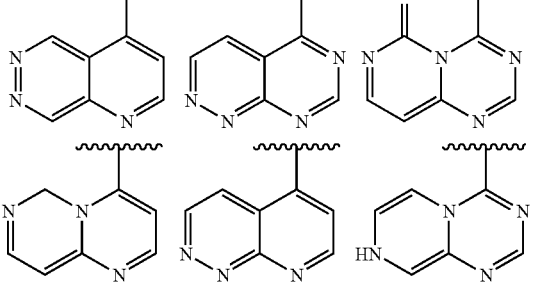

-continued

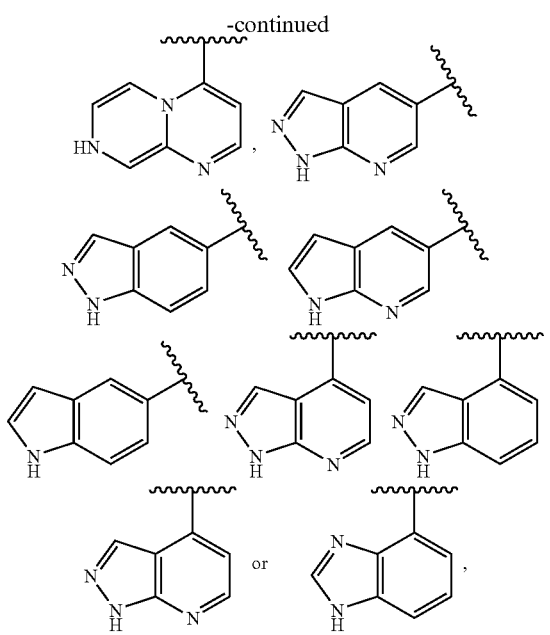

each of which can be optionally substituted with up to 3 substituents, which are the same or different, and are selected from alkyl, cycloalkyl, heterocycloalkyl, heterocycloalkenyl, halo, haloalkyl, —O-haloalkyl, —OH, —CN, —NH$_2$, —NH-alkyl, —N(alkyl)$_2$ or —NHSO$_2$-alkyl; wherein the letter "N" inside a ring indicates that the ring has 1 or 2 ring nitrogen atoms.

In one embodiment, $R^{10}$ is:

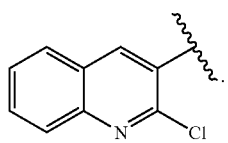 [SMILES: *c1cc2ccccc2nc1Cl]

In one embodiment, $R^2$ is —C(O)OH; the optional bond is absent; and $R^{10}$ is phenyl, pyridyl or pyrimidinyl, each of which is unsubstituted or optionally substituted with up to 3 substituents, which are the same or different, and are selected from alkyl, aryl, heteroaryl, heterocycloalkyl, heterocycloalkenyl, halo, haloalkyl, —OH, hydroxyalkyl, —CN, —C(O)alkyl, —C(O)Oalkyl, —C(O)N(R$^9$)$_2$, -alkylene-OR$^9$, —OR$^9$, —N(R$^9$)$_2$, —NHC(O)R$^8$, —NHSO$_2$R$^{11}$, —S(O)$_p$R$^{11}$ or —SO$_2$N(R$^9$)$_2$.

In another embodiment, $R^2$ is —C(O)OH; the optional bond is absent; and $R^{10}$ is bicyclic aryl or bicyclic heteroaryl, each of which can be unsubstituted or optionally substituted with up to 3 substituents, which are the same or different, and are selected from alkyl, aryl, heteroaryl, halo, haloalkyl, heterocycloalkyl, heterocycloalkenyl, hydroxyalkyl, —CN, —C(O)alkyl, —C(O)Oalkyl, —C(O)N(R$^9$)$_2$, -alkylene-OR$^9$, —OR$^9$, —N(R$^9$)$_2$, —NHC(O)R$^8$, —NHSO$_2$R$^{11}$, —S(O)$_p$R$^{11}$ or —SO$_2$N(R$^9$)$_2$.

In another embodiment, $R^2$ is —C(O)OH; the optional bond is absent; and $R^{10}$ is quinoline, quinolinone, pteridine or pteridinone, each of which can be optionally substituted with up to 3 substituents, which are the same or different, and are selected from alkyl, cycloalkyl, heterocycloalkyl, heterocycloalkenyl, halo, haloalkyl, —O-haloalkyl, —OH, —CN, —NH$_2$, —NH-alkyl, —N(alkyl)$_2$ or —NHSO$_2$-alkyl.

In one embodiment, for the Compounds of Formula (I), $R^1$, $R^2$, $R^3$, $R^6$, $R^7$, $R^{10}$ and Z are selected independently from each other.

In another embodiment, a Compound of Formula (I) is in purified form.

Non-limiting examples of the Compounds of Formula (I) include, but are not limited to, the following compounds:

1

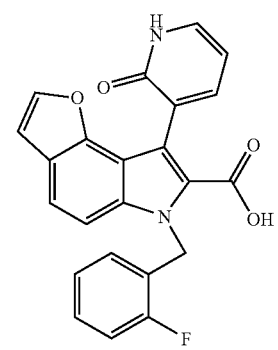

2

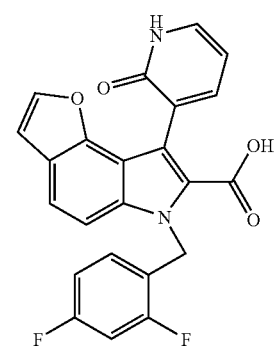

3

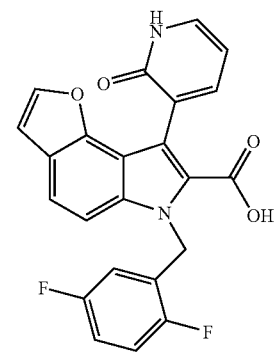

4

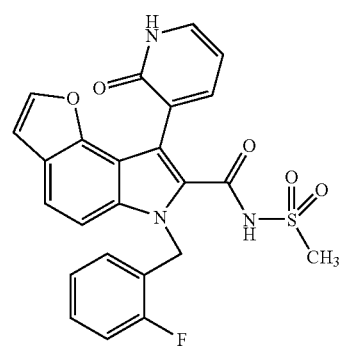

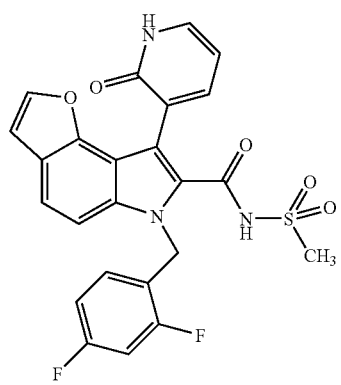
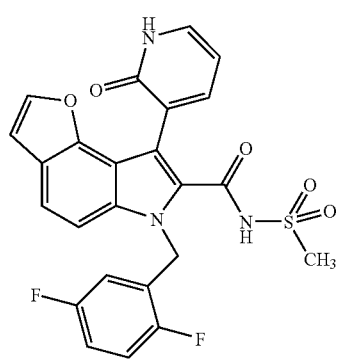
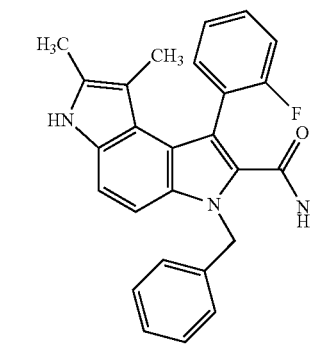
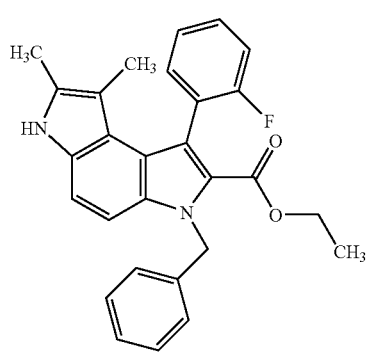
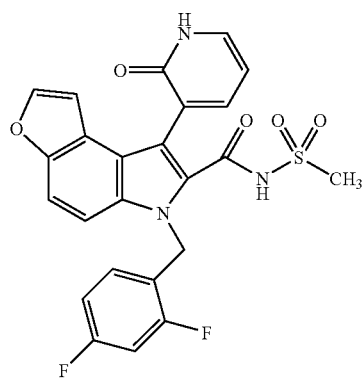
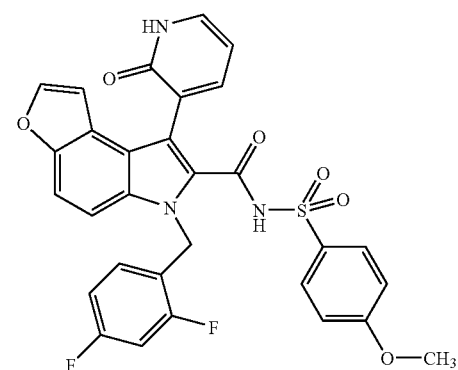
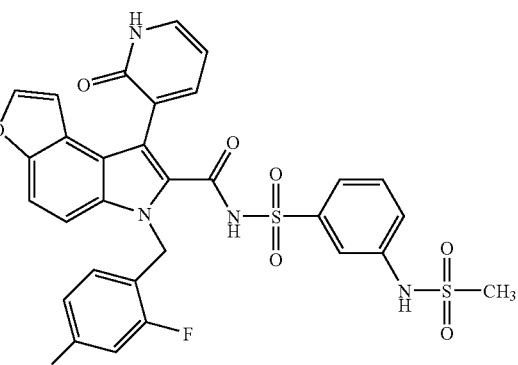
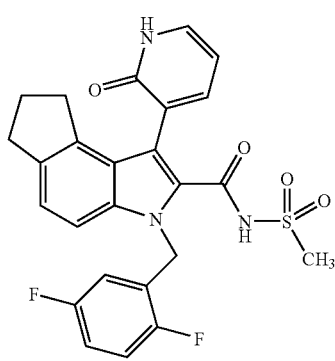

13
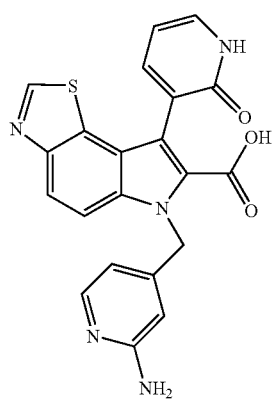
14
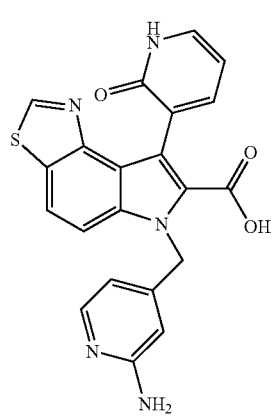
15
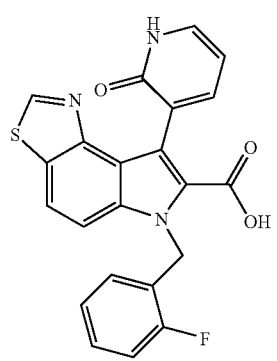
16
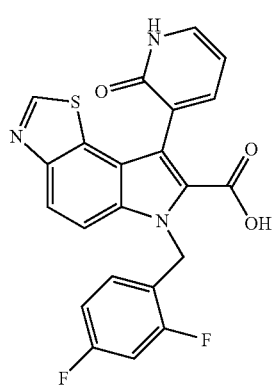
17
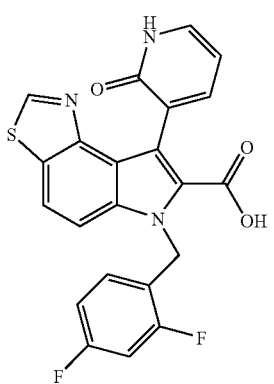
18
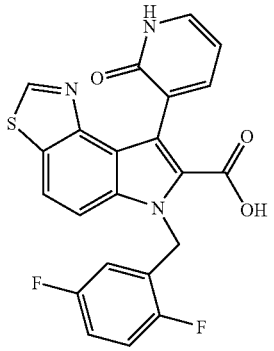
19
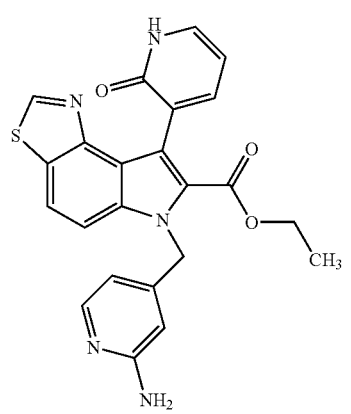
20
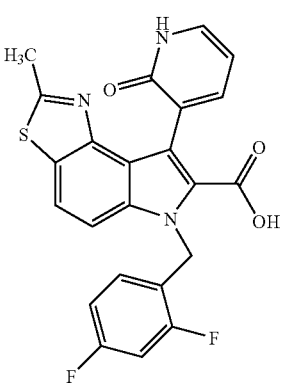

21
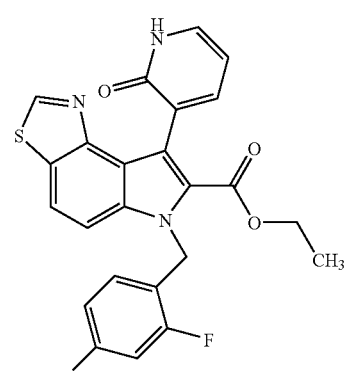
22
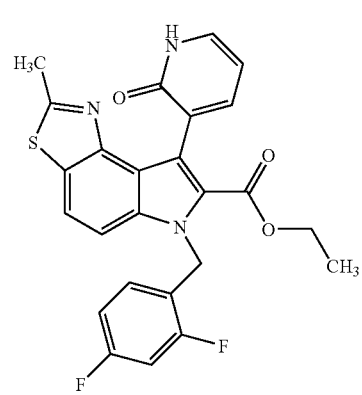
23
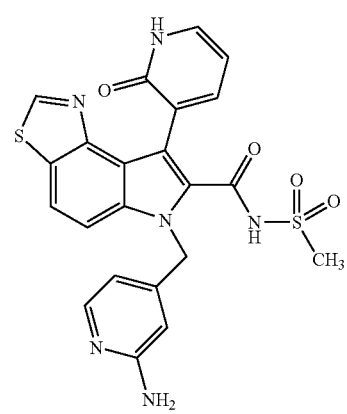
24
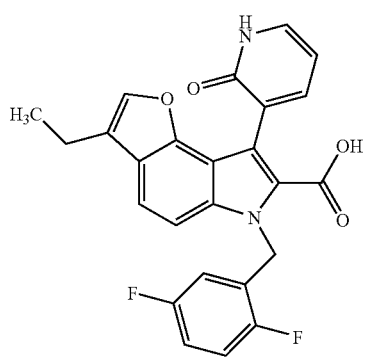
25
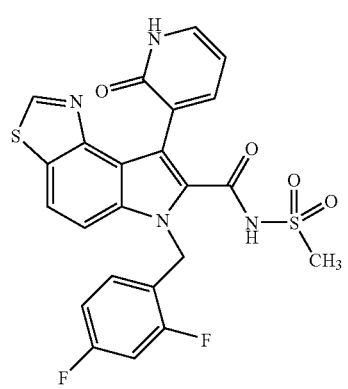
26
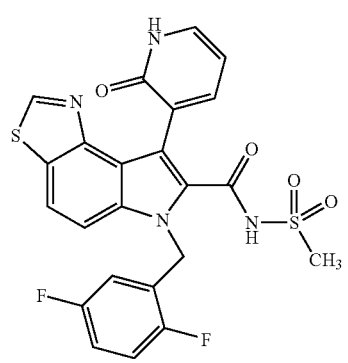
27
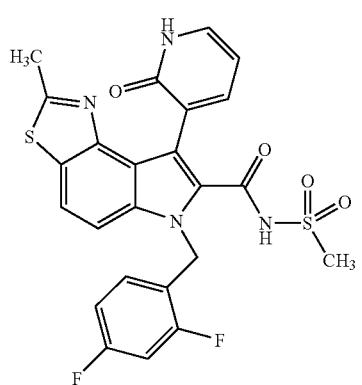
28
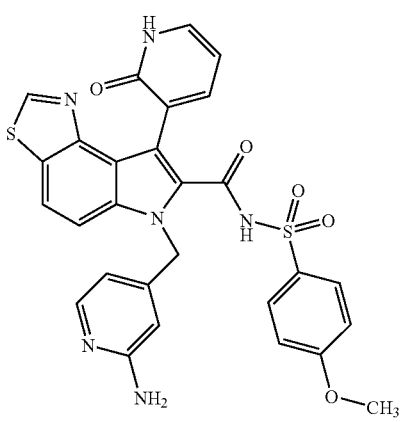

29
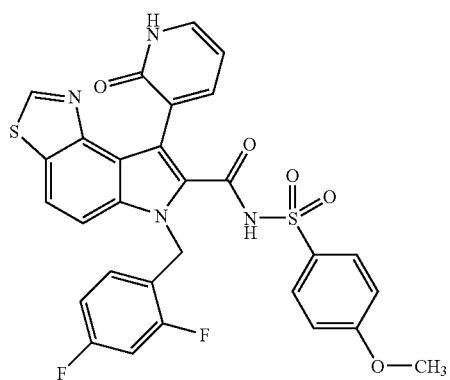
30
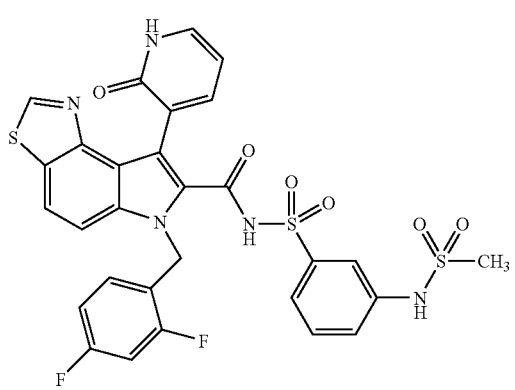
31
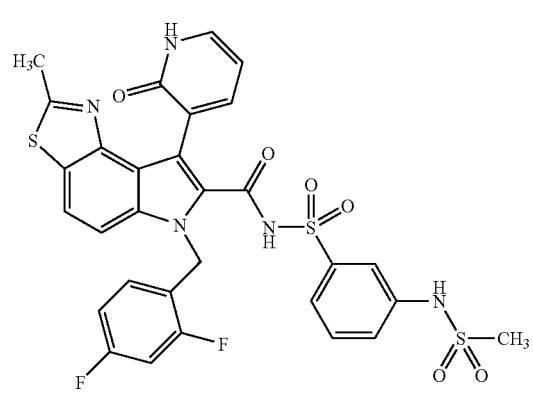
32
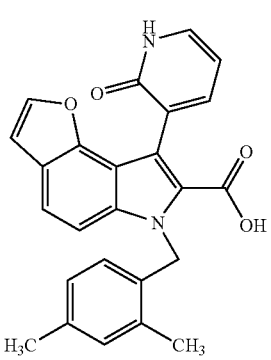
33
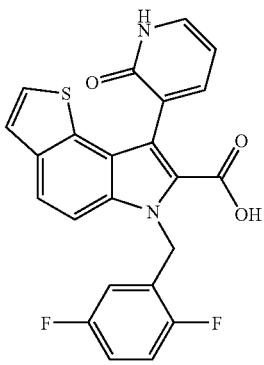
34
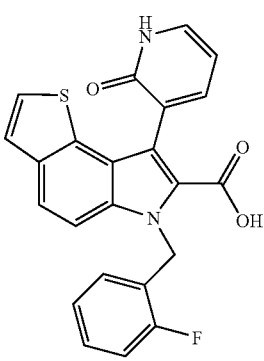
35
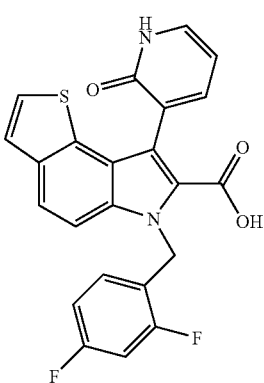
36
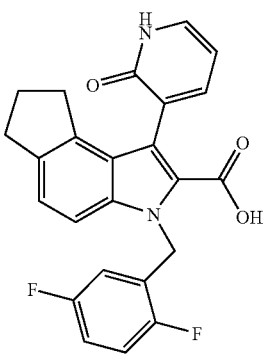

US 8,557,848 B2
97
-continued
37
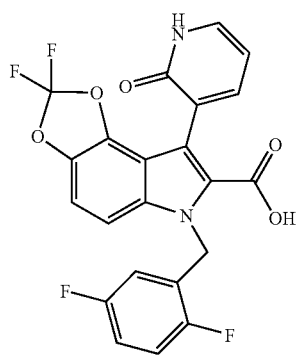
38
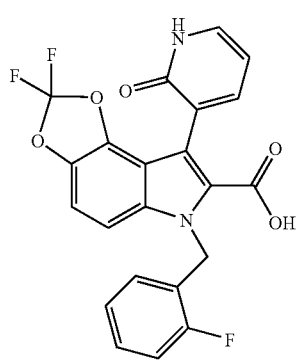
39
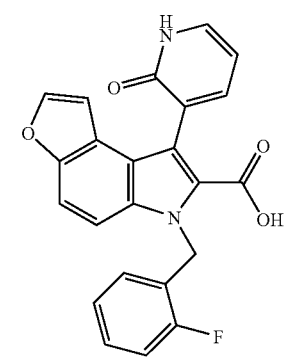
40
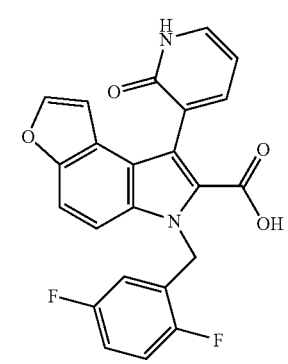
98
-continued
41
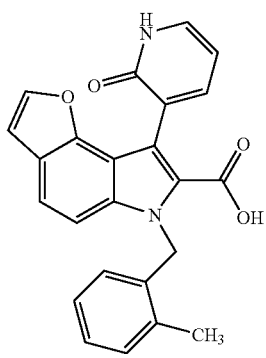
42
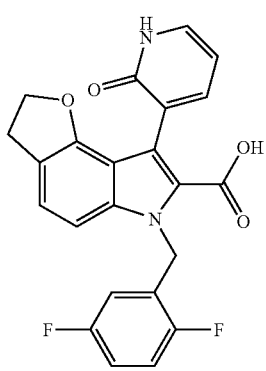
43
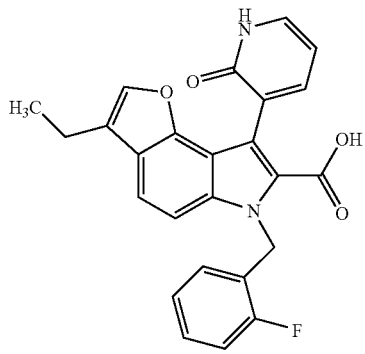
44
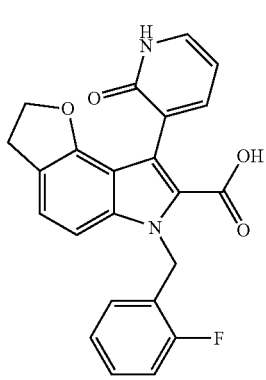

99
-continued
45
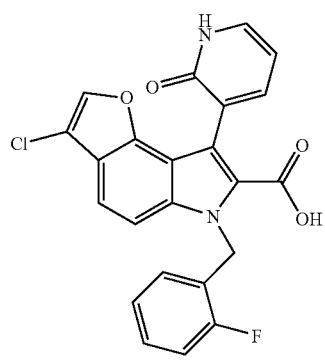
46
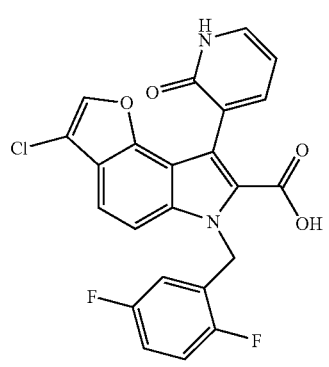
47
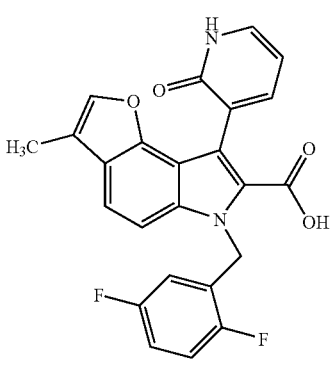
48
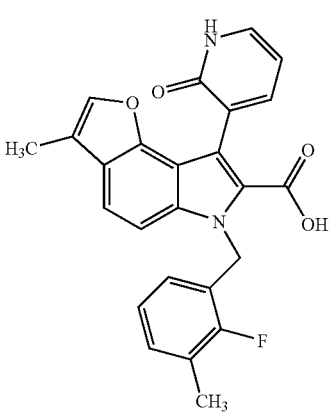
100
-continued
49
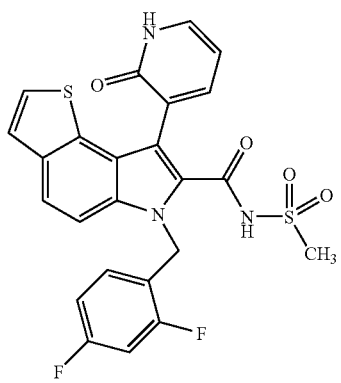
50
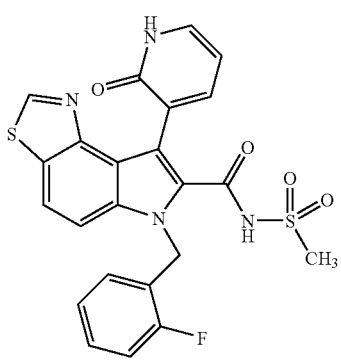
51
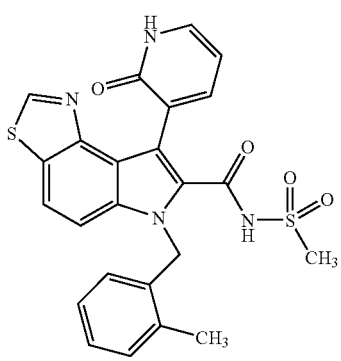
52
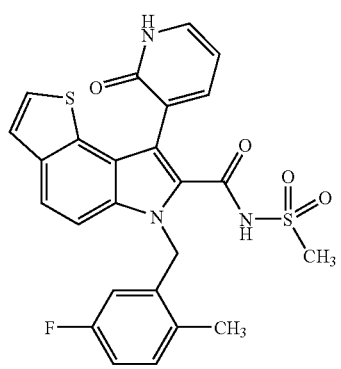

| 101 | 102 |
|---|---|
| 53 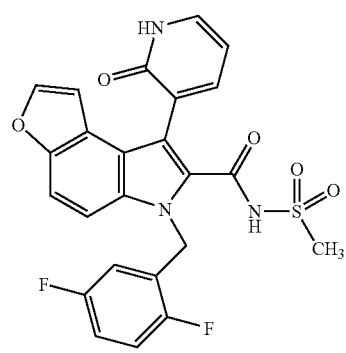 | 57 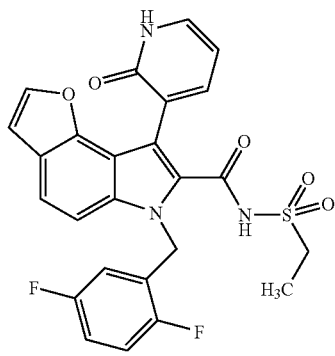 |
| 54 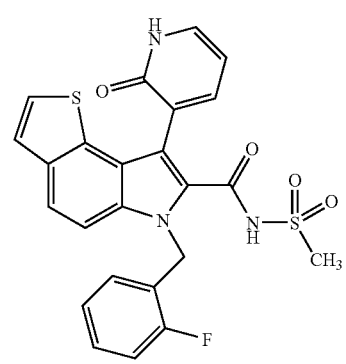 | 58 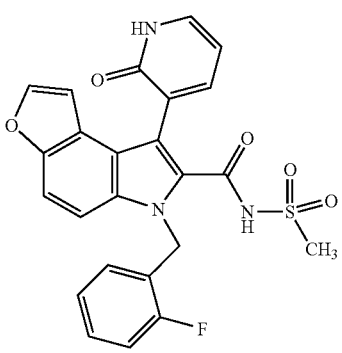 |
| 55 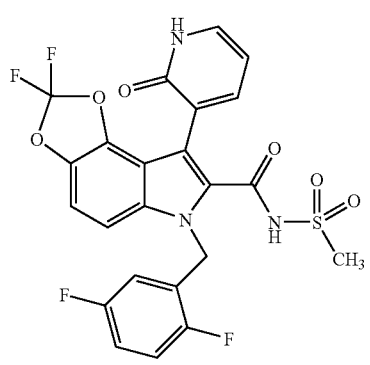 | 59 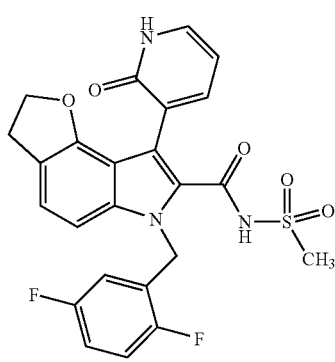 |
| 56 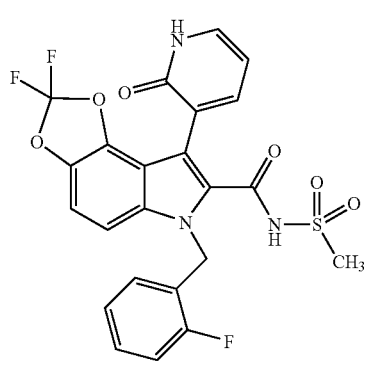 | 60 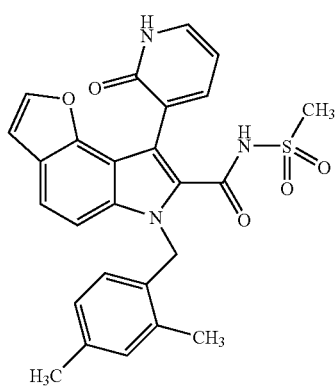 |

-continued
61
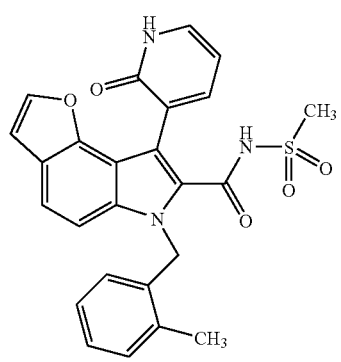
62
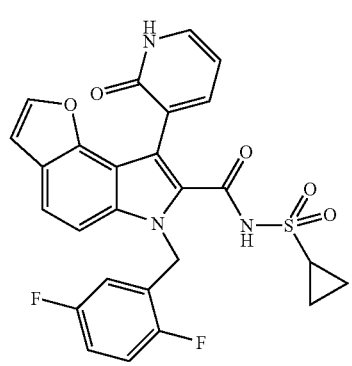
63
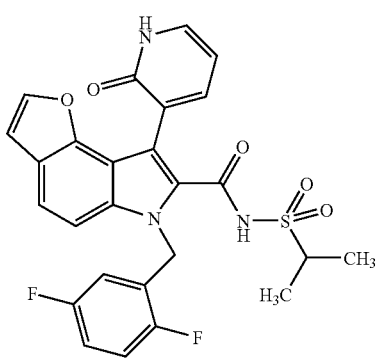
64
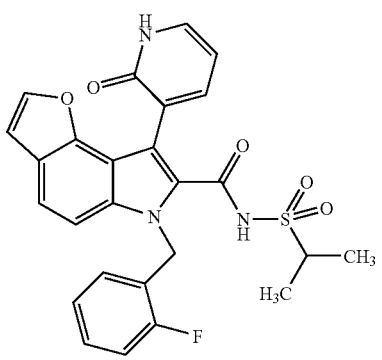
-continued
65
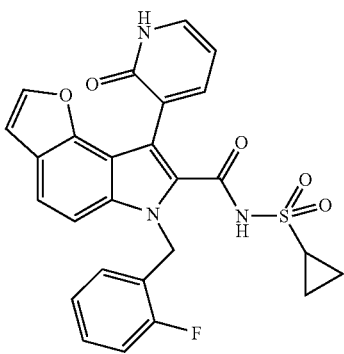
66
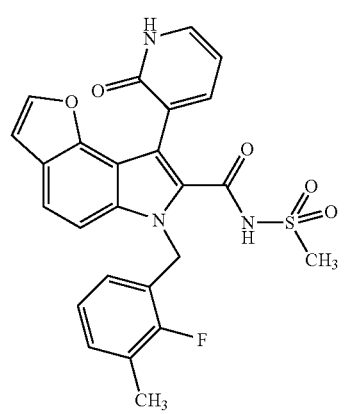
67
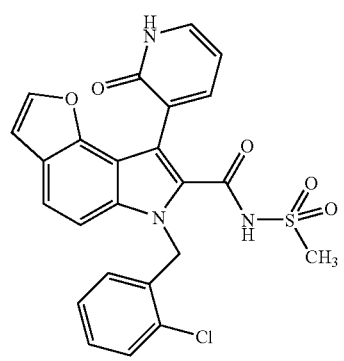
68
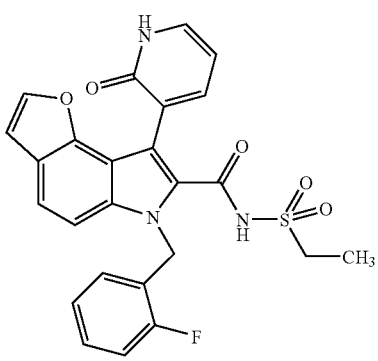

| | |
|---|---|
| 69 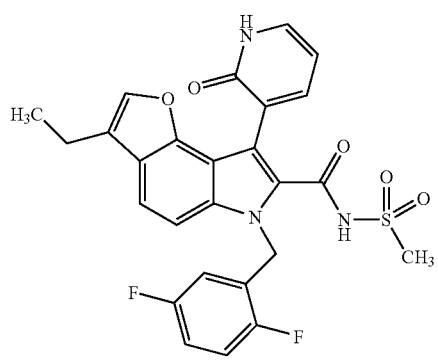 | 73 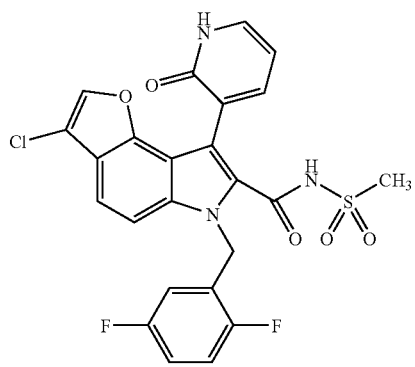 |
| 70 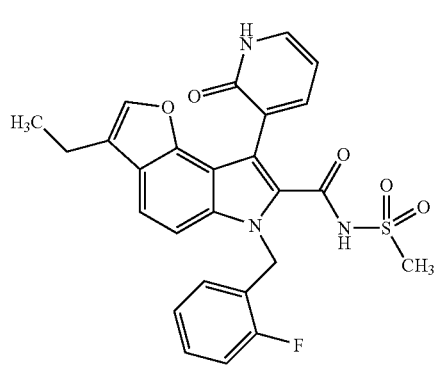 | 74 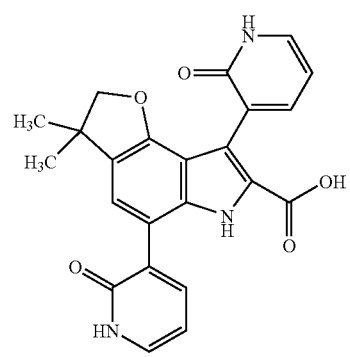 |
| 71 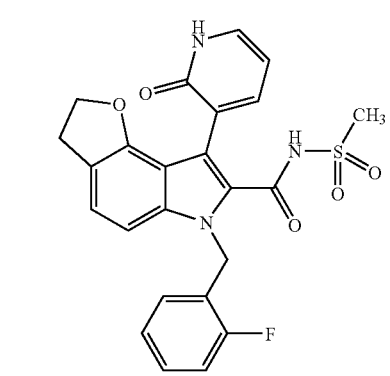 | 75 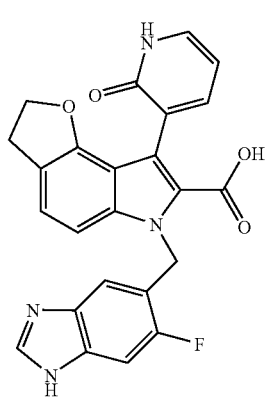 |
| 72 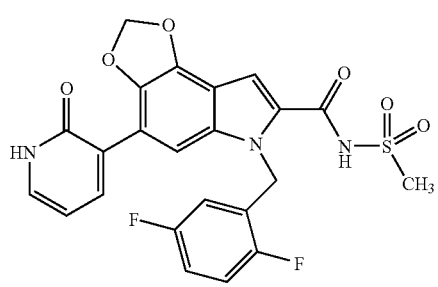 | 76 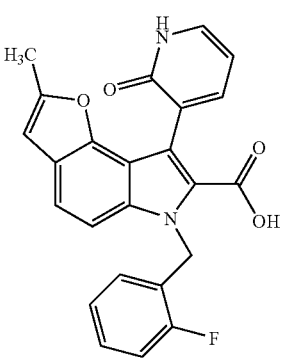 |

77 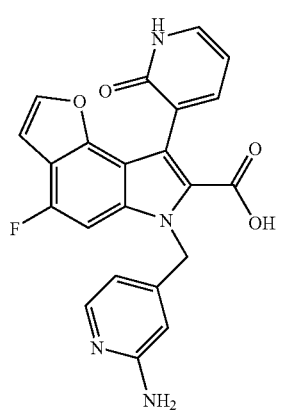
78 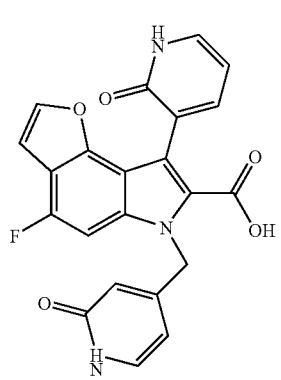
79 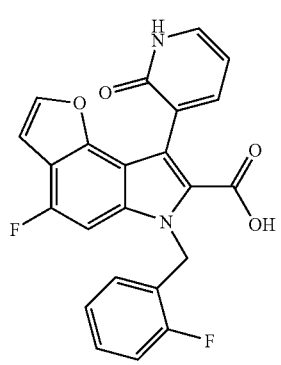
80 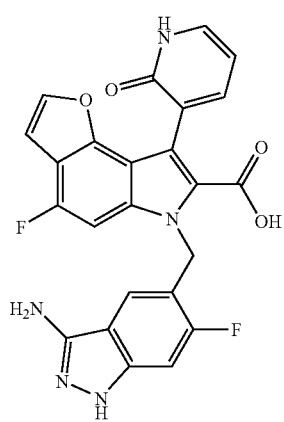
81 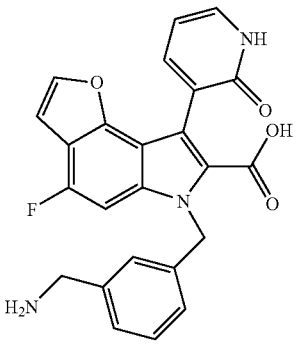
82 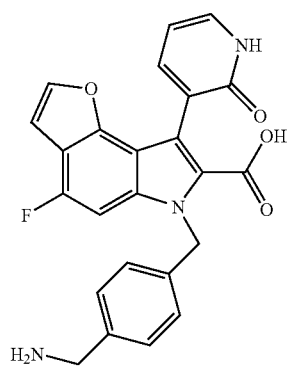
83 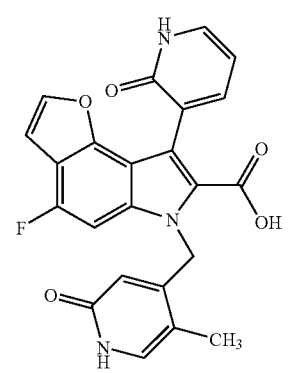
84 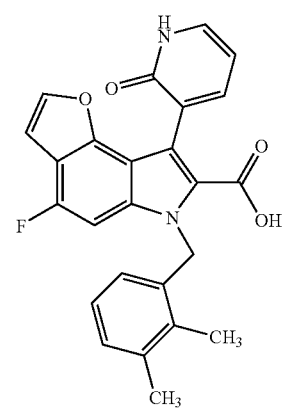

| 85 | 89 |
|---|---|
| 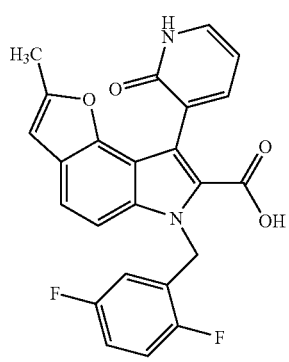 | 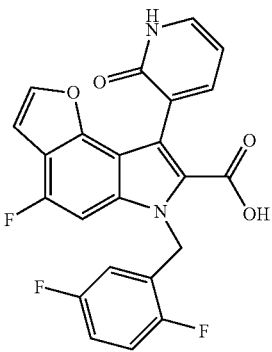 |
| 86 | 90 |
| 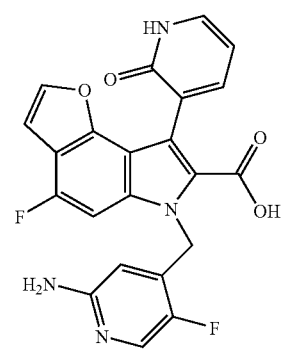 | 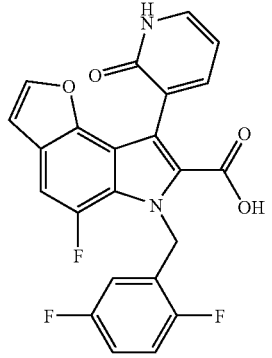 |
| 87 | 91 |
| 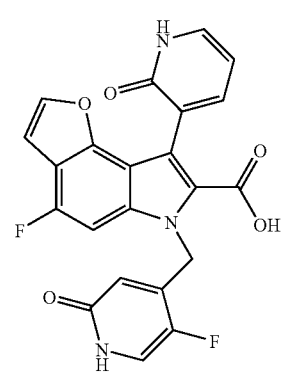 | 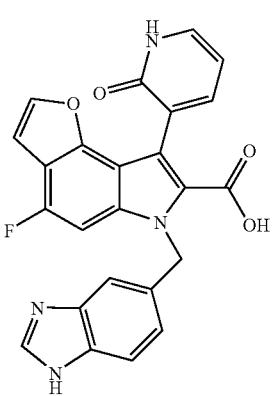 |
| 88 | 92 |
| 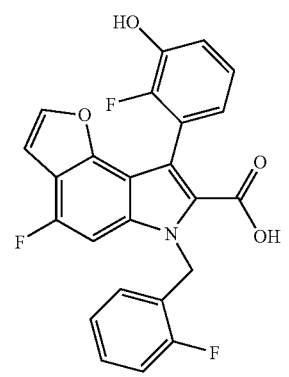 | 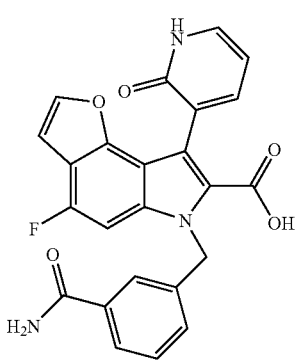 |

| 93 | 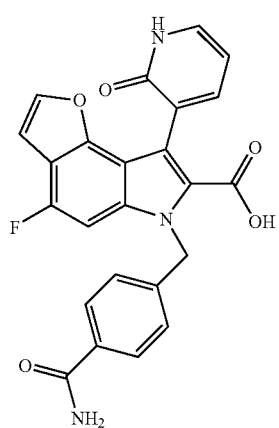 |
| --- | --- |
| 94 | 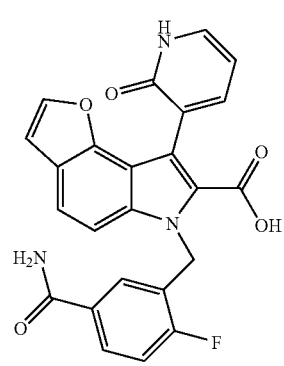 |
| 95 | 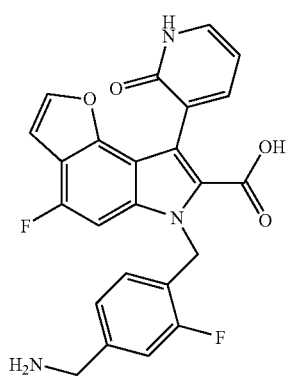 |
| 96 | 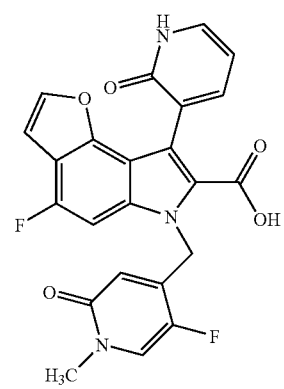 |
| 97 | 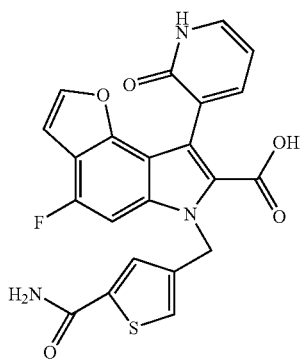 |
| --- | --- |
| 98 | 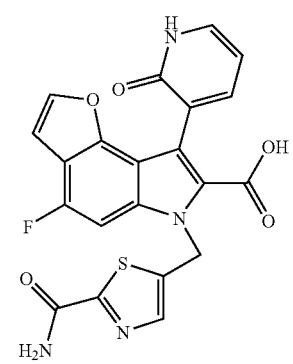 |
| 99 | 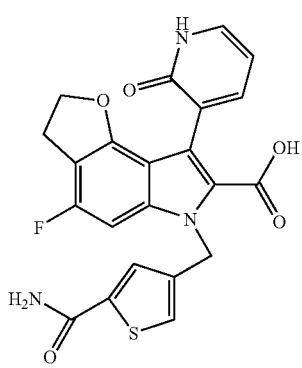 |
| 100 | 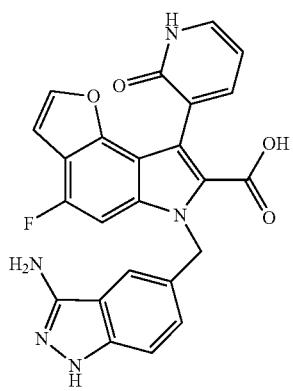 |

| 101 | 105 |
|---|---|
| 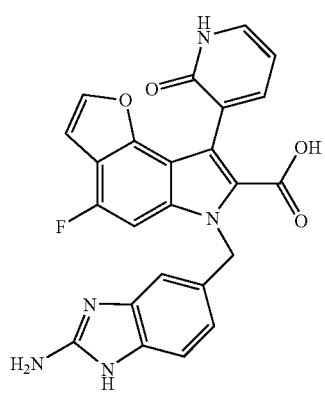 | 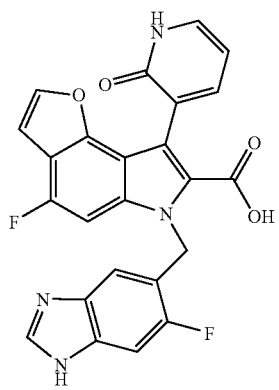 |
| 102 | 106 |
|---|---|
| 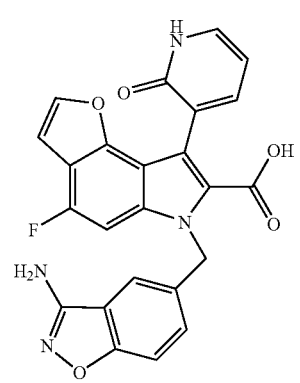 | 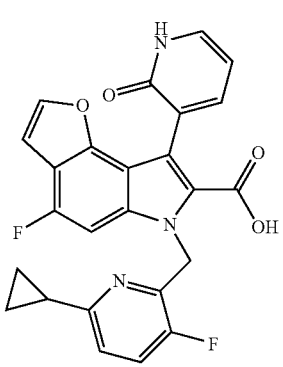 |
| 103 | 107 |
|---|---|
| 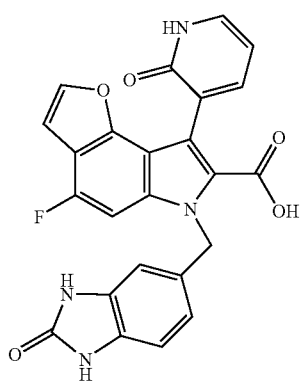 | 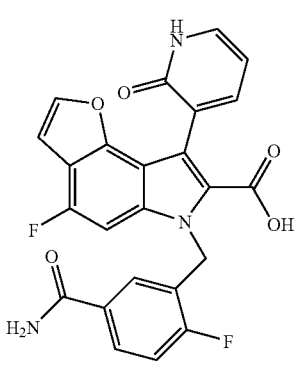 |
| 104 | 108 |
|---|---|
| 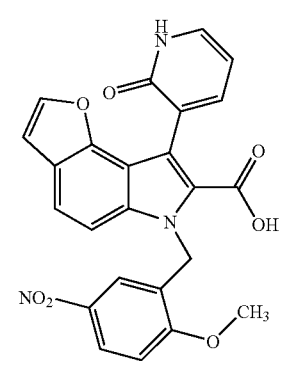 | 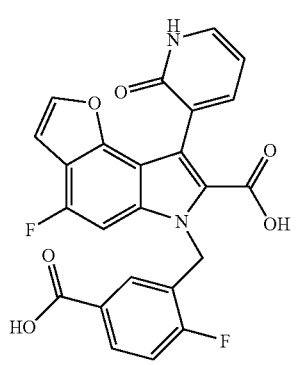 |

109
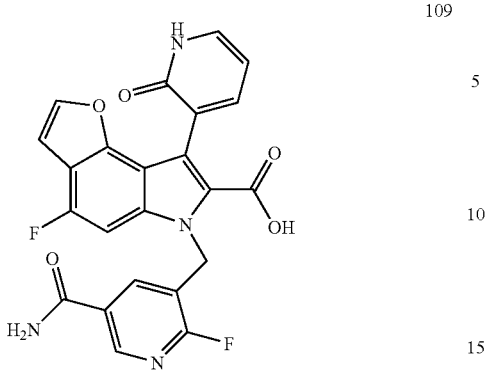
110
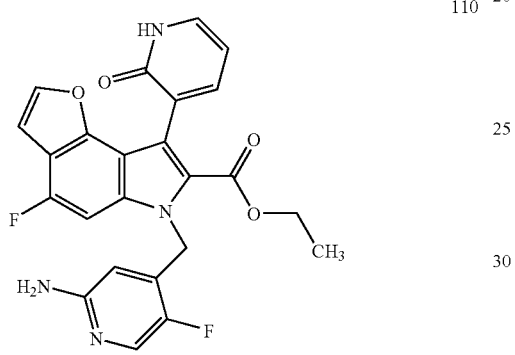
111
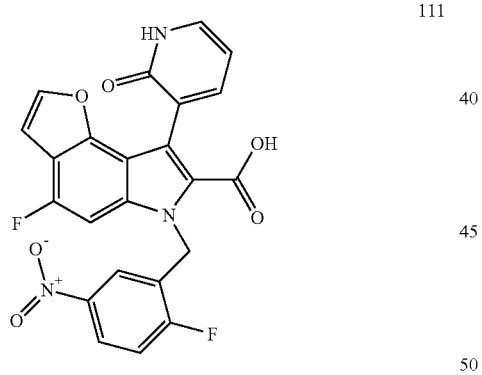
112
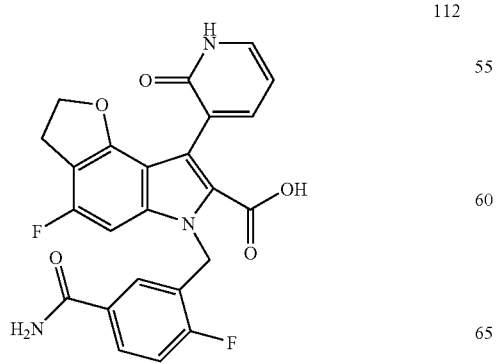
113
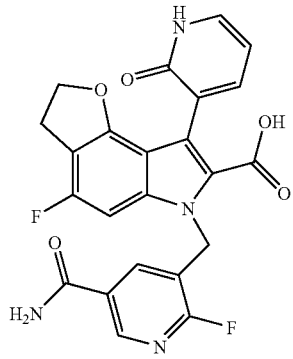
114
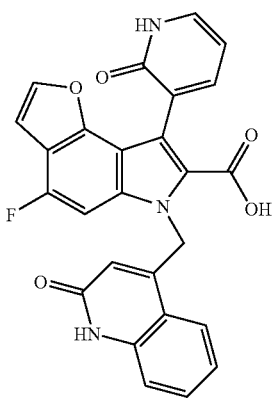
115
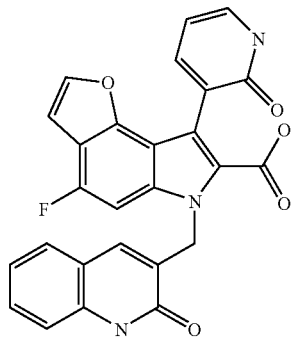
116
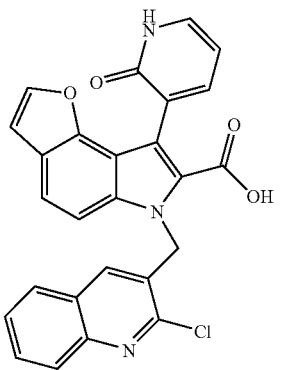

-continued
| | |
|---|---|
| 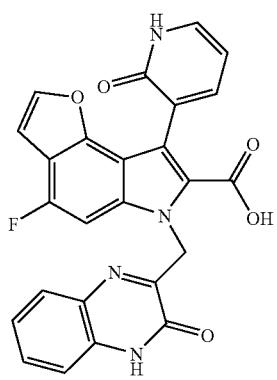 117 | 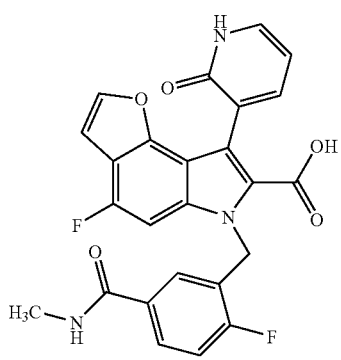 121 |
| 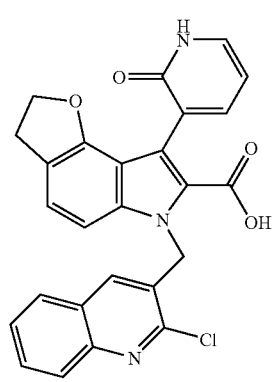 118 | 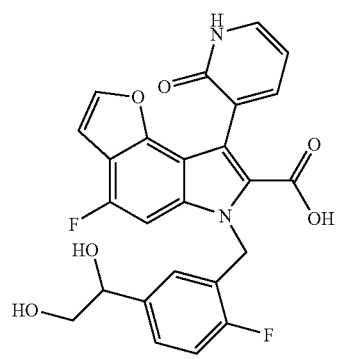 122 |
| 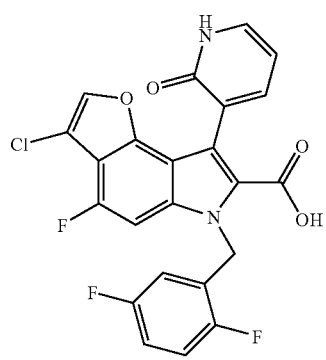 119 | 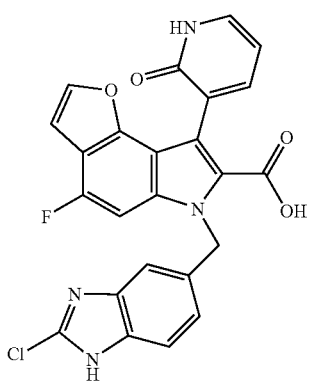 123 |
| 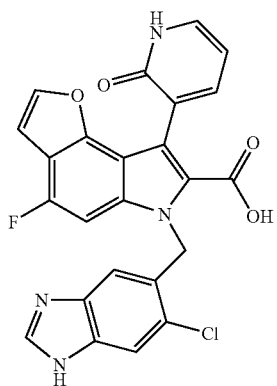 120 | 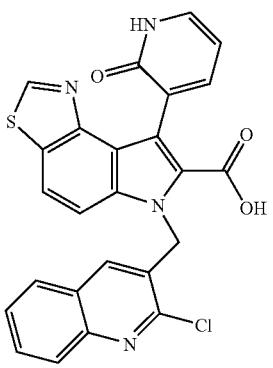 124 |

-continued
125
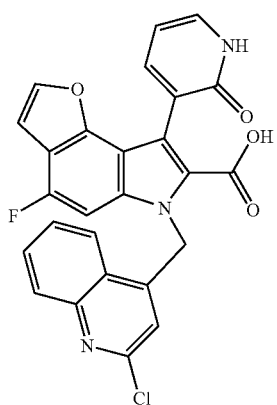
126
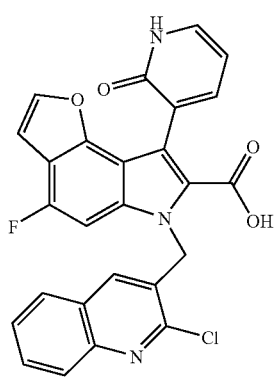
127
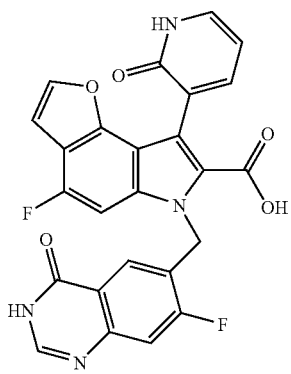
128
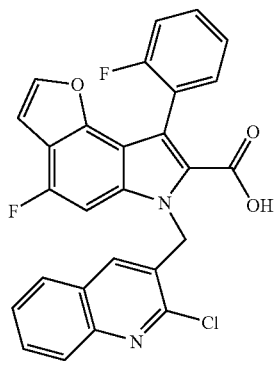
-continued
129
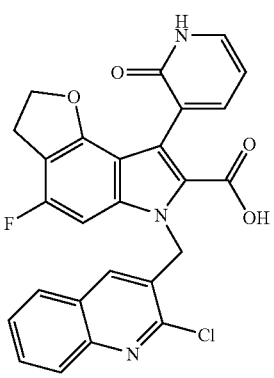
130
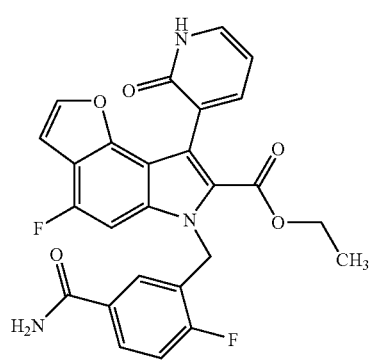
131
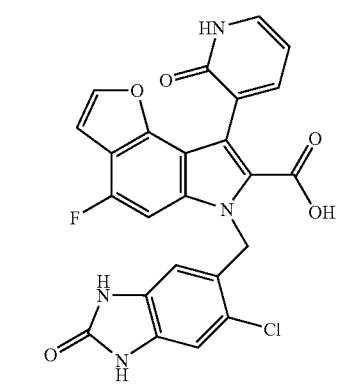
132
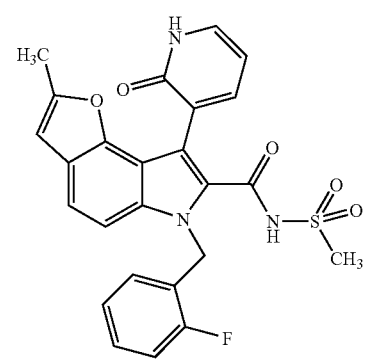

133
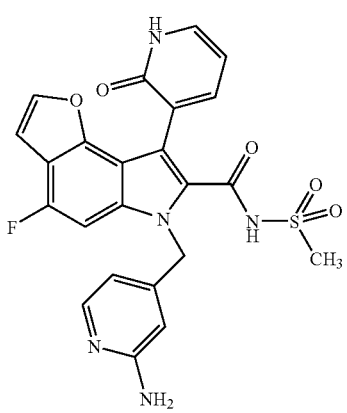
134
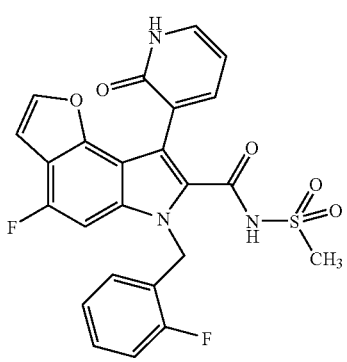
135
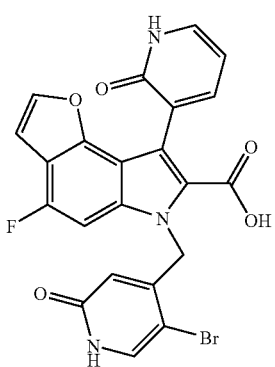
136
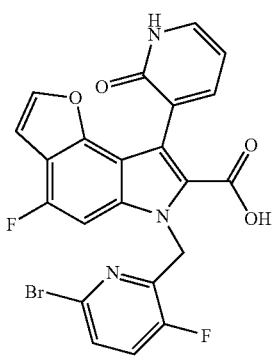
137
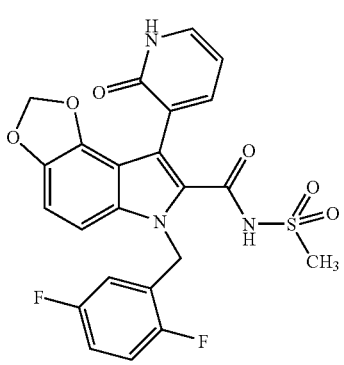
138
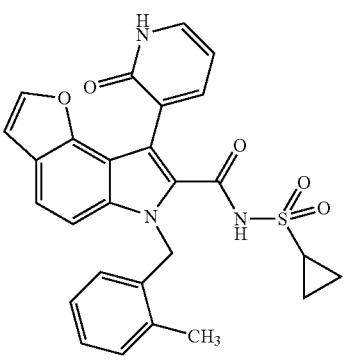
139
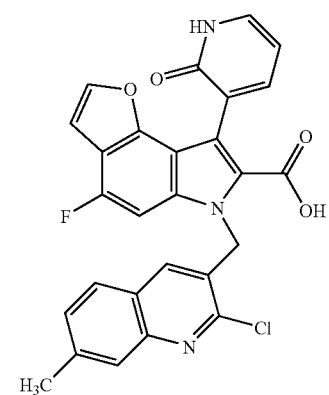
140
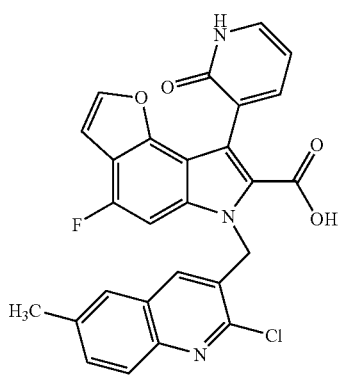

141 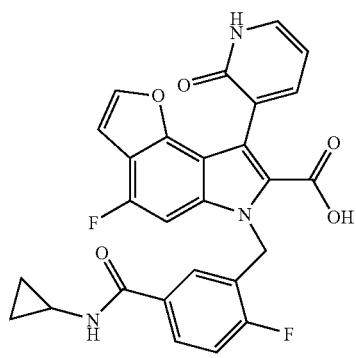
142 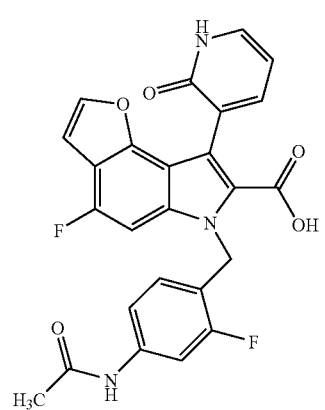
143 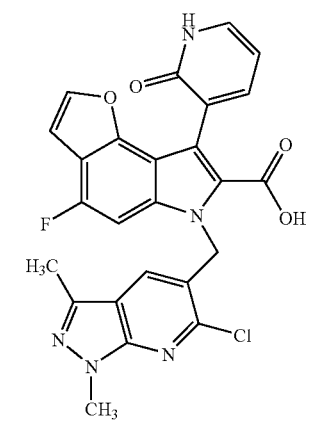
144 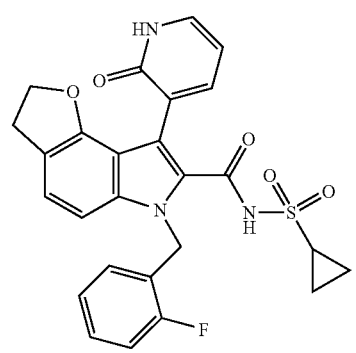
145 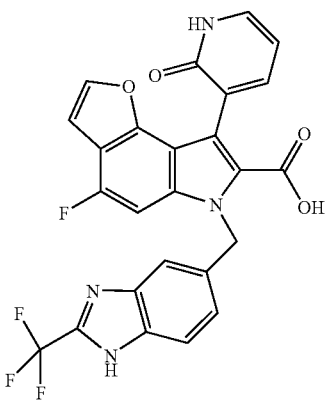
146 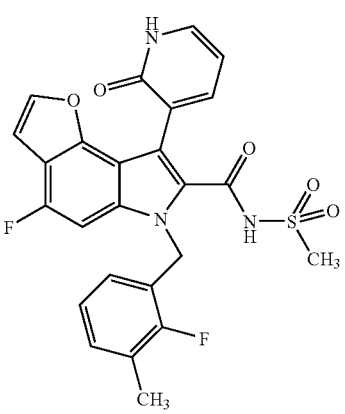
147 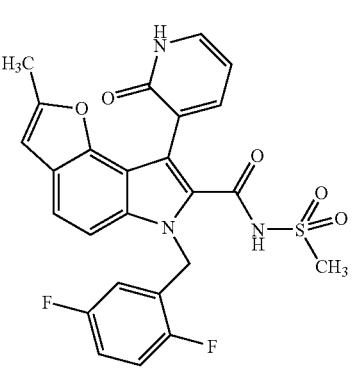
148 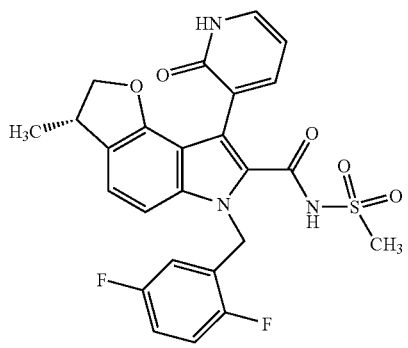

149 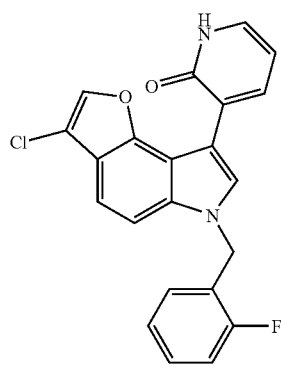
150 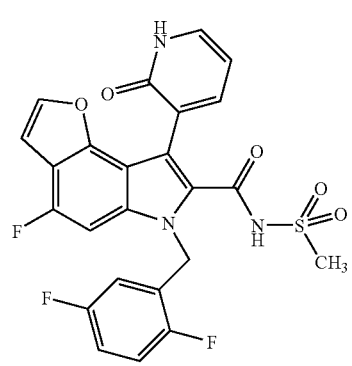
151 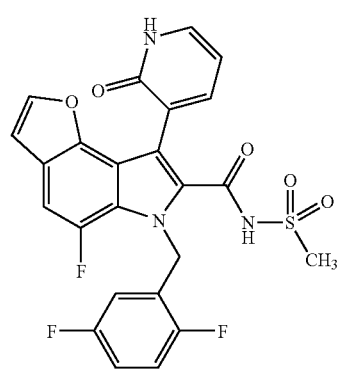
152 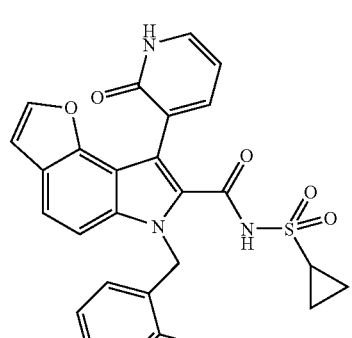
153 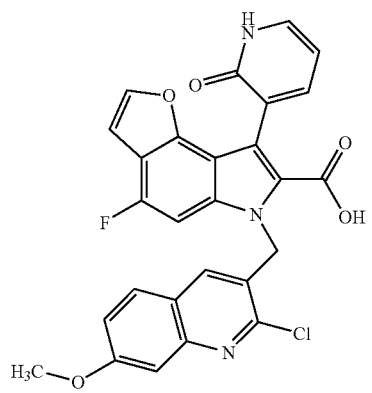
154 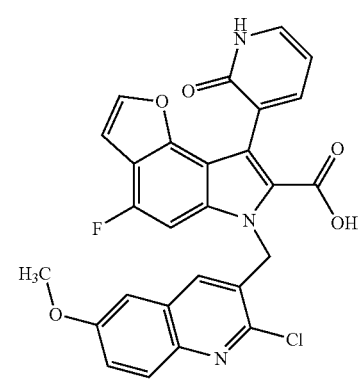
155 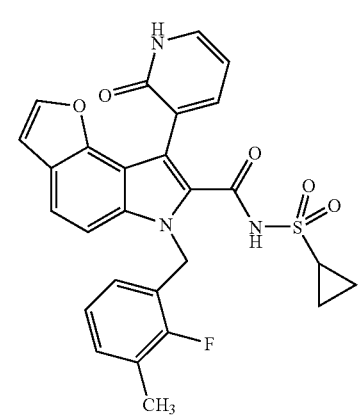
156 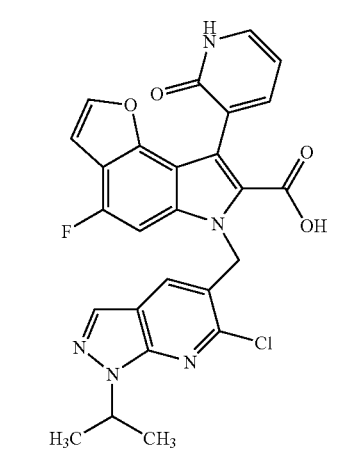

127
-continued
157
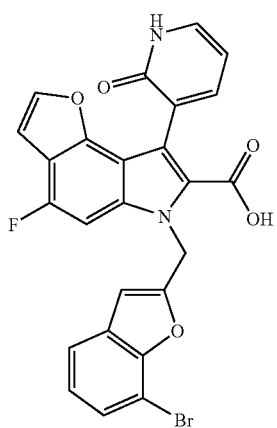
158
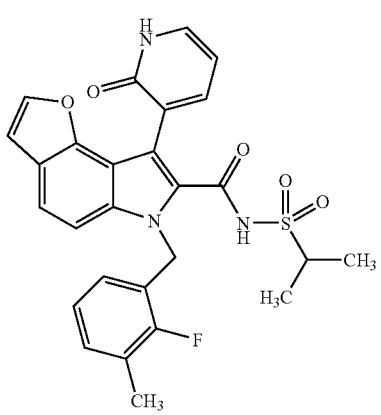
159
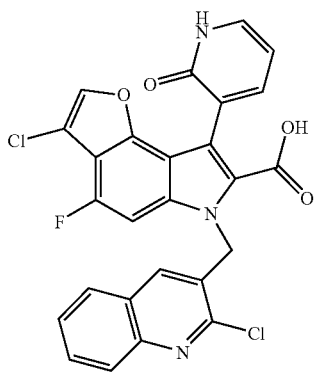
160
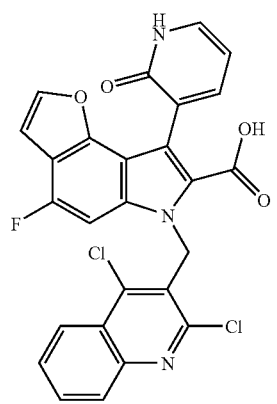
128
-continued
161
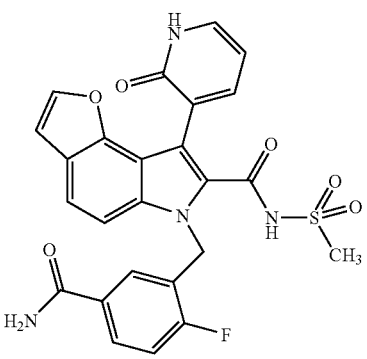
162
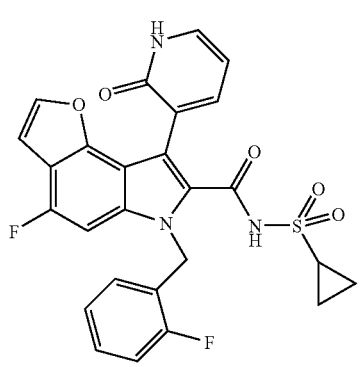
163
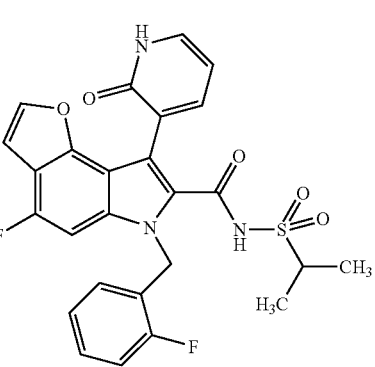
164
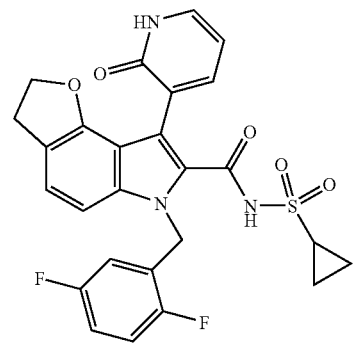

-continued
165
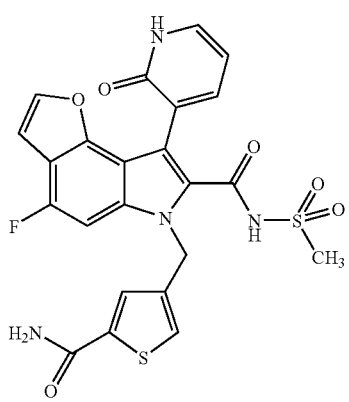
166
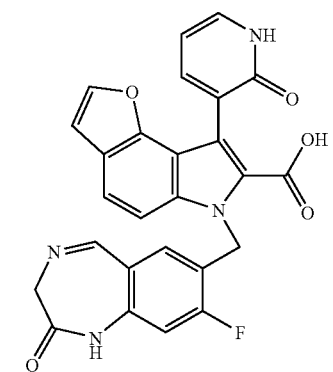
167
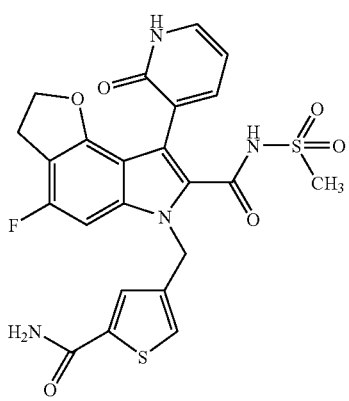
168
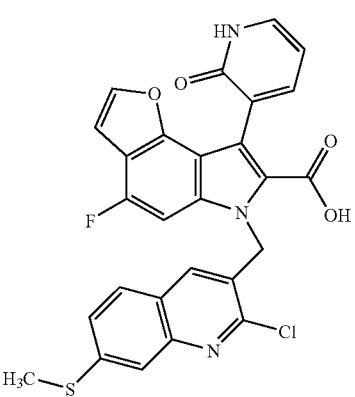
-continued
169
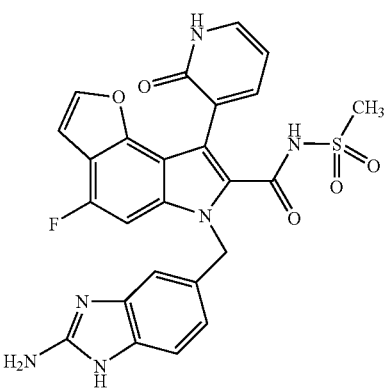
170
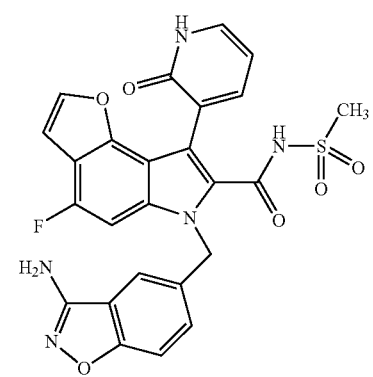
171
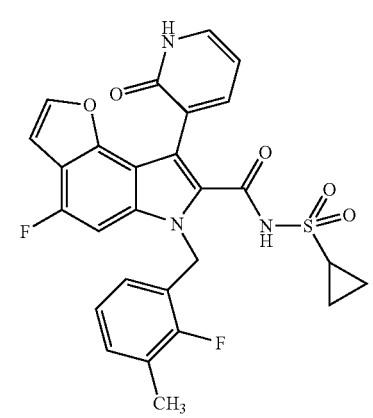
172
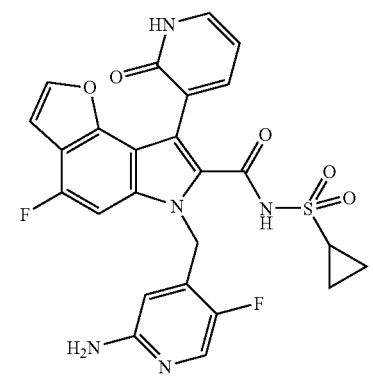

173 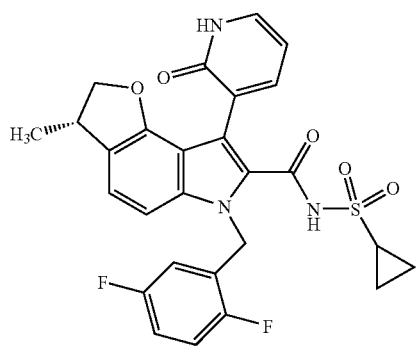
174 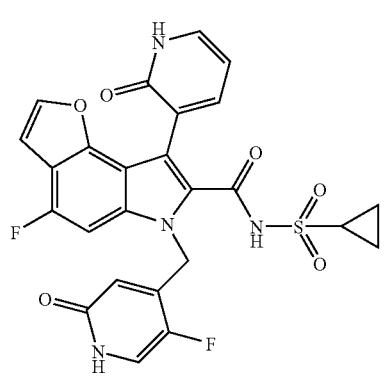
175 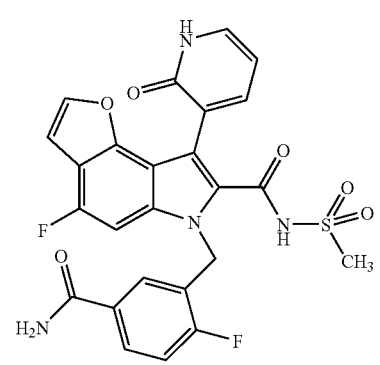
176 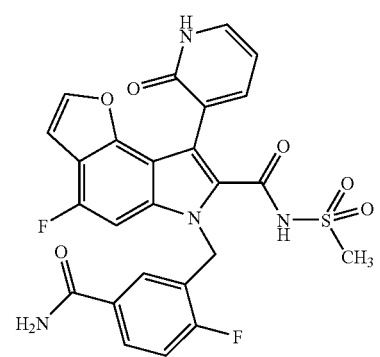
177 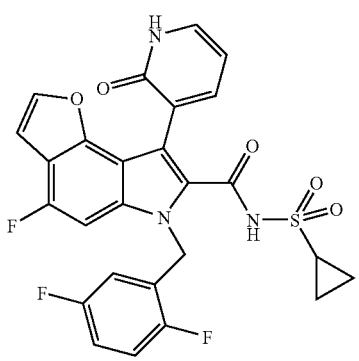
178 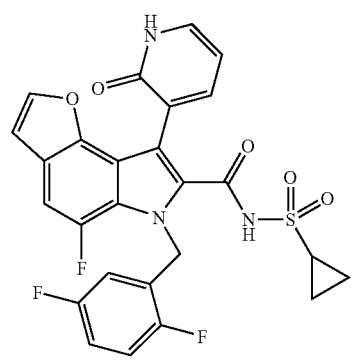
179 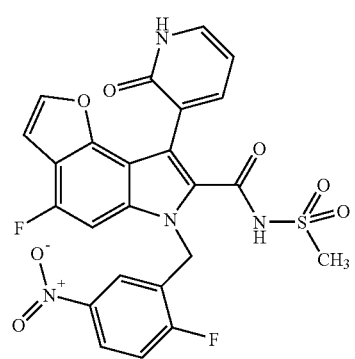
180 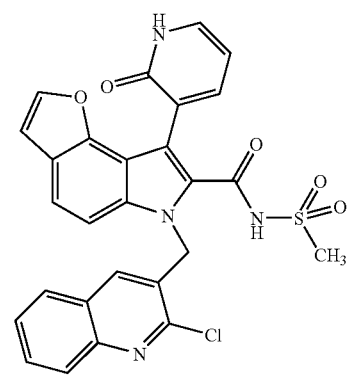

133
-continued
181
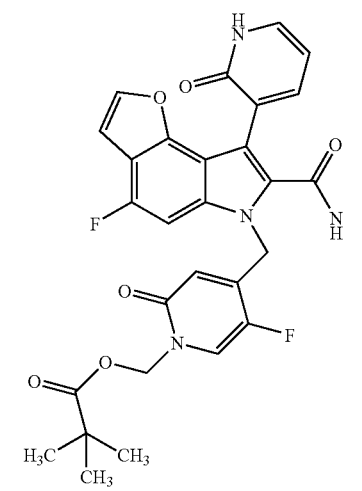
182
183
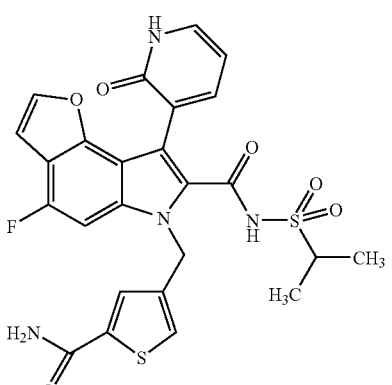
184
134
-continued
185
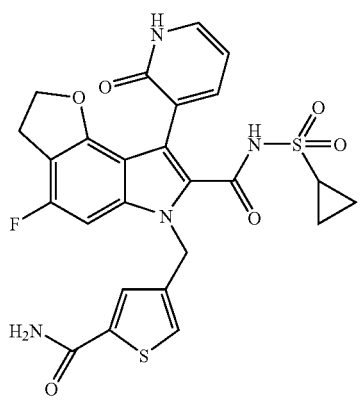
186
187
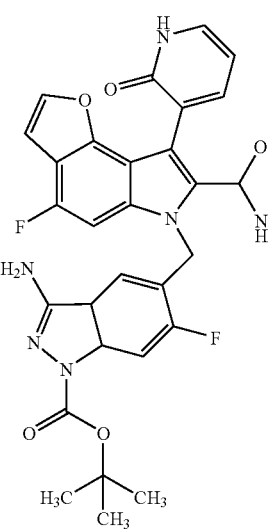

188 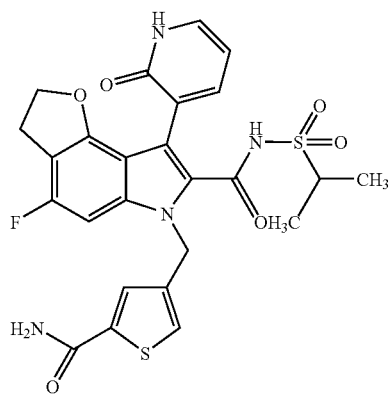
189 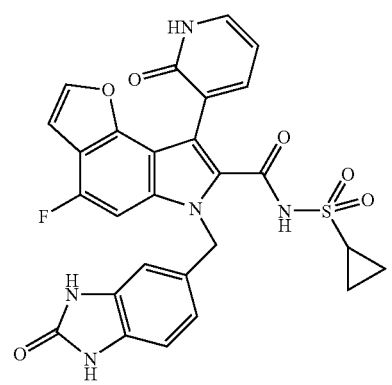
190 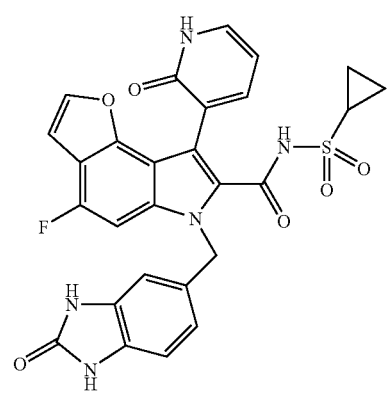
191 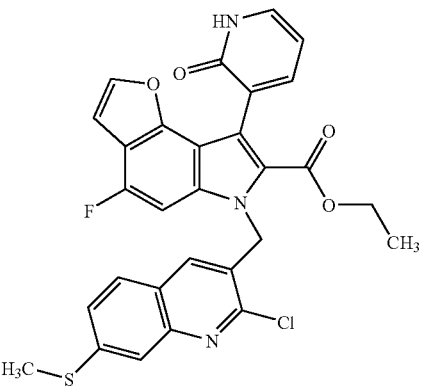
192 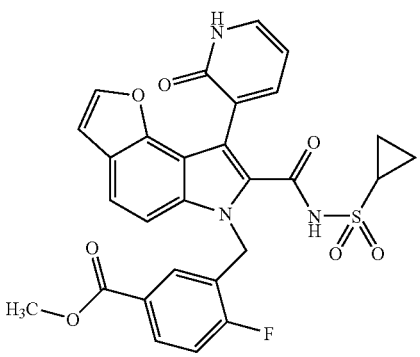
193 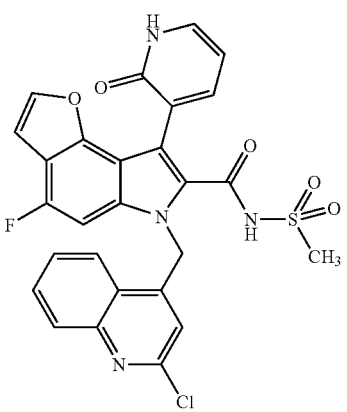
194 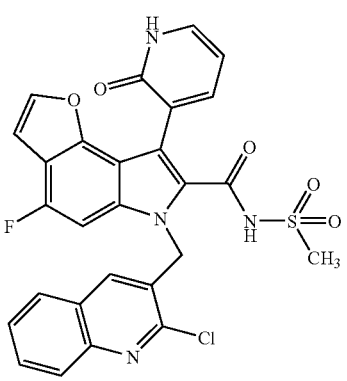
195 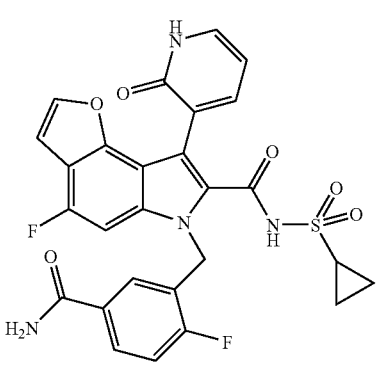

| 196 | 200 |
|---|---|
| 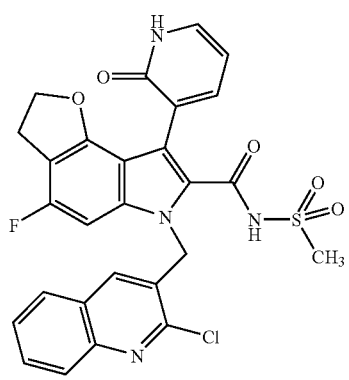 | 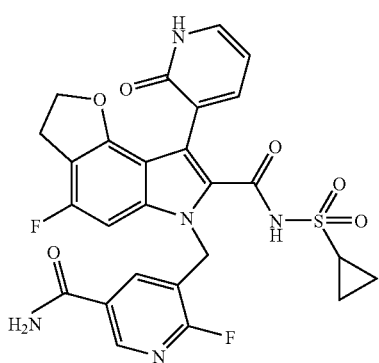 |
| 197 | 201 |
| 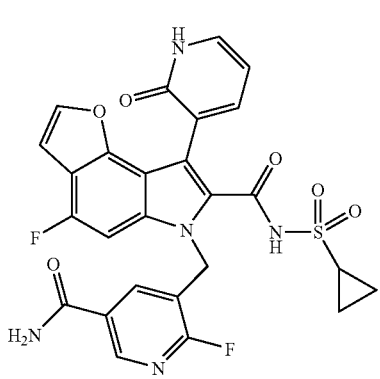 | 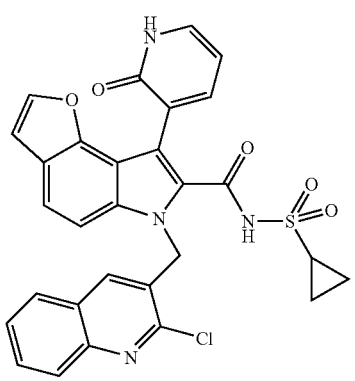 |
| 198 | 202 |
| 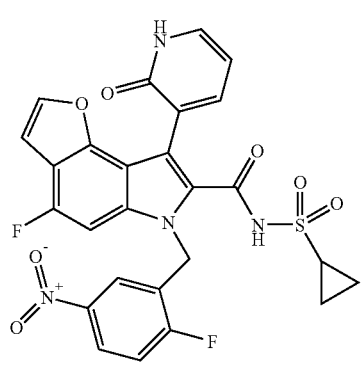 | 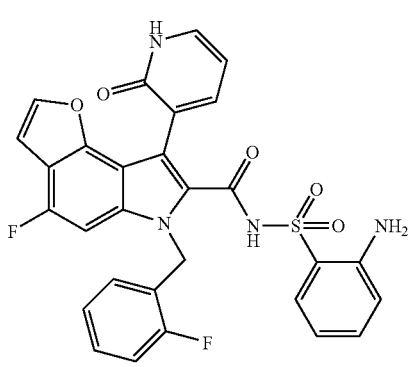 |
| 199 | 203 |
| 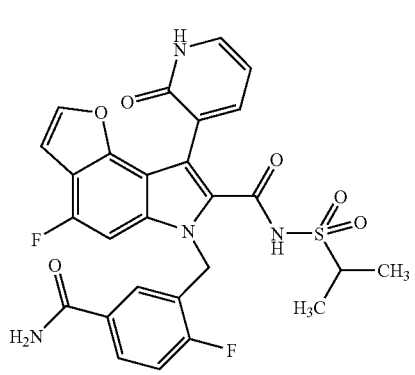 | 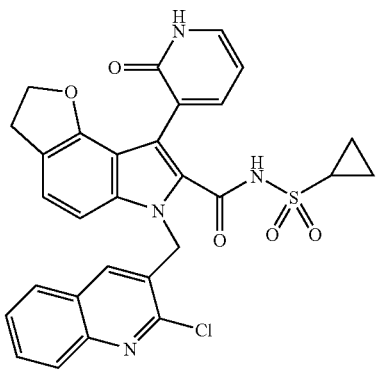 |

| | |
|---|---|
| 204 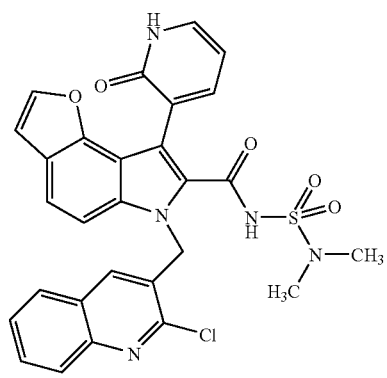 | 208 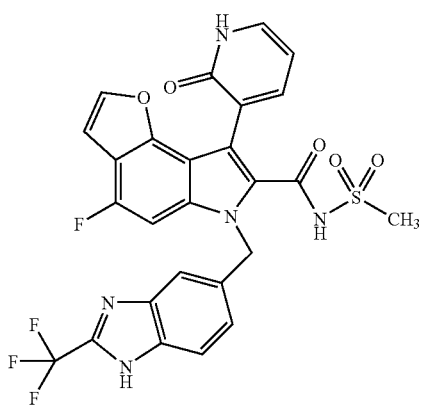 |
| 205 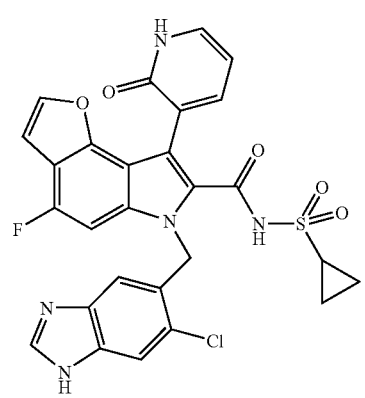 | 209 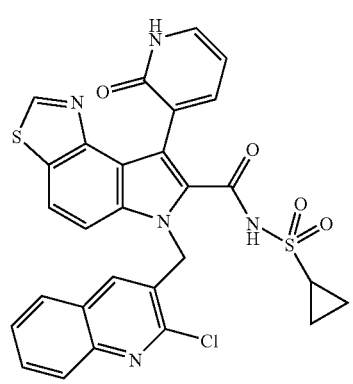 |
| 206 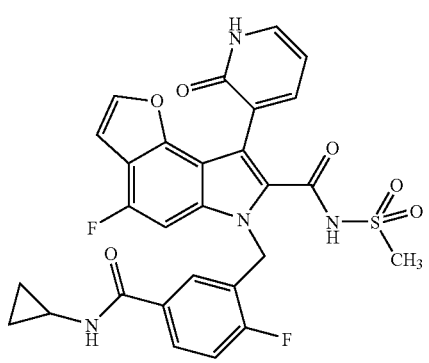 | 210 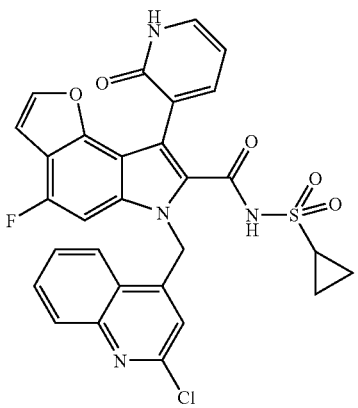 |
| 207 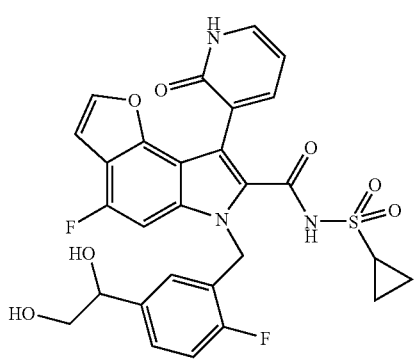 | 211 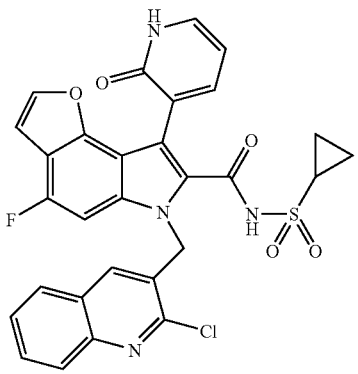 |

-continued
212 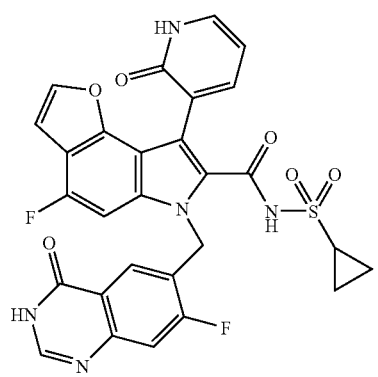
213 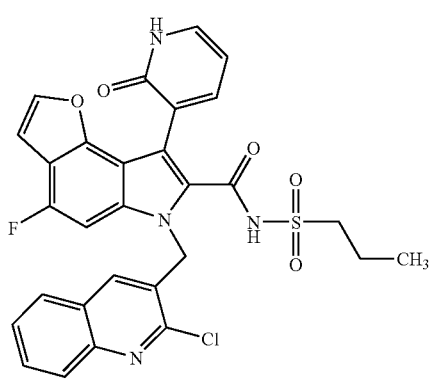
214 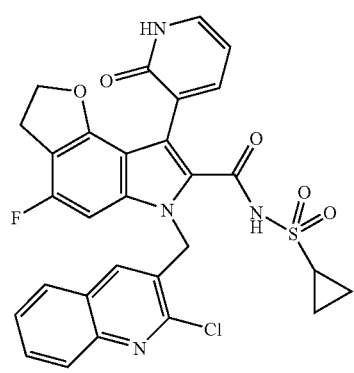
215 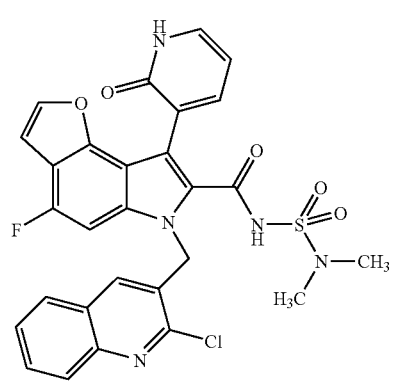
-continued
216 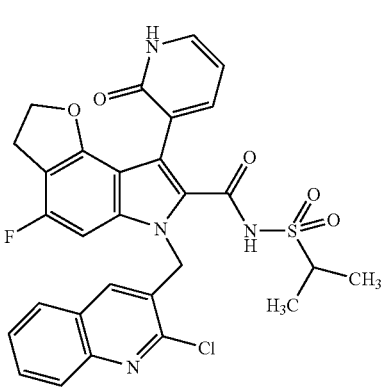
217 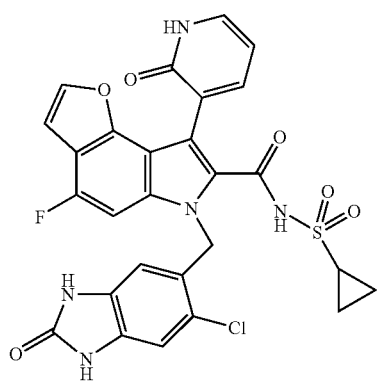
218 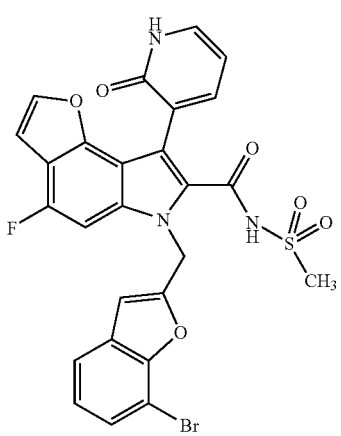
219 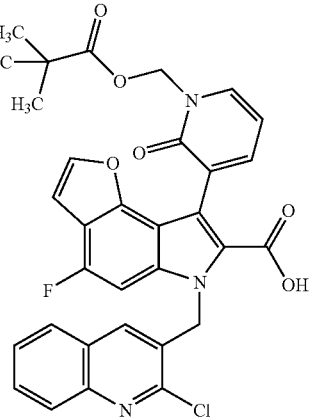

220 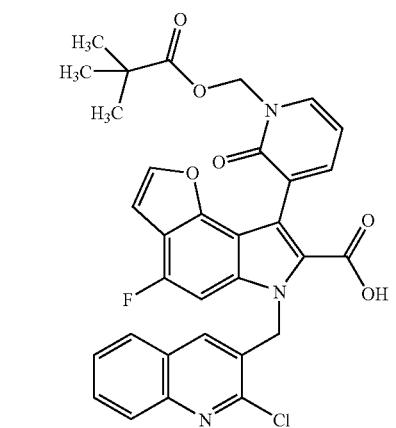
221 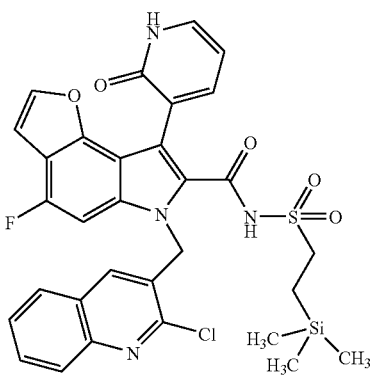
222
223
224 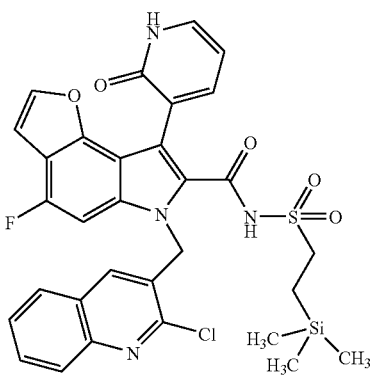
225 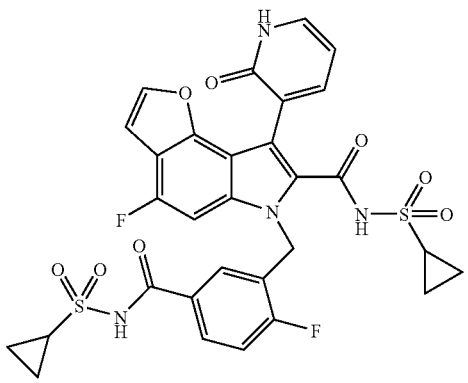
226 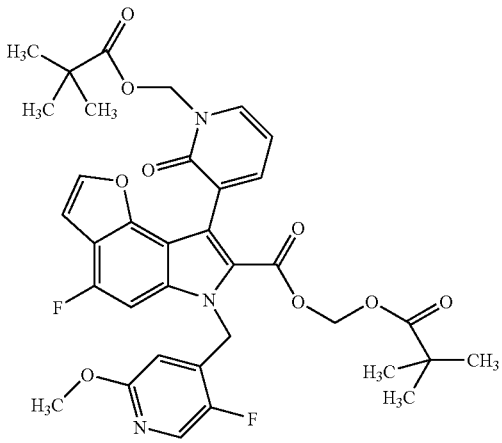
227 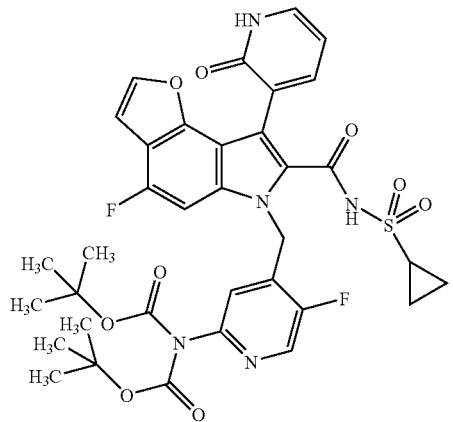

228
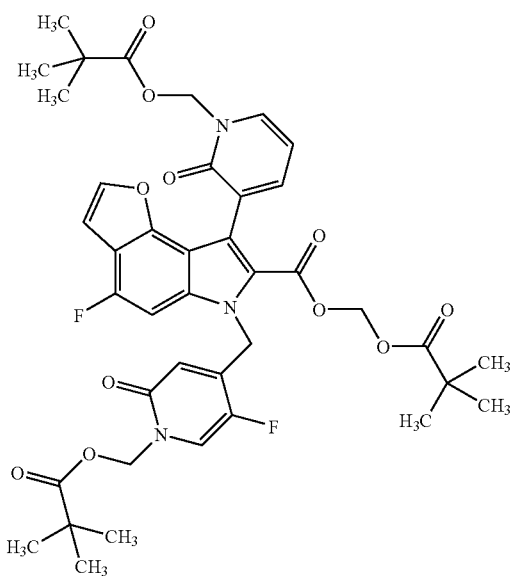
229
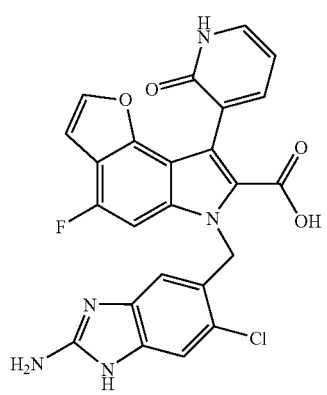
230
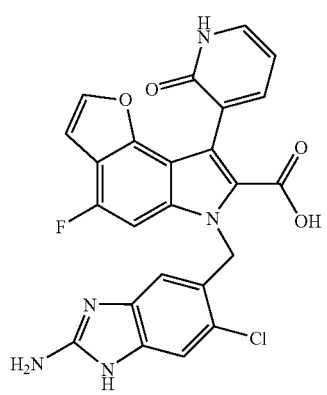
231
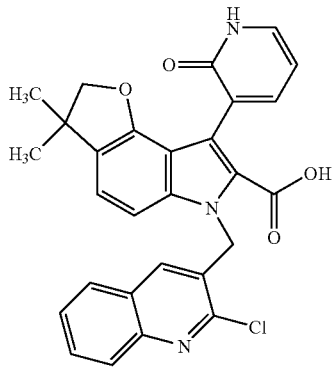
232
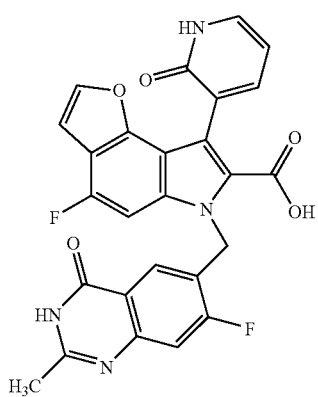
233
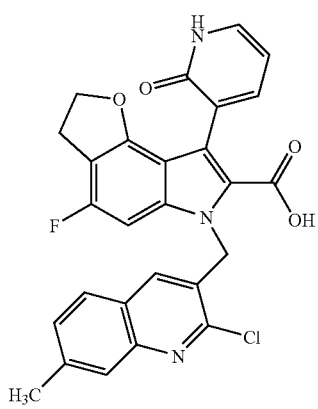
234
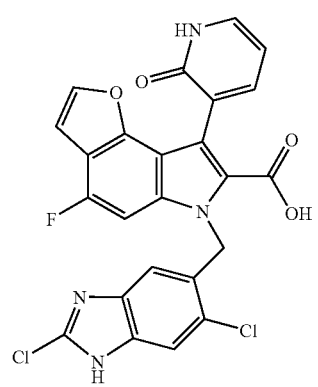

235 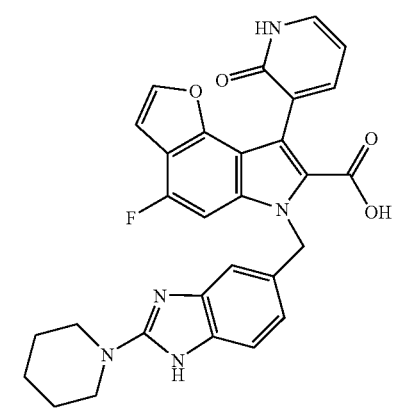
236 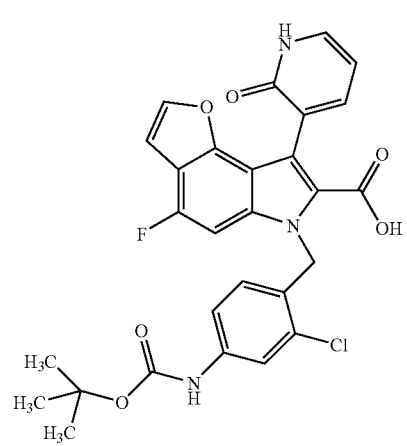
237 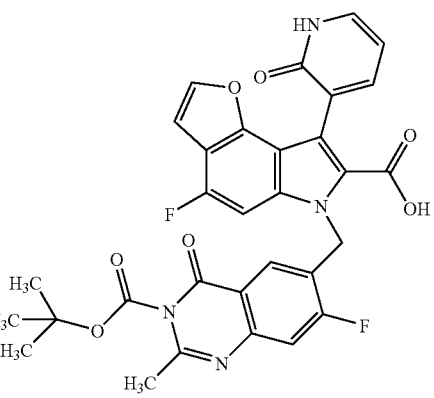
238 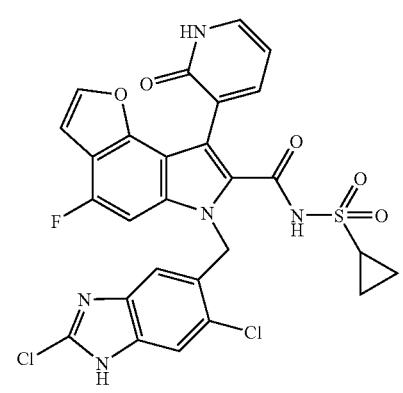
239 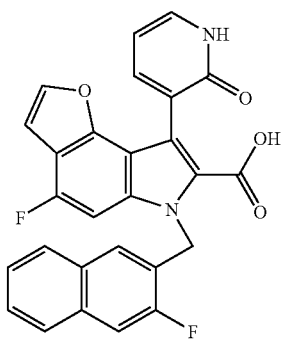
240 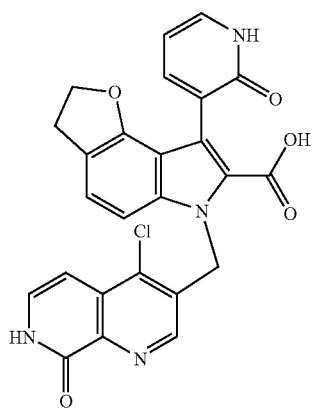
241 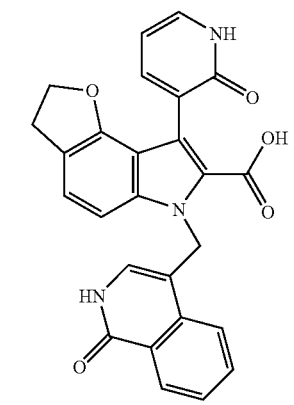
242 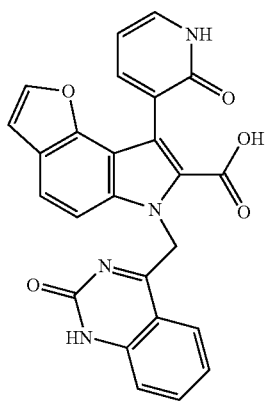

-continued
243
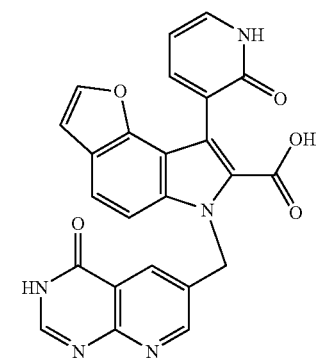
244
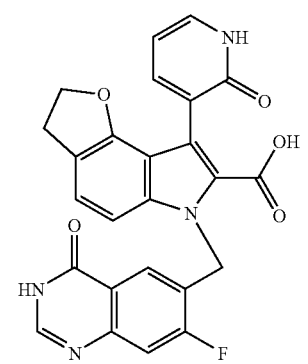
245
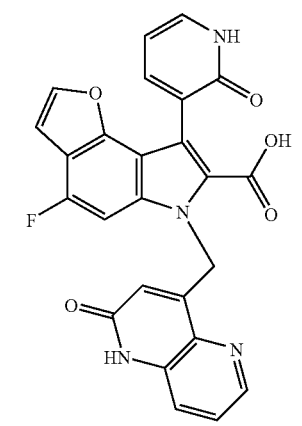
246
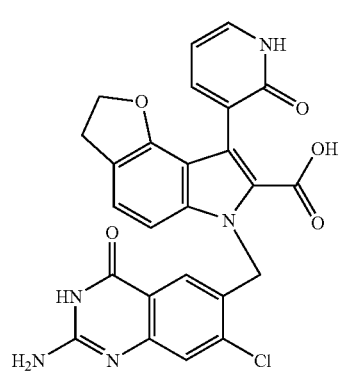
-continued
247
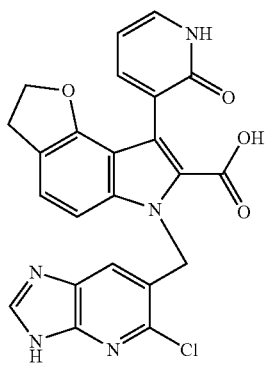
248
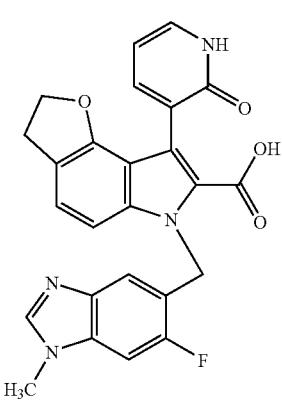
249
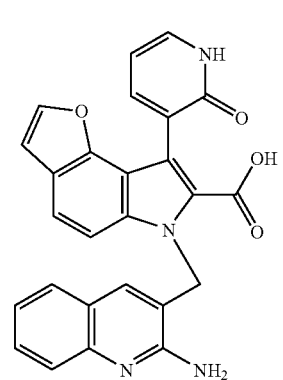
250
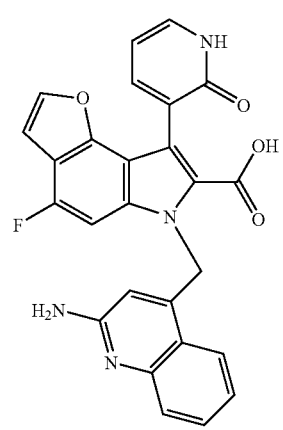

-continued
251
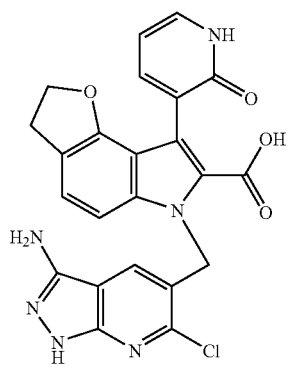
252
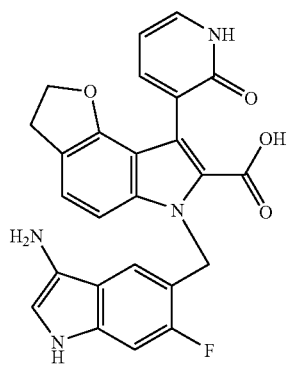
253
254
255
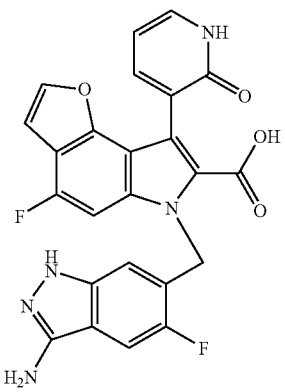
256
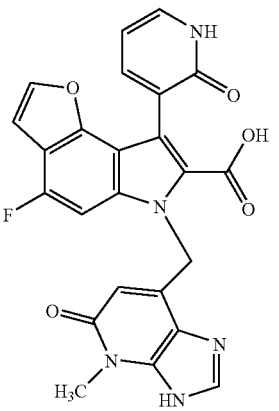
257
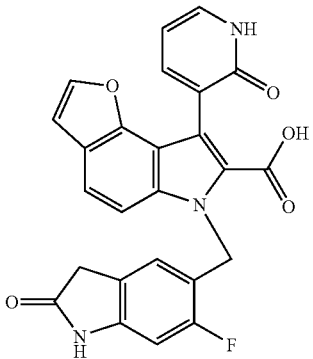
258
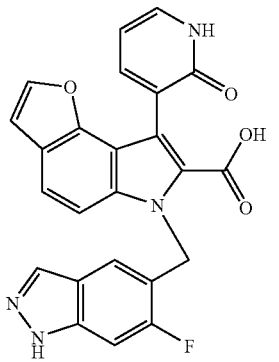

259
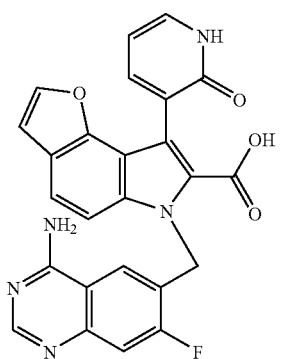
260
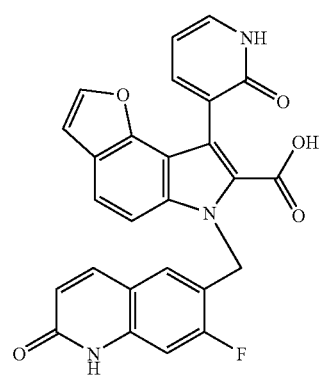
261
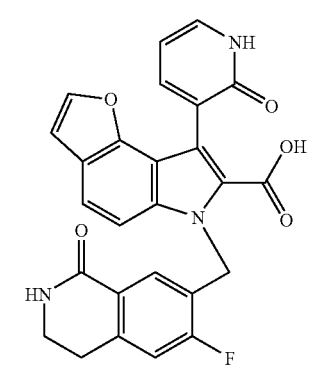
262
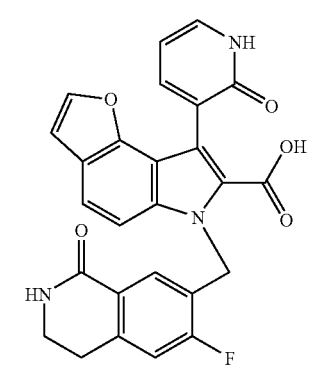
263
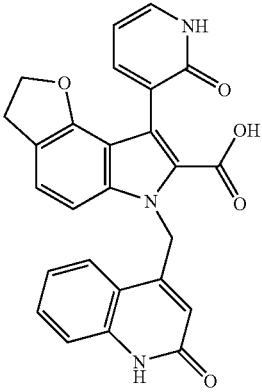
264
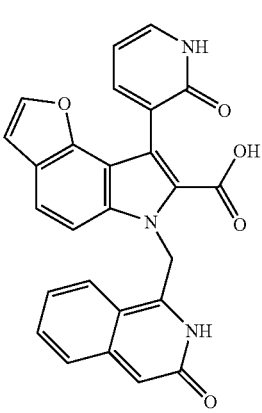
265
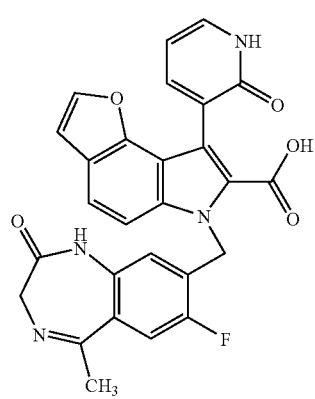
and pharmaceutically acceptable salts, solvates, esters and prodrugs thereof.
Methods for Making the Compounds of Formula (I)
Methods useful for making the Compounds of Formula (I) are set forth in the Examples below and generalized in Schemes 1-9.

Scheme 1 shows one method for preparing compounds of formula A4, which are useful intermediates for making of the Compounds of Formula (I).

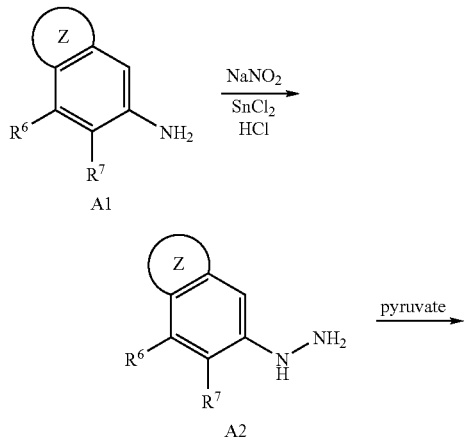

wherein $R^6$, $R^7$ and Z are defined above for the Compounds of Formula (I), and R is any carbonyl substituent that is encompassed by $R^2$, as defined above for the compounds of formula (I).

A 3,4-ring fused aniline compound of formula A1 can be converted to an indole compound of formula A4 using various indole syntheses that are well-known to those skilled in the art of organic synthesis, including but not limited to, a Fischer indole synthesis through intermediates of type A2 and A3, the method set forth in Nazare et al., *Angew. Chem.*, 116:4626-4629 (2004).

Scheme 2 shows methods useful for making compounds B4 and B6, which are useful intermediates for making of the Compounds of Formula (I).

wherein $R^6$, $R^7$ and Z are defined above for the Compounds of Formula (I), and R is any carbonyl substituent that is encompassed by $R^2$, as defined above for the compounds of formula (I).

A bicyclic benzene derivative of formula B1, wherein $R^7$ is H, can be di-brominated to give compound B2. Selective de-bromination provides the corresponding monobromo analog B3, which under palladium catalyzed cyclization conditions provides the desired intermediate B4, wherein $R^7$ is H. Alternatively a compound of formula B1, wherein $R^7$ is other than H, can be monobrominated to give compound B5. Compound B5 can then undergo under palladium catalyzed cyclization conditions provides the desired intermediate B6, wherein $R^7$ is other than H.

Scheme 3 shows an alternative method to make compounds of formula C5, which are analogous to compounds B4 and B6 and are also useful intermediates for making of the Compounds of Formula (I).

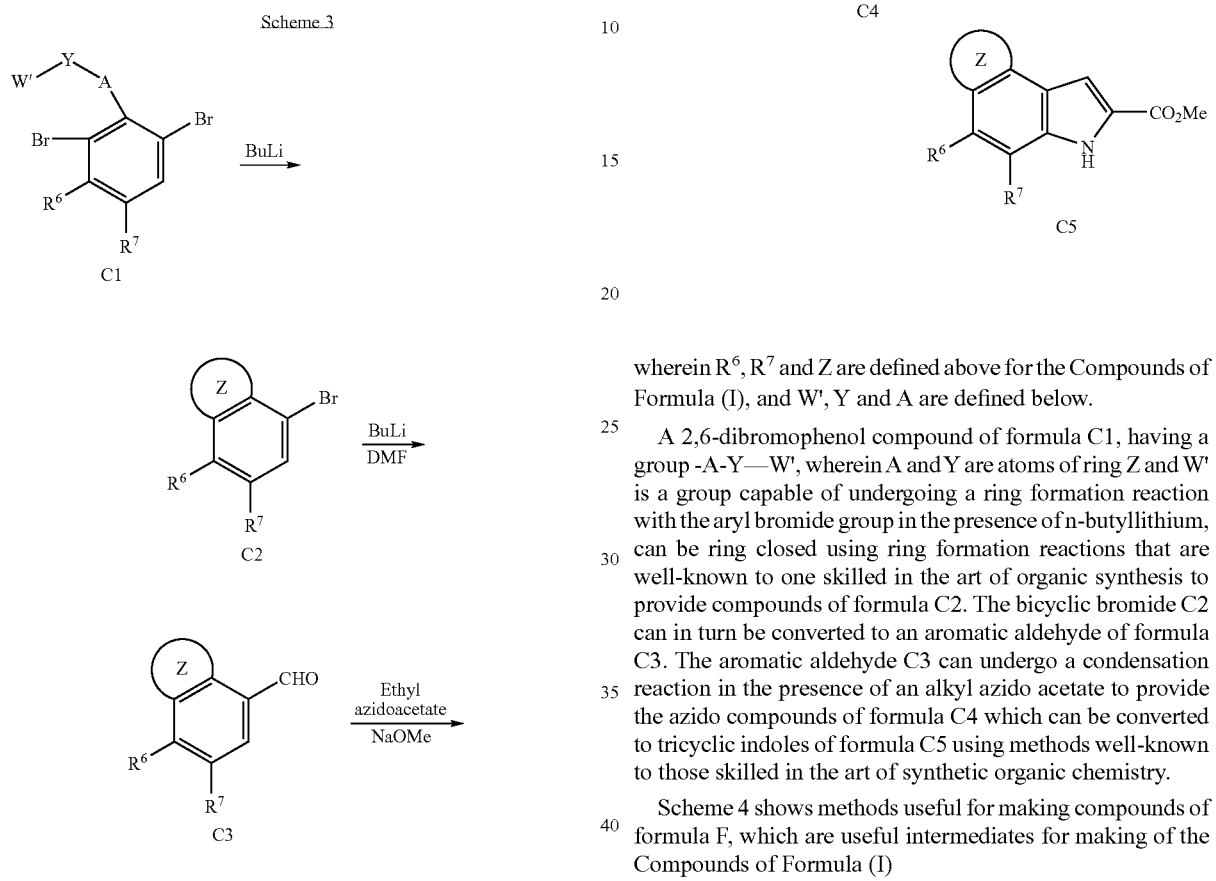
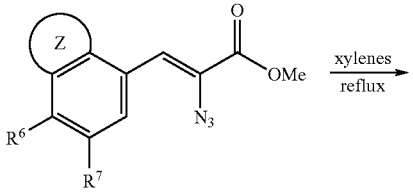
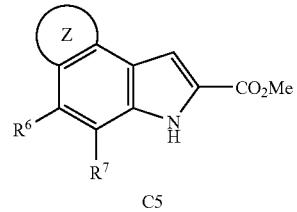

wherein $R^6$, $R^7$ and Z are defined above for the Compounds of Formula (I), and W', Y and A are defined below.

A 2,6-dibromophenol compound of formula C1, having a group -A-Y—W', wherein A and Y are atoms of ring Z and W' is a group capable of undergoing a ring formation reaction with the aryl bromide group in the presence of n-butyllithium, can be ring closed using ring formation reactions that are well-known to one skilled in the art of organic synthesis to provide compounds of formula C2. The bicyclic bromide C2 can in turn be converted to an aromatic aldehyde of formula C3. The aromatic aldehyde C3 can undergo a condensation reaction in the presence of an alkyl azido acetate to provide the azido compounds of formula C4 which can be converted to tricyclic indoles of formula C5 using methods well-known to those skilled in the art of synthetic organic chemistry.

Scheme 4 shows methods useful for making compounds of formula F, which are useful intermediates for making of the Compounds of Formula (I)

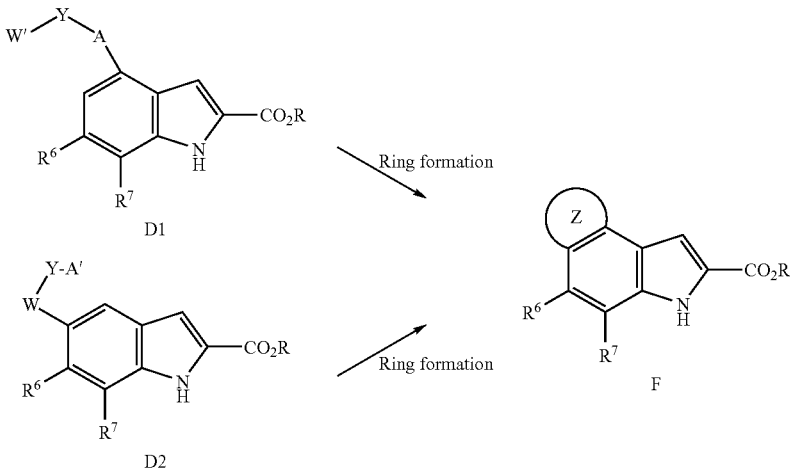

wherein $R^6$, $R^7$ and Z are defined above for the Compounds of Formula (I); R is any carbonyl substituent that is encompassed by $R^2$, as defined above for the compounds of formula (I); and W, W', Y, A and A' are defined below.

A compound of formula D1, having a group -A-Y—W', wherein A and Y are atoms of ring Z and W' is a group capable of undergoing a ring formation reaction with the benzene ring to which -A-Y—W' is attached, can undergo numerous ring formation reactions that are well-known to one skilled in the art of organic synthesis to form the tricyclic compounds of formula F. Similarly, a compound of formula D2, having a group —W—Y-A', wherein W and Y are atoms of ring Z and A' is a group capable of undergoing a ring formation reaction with the benzene ring to which —W—Y-A' is attached, can undergo numerous ring formation reactions that are well-known to one skilled in the art of organic synthesis to form the tricyclic compounds of formula F. Examples of ring formation methods include, but are not limited to, those disclosed in as *Comprehensive Heterocyclic Synthesis* (Pergamon Press); John et al., *J. Org. Chem.*, 47:2196 (1982); Maria et al., *Synthesis*, 1814 (2000); Martin et al., *J. Med. Chem.*, 44:1561 (2001); Morsy et al., *Pak. J. Sci. Ind. Res*, 43:208 (2000); Koguro et al., *Synthesis*, 911 (1998); Cowden et al., *Tet. Lett.*, 8661 (2000); Norton et al., *Synthesis*, 1406 (1994); Carl et al., *Tet. Lett.*, 2935 (1996); Gunter et al., *J. Org. Chem.*, 46:2824 (1981).

Scheme 5 illustrates methods by which intermediate compounds of formula F can be further derivatized to provide the Compounds of Formula (I), wherein $R^2$ is —C(O)OH.

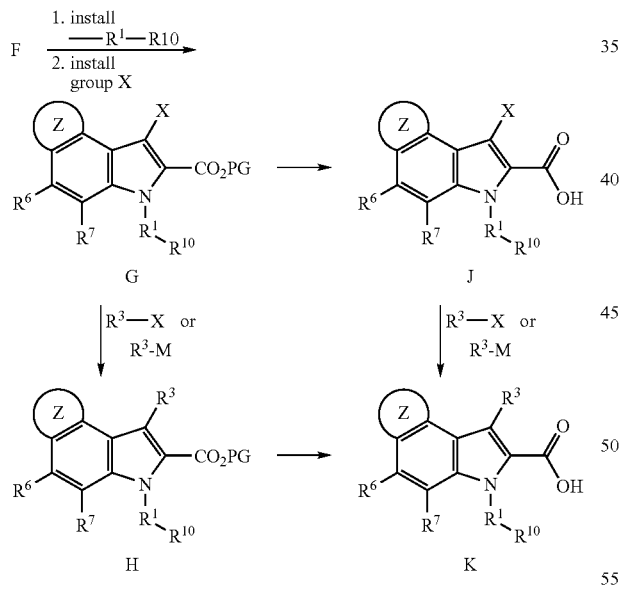

Scheme 5 wherein $R^1$, $R^3$, $R^6$, $R^7$, $R^{10}$ and Z are defined above for the Compounds of Formula (I); PG is a carboxy protecting group; and X is halo, —O-triflate, —B(OH)$_2$, —Sn(alkyl)$_3$, —MgBr, —MgCl, —ZnBr, —ZnCl, or any metal which can participate in an organometallic cross-coupling reaction.

An intermediate compound of formula F can be converted to a 3-substituted indole of formula G using methods well-known to one skilled in the art of organic synthesis. A compound of formula G, wherein X is halo or —O-triflate can then be coupled with an appropriate compound of formula $R^3$—M (wherein M is —B(OH)$_2$, —Sn(alkyl)$_3$, —MgBr, —MgCl, —ZnBr, —ZnCl, or any metal which can participate in an organometallic cross-coupling reaction) using an organometallic cross-coupling method. Alternatively, a compound of formula G, wherein X is —B(OH)$_2$, —Sn(alkyl)$_3$, —MgBr, —MgCl, —ZnBr, —ZnCl, or any metal which can participate in an organometallic cross-coupling reaction, can then be coupled with an appropriate compound of formula $R^3$—M (wherein M is halo or —O-triflate) using an organometallic cross-coupling method. Suitable cross-coupling methods include, but are not limited to, a Stille coupling (see Choshi et al., *J. Org. Chem.*, 62:2535-2543 (1997), and Scott et al., *J. Am. Chem. Soc.*, 106:4630 (1984)), a Suzuki coupling (see Miyaura et al., *Chem. Rev.*, 95:2457 (1995)), a Negishi coupling (see Zhou et al., *J. Am. Chem. Soc.*, 127:12537-12530 (2003)), and a Kumada coupling (see Kumada, *Pure Appl. Chem.*, 52:669 (1980) and Fu et al., *Angew. Chem.* 114:4363 (2002)) to provide a compound of formula H. The carboxy protecting group, PG, can then be removed from the compound of formula H and the resulting carboxylic acid can be derivatized using the methods described below in Schemes 6-8 in order to make the appropriate $R^2$ groups and make the compounds of formula K, which correspond to the compounds formula (I), wherein $R^2$ is —C(O)OH. Alternatively, a compound of formula F can first be deprotected and the $R^2$ group attached using the above methods to provide a compound of formula J. A compound of formula J can then be cross-coupled with a compound of $R^3$—X or $R^3$—M as described above to provide make the compounds of formula K.

Scheme 6 shows a method useful for making the Compounds of Formula (I), wherein $R^2$ is —C(O)N($R^9$)SO$_2R^{11}$.

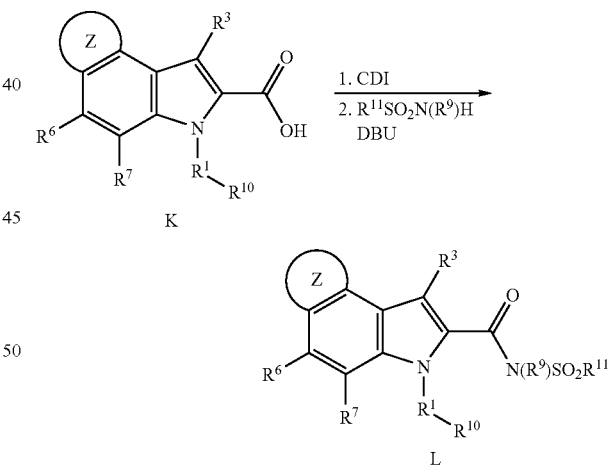

Scheme 6 wherein $R^1$, $R^3$, $R^6$, $R^7$, $R^9$, $R^{10}$, $R^{11}$ and Z are as defined for the Compounds of Formula (I).

A 2-carboxy indole compound of formula K can be coupled with a compound of formula $R^{11}SO_2NH_2$ in the presence of carbonyldiimidazole (CDI) and 1,8-diazabicyclo [5.4.0]undec-7-ene (DBU) to provide the compounds of formula L, which correspond to the Compounds of Formula (I) wherein $R^2$ is —C(O)NHSO$_2R^{11}$.

Scheme 7 shows a method useful for making the Compounds of Formula (I), wherein $R^2$ is —C(O)N($R^9$)$_2$.

Scheme 7

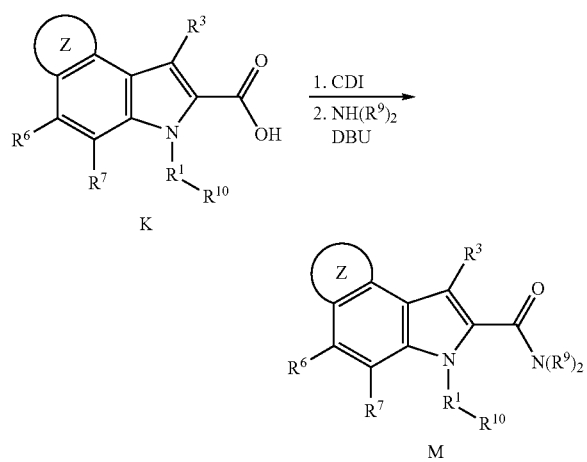

wherein $R^1$, $R^3$, $R^6$, $R^7$, $R^9$, $R^{10}$ and Z are as defined for the Compounds of Formula (I).

A 2-carboxy indole compound of formula K can be coupled with an amine of formula $NH(R^9)_2$ in the presence of carbonyldiimidazole (CDI) and 1,8-diazabicyclo[5.4.0]undec-7-ene (DBU) to provide the compounds of formula M, which correspond to the Compounds of Formula (I) wherein $R^2$ is —$C(O)N(R^9)_2$.

Scheme 8 shows a method useful for making the Compounds of Formula (I), wherein $R^2$ is:

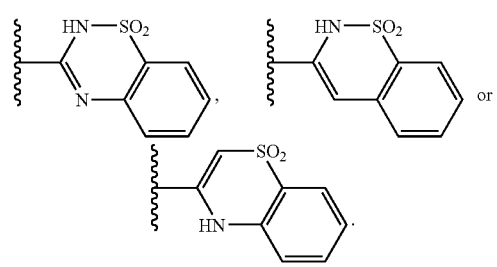

Scheme 8

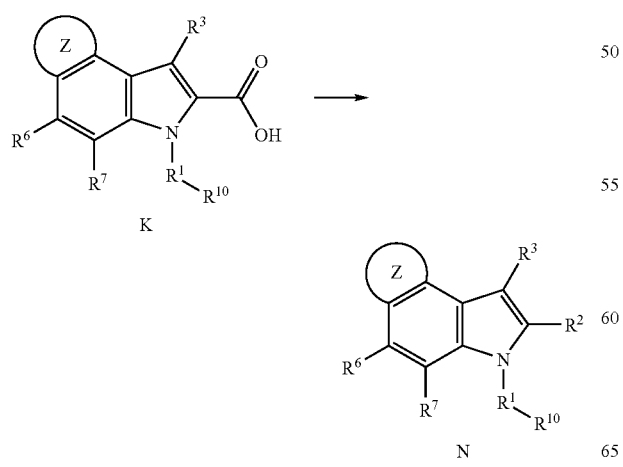

wherein $R^1$, $R^3$, $R^6$, $R^7$, $R^{10}$ and Z are as defined for the Compounds of Formula (I) and $R^2$ is:

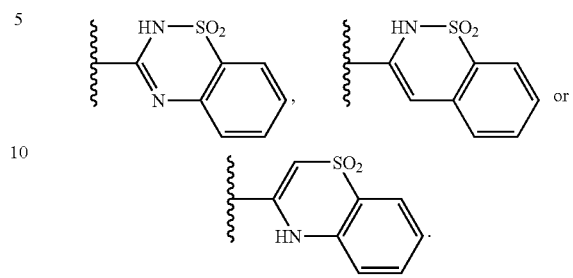

A 2-carboxy indole compound of formula K can be converted to the compounds of formula N, which correspond to the Compounds of Formula (I) wherein $R^2$ is:

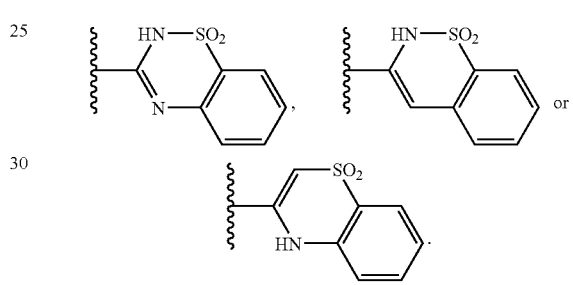

using the methods set forth in U.S. Patent Application No. US2005/0075331.

Scheme 9 shows a method useful for making the Compounds of Formula (I), wherein $R^3$ is 1H-pyridin-2-one-3-yl.

Scheme 9

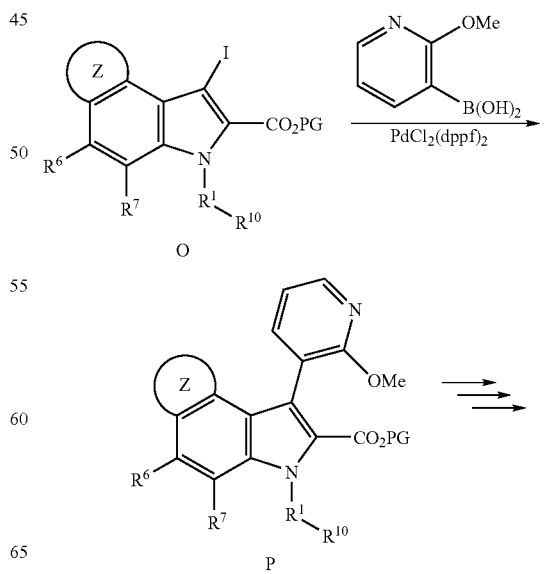

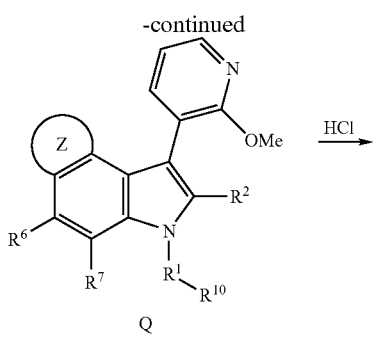

Q

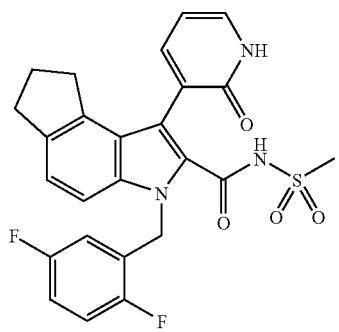

R wherein $R^1$, $R^2$, $R^6$, $R^7$, $R^{10}$ and Z are as defined for the Compounds of Formula (I), and PG is a carboxy protecting group.

A 3-iodoindole compound of formula O can be coupled with 2-hydroxypyridine-3-boronic acid using a Suzuki coupling reaction to provide the $R^3$-substituted indole compounds of formula P. A compound of formula P can be further elaborated using methods set forth above to provide the compounds of formula Q. The 2-hydroxypyridyl moiety of a compound of formula Q can then be reacted with hydrochloric acid to provide a compound of formula R, which corresponds to the Compounds of Formula (I), wherein $R^3$ is 1H-pyridin-2-one-3-yl.

The starting material and reagents depicted in Schemes 1-9 are either available from commercial suppliers such as Sigma-Aldrich (St. Louis, Mo.) and Acros Organics Co. (Fair Lawn, N.J.), or can be prepared using methods well-known to those of skill in the art of organic synthesis.

One skilled in the art will recognize that the synthesis of Compounds of Formula (I) may require the need for the protection of certain functional groups (i.e., derivatization for the purpose of chemical compatibility with a particular reaction condition). Suitable protecting groups for the various functional groups of the Compounds of Formula (I) and methods for their installation and removal can be found in Greene et al., *Protective Groups in Organic Synthesis*, Wiley-Interscience, New York, (1999).

One skilled in the art will also recognize that one route will be optimal depending on the choice of appendage substituents. Additionally, one skilled in the art will recognize that in some cases the order of steps may differ from that presented herein to avoid functional group incompatibilities and amend the synthetic route accordingly.

One skilled in the art will recognize that the synthesis of certain compounds of Formula 1 require the construction of an amide bond. Methods useful for making such amide bonds, include but are not limited to, the use of a reactive carboxy derivative (e.g. acid halide, or ester at elevated temperatures) or the use of an acid with a coupling reagent (e.g. DECI, DCC) with an amine.

The starting materials used and the intermediates prepared using the methods set forth in Schemes 1-9 may be isolated and purified if desired using conventional techniques, including but not limited to filtration, distillation, crystallization, chromatography and the like. Such materials can be characterized using conventional means, including physical constants and spectral data.

EXAMPLES

General Methods

Solvents, reagents, and intermediates that are commercially available were used as received. Reagents and intermediates that are not commercially available were prepared in the manner as described below. $^1$H NMR spectra were obtained on a Bruker Avance 500 (500 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min-10% CH$_3$CN, 5 min-95% CH$_3$CN, 5-7 min-95% CH$_3$CN, 7 min-stop. The retention time and observed parent ion are given. Flash column chromatography was performed using pre-packed normal phase silica from Biotage, Inc. or bulk silica from Fisher Scientific. Unless otherwise indicated, column chromatography was performed using a gradient elution of hexanes/ethyl acetate, from 100% hexanes to 100% ethyl acetate.

Example 1

Preparation of Compound 12

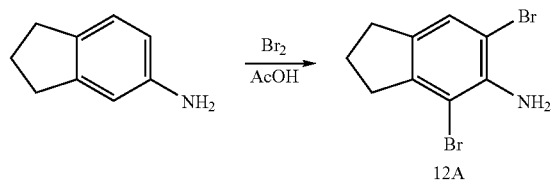

Step A—Synthesis of Compound 12A

To a solution of 5-aminoindane (5.00 g, 37.55 mmol) in acetic acid (200 mL) was added bromine (15 mL). The resulting mixture was allowed to stir for 1 hour and then concentrated to ~100 mL. Chloroform was added to give a precipitate. The solid was isolated by filtration, and washed with chloroform to provide compound 12A as a lightly tinted solid (12.63 g). mp 220-221° C.; $^1$H NMR (400 MHz, d$_6$-DMSO) δ 2.07 (m, 2H), 2.90 (m, 4H), 7.33 (s, 1H).

Step B—Synthesis of Compound 12B

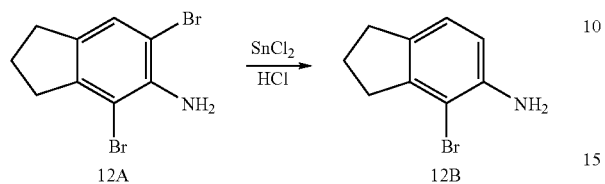

Stannous chloride (0.89 g) was added to a solution of compound 12A (1.0 g, 3.5 mmol) in acetic acid (5 mL) and aqueous concentrate HCl (4 mL). The resulting mixture was heated at reflux for 30 minutes, then cooled to room temperature. The solvents were then removed in vacuo and the resulting residue was partitioned between aqueous NaOH and CH$_2$Cl$_2$. The organic phase was separated and the aqueous phase was extracted with CH$_2$Cl$_2$. The combined organic phases were dried with MgSO$_4$ and concentrated to provide a crude residue that was purified using silica gel chromatography (EtOAc:Hexane=1:20) to provide compound 12B (0.501 g) as a white solid. $^1$H NMR (400 MHz, CDCl3) δ 6.95 & 6.93 (d, J=8.05 Hz, 1H), 6.59 & 6.57 (d, J=7.32 Hz, 1H), 3.96 (s, 2H), 2.91 (q, J=7.32 & 15.38 Hz, 4H), 2.07 (qintet, J=7.32 Hz, 2H).

Step C—Synthesis of Compound 12C

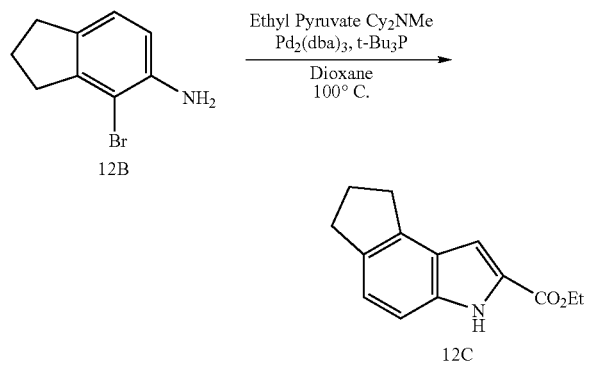

Pd$_2$(dba)$_3$ (185 mg) was added to a dioxane (20 mL) solution of compound 12B (0.455 g, 2.1 mmol), tri-tert-butylphosphine (0.81 mL of a 1.0 M solution in toluene), dicyclohexylmethylamine (2.92 mL) and ethyl pyruvate (0.9 mL). The mixture was heated at 100° C. under an atmosphere of nitrogen overnight. After cooling, the reaction mixture was partitioned between CH$_2$Cl$_2$ and diluted with aqueous HCl (1N). The organic phase was separated and extracted with CH$_2$Cl$_2$ (2X). The combined organic phases were dried (MgSO$_4$) and concentrated in vacuo. The crude reaction product was purified using flash column chromatography on silica gel (EtOAc/Hexane=1:10) to provide compound 12C (0.263 g). MS found for C$_{14}$H$_{15}$NO$_2$=230.07 (M+H).

Step D—Synthesis of Compound 12D

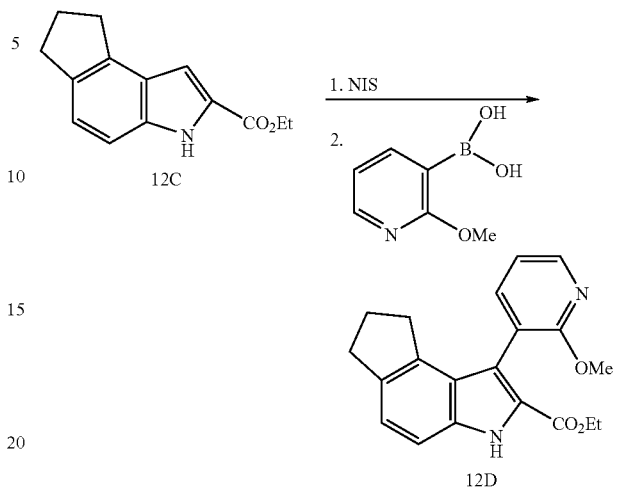

N-iodosuccinimide (0.402 g, 2.05 mmol) was added to a allowed to stir solution of solution of compound 12C (0.47 g, 2.05 mmol) in CH$_2$Cl$_2$ (15 mL) at 4° C. The reaction was monitored by TLC until no starting materials remained (about 1 hour). The reaction was partitioned between EtOAc and diluted with aqueous sodium thiosulfate (5%). The organic phase was separated, washed with sat. aqueous sodium bicarbonate and water. The crude product was used directly in the next step without purification. The SME (30 mL) solution of the above crude indole and PdCl$_2$ (DPPF)$_2$ (0.141 g, 0.1 eq) was heated to 90° C. (oil bath temperature) for a period of 0.5 hour and a solution of the boronic acid (0.318 g, 1.2 eq) and potassium carbonate (1.197 g, 5 eq) in H$_2$O/DME (6 mL/6 mL) was added dropwise. When the addition was complete the reaction mixture was heated to 150° C. (oil bath) for 2 hours. After cooling, 3% aqueous sodium sulfate was added followed by EtOAc and filtered through celite. The filtrate was partitioned between water and CH$_2$Cl$_2$. The organic phase was separated and the aqueous phase was further extracted with CH$_2$Cl$_2$. The combined organic phase was dried (MgSO$_4$) and concentrated. The residue was purified using silica gel chromatography (EtOAc:Hexane=1:10) to provide compound 12D. MS found for C$_{20}$H$_{20}$N$_2$O$_3$=337.18 (M+H).

Step E—Synthesis of Compound 12E

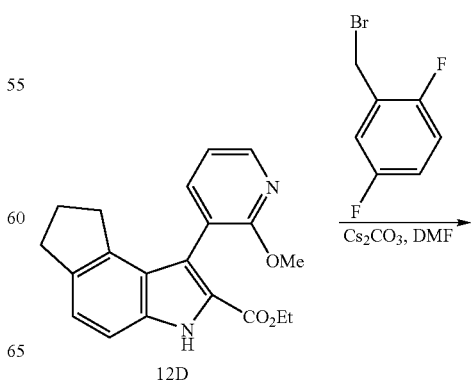

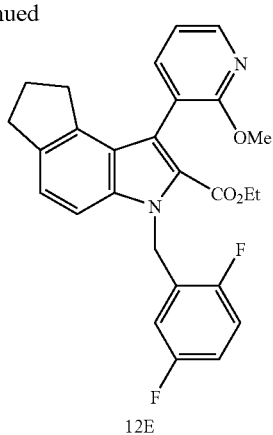

12E 2,4-difluorobenzylbromide (0.187 g, 1.5 eq) was added dropwise to a allowed to stir solution of compound 12D (202 mg, 0.6 mmol) and Cs$_2$CO$_3$ in DMF at room temperature under an atmosphere of nitrogen. After 16 hours, the reaction mixture was partitioned between EtOAc and water. The aqueous phase was separated, washed with water three times, dried (MgSO$_4$) and concentrated. The residue was purified using flash column chromatography on silica gel (EtOAc:Hexane=1:20) to provide compound 12E (0.263 g) as a white solid. MS found for C$_{27}$H$_{24}$N$_2$O$_3$=463.18 (M+H).

Step F—Synthesis of Compound 12F

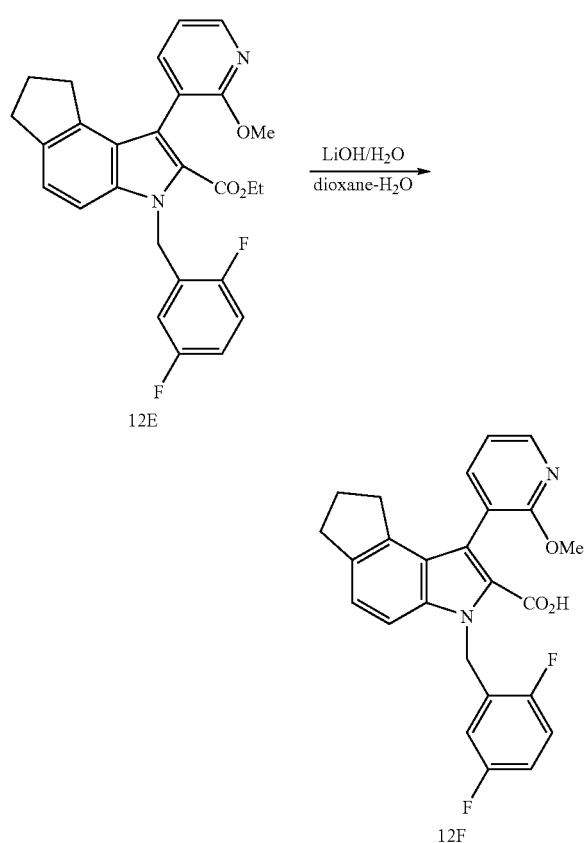

12E

12F

Lithium hydroxide (53 mg, 3 eq) was added to a allowed to stir solution of the ethylester 12E (196 mg, 0.42 mmol) in aqueous THF/H$_2$O (3 mL/1 mL) under an atmosphere of nitrogen. The resulting reaction mixture was heated to 100° C. for 4 hours (oil bath). After cooling, the reaction was partitioned between CH$_2$Cl$_2$ and diluted with aqueous HCl (1N). The organic phases were separated and extracted with CH$_2$Cl$_2$. The combined organic phases were dried (MgSO$_4$) and concentrated in vacuo to provide a crude residue that was purified using flash column chromatography on silica gel (EtOAc/Hexane=1:10) followed by EtOAc as eluent to provide compound 12F as a white solid (95.2 mg). MS found for C$_{25}$H$_{20}$F$_2$N$_2$O$_3$=435.11 (M+H).

Step G—Synthesis of Compound 12G

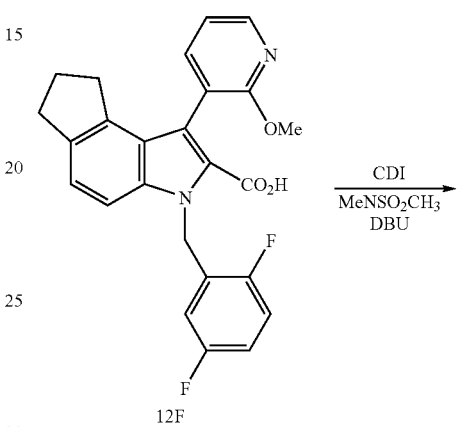

12F

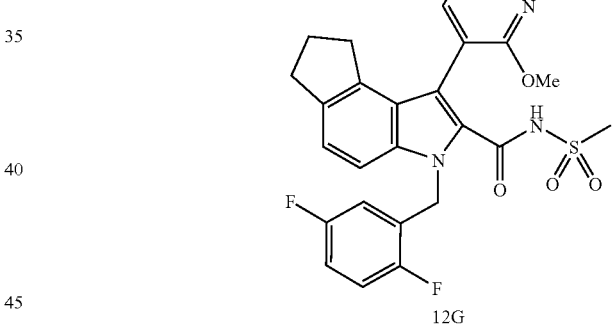

12G

CDI (35 mg, 1 eq) was added to a allowed to stir solution of the acid 12F (95 mg) in THF and the reaction mixture was heated at reflux under an atmosphere of nitrogen for a period of 2 hours. After cooling, methane sulfonamide (31 mg, 1.5 eq) followed by DBU (0.26 mmol) were added. After 6 hours the mixture was partitioned between EtOAc and diluted with aqueous HCl (1N), the organic phase was separated and the aqueous phase was further extracted with EtOAc. The combined organic phases were dried (MgSO$_4$) and concentrated in vacuo to provide a crude residue that was purified using flash column chromatography on silica gel (CH$_2$Cl$_2$:MeOH=20:1) to provide compound 12G (20.6 mg). MS found for C$_{26}$H$_{23}$F$_2$N$_3$O$_4$S=517.12

Step H—Synthesis of Compound 12

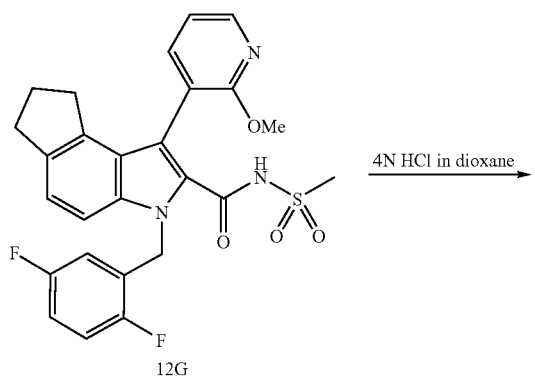

HCl (4N in dioxane, 10 mL) was added to compound 12G (50 mg) in a sealed tube and the resulting suspension was heated to 80° C. (oil bath) and allowed to stir at this temperature overnight. The reaction mixture was then cooled to room temperature and the solvent was removed in vacuo to provide a crude residue which was triturated with ether and the resulting solid was collected to provide compound 12 (35.2 mg). MS found for $C_{25}H_{21}F_2N_3O_4S$: 498.03 (M+H)$^+$. $^1$H NMR (500 MHz, d$_6$-DMSO) δ 12.68 (bs, 1H), 12.50 (bs, 1H), 7.74 (d, J=6.59 Hz, 1H), 7.67 (m, 1H), 7.37 (d, J=8.79 Hz, 1H), 7.32-7.26 (m, 1H), 7.24 (d, J=8.79 Hz, 1H), 7.17-7.12 (m, 1H), 6.59-6.54 (m, 2H), 5.69 (s, 2H), 3.23 (s, 3H), 2.86-2.83 (m, 2H), 2.8-2.0 (bs, 2H), 1.95 (s, 2H). $^{13}$C NMR (125 MHz, DMSO-d$_6$) δ 162.864, 161.097, 158.974, 157.059, 156.602, 154.687, 144.974, 136.933, 136.884, 135.826, 135.781, 128.571, 127.140, 127.083, 127.004, 126.944, 123.307, 123.155, 122.083, 117.030, 116.962, 116.837, 116.769, 115.700, 115.628, 115.511, 114.911, 114.726, 108.947, 106.806, 106.194, 72.068, 66.255, 41.665, 41.102, 32.178, 31.747, 24.874.

Example 2

Preparation of Compound 16

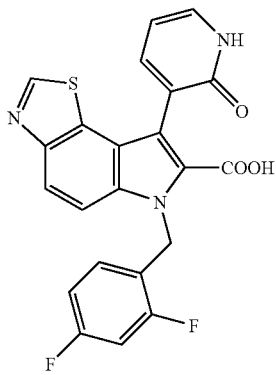

Step A—Synthesis of Compound 16A

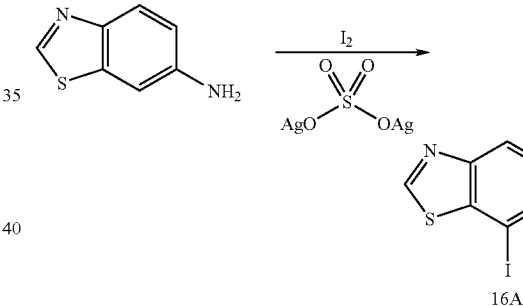

To a solution of benzothiazol-6-ylamine (5.00 g, 33.25 mmol) in ethanol (50 mL) was added silver sulfate (10.5 g, 33.25 mmol) and iodine (8.45 g, 33.25 mmol) and the reaction was allowed to stir at room temperature for 48 hours. The reaction mixture was added sodium thiosulfate and allowed to stir for 1 h and filtered. The reaction mixture was extracted with EtOAc (350 mL), washed with brine, dried (MgSO$_4$), filtered, and concentrated in vacuo. The resulting residue was purified using flash column chromatography on silica gel (EtOAc/Hexanes, 0-100%) to provide compound 16A as a colorless solid (1.7 g).

Step B—Synthesis of Compound 16B

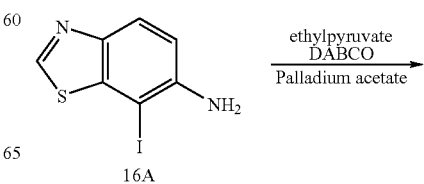

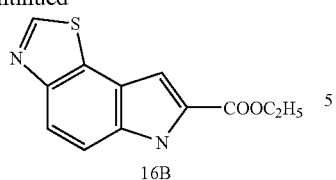

16B

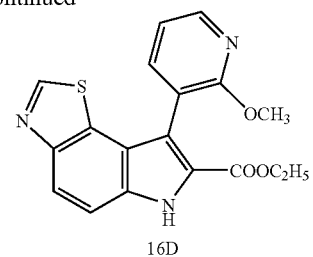

16D

A solution of compound 16A (1.7 g, 6.16 mmol) in DMF (15 mL) was extensively degassed and treated with ethyl pyruvate (0.965 g, 8.4 mmol), DABCO and palladium acetate (139 mg, 0.616 mmol) and then heated at 105° C. for 12 hours. The reaction mixture was poured into water and extracted with ethyl acetate and the organic layer was dried (MgSO$_4$), filtered, concentrated in vacuo and purified using flash column chromatography on silica gel (EtOAc/Hexanes 0-70%) to provide compound 16B (500 mg).

Step C—Synthesis of Compound 16C

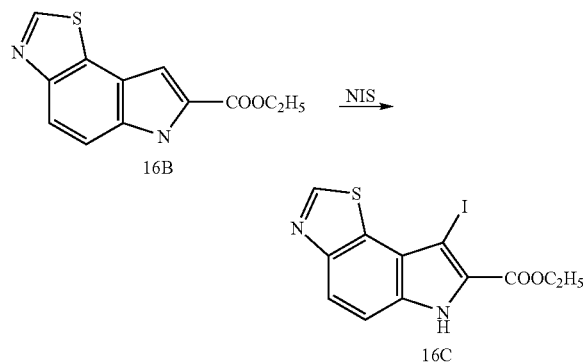

To a solution of compound 16B (430 mg, 1.75 mmol) in chloroform (30 mL) was added N-iodosuccinimide and the resulting reaction was allowed to stir at room temperature for 12 hours. The reaction mixture was diluted with water, and extracted with ethyl acetate (500 mL). The combined organic layers were extracted with brine, dried (MgSO$_4$), filtered, concentrated under vacuum, pre-absorbed on silica and purified using flash column chromatography (1:1 EtOAc/Hexanes) to provide compound 16C as a colorless solid.

Step D—Synthesis of Compound 16D

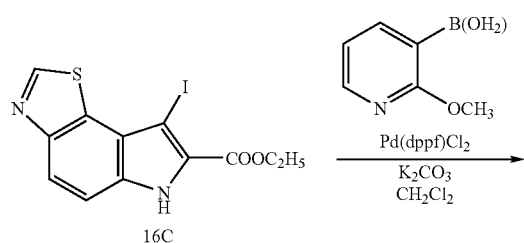

To a solution of compound 16C (500 mg, 1.35 mmol) in DME (15 mL) was added 2-methoxy-3-pyridyl boronic acid (413 mg, 2.7 mmol) and Pd(dppf)Cl$_2$ (130 mg) and the reaction was allowed to stir at room temperature under nitrogen for 0.5 hours. The reaction mixture was then treated with a solution of potassium carbonate (932 mg, 6.75 mmol) in 10 mL of water and heated at 90° C. for 3 hours. The reaction mixture was diluted with EtOAc (250 mL), concentrated in vacuo and purified using flash column chromatography on silica gel using EtOAc/Hexanes (0 to 100% EtOAc) to provide compound 16D.

Step E—Synthesis of Compound 16E

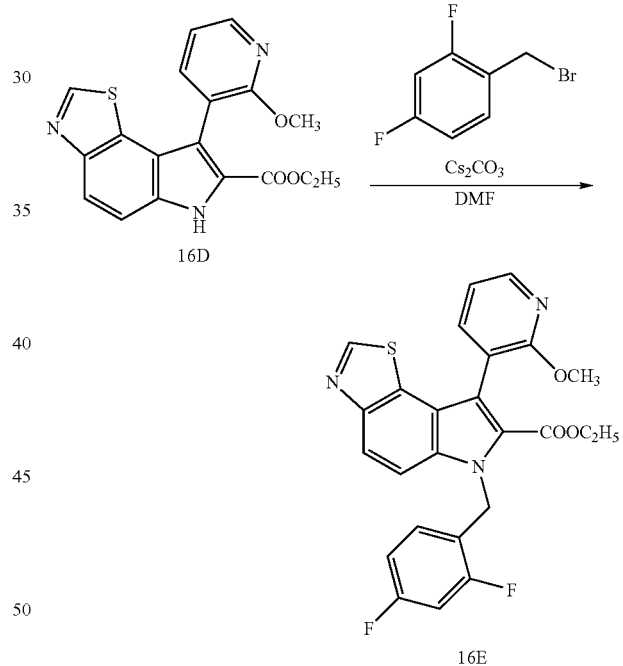

To a solution of compound 16D (100 mg, 0.29 mmol) in DMF (3 mL) was added cesium carbonate (189 mg, 0.58 mmol) and 2,4-difluorobenzyl bromide and the resulting reaction was allowed to stir at room temperature for 1 hour. The reaction mixture was diluted with EtOAc (300 mL) and washed with brine (2×100 mL). The combined organic layers were dried (MgSO$_4$), filtered, and concentrated in vacuo. The resulting residue was purified using flash column chromatography on silica gel (EtOAc/Hexane, 0 to 100% EtOAc) to provide compound 16E as a colorless solid.

Step F—Synthesis of Compound 16

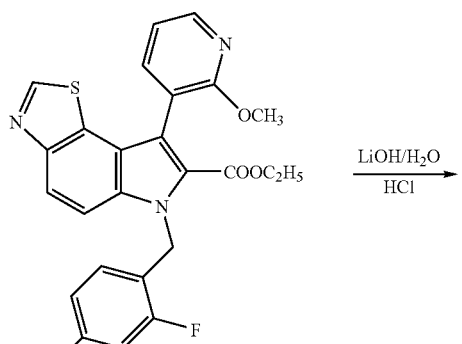

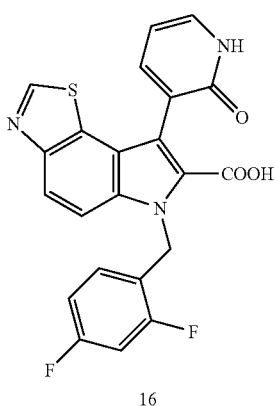

To a solution of compound 16E (200 mg, 0.041 mmol) in methanol/water/THF (5 mL each) was added lithium hydroxide and the resulting reaction was allowed to stir at reflux overnight. The reaction mixture was diluted with aqueous HCl and extracted into ethyl acetate (100 mL). The combined organic layers were dried (MgSO$_4$), filtered, concentrated in vacuo and used as it is in the next step. The residue was taken up in methanol (1 mL) and treated with aqueous HCl (4M) and heated for 1 h at 80° C. A large amount of white solid separated out which was filtered and dried to provide compound 16. MS found for $C_{22}H_{13}F_2N_3O_3S$: 438.00 (M+H)$^+$.
$^1$H NMR (400 MHz, d$_6$-DMSO) δ 9.15 (s, 1H), 8.01+7.98 (d, J=9.52 Hz, 1H), 7.79 & 7.77 (d, J=8.79 Hz, 1H), 7.59 & 7.57 (d, J=6.59 Hz, 1H), 7.497 & 7.48 (d, J=5.86 Hz, 1H), 7.29 (t, J=9.52 Hz, 1H), 6.96 (t, J=9.50 Hz, 1H), 6.70 (q, J=8.79 & 15.38 Hz, 1H), 6.34 (t, J=7.32 Hz, 1H), 5.98 (q, J=16.11 & 46.87 Hz, 2H).

Example 3

Preparation of Compound 9

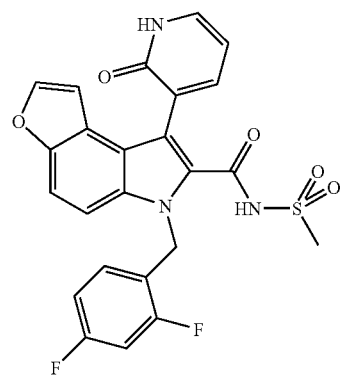

Step A—Synthesis of Compound 9A

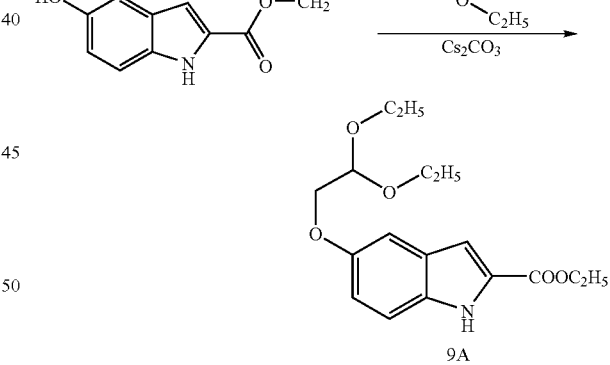

To a solution of 5-hydroxy-1H-indole-2-carboxylic acid ethyl ester (5.00 g, 25.00 mmol) in DMF (30 mL) was added Cs$_2$CO$_3$ (9.00 g, 1.1 mmol) and bromoacetaldehyde-diethylacetal (20 g, 5.00 mmol) and the resulting reaction was allowed to stir at reflux for 2 hours. The reaction mixture was cooled to room temperature, treated with aqueous NaOH (1M, 500 mL) and extracted into EtOAc (500 mL). The organic layers were dried (MgSO$_4$), filtered, concentrated in vacuo (high vacuo to distill out DMF and bromoacetaldehyde) and purified using flash column chromatography (Hexanes/EtOAc, 0 to 100%) to provide compound 9A as a colorless solid.

Step B—Synthesis of Compound 9B

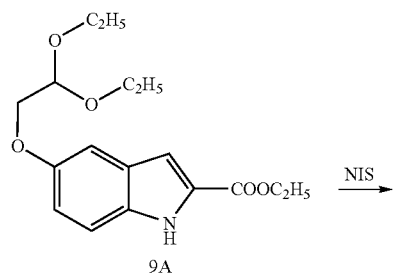

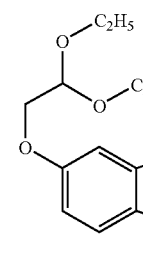

To a solution of compound 9A (2.3 g, 7.1 mmol) in chloroform (20 mL) was added N-iodosuccinimide (1.77 g, 7.8 mmol) and the reaction was allowed to stir at room temperature for 12 hours. The reaction mixture was diluted with EtOAc (200 mL) and washed three times with water. The organic layer was dried ($MgSO_4$), filtered, concentrated in vacuo and purified using flash column chromatography (eluent: EtOAc/Hexanes, 0 to 50% EtOAc) to provide compound 9B as a colorless solid (2.7 g).

Step C—Synthesis of Compound 9C

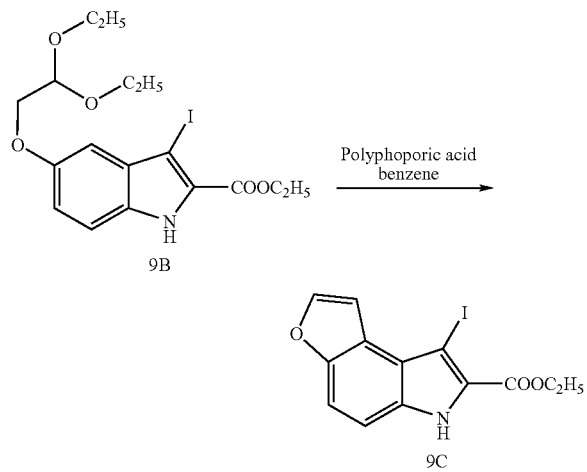

To a solution of compound 9B (2.7 g, 6.00 mmol) in benzene (30 mL) was added polyphosphoric acid (3 g) and the resulting reaction was allowed to stir at reflux for about 1 hour. The reaction was then quenched using cold water and the resulting solution was extracted into EtOAc. The organic layer were dried ($MgSO_4$), filtered, concentrated in vacuo and purified using flash column chromatography (Hexane: EtOAc, 1:1) to provide compound 9C.

Step D—Synthesis of Compound 9D

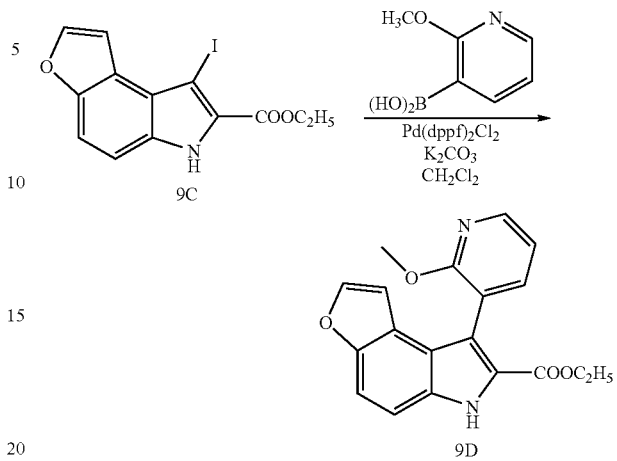

To a solution of compound 9C (1.5 g, 4.33 mmol) in DME (20 mL) was added 2-methoxy-3-pyridyl boronic acid (795 mg, 5.2 mmol) and Pd(dppf)$_2$Cl$_2$ (408 mg) and the reaction was allowed to stir at room temperature under nitrogen for 30 minutes. The reaction mixture was added a solution of potassium carbonate (2.4 g, 17.3 mmol) in 10 mL of water and heated at 90° C. for 1 hour. The reaction mixture was diluted with EtOAc (250 mL), concentrated in vacuo, and purified using flash column chromatography (EtOAc/Hexanes, 1:1) to provide compound 9D as a colorless solid (620 mg).

Step E—Synthesis of Compound 9E

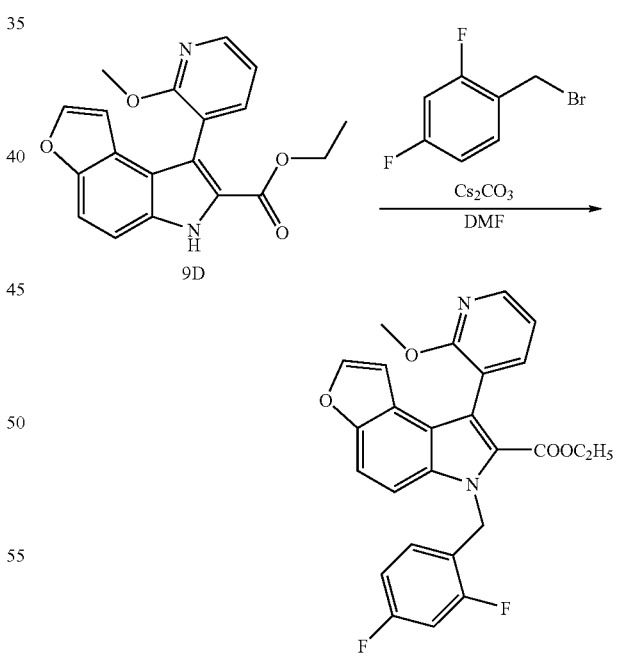

To a solution of compound 9D (620 mg, 1.86 mmol) in DMF (5.00 mL) was added Cs$_2$CO$_3$ (1.21 g, 3.72 mmol) and 2,4-difluorobenzylbromide (577, 2.79 mmol) and the resulting reaction was allowed to stir overnight. The reaction mixture was then diluted with water (250 mL) and extracted into EtOAc (300 mL). The combined organic layers were dried (MgSO₄), filtered, concentrated in vacuo and purified using flash column chromatography (EtOAc/Hexanes, 1:1) to provide compound 9E (900 mg).

Step F—Synthesis of Compound 9F

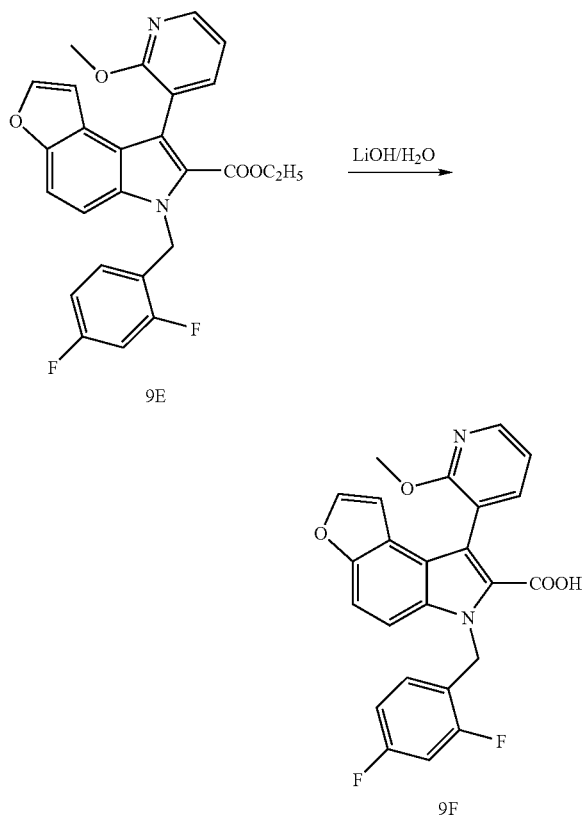

To a solution of compound 9E (1.95 mmol) in methanol/water/THF (15 mL, 1:1:1) was added lithium hydroxide (10 mmol) and the resulting reaction was allowed to stir for 4 hours at reflux. The reaction mixture was acidified with aqueous HCl (1N, 20 mL) and extracted into EtOAc (250 mL). The combined organic layers were dried (MgSO₄), filtered, and concentrated in vacuo to provide compound 9F, which was used without further purification.

Step G—Synthesis of Compound 9G

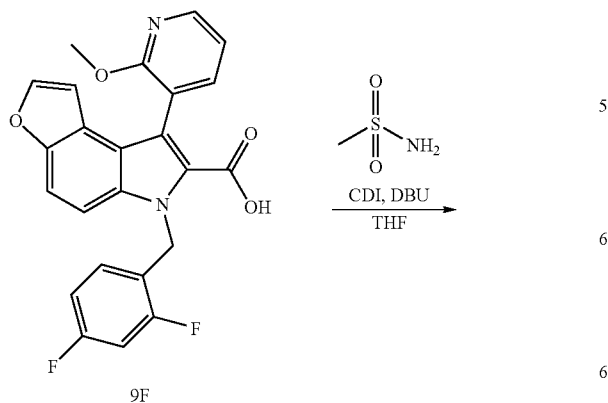

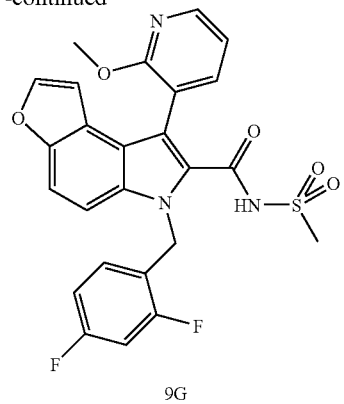

To a solution of compound 9F (0.34 mmol) in 3 mL of THF was added CDI (0.5 mmol) and the resulting reaction was heated to reflux and allowed to stir at this temperature for 3 hours. The reaction mixture was then cooled to 0° C. and treated with methane sulfonamide and DBU. The resulting reaction mixture was allowed to stir at room temperature for 48 hours, then diluted with EtOAc (100 mL) and the resulting solution was washed with water and aqueous HCl (1N). The combined organic layers were dried (MgSO₄), filtered, and concentrated in vacuo and the resulting residue was purified using flash column chromatography on silica gel (acetone/CH₂Cl₂, 0 to 70% acetone) to provide compound 9G (100 mg).

Step H—Synthesis of Compound 9

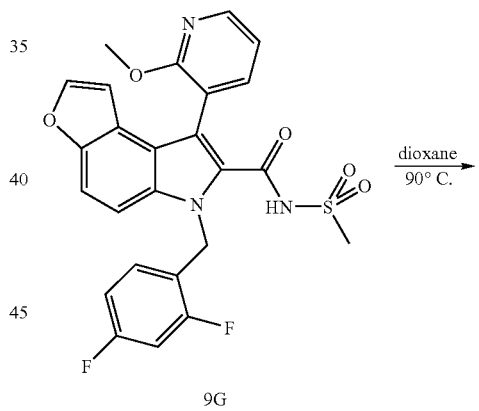

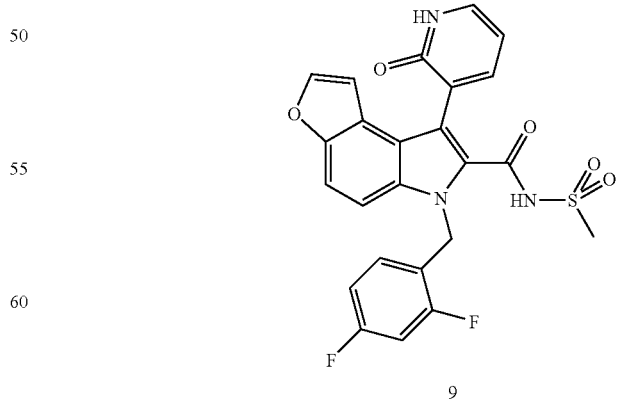

A solution of compound 9G (100 mg, 0.2 mmol) in 4M solution of dioxane (5 mL) was heated to 90° C. and allowed to stir at this temperature for 3 hours. The reaction mixture was then concentrated in vacuo and the resulting residue was diluted with EtOAc. The solid product was filtered and washed with EtOAc, then diethyl ether, to provide compound 9. MS found for C$_{24}$H$_{17}$F$_2$N$_3$O$_5$S: 498.05 (M+H)$^+$. $^1$H NMR (400 MHz, d$_6$-DMSO) δ 12.77 (s, 1H), 12.70 (s, 1H), 7.97 & 7.966 (d, J=2.14 Hz, 1H), 7.87 (q, J=2.14 & 7.26 Hz, 1H), 7.76-7.72 (m, 1H), 7.66 & 7.63 (d, J=8.97 Hz, 1H), 7.56 & 7.54 (d, J=9.40 Hz, 1H), 7.30-7.25 (m, 1H), 6.99-6.86 (m, 2H), 6.65 (t, J=6.41 Hz, 1H), 6.468 & 6.464 (d, J=1.71 Hz, 1H), 5.78 (s, 2H), 3.26 (s, 3H).

Example 4

Preparation of Compound 1

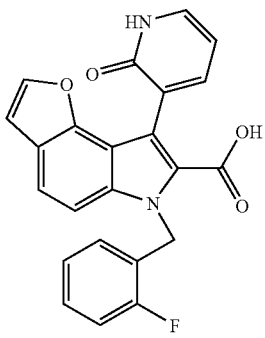

Step A—Synthesis of Compound 1A

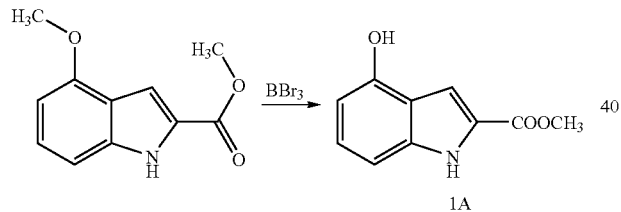

A solution of 4-methoxy-1H-indole-2-carboxylic acid methyl ester (410 mg, 2.00 mmol) in CH$_2$Cl$_2$ (5 mL) was cooled to −78° C. and BBr$_3$ (6 mL solution, 1M) was added. The resulting reaction was then allowed to stir at 0° C. for 3 hours. The reaction mixture was then quenched using water and the resulting solution was extracted with EtOAc (200 mL). The combined organic layers were dried (MgSO$_4$), filtered, concentrated in vacuo and purified using flash column chromatography to provide compound 1A.

Step B—Synthesis of Compound 1B

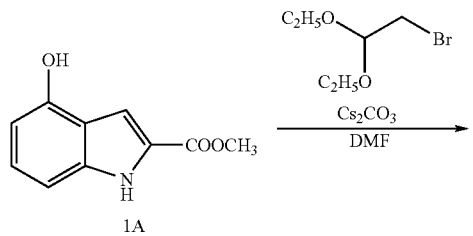

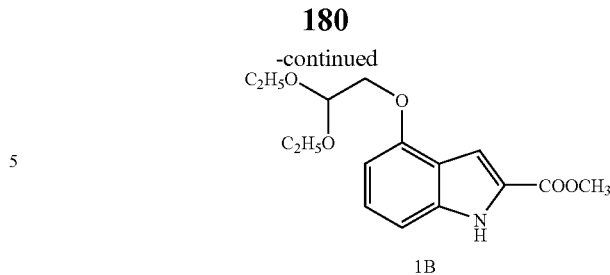

To a solution of compound 1A (2.5 g, 13.10 mmol) in DMF (50 mL) was added Cs$_2$CO$_3$ (5.12 g, 15.72 mmol), then bromoacetaldehyde-diethylacetal (12.90 g, 65.6 mmol), and the resulting reaction was allowed to stir at reflux for 2 hours. The reaction mixture was cooled to room temperature, treated with aqueous NaOH (1M, 50 mL) and extracted into EtOAc (250 mL). The organic layers were combined, dried (MgSO$_4$), filtered, and concentrated in vacuo to provide a crude residue which was purified using flash column chromatography (Hexanes/EtOAc 0 to 100%) to provide compound 1B as a colorless solid.

Step C—Synthesis of Compound 1C

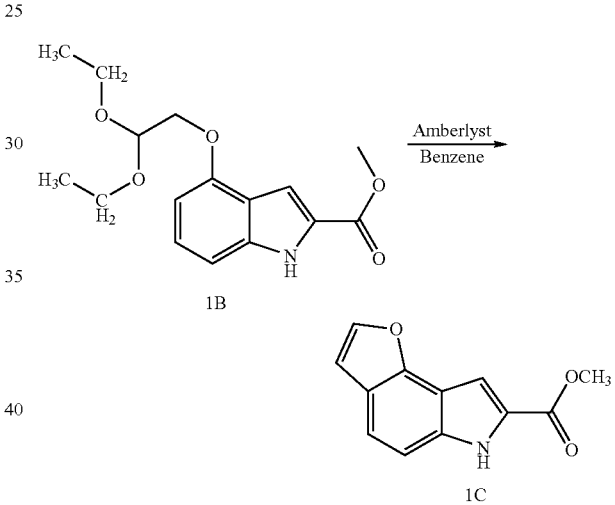

To a solution of compound 1B in benzene (60 mL) was added Amberlyst-15 strongly acidic resin (4.5 g) and the resulting reaction was heated to 70° C. and allowed to stir at this temperature for 4 hours. The reaction mixture was then cooled to room temperature, diluted with EtOAc (300 mL) and washed with aqueous NaHCO$_3$. The combined organic layers were dried (MgSO$_4$), filtered, concentrated in vacuo and purified using flash column chromatography on silica gel (EtOAc/Hexanes, 0-30% EtOAc) to provide compound 1C (1.2 g).

Step D—Synthesis of Compound 1D

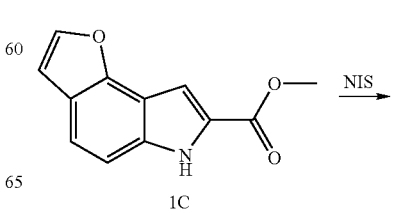

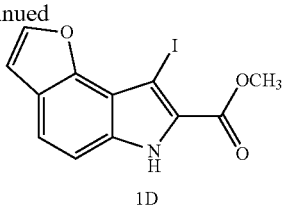

1D

To a solution of compound 1C (2.00 g, 9.3 mmol) in DMF (20 mL) was added N-iodosuccinimide (2.29 g, 10.2 mmol) and the resulting reaction was allowed to stir at room temperature for 12 hours. The reaction mixture was then concentrated in vacuo, diluted with water and extracted into EtOAc (300 mL). The combined organic layers were dried (MgSO$_4$), filtered, and concentrated in vacuo. The resulting brown residue was diluted with a minimum amount of CH$_2$Cl$_2$ and triturated using hexanes. Compound 1D separated out as a brown solid, which was filtered, then dried in vacuo. (Yield 2.6 g, 84%).

Step E—Synthesis of Compound 1E

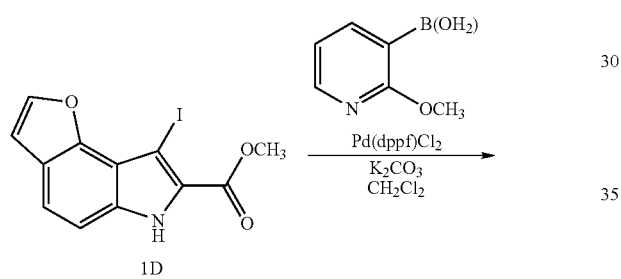

To a solution of compound 1D (2.6 g, 7.6 mmol) in DME (40 mL) under nitrogen atmosphere was added with 2-methoxy-3-pyridyl boronic acid (3.5 g, 22.8 mmol) and Pd (dppf)$_2$Cl$_2$ (616 mg) and the resulting reaction was allowed to stir at room temperature under nitrogen for 0.5 hours. The reaction mixture was then treated with a solution of potassium carbonate (6.3 g, 45.6 mmol) in water (40 mL) and the resulting solution was heated to 90° C. and allowed to stir at this temperature for 1 hour. The reaction mixture was then diluted with EtOAc (300 mL) and the resulting solution was concentrated in vacuo to provide a crude residue which was purified using flash column chromatography (EtOAc/Hexanes, 0 to 50% EtOAc) to provide compound 1E as a solid (2.0 g).

Step F—Synthesis of Compound 1F

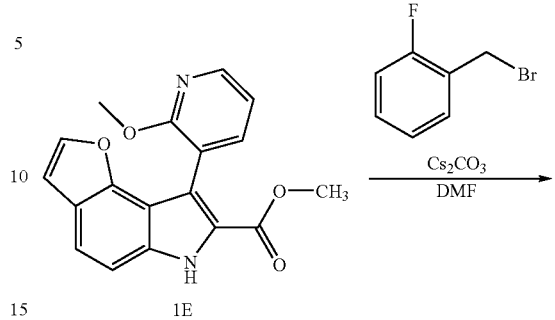

To a solution of indole 1E (300 mg, 0.93 mmol) in DMF (10 mL) was added cesium carbonate (604 mg, 1.86 mmol) and 2-fluorobenzyl bromide (351 mg, 1.86 mmol) and allowed to stir at room temperature for 12 hours. The reaction mixture was diluted with EtOAc (250 mL) and washed with brine (2×100 mL). The combined organic layers were dried (MgSO$_4$), filtered, and concentrated in vacuo and purified using flash column chromatography on silica gel to provide compound 1F as a colorless solid.

Step G—Synthesis of Compound 1

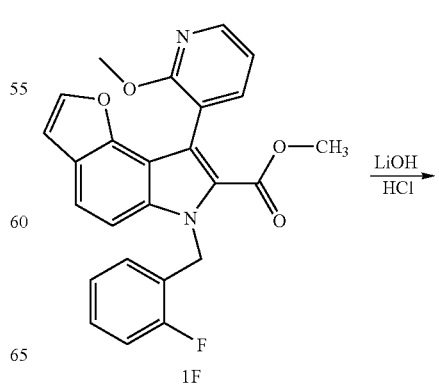

-continued

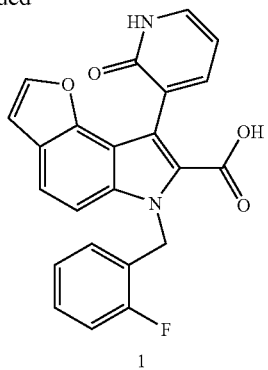

1

To a solution of compound 1F (100 mg, 0.23 mmol) in THF/water/methanol (4 mL each) was added lithium hydroxide (40 mg, 1 mmol) and the resulting reaction was allowed to stir at reflux for 4 hours. The reaction mixture was diluted with acid and extracted with EtOAc (200 mL). The organic layer was dried (MgSO$_4$), concentrated in vacuo and used as it is in next step. A solution of crude acid (80 mg) in 4 M HCl in dioxane (5 mL) and methanol (1 mL) was heated at 80° C. for 3 hours. The reaction mixture was concentrated in vacuo and the crude was purified using reverse-phase HPLC using the following conditions, to provide compound 1: Waters: Delta Pk, P/No 11805, Wat 011805, 300×30 mm (L/ID) C18, 15 mM, 300 A, 343K16006 (W): Flow Rate: 30 mL/min; Mobile Phase: 30-70% ramp acetonitrile, water; 0→40 minutes.

For compound 1: MS found for $C_{23}H_{15}FN_2O_4$: 403.08 (M+H)$^+$. $^1$H NMR (300 MHz, d$_6$-DMSO) δ 11.72 (bs, 1H), 7.84 & 7.83 (d, J=2.20 Hz, 1H), 7.68 & 7.66 (dd, J=6.59 & 2.20 Hz, 1H), 7.55 & 7.53 (d, J=8.79 Hz, 1H), 7.45 & 7.43 (d, J=8.79 Hz, 1H), 7.41-7.39 (m, 1H), 7.30-7.19 (m, 2H), 7.02 (t, J=7.32 Hz, 1H), 6.963 & 6.957 (d, J=2.20 Hz, 1H), 6.60 (t, J=7.32 Hz, 1H), 6.33 (t, J=7.32 Hz, 1H), 5.95 (s, 2H).

Example 5

Preparation of Compound 4

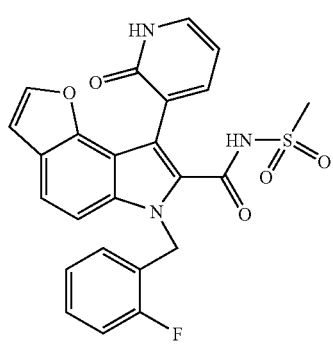

4

Step A—Synthesis of Compound 4A

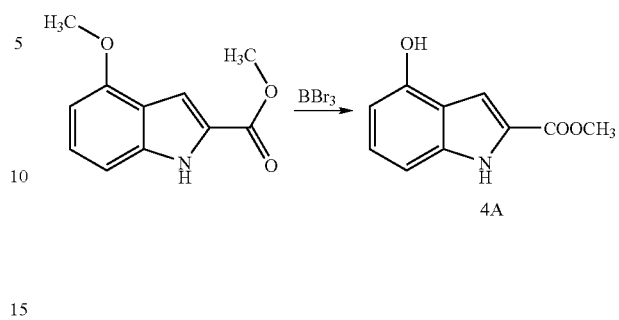

To a solution of 3-methoxy-1H-indole-2-carboxylic acid methyl ester (410 mg, 2.00 mmol) in CH$_2$Cl$_2$ (5 mL) was added BBr$_3$ (6 mL solution, 1M) at −78° C. and the reaction was allowed to stir at 0° C. for 3 hours. The reaction mixture was quenched with water and extracted with EtOAc (200 mL). The combined organic layers were dried (MgSO$_4$), filtered, and concentrated in vacuo and purified using flash column chromatography to provide compound 4A.

Step B—Synthesis of Compound 4B

To a solution of compound 4A (2.5 g, 13.10 mmol) in DMF (50 mL) was added Cs$_2$CO$_3$ (5.12 g, 15.72 mmol) and bromoacetaldehyde-diethylacetal (12.90 g, 65.6 mmol) and the resulting reaction was allowed to stir at reflux for 2 hours. The reaction mixture was cooled to room temperature, diluted treated with aqueous NaOH (1M, 50 mL) and extracted into EtOAc (250 mL). The combined organic layers were dried (MgSO$_4$), filtered, and concentrated in vacuo to provide a crude residue which was purified using flash column chromatography (Hexane/EtOAc 0 to 100%) to provide compound 4B as a colorless solid.

Step C—Synthesis of Compound 4C

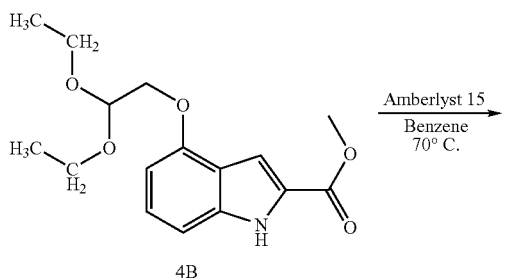

To a solution of compound 4B in benzene (60 mL) was added Amberlyst-15 strongly acidic resin (4.5 g) and the reaction was heated at 70° C. and allowed to stir at this temperature for 4 hours. The reaction mixture was cooled diluted with EtOAc (300 mL) and washed with aqueous NaHCO$_3$. The combined organic layers were dried (MgSO$_4$), filtered, and concentrated in vacuo and purified using flash column chromatography (SiO$_2$) EtOAc/Hexanes (0-30%) to provide compound 4C (1.2 g).

Step D—Synthesis of Compound 4D

To a solution of compound 4C (2.00 g, 9.3 mmol) in DMF (20 mL) was added N-iodosuccinimide (2.29 g, 10.2 mmol) and the reaction allowed to stir at room temperature for 12 hours. The reaction mixture concentrated in vacuo and diluted with water and extracted in EtOAc (300 mL). The combined organic layers were dried (MgSO$_4$), filtered, and concentrated in vacuo. The brown residue was taken in minimum amount of CH$_2$Cl$_2$ and triturated with hexanes. Compound 4D separated out as a brown solid which was filtered, and dried in vacuo. (Yield 2.6 g, 84%)

Step E—Synthesis of Compound 4E

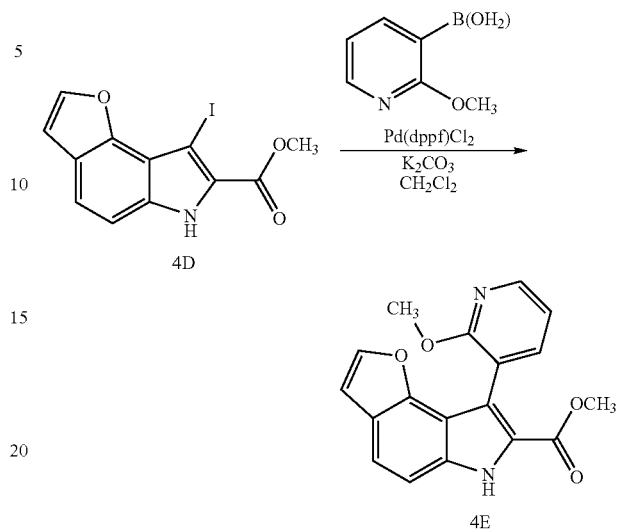

To a solution of compound 4D (2.6 g, 7.6 mmol) in DME (40 mL) was added 2-methoxypyridyl boronic acid (3.5 g, 22.8 mmol) and Pd(dppf)$_2$Cl$_2$ (616 mg) was allowed to stir at room temperature under nitrogen for 0.5 hours. The reaction mixture was then treated with a solution of potassium carbonate (6.3 g, 45.6 mmol) in 40 mL of water and the resulting solution was heated to 90° C. and allowed to stir at this temperature for 1 hour. The reaction mixture was diluted with EtOAc (300 mL), concentrated in vacuo and purified using flash column chromatography on silica gel (EtOAc/Hexanes, 0 to 50%) to provide compound 4E (2.00 g).

Step F—Synthesis of Compound 4F

To a solution of compound 4E (300 mg, 0.93 mmol) in DMF (10 mL) was added cesium carbonate (604 mg, 1.86 mmol) and 2-fluorobenzyl bromide (351 mg, 1.86 mmol) and the resulting reaction was allowed to stir at room temperature for 12 hours. The reaction mixture was diluted with EtOAc (250 mL) and washed with brine (2×100 mL). The combined organic layers were dried (MgSO₄), filtered, and concentrated in vacuo and the resulting residue was purified using flash column chromatography on silica gel to provide compound 4F as a colorless solid.

Step G—Synthesis of Compound 4G

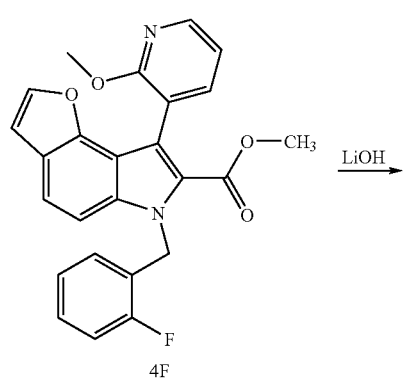

4F

To a solution of compound 4F (100 mg, 0.23 mmol) in THF/water/methanol (4 mL each) was added lithium hydroxide (40 mg, 1 mmol) and the resulting reaction was heated to reflux and allowed to stir at this temperature for 4 hours. The reaction mixture was diluted with aqueous HCl (1N) and extracted with EtOAc (200 mL). The organic layer was dried (MgSO₄) and concentrated in vacuo to provide compound 4G which was used without further purification.

Step H—Synthesis of Compound 4H

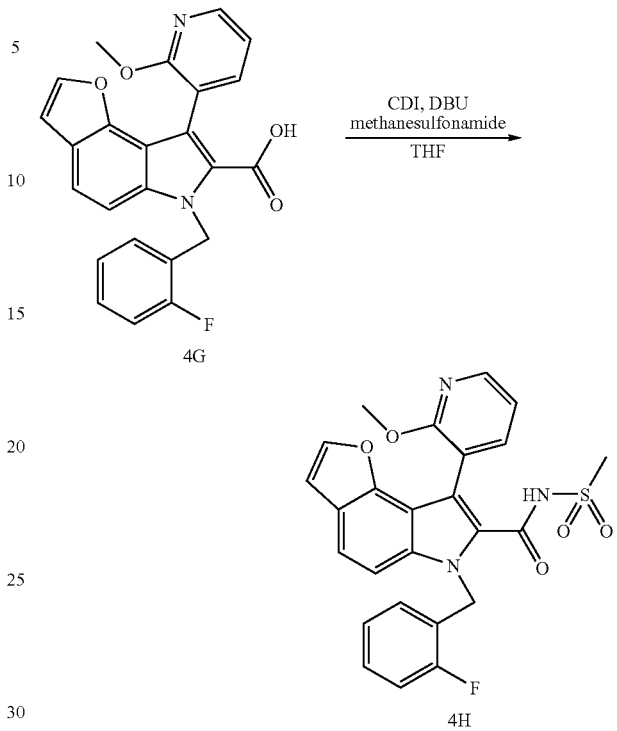

4G

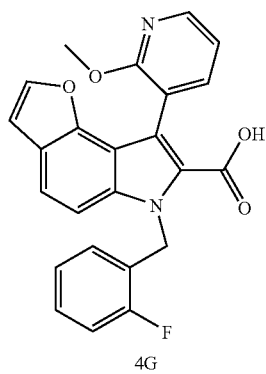

4G

To a solution of compound 4G (150 mg, 0.36 mmol) in 5 mL of THF was added CDI (70 mg, 0.43 mmol) and the resulting reaction was heated at reflux for 3 hours. The reaction mixture was cooled to room temperature and methanesulfonamide (40 mg, 0.43 mmol) and DBU (100 mg, 0.65 mmol) were added. The resulting reaction mixture was allowed to stir at 65° C. for 48 hours, diluted with EtOAc (150 mL) and washed with water and aqueous HCl (1N). The combined organic layers were dried (MgSO₄), filtered and concentrated in vacuo to provide a crude residue which was purified using flash column chromatography on silica gel (acetone/CH₂Cl₂, 0 to 70% acetone) to provide compound 4H as a colorless solid.

Step I—Synthesis of Compound 4

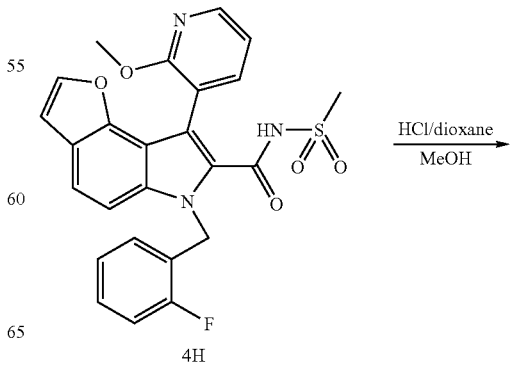

4H

-continued

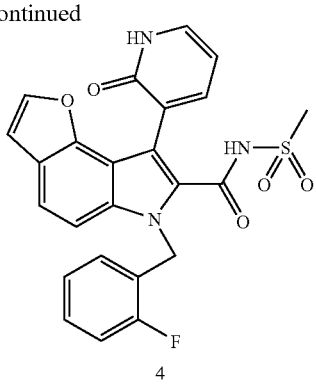

4

To a solution of compound 4H (80 mg, 0.16 mmol) in 4 M HCl in dioxane (5 mL) and methanol (1.5 mL) was heated at 80° C. and allowed to stir at this temperature for 4 hours. The reaction mixture was concentrated in vacuo and the resulting crude residue was purified using HPLC (reverse phase) using following conditions: Column: Waters: Delta Pk, P/No 11805, Wat 011805, 300×30 mm (L/ID) C18, 15 mM, 300 A, 343K16006 (W): 30 ml/min flow; 30-70% ramp acetonitrile, water; 0→40 minutes, to provide compound 4 as colorless solid (60 mg). MS found for $C_{24}H_{18}FN_3O_5S$: 480.05 (M+H)$^+$. $^1$H NMR (300 MHz, $d_6$-DMSO) δ 12.77 (bs, 1H), 12.61 (bs, 1H), 7.98+7.96 (d, J=6.04 Hz, 1H), 7.86-7.83 (m, 1H), 7.67 (s, 1H), 7.60 & 7.58 (d, J=7.69 Hz, 1H), 7.51 & 7.49 (d, J=8.24 Hz, 1H), 7.32-7.27 (m, 1H), 7.21 (t, J=8.79 Hz, 1H), 7.05 (t, J=7.69 Hz, 1H), 6.82 (t, J=7.69 Hz, 1H), 6.67-6.60 (m, 1H), 5.81 (s, 2H), 3.22 (s, 3H).

Example 6

Preparation of Compound 49

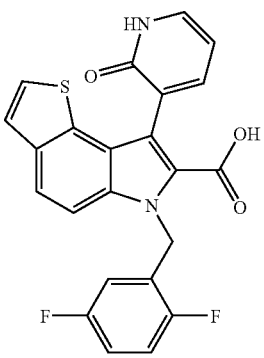

49

Step A—Synthesis of Compound 49A

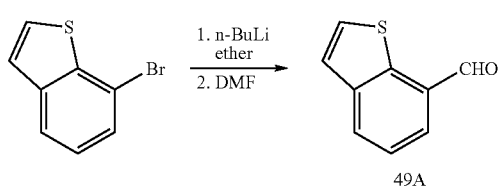 [SMILES: Brc1cccc2ccsc12 ; O=Cc1cccc2ccsc12]

A solution of 7-bromothiophene (8.0 g, 37.5 mmol) in ether (50 mL) was cooled to −78° C. and treated dropwise with n-BuLi (1.6 M solution in hexanes, 1.0 eq.) and the resulting reaction was allowed to stir at −78° C. for 20 minutes. The reaction mixture was then diluted with DMF (dry 5.4 g, 67.4 mmol) and allowed to stir at −78° C. for 1 hour. The reaction mixture was then diluted with water and extracted into ether. The combined organic layers were dried (MgSO$_4$), filtered, concentrated in vacuo and purified using flash column chromatography on silica gel to provide compound 49A as a colorless liquid.

Step B—Synthesis of Compound 49B

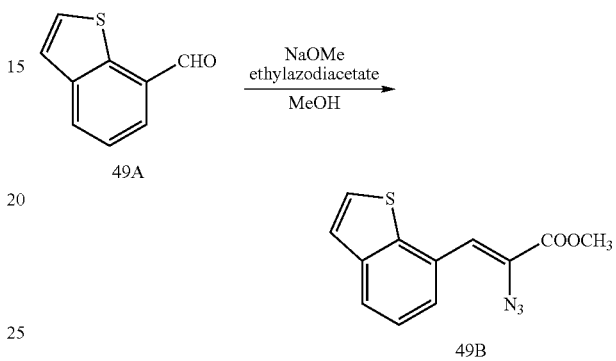

To a solution of freshly made sodium methoxide (prepared by dissolving (1.42 g, 62.0 mmol) in methanol (30 mL)) was added dropwise to a solution of ethylazidoacetate (7.99 g, 62 mmol) and compound 49A (5.1 g, 31 mmol) in methanol (30 mL) which was precooled to −20° C. The reaction mixture was allowed to stir at room temperature for 3 hours, then diluted with EtOAc (200 mL). The organic layer was dried (MgSO$_4$), filtered, concentrated in vacuo and the resulting residue was purified using flash column chromatography on silica gel to provide a crude yellow residue which was recrystallized from ether and hexanes to provide compound 49B (1.95 g).

Step C—Synthesis of Compound 49C

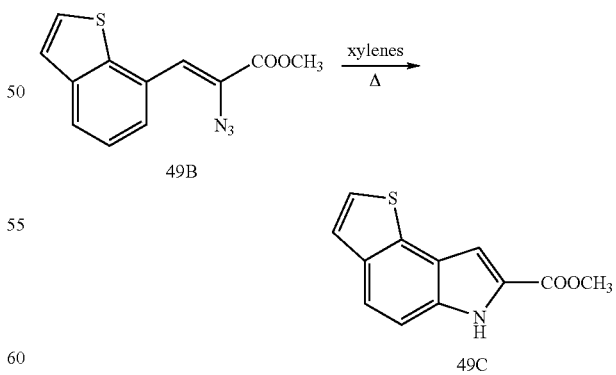

A solution of compound 49B (1.95 g) in xylenes (20 mL) was heated at reflux for 30 minutes, then cooled to room temperature. The reaction mixture was then concentrated in vacuo until a solid precipitate appeared and was collected to provide compound 49C as a colorless solid (1.1 g).

Step D—Synthesis of Compound 49D

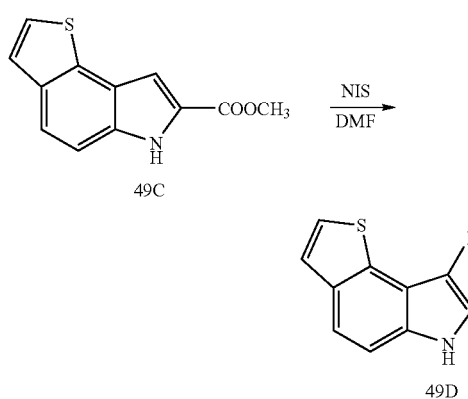

To a solution of compound 49C (1.00 g, 4.33 mmol) in DMF (20 mL) was added N-iodosuccinimide and the resulting reaction was allowed to stir at room temperature for 12 hours. The reaction mixture was concentrated in vacuo and the resulting residue was diluted with water and extracted into EtOAc (300 mL). The combined organic layers were dried (MgSO₄), filtered, concentrated in vacuo and the resulting residue was purified using flash column chromatography on silica gel to provide compound 49D as a colorless solid.

Step E—Synthesis of Compound 49E

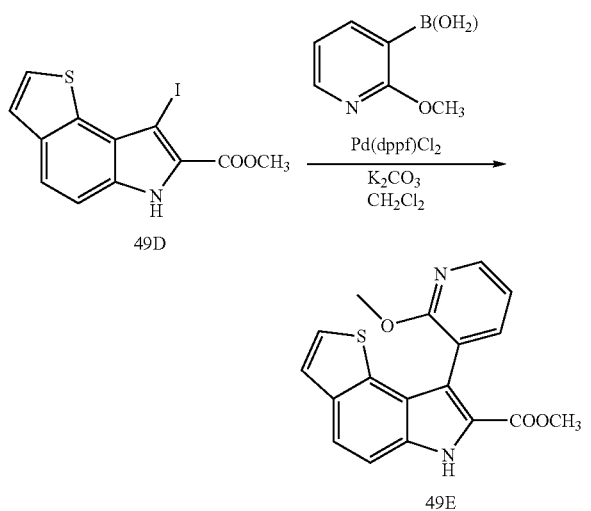

To a solution of compound 49D (1.2 g, 3.35 mmol) in DME (25 mL) was added 2-methoxy-3-pyridyl boronic acid (1.52 g, 10 mmol) and Pd(pddf)₂Cl₂ (324 mg) was allowed to stir at room temperature under nitrogen for 15 minutes. The reaction mixture was then treated with a solution of potassium carbonate (2.77 g, 20.1 mmol) in 25 mL of water and the resulting reaction was heated at 90° C. and allowed to stir at this temperature for 1 hour. The reaction mixture was diluted with EtOAc (300 mL), concentrated in vacuo and the resulting residue was purified using flash column chromatography on silica gel (EtOAc/Hexanes, 0 to 70% EtOAc) to provide compound 49E.

Step F—Synthesis of Compound 49F

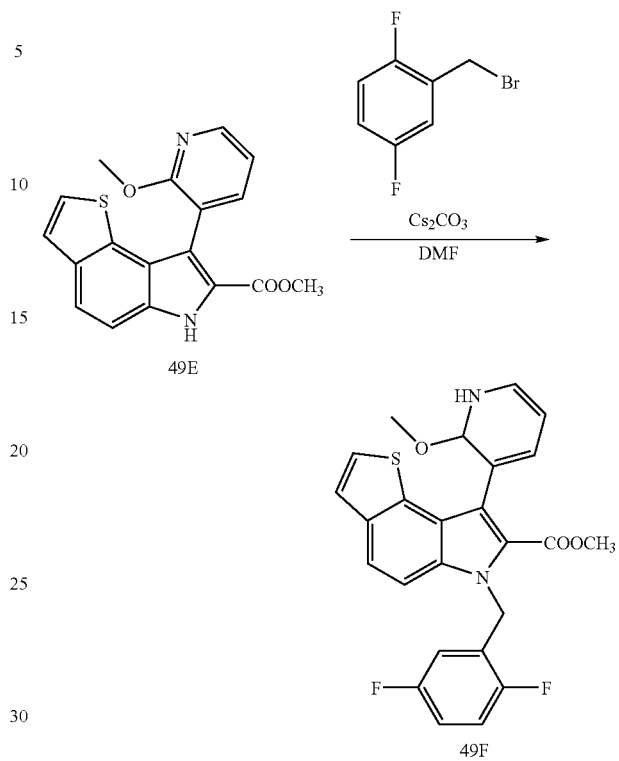

To a solution of compound 49E (300 mg, 0.90 mmol) in DMF (10 mL) was added cesium carbonate (585 mg, 1.80 mmol) and 2,4-difluorobenzyl bromide (372 mg, 1.80 mmol) and the resulting reaction was allowed to stir at room temperature for 12 hours. The reaction mixture was then diluted with EtOAc (250 mL) and the organic layer was washed with brine (2×100 mL), then dried (MgSO₄), filtered, and concentrated in vacuo. The resulting residue was purified a first time using flash column chromatography on silica gel (EtOAc/Hexanes, 0 to 70% EtOAc) and a second time using acetone/CH₂Cl₂ (0 to 50% acetone) as eluent to provide compound 49F as a colorless solid.

Step G—Synthesis of Compound 49

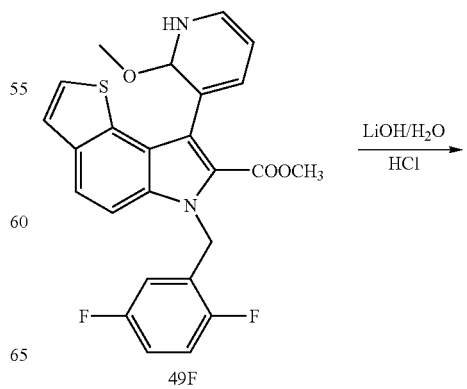

Step A—Synthesis of Compound 52A

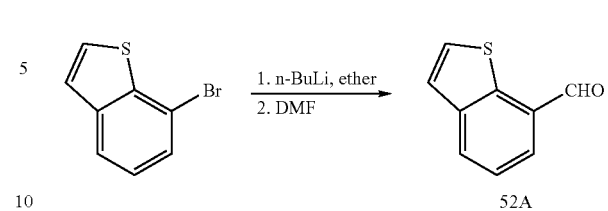

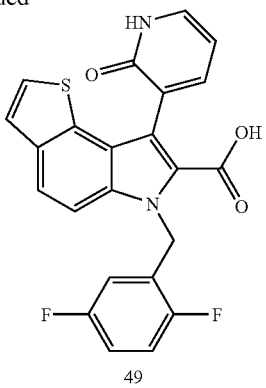

49

A solution of 7-bromothiophene (8.0 g, 37.5 mmol) in ether (50 mL) was cooled to −78° C., then n-BuLi (1.6 M soln in hexanes, 1.0 eq.) was added dropwise and the resulting reaction was allowed to stir at −78° C. for 20 minutes. The reaction mixture was diluted with DMF (dry 5.4 g, 67.4 mmol) and allowed to stir at −78° C. for 1 hour. The reaction mixture was then quenched with water and the resulting solution was extracted into ether. The combined organic layers were dried (MgSO$_4$), filtered, and concentrated in vacuo to provide a crude residue which was purified using flash column chromatography on silica gel to provide compound 52A as a colorless liquid.

To a solution of compound 49F (100 mg, 0.23 mmol) in THF/water/methanol (4 mL each) was added lithium hydroxide (40 mg, 1 mmol) and the resulting reaction was allowed to stir at reflux for 4 hours. The reaction mixture was diluted with aqueous HCl(1N) and extracted with EtOAc (200 mL). The organic layer was dried (MgSO$_4$) then concentrated in vacuo, and the crude residue was diluted with hydrochloric acid (4M solution in dioxane). To the resulting acidic solution was added 1 mL of methanol and the resulting mixture was allowed to stir at 90° C. for 3 hours. The reaction mixture was concentrated in vacuo and the resulting residue was dissolved in EtOAc. To resulting solution was added hexanes, until compound 49 separated out and was filtered and used as it is (45 mg). MS found for $C_{23}H_{14}F_2N_2O_3S$: 437.10 (M+H)$^+$. $^1$H NMR (300 MHz, d$_6$-DMSO) δ 11.76 (bs, 1H), 7.81+7.87 (d, J=8.79 Hz, 1H), 7.62 (s, 1H), 7.61-7.58 (m, 1H), 7.50-7.46 (m, 1H), 7.33-7.28 (m, 1H), 7.16-7.10 (m, 1H), 6.35-6.31 (m, 2H), 5.98 (q, J=16.84 & 40.27 Hz, 2H).

Step B—Synthesis of Compound 52B

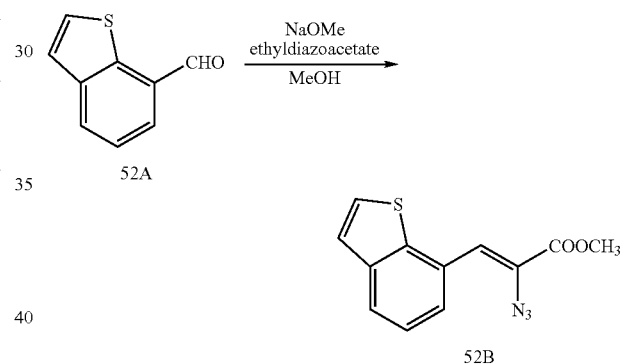

A solution of freshly made sodium methoxide (prepared by dissolving (1.42 g, 62.0 mmol) in methanol (30 mL)) was added dropwise to a solution of ethylazidoacetate (7.99 g, 62 mmol) and 5.1 g (31 mmol) of compound 52A in methanol (30 mL) which was precooled to −20° C. The resulting reaction was allowed to stir at room temperature for 3 hours and was then diluted with EtOAc (200 mL). The organic layer were dried (MgSO$_4$), filtered, and concentrated in vacuo to provide a crude residue which was purified using flash column chromatography on silica gel to provide a yellow solid which was recrystallized from ether and hexanes to provide compound 52B (1.95 g).

Step C—Synthesis of Compound 52C

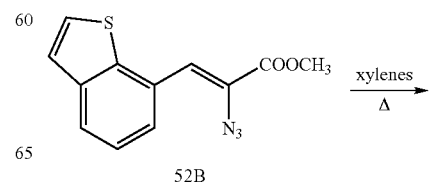

Example 7

Preparation of Compound 52

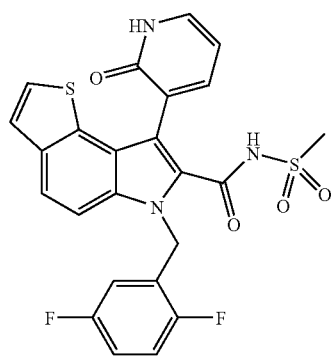

52

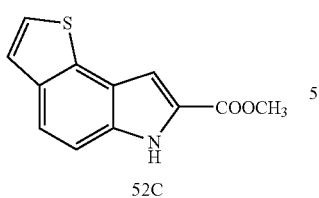

52C

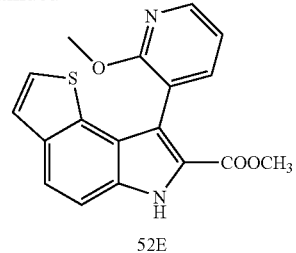

52E

A solution of compound 52B in xylene was heated at reflux for 30 minutes, then cooled to room temperature and concentrated in vacuo until a solid precipitate appeared. The solid was collected to provide compound 52C (1.1 g) as a colorless solid which was used without further purification.

Step D—Synthesis of Compound 52D

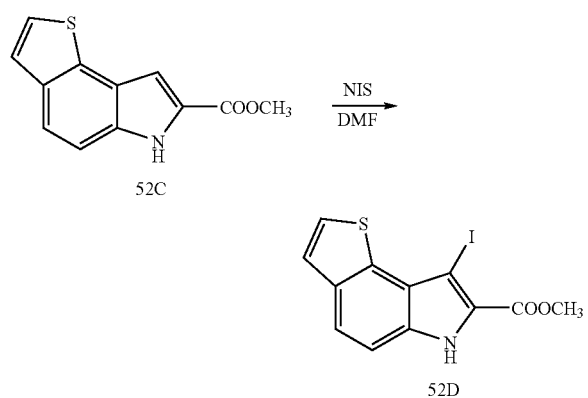

To a solution of compound 52C (1.00 g, 4.33 mmol) in DMF (20 mL) was added N-iodosuccinimide and the resulting reaction was allowed to stir at room temperature for 12 hours. The reaction mixture was then concentrated in vacuo and the resulting residue was diluted with water and extracted into EtOAc (300 mL). The combined organic layers were dried (MgSO$_4$), filtered and concentrated in vacuo and the resulting residue was purified using flash column chromatography on silica gel (EtOAc/Hexanes, 0 to 50% EtOAc) to provide compound 52D as a colorless solid.

Step E—Synthesis of Compound 52E

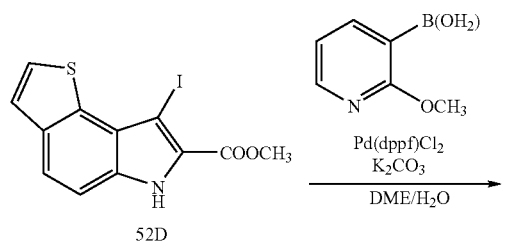

To a solution of compound 52D (1.2 g, 3.35 mmol) in DME (25 mL) was added 2-methoxy-3-pyridyl boronic acid (1.52 g, 10 mmol) and Pd(dppf)$_2$Cl$_2$ (324 mg) and the resulting reaction was allowed to stir under a nitrogen atmosphere at room temperature for 15 minutes. The reaction mixture was then treated with a solution of potassium carbonate (2.77 g, 20.1 mmol) in 25 mL of water and the resulting reaction was heated to 90° C. and allowed to stir at this temperature for 1 hour. The reaction mixture was then diluted with EtOAc (300 mL), concentrated in vacuo and the resulting residue was purified using flash column chromatography on silica gel using EtOAc/Hexanes (0-70% EtOAc) to provide compound 52E.

Step F—Synthesis of Compound 52F

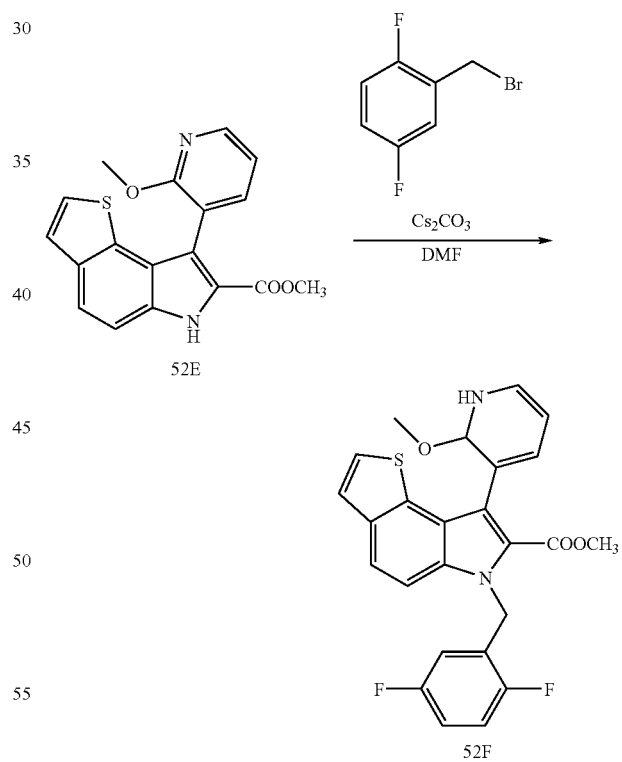

To a solution of compound 52E (300 mg, 0.90 mmol) in DMF (10 mL) was added cesium carbonate (585 mg, 1.80 mmol) and 2,4-difluorobenzyl bromide (372 mg, 1.80 mmol) and the resulting reaction was allowed to stir at room temperature for 12 hours. The reaction mixture was then diluted with EtOAc (250 mL) and washed with brine (2×100 mL). The organic layer were dried (MgSO$_4$), filtered, and concentrated in vacuo to provide a crude residue which was purified first using flash column chromatography on silica gel (EtOAc/Hexanes, 0 to 70% EtOAc) and once again using (acetone/CH$_2$Cl$_2$, 0 to 50% acetone) to provide compound 52F as a colorless solid.

Step G—Synthesis of Compound 52G

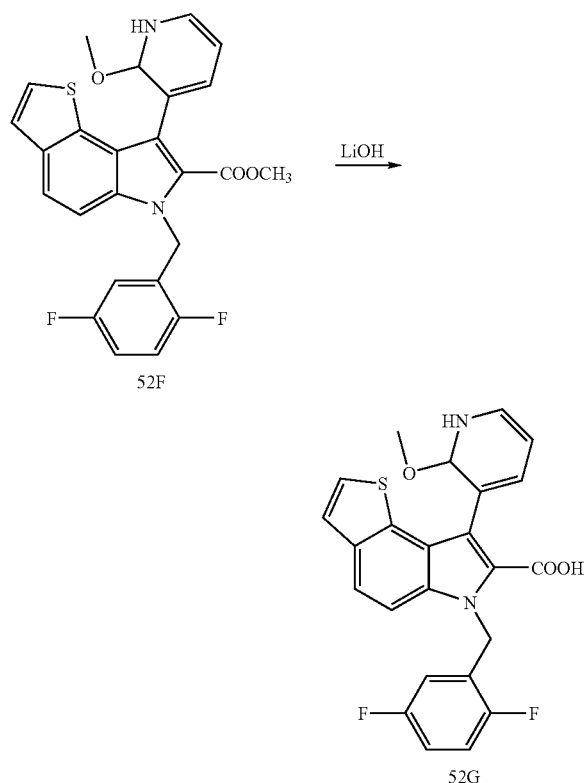

52F

52G

To a solution of compound 52F (100 mg, 0.23 mmol) in THF/water/methanol (4 mL each) was added lithium hydroxide (40 mg, 1 mmol) and the resulting reaction was heated to refluxed and allowed to stir at this temperature for 4 hours. The reaction mixture was diluted with aqueous HCl (1N) and extracted into EtOAc (200 mL). The organic layer was dried (MgSO$_4$), filtered and concentrated in vacuo to provide compound 52G which was used without further purification.

Step H—Synthesis of Compound 52H

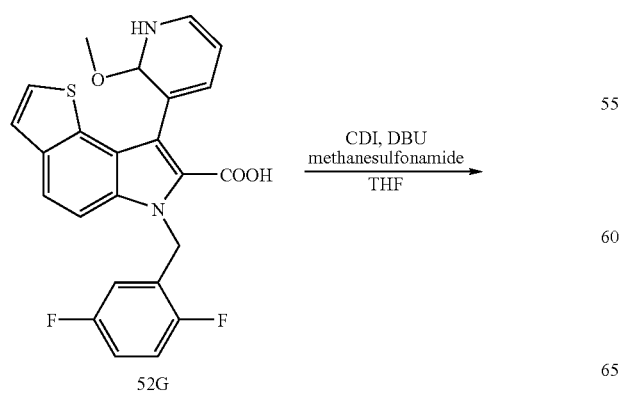

52G

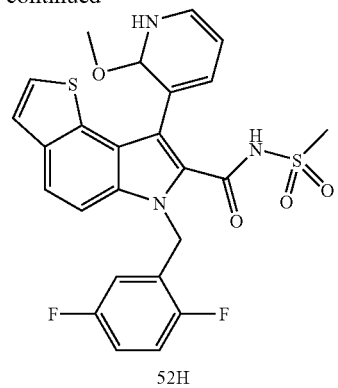

52H

To a solution of compound 52G (170 mg, 0.37 mmol) in 5 mL of THF was added CDI (74 mg, 0.45 mmol) and the resulting reaction was heated to reflux and allowed to stir at this temperature for 2 hours. The reaction mixture was then cooled to room temperature and treated with methanesulfonamide (43 mg, 0.45 mmol) and DBU (100 mg, 0.65 mmol). The resulting reaction was heated to 65° C. and allowed to stir at this temperature for 12 hours, after which time it was diluted with EtOAc (150 mL) and washed with water and aqueous HCl (1N). The combined organic layers were dried (MgSO$_4$), filtered and concentrated in vacuo to provide a crude residue which was purified using flash column chromatography on silica gel (acetone/CH$_2$Cl$_2$, 0 to 50% acetone) to provide compound 52H.

Step I—Synthesis of Compound 52

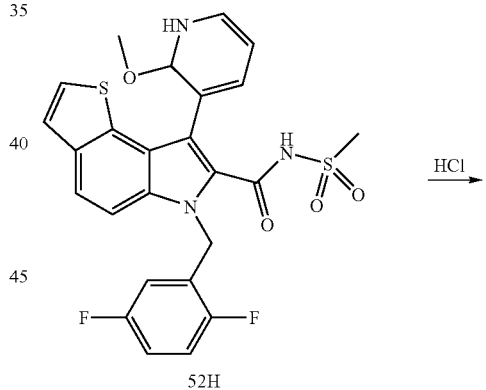

52H

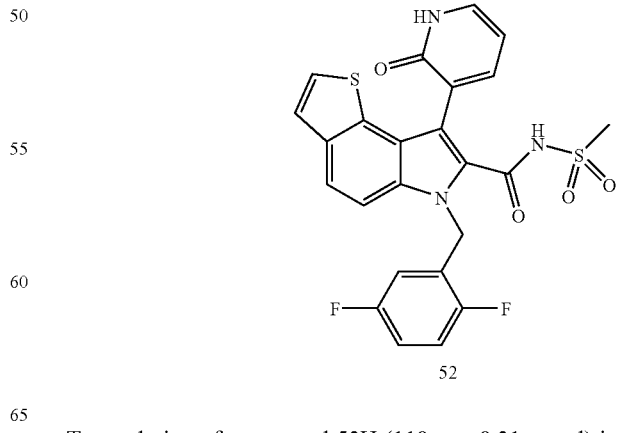

52

To a solution of compound 52H (110 mg, 0.21 mmol) in HCl (4M in dioxane) was added 1 mL of methanol and the resulting reaction was heated to 90° C. and allowed to stir at this temperature for 3 hours. The reaction mixture was concentrated in vacuo and the resulting residue was dissolved in EtOAc, then purified using HPLC (reverse phase) using following conditions to provide compound 52: Column: Waters Delta Pk, P/No 11805, Watman 011805, 300×30 mm (MD) C18, 15 mM, 300 A, 343K16006 (W); Flow Rate: 30 mL/min; Mobile Phase: 30-70% ramp acetonitrile/water over 40 minutes.

For compound 52: MS found for $C_{24}H_{17}F_2N_3O_4S_2$: 513.97 $(M+H)^+$. $^1$H NMR (300 MHz, $d_6$-DMSO) δ 12.77 (bs, 1H), 12.50 (bs, 1H), 7.97 & 7.95 (d, J=6.59 Hz, 1H), 7.84 & 7.82 (d, J=8.79 Hz, 1H), 7.76 (s, 1H), 7.65 & 7.63 (d, J=8.79 Hz, 1H), 7.52-7.47 (m, 2H), 7.34-7.28 (m, 1H), 7.19-7.13 (m, 1H), 6.66-6.59 (m, 2H), 5.82 (s, 2H), 3.25 (s, 3H).

Example 8

Preparation of Compound 51

Step A—Synthesis of Compound 51A

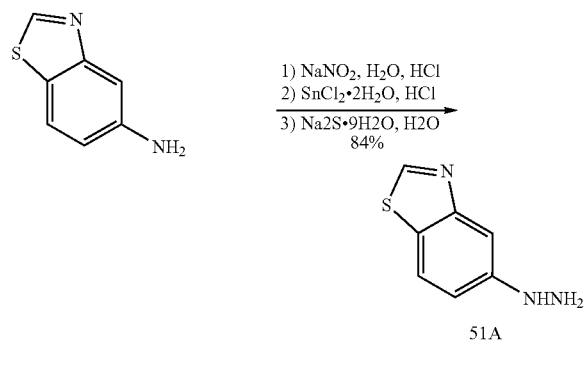

To a suspension of 1,3-benzothiazol-5-amine (16 g, 107 mmol) in concentrated HCl (180 mL) at −10° C. was added very slowly a solution of sodium nitrite (7.66 g, 111 mmol) in water (35 mL). After addition, the mixture was vigorously allowed to stir at −5° C. to 0° C. for 0.5 hours. To the reaction mixture was then added dropwise a solution of tin(II) chloride (81.0 g, 359 mmol) in concentrated HCl (60 mL). The internal temperature was maintained at or below −5° C. during the addition and the resulting suspension was allowed to stir at −10° C. to 20° C. for about 1.5 hours. The precipitate was filtered off and the flask was rinsed with a small amount of water. The collected solids were dissolved into water (100 mL), and to the resulting solution was added $Na_2S.9H_2O$ (39 g). The aqueous layer was adjusted to pH 11 using 50% aqueous sodium hydroxide solution (4 mL). The solids were removed by filtration and washed with water. The aqueous layer was extracted with THF/ethyl acetate (1:2) (2×200 mL). The combined organic layer was dried (magnesium sulfate), filtered, and concentrated in vacuo to provide compound 51A (14.8 g, 84%), which was used without further purification.

Step B—Synthesis of Compound 51B

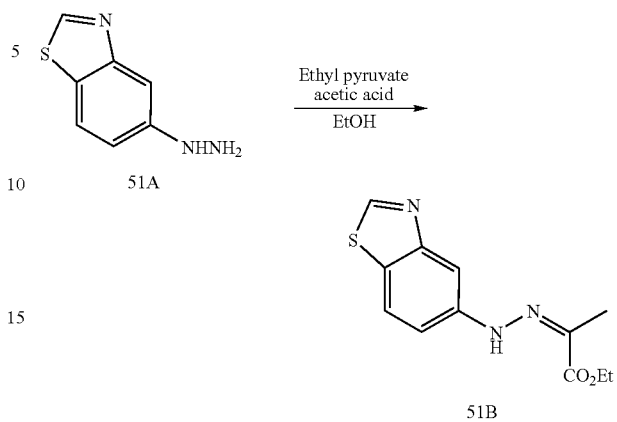

To a solution of compound 51A (14.8 g, 89.6 mmol) in ethanol (300 mL) at room temperature, was added ethyl pyruvate (15 mL, 137 mmol) and acetic acid (1.35 mL). The reaction was heated to reflux and allowed to stir at this temperature for 2.5 hours. After being cooled to room temperature, the reaction mixture was concentrated in vacuo and the resulting residue was diluted with ethyl acetate (300 mL) and 0.1 N aqueous sodium carbonate solution (300 mL). The separated organic layer was dried (magnesium sulfate), filtered and concentrated in vacuo to provide a crude residue which was purified using flash chromatography on silica gel (EtOAc:Hexanes, 0 to 50% EtOAc) to provide compound 51B (22.7 g, 96%).

Step C—Synthesis of Compound 51C

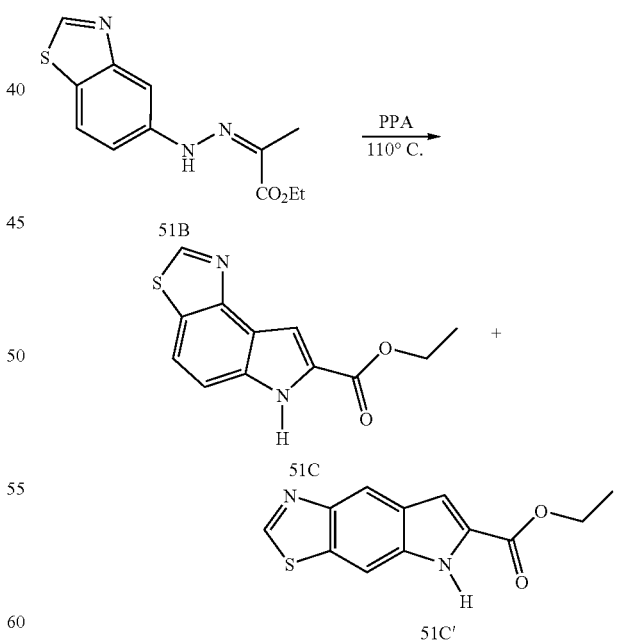

Compound 51B (22 g, 83.6 mmol) was ground into a powder, then was mixed with polyphosphoric acid (180 g). The bi-phasic mixture was vigorously allowed to stir at 110° C. for 1.5 h, then cooled to room temperature and poured into ice water. The aqueous layer of the mixture was basified to pH 11 using aqueous ammonium hydroxide (37 N). The resulting mixture was extracted with 300 mL of ethyl acetate/THF (2:1) four times. The combined organics were dried (magnesium sulfate), filtered, and concentrated in vacuo to provide a crude residue which contained compounds 51C and 51C'. The crude residue was purified using flash chromatography on silica gel (EtOAc:Hexanes, 0 to 50% EtOAc) to provide compound 51C (2.55 g, 12%). $^1$H NMR (500 MHz, d$_6$-DMSO): δ 12.28 (s, 1H), 7.86 (d, J=8.8 Hz, 1H), 7.52 & 7.50 (dd, J=0.6 Hz & 8.5 Hz, 1H), 7.40 & 7.39 (dd, J=0.9 Hz & 2.2 Hz, 1H), 4.37 (q, J=6.9 Hz & 7.3 Hz, 2H), 2.85 (s, 3H), 1.36 (t, J=6.9 Hz, 3H). $^{13}$C NMR (125 MHz, d$_6$-DMSO): δ 166.4, 161.0, 136.3, 126.9, 126.7, 120.5, 117.8, 110.8, 109.1, 105.1, 60.4, 19.6, 14.2. HRMS calcd for $C_{13}H_{12}N_2O_2S$: 261.0698 (M+H)$^+$. Found: 261.0701.

Step D—Synthesis of Compound 51D

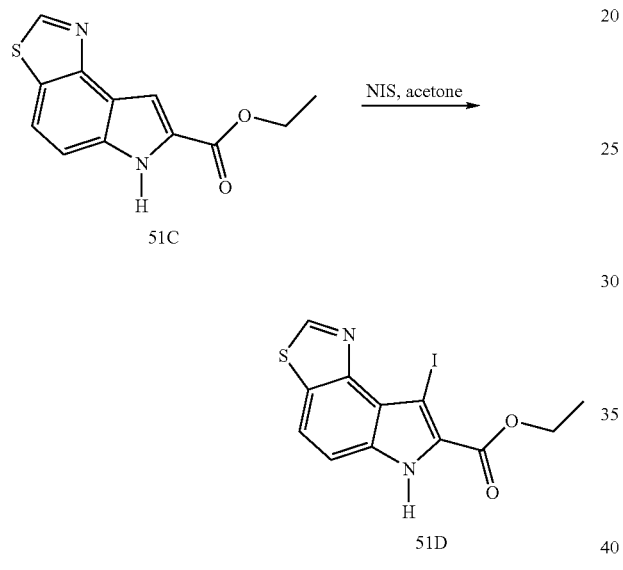

To a solution of compound 51C (2.55 g, 10.4 mmol) in acetone (400 mL) at room temperature, was added N-iodosuccinimide (15.8 mmol). The resulting reaction was allowed to stir at room temperature for 18 hours, then concentrated in vacuo, and the resulting residue was dissolved with ethyl acetate (150 mL). The organic layer was collected and washed with saturated aqueous sodium thiosulfate solution (80 mL). The aqueous layer was then extracted with ethyl acetate (2×100 mL) and the combined organic layers were dried (magnesium sulfate), filtered and concentrated in vacuo to provide compound 51D (quant.), which was used without further purification. $^1$H NMR (500 MHz, d$_6$-DMSO) δ 12.66 (s, 1H), 9.49 (s, 1H), 8.06 & 8.04 (dd, J=3.47 Hz & 8.83 Hz, 1H), 7.66 & 7.65 (dd, J=3.15 Hz & 8.51 Hz, 1H), 4.40 (q, J=4.42 Hz & 4.39 Hz, 2H), 1.40 (dt, J=3.47 Hz & 7.09 Hz, 3H); $^{13}$C NMR (125 MHz, d$_6$-DMSO): δ 160.25, 154.74, 146.47, 146.25, 135.83, 127.14, 126.49, 125.64, 119.00, 111.86, 60.71, 14.19. M.S. found for $C_{12}H_9IN_2O_2S$: 373.17 (M+H)$^+$.

Step E—Synthesis of Compound 51E

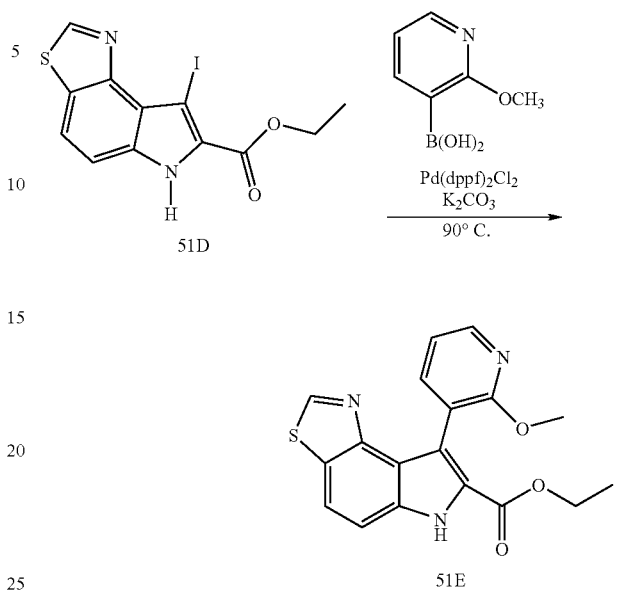

To a solution of compound 51D (10.4 mmol) in 1,2-dimethoxyethane (225 mL) was added Pd(dppf)$_2$Cl$_2$ (1.05 mmol) and the resulting solution was degassed using argon bubbling for 5 minutes. The degassed solution was then heated to 90° C. and allowed to stir for 0.5 hours. In a second flask, 2-methoxy-3-pyridine boronic acid (14.6 mmol) and potassium carbonate (52.1 mmol) were dissolved into dimethoxyethane (75 mL) and water (75 mL) and the resulting solution was degassed with argon bubbling for 5 minutes, then the contents of the second flask were added to the solution containing compound 51D. The resulting bi-phasic mixture was heated to 90° C. and vigorously allowed to stir at this temperature. After 4 hours the reaction was cooled to room temperature and quenched by addition of a solution of sodium sulfite (3.6 g) in water (80 mL) at room temperature. Ethyl acetate (200 mL) and water (100 mL) were added to the quenched reaction and the layers were separated. The aqueous layer was extracted with ethyl acetate (2×200 mL) and the combined organic layers was dried (magnesium sulfate), filtered and concentrated in vacuo to provide compound 51E (100%). NMR (500 MHz, d$_6$-DMSO): δ 12.41 (s, 1H), 9.21 (s, 1H), 8.19 & 8.18 (ddd, J=0.63 Hz, 1.89 Hz & 5.04 Hz, 1H), 7.99 (d, J=8.83 Hz, 1H), 7.72 (s, 1H), 7.66 (d, J=8.83 Hz, 1H), 7.04 (q, J=5.04 Hz & 2.21 Hz, 1H), 4.17 (q, J=7.25 Hz & 6.94 Hz, 2H), 3.69 (s, 3H), 1.09 (t, J=7.09 Hz, 3H). $^{13}$C NMR (125 MHz, d$_6$-DMSO): δ 161.42, 160.80, 154.43, 152.61, 146.80, 145.17, 140.71, 135.05, 126.34, 123.64, 120.32, 118.25, 116.36, 116.02, 111.75, 60.10, 39.00, 13.78. M.S. found for $C_{18}H_{15}N_3O_3S$: 354.04 (M+H)$^+$.

Step F—Synthesis of Compound 51F

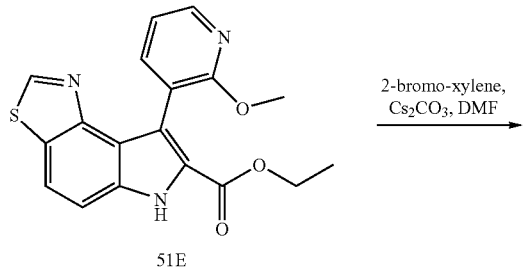

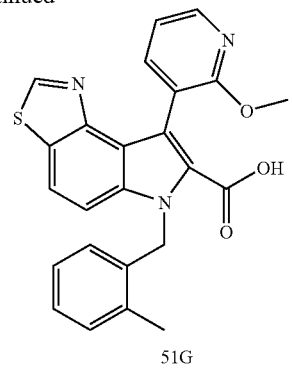

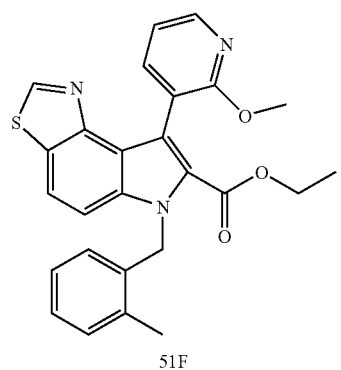

To a solution of compound 51E (0.71 mmol) in DMF (25 mL) at room temperature, was added 2-bromo-xylene (1.00 mmol) and cesium carbonate (1.23 mmol). The resulting suspension was allowed to stir at room temperature for 18 hours, then ethyl acetate (200 mL) and water (100 mL) were added to the reaction mixture, and the layers were separated. The aqueous layer was extracted with ethyl acetate (2×100 mL). The combined organic layer was washed with water (2×100 mL). The separated organic layer was dried (magnesium sulfate), filtered and concentrated in vacuo to provide a crude residue which was purified using flash chromatography to provide compound 51F (0.21 g, 65%). M.S. found for $C_{26}H_{23}N_3O_3S$: 458.11 $(M+H)^+$.

Step G—Synthesis of Compound 51G

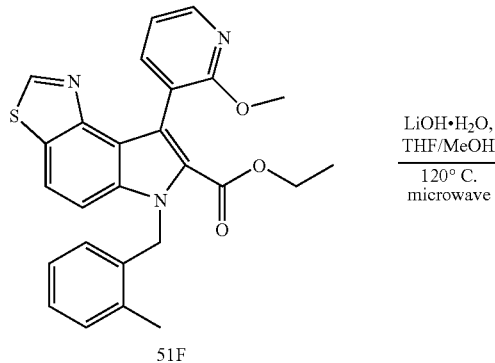

To a solution of compound 51F (0.21 g, 0.45 mmol) in tetrahydrofuran (2 mL) and methanol (3 mL) was added lithium hydroxide monohydrate (60 mg, 1.43 mmol). The resulting suspension was allowed to stir at room temperature for 5 minutes before being placed in microwave reactor for 20 minutes (120° C., high power). The reaction was then concentrated in vacuo and ethyl acetate (50 mL) and tetrahydrofuran (50 mL) were added to the residue. The aqueous layer was acidified to pH=1 by adding 5% phosphoric acid, and the layers were separated. The aqueous layer was further extracted with ethyl acetate (2×50 mL). The combined organic layer was dried (magnesium sulfate) and filtered and concentrated in vacuo to provide compound 51G (100%). M.S. found for $C_{24}H_{19}N_3O_3S$: 430.10 $(M+H)^+$.

Step H—Synthesis of Compound 51H

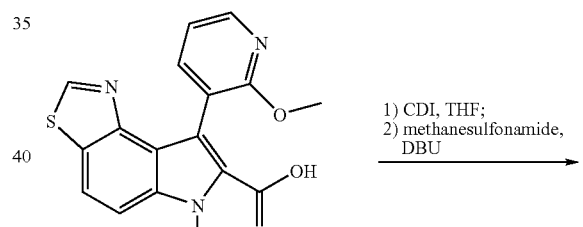

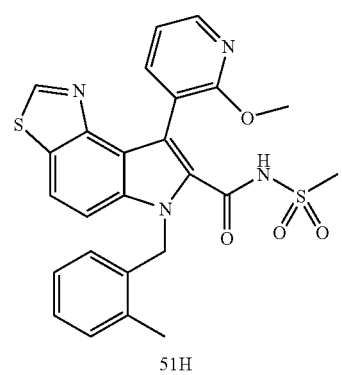

To a solution of compound 51G (132 mg, 0.31 mmol) in tetrahydrofuran (5 mL) was added carbonyl diimidazole (60 mg). The resulting suspension was refluxed at 75° C. for 1 hour, and then cooled to room temperature before adding methanesulfonamide (70 mg, 0.74 mmol) and 1,8-diazabicyclo(5.4.0) undec-7-ene (0.11 mL). The resulting reaction mixture was allowed to stir at room temperature for 48 hours. Ethyl acetate (80 mL), tetrahydrofuran (10 mL) and 1% aqueous phosphoric acid (50 mL) were added to the reaction mixture, and the layers were separated. The aqueous layer was extracted with ethyl acetate (2×50 mL). The combined organic layer was dried (magnesium sulfate), filtered and concentrated in vacuo. The crude product was purified using flash chromatography on silica gel to provide compound 51H (106 mg, 68%).

Step I—Synthesis of Compound 51

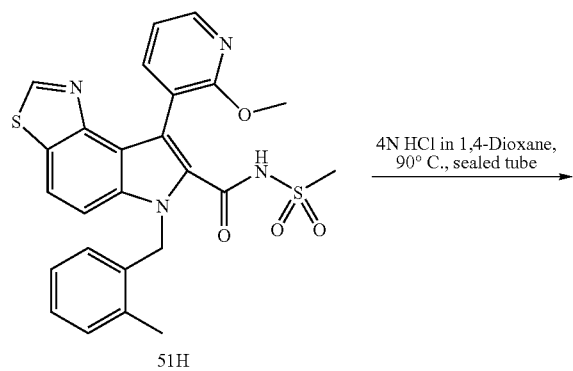

A solution of compound 51H (103 mg, 0.20 mmol) in 4N HCl (4.5 mL in 1,4-dioxane) was placed in a sealed tube, heated to 90° C., and allowed to stir at this temperature for 3 hours. The reaction mixture was then cooled to room temperature and concentrated in vacuo. The crude product was purified using reverse phase HPLC to provide compound 51 (35 mg, 35%). $^1$H NMR (500 MHz, d$_6$-DMSO): δ 12.72 (s, 1H), 12.57 (s, 1H), 9.32 (s, 1H), 8.04 (d, J=8.83 Hz, 1H), 7.98 (d, J=6.62 Hz, 1H), 7.68-7.64 (m, 2H), 7.21 (d, J=7.57 Hz, 1H), 7.12 (t, J=7.41 Hz, 1H), 6.98 (t, J=7.57 Hz, 1H), 6.59 (t, J=6.62 Hz, 1H), 6.23 (d, J=7.88 Hz, 1H), 5.79 (s, 2H), 3.09 (s, 3H), 2.40 (s, 3H). $^{13}$C NMR (125 MHz, d$_6$-DMSO): δ 163.64, 162.74, 160.88, 155.03, 146.60, 142.59, 136.12, 135.32, 134.60, 132.27, 129.89, 129.01, 127.38, 127.07, 126.72, 125.92, 124.64, 119.03, 114.42, 110.27, 106.96, 73.69, 45.91, 18.71. M.S. found for C$_{24}$H$_{20}$N$_4$O$_4$S$_2$: 493.06 (M+H)$^+$.

Example 9

Preparation of Compound 56

Step A—Synthesis of Compound 56A

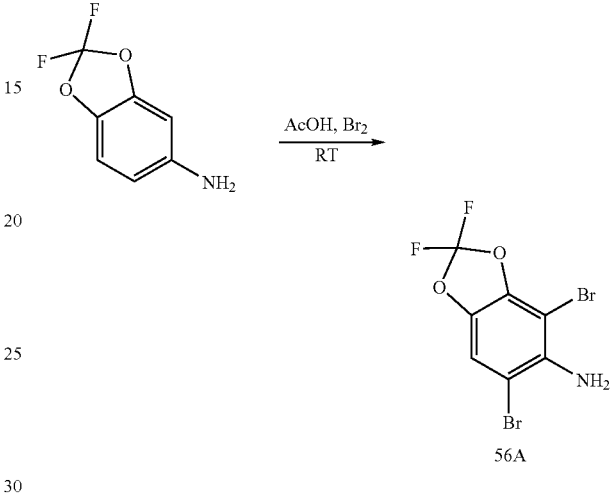

Bromine (11.3 mL) was added into a solution of 5-amino-2,2-difluorobenzodioxole (Maybridge, 5.0 g, 28.9 mmol) in acetic acid (150 mL). The mixture was allowed to stir at room temperature for 1 hour, then concentrated in vacuo. The resulting residue was diluted with methylene chloride (50 mL) and the solid was filtered, washed with methylene chloride (4×15 mL) and dried under vacuum to provide compound 56A (8.2 g, 86%) as a yellow solid. M.S. found for C$_7$H$_3$Br$_2$F$_2$NO$_2$: 331.93 (M+H)$^+$.

Step B—Synthesis of Compound 56B

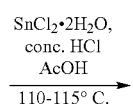

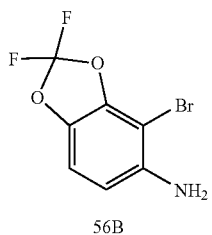

To a suspension of compound 56A (4.48 g, 13.5 mmol) in acetic acid (glacial, 20 mL) and concentrated HCl (16.0 mL) was added stannous chloride (3.36 g, 14.9 mmol). The resulting suspension was heated to 110-115° C. and allowed to stir at this temperature for 30 minutes. The reaction mixture was cooled to room temperature and concentrated in vacuo. To the residue were added methylene chloride (80 mL) and aqueous 1N sodium hydroxide (80 mL), and the layers were separated. The aqueous layer was extracted with methylene chloride (2×80 mL). The combined organic layer was dried (magnesium sulfate), filtered, and concentrated in vacuo to provide compound 56B (2.68 g, 79%) as a white solid. $^1$H NMR (500 MHz, d$_6$-DMSO): δ 7.12 (d, J=8.5 Hz, 1H), 6.54 (d, J=8.8 Hz, 1H), 5.48 (s, 2H). $^{13}$C NMR (125 MHz, d$_6$-DMSO): δ 143.7, 141.6, 133.1, 130.7, 109.5, 108.4, 87.5. M.S. found for $C_7H_4BrF_2NO_2$: 254.00 (M+H)$^+$.

Step C—Synthesis of Compound 56C

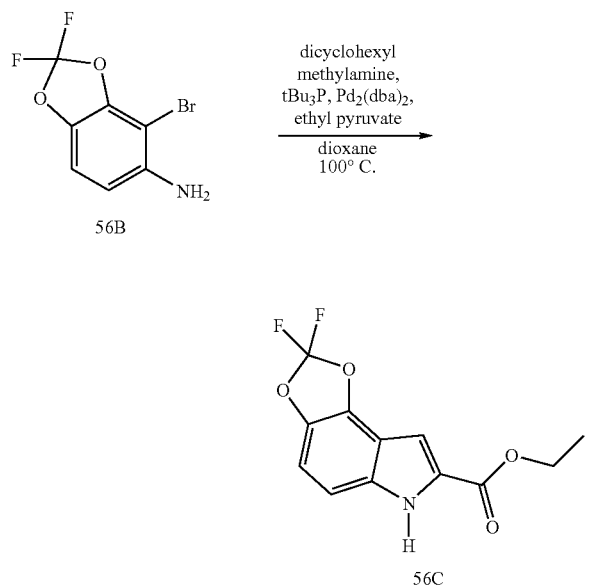

Compound 56B (2.66 g, 10.6 mmol) was dissolved into anhydrous dioxane (100 mL). To the solution was added dicyclohexyl methylamine (14.8 mL, 69.1 mmol), tri-tert-butyl phosphine (0.83 g, 4.10 mmol), Pd$_2$(dba)$_3$ (971 mg, 1.06 mmol) and ethyl pyruvate (4.60 mL, 42.0 mmol). The mixture was heated to 100° C. and allowed to stir for 18 hours. The reaction mixture was cooled to room temperature, and was diluted with methylene chloride (300 mL) and aqueous 1N HCl solution (300 mL). The layers were separated, and the aqueous layer was extracted with methylene chloride (2×150 mL). The combined organic layer was dried (magnesium sulfate), filtered and concentrated in vacuo. The crude product was purified using flash chromatography on silica gel to provide compound 56C (1.79 g, 62%). $^1$H NMR (500 MHz, d$_6$-DMSO): δ 12.40 (s, 1H), 7.38 (d, J=9.1 Hz, 1H), 7.31 & 7.30 (dd, J=0.9 Hz & 8.8 Hz, 1H), 7.17 (d, J=2.2 Hz, 1H), 4.37 (q, J=6.9 Hz & 7.3 Hz, 2H), 1.35 (t, J=7.1 Hz, 3H). $^{13}$C NMR (125 MHz, d$_6$-DMSO): δ 160.5, 136.1, 135.8, 134.4, 133.6, 130.1, 111.6, 108.1, 107.4, 101.6, 60.9, 14.1.

Step D—Synthesis of Compound 56D

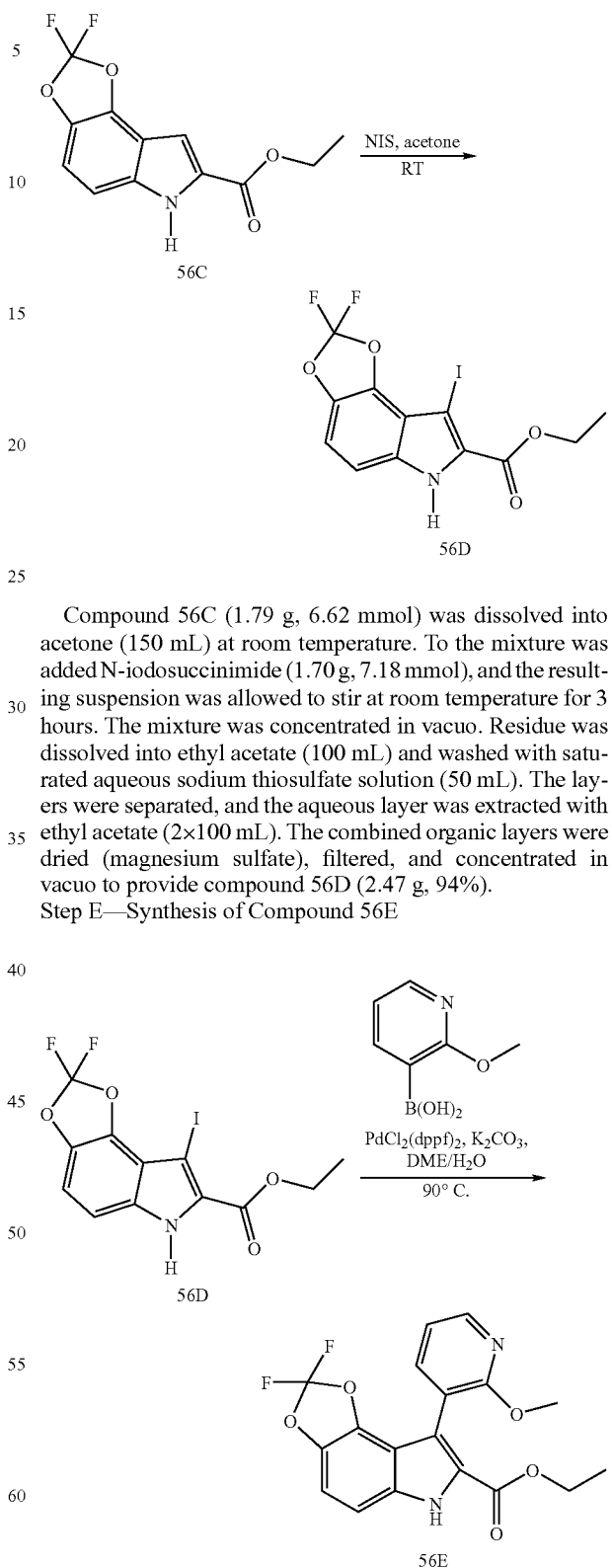

Compound 56C (1.79 g, 6.62 mmol) was dissolved into acetone (150 mL) at room temperature. To the mixture was added N-iodosuccinimide (1.70 g, 7.18 mmol), and the resulting suspension was allowed to stir at room temperature for 3 hours. The mixture was concentrated in vacuo. Residue was dissolved into ethyl acetate (100 mL) and washed with saturated aqueous sodium thiosulfate solution (50 mL). The layers were separated, and the aqueous layer was extracted with ethyl acetate (2×100 mL). The combined organic layers were dried (magnesium sulfate), filtered, and concentrated in vacuo to provide compound 56D (2.47 g, 94%).

Step E—Synthesis of Compound 56E

Compound 56D (2.46 g, 6.21 mmol) was dissolved into 1,2-dimethoxyethane (75 mL). To the mixture was added PdCl$_2$(dppf)$_2$ (510 mg, 0.63 mmol). The resulting suspension was heated to 90° C. and was de-gassed with nitrogen bubbling for 15 minutes. In a second flask, 2-methoxy-3-pyridine boronic acid (1.15 g, 7.52 mmol) and potassium carbonate (4.30 g, 31.1 mmol) were dissolved into dimethoxyethane (25 mL) and water (25 mL). The mixture was de-gassed with nitrogen bubbling for 5 minutes before being transferred to the first flask. The resulting mixture was vigorously allowed to stir at 90° C. for 3.5 h, then cooled to room temperature. A solution of sodium sulfite (4.3 g) in water (57 mL) was then added to the mixture, followed by ethyl acetate (150 mL), and the layers were separated. The aqueous layer was extracted with ethyl acetate (2×100 mL) and the combined organic layers were dried (magnesium sulfate), filtered, and concentrated in vacuo. The resulting residue was purified using flash chromatography on silica gel to provide compound 56E (0.96 g, 41%). M.S. found for $C_{18}H_{14}F_2N_2O_5$: 377.02 $(M+H)^+$.

Step F—Synthesis of Compound 56F

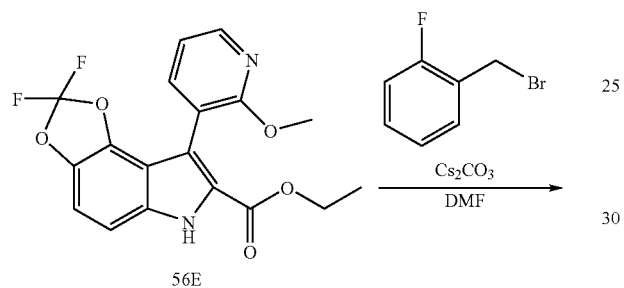

56E

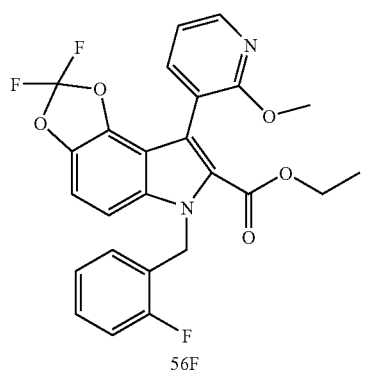

56F

Compound 56E (250 mg, 0.66 mmol) was dissolved into N,N-dimethyl formamide (20 mL) at room temperature. To the mixture were added 2-fluorobenzyl bromide (175 mg, 0.92 mmol) and cesium carbonate (325 mg, 1.00 mmol). The resulting suspension was allowed to stir at room temperature for 18 hours. Ethyl acetate (200 mL) and water (100 mL) were added to the reaction mixture, and then the layers were separated. The aqueous layer was extracted with ethyl acetate (2×50 mL). The combined organic layer was washed with water (2×50 mL), and then was dried (magnesium sulfate), filtered and concentrated in vacuo to provide compound 56F (0.27 g, 84%). M.S. found for $C_{25}H_{19}F_3N_2O_5$: 485.10 $(M+H)^+$.

Step G—Synthesis of Compound 56G

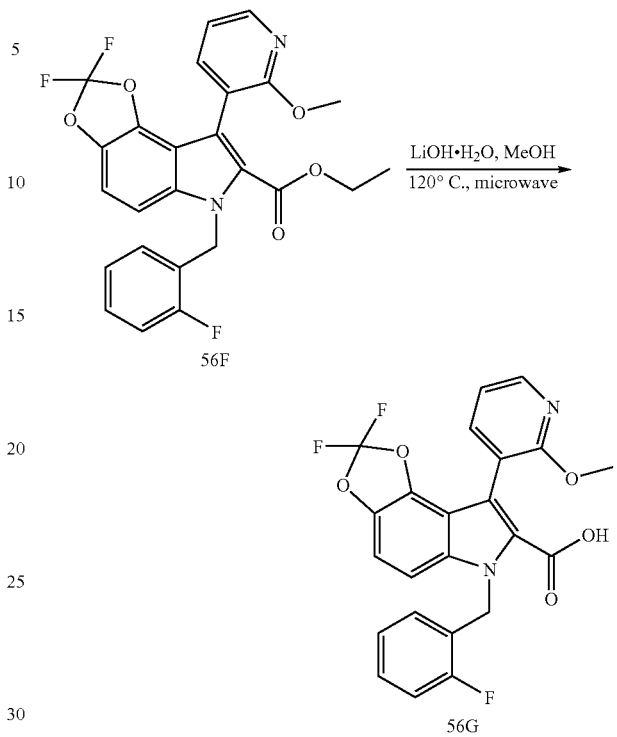

To a solution of compound 56F (0.55 mmol) in methanol (5 mL) was added lithium hydroxide monohydrate (2.19 mmol) and the resulting suspension was allowed to stir at room temperature for 5 minutes before being placed in a microwave reactor for 20 min (120° C., high power). The mixture was then concentrated in vacuo and the resulting residue was diluted with ethyl acetate (50 mL) and tetrahydrofuran (50 mL). The aqueous layer was acidified to pH 1 using 1N HCl solution, and the layers were separated. The aqueous layer was further extracted with ethyl acetate (2×50 mL), and the combined organic layer was dried (magnesium sulfate), filtered and concentrated in vacuo to provide compound 56G (100%). M.S. found for $C_{23}H_{15}F_3N_2O_5$: 457.09 $(M+H)^+$.

Step H—Synthesis of Compound 56H

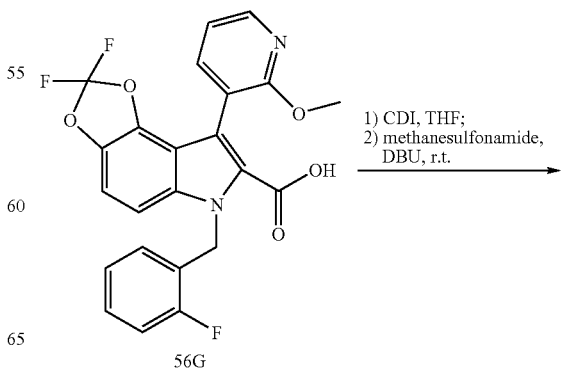

56G

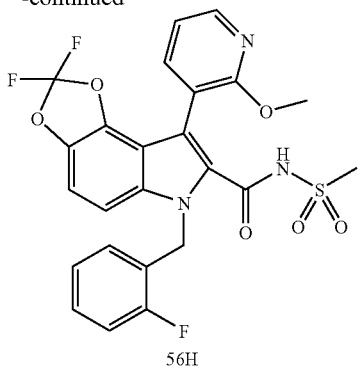

56H

Compound 56G (143 mg, 0.31 mmol) was dissolved into tetrahydrofuran (5.0 mL) at room temperature. To the mixture was added carbonyl diimidazole (65 mg, 0.40 mmol). The suspension was refluxed at 75° C. for 1 h, and then cooled to room temperature before adding methanesulfonamide (60 mg, 0.63 mmol) and 1,8-diazabicyclo(5.4.0) undec-7-ene (1.00 mmol). The resulting reaction mixture was allowed to stir at room temperature for 68 hours. Ethyl acetate (80 mL), tetrahydrofuran (10 mL) and 1% aqueous phosphoric acid (50 mL) were added to the reaction mixture, and the layers were separated. The aqueous layer was extracted with ethyl acetate (2×50 mL). The combined organic layer was dried (magnesium sulfate), filtered and concentrated in vacuo to provide compound 56H (113 mg, 68%). M.S. found for $C_{24}H_{18}F_3N_3O_6S$: 534.04 $(M+H)^+$.

Step I—Synthesis of Compound 56

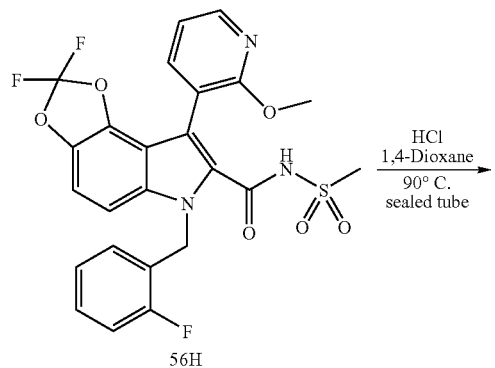

A solution of Compound 56H (65 mg, 0.12 mmol) in HCl (4N in dioxane, 5.0 mL) in a sealed tube was heated to 90° C. and allowed to stir at this temperature for 2 hours. The reaction mixture was then cooled to room temperature, then concentrated in vacuo to provide a crude residue which was purified using reverse phase HPLC to provide compound 56 (44 mg, 69%). $^1$H NMR (500 MHz, $d_6$-DMSO): δ 12.77 (s, 1H), 12.49 (s, 1H), 7.82 & 7.81 (dd, J=1.58 Hz & 6.94 Hz, 1H), 7.61 (t, J=5.20 Hz, 1H), 7.50 (d, J=8.83 Hz, 1H), 7.45 (d, J=9.14 Hz, 1H), 7.33 (q, J=6.31 Hz & 7.57 Hz, 1H), 7.22 (t, J=9.46 Hz, 1H), 7.09 (t, J=7.57 Hz, 1H), 6.89 (t, J=7.72 Hz, 1H), 6.56 (t, J=6.62 Hz, 1H), 5.76 (s, 2H), 3.23 (s, 3H). $^{13}$C NMR (125 MHz, $d_6$-DMSO): δ 161.81, 160.59, 158.65, 157.27, 145.62, 143.33, 137.17, 135.62, 135.24, 134.57, 129.54, 128.67, 127.17, 124.10, 123.99, 123.79, 115.23, 111.32, 107.34, 106.68, 106.45, 42.10, 40.95. M.S. found for $C_{23}H_{16}F_3N_3O_6S$: 520.04 $(M+H)^+$.

Example 10

Preparation of Compound 59

Step A—Synthesis of Compound 59A

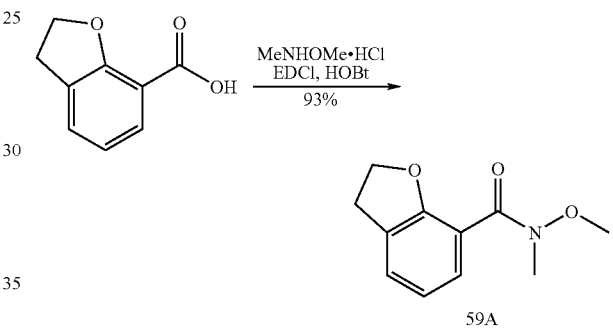

A suspension of 2,3-dihydro-benzofuran-7-carboxylic acid, (TCI, 20.0 g, 121.8 mmol) in 600 mL of dry acetonitrile was cooled to 0° C. and treated with N,O-dimethylhydroxylamine hydrochloride (14.25 g, 146.1 mmol). The reaction was allowed to stir for 10 minutes and EDCI (24.6 g, 158.3 mmol) was added, followed by HOBT (3.2 g, 24.2 mmol) and the resulting mixture was allowed to stir for 5 minutes. Triethylamine (365.4 mmol) was then added and the reaction mixture was allowed to stir for 18 hours at room temperature, then diluted with aqueous 1N HCl (250 mL) and extracted with ethyl acetate (1.0 L). The organic layer was sequentially washed with aqueous 10% potassium carbonate (200 mL), aqueous 1N HCl (200 mL), and brine (200 mL). The organic layer was then dried over magnesium sulfate, filtered and concentrated in vacuo to provide compound 59A (23.37 g, 93%) as a colorless oil. M.S. found for $C_{11}H_{13}NO_3$: 230.11 $(M+Na)^+$.

Step B—Synthesis of Compound 59B

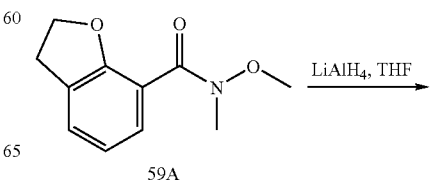

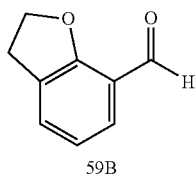

59B

A suspension of lithium aluminum hydride (pellets, 5.56 g, 146.5 mmol) in 500 mL of dry THF was allowed to stir at 55° C. for 18 hours under anhydrous atmosphere, then cooled to 0° C., and a solution of compound 59A (23.37 g, 112.7 mmol) in 500 mL of dry THF was added over 45 minutes. The reaction mixture was allowed to stir at 0° C. for 30 minutes, then quenched by careful addition of aqueous 20% sodium hydrogen sulfate until gas evolution stopped. Additional aqueous 20% sodium hydrogen sulfate (approx. 5 mL) was added, and the resulting solution was vigorously allowed to stir for 15 minutes. The reaction mixture was diluted with ether (500 mL) and hexanes (500 mL) and filtered through a short path of celite. The filtrate was concentrated in vacuo to afford a crude residue which was purified using medium pressure liquid chromatography (Biotage 75-M silica gel column, gradient: 0 to 30% ethyl acetate in hexanes) to provide compound 59B (9.00 g, 54%) as a white solid. $^1$H NMR (400 MHz, d$_6$-DMSO): δ 10.10 (s, 1H), 7.51 (q, J=7.32 Hz & 5.13 Hz, 2H), 6.95 (t, J=7.69 Hz, 1H), 4.69 (t, J=8.79 Hz, 2H), 3.22 (t, J=8.42 Hz, 2H).

Step C—Synthesis of Compound 59C

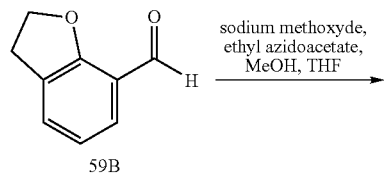

59B

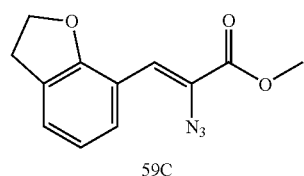

59C

A solution of freshly prepared sodium methoxyde in methanol (2.5 eq, prepared by dissolving 1.94 g of sodium in 80 mL of methanol) was added dropwise (over 20 minutes) to a cooled (−20° C., internal temperature) solution of compound 59B (5.0 g, 33.74 mmol) and ethyl azidoacetate (10.9 g, 84.36 mmol) in 20 mL of dry methanol and 20 mL of dry THF. The addition was carried such that the internal reaction temperature was not permitted to rise above −10° C. The reaction was then allowed to stir at −10° C. for 1 hour, then allowed to warm to room temperature over 1 hour. The reaction mixture was then allowed to stir at room temperature for 1 hour (a white precipitate formed), and was then quenched with aqueous saturated ammonium chloride solution (10 mL). The resulting solution mixture was partitioned between ethyl acetate (500 mL) and water (100 mL). The organic layer was washed with brine (80 mL), dried over magnesium sulfate, filtered, and concentrated in vacuo. The resulting residue was purified using column chromatography on silica gel (Biotage 75-M column; gradient: 0 to 25% ethyl acetate in hexanes) to provide compound 59C (4.20 g, 52%) as a slightly yellow solid. $^1$H NMR (400 MHz, d$_6$-DMSO): δ 7.96 (d, J=8.06 Hz, 1H), 7.24 (d, J=6.59 Hz, 1H), 7.01 (s, 1H), 6.88 (t, J=7.69 Hz, 1H), 4.58 (t, J=8.79 Hz, 2H), 3.84 (s, 3H), 3.21 (t, J=8.79 Hz, 2H).

Step D—Synthesis of Compound 59D

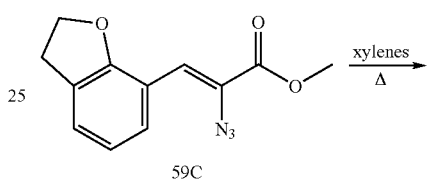

59C

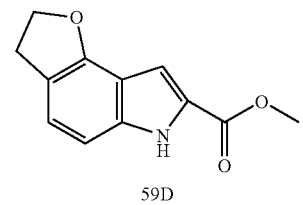

59D

A solution of compound 59C (4.0 g, 16.31 mmol) in 60 mL of xylenes was heated to 150° C. and allowed to stir at this temperature for 10 minutes, then was cooled to room temperature, during which time a white solid formed. The suspension was stored as −20° C. in freezer for 1 hour, then filtered to provide compound 59D as a white solid (1.0 g). The filtrate was concentrated in vacuo, and the resulting residue was purified using column chromatography on silica gel (Biotage 40-S column; gradient: 0 to 35% ethyl acetate in hexanes) to provide an additional amount of compound 59D (290 mg). (Total yield=1.29 g, 37%). $^1$H NMR (400 MHz, d$_6$-DMSO): δ 11.91 (s, 1H), 7.12 (d, J=8.06 Hz, 1H), 6.96 (s, 1H), 6.95 (d, J=8.06 Hz, 1H), 4.65 (t, J=8.79 Hz, 2H), 3.85 (s, 3H), 3.22 (t, J=8.79 Hz, 2H).

Step E—Synthesis of Compound 59E

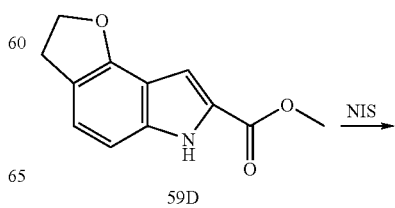

59D

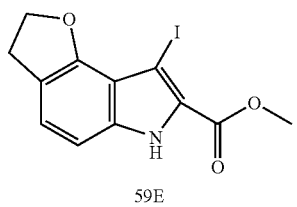

59E

To a solution of compound 59D (1.45 g, 6.67 mmol) in 50 mL of chloroform and 20 mL of THF at 0° C. was added N-iodosuccinimide (1.65 g, 7.34 mmol). The resulting reaction was allowed to stir at 0° C. for 30 minutes, then warmed to room temperature and allowed to stir at this temperature for 30 minutes. The reaction mixture was then diluted with ethyl acetate (100 mL), and the resulting solution was sequentially washed with aqueous saturated sodium thiosulfate (20 mL), aqueous saturated sodium bicarbonate (20 mL) and brine (20 mL). The organic layer was dried over magnesium sulfate, filtered, and concentrated in vacuo. The crude product was purified using column chromatography on silica gel (Biotage 40-S column; gradient: 0 to 40% ethyl acetate in hexanes) to provide compound 59E (190 mg, 10%) as a white solid. M.S. found for $C_{12}H_{10}INO_3$: 343.87 (M+H)$^+$.

Step F—Synthesis of Compound 59F

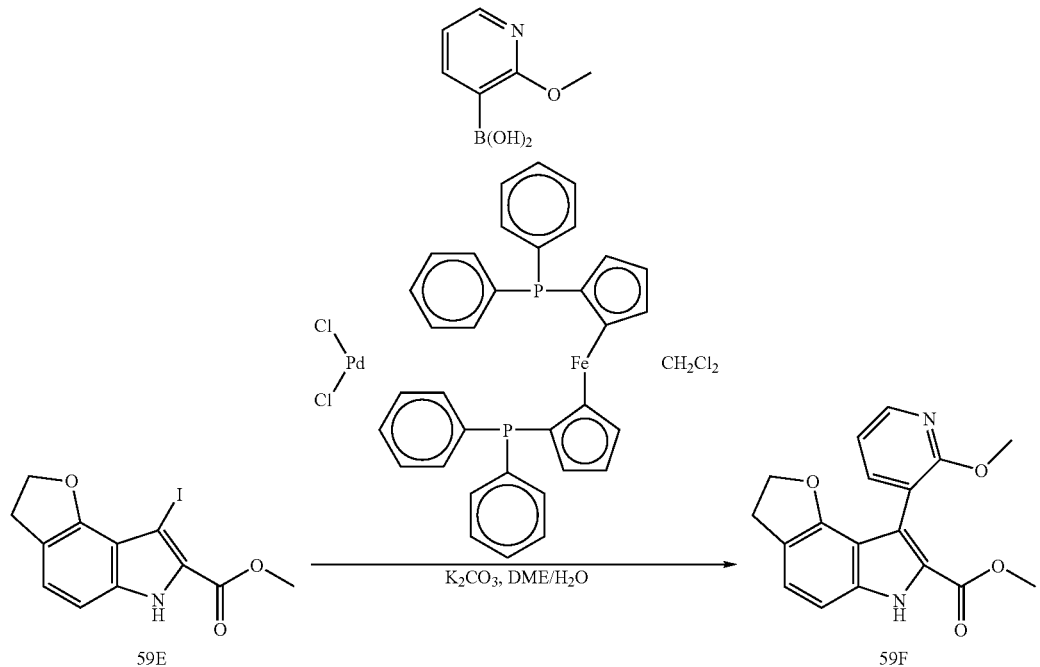

To a solution of compound 59E (180 mg, 0.524 mmol) in 10 mL of 1,2-dimethoxyethane was added 2-methoxy-3-pyridine boronic acid (240 mg, 1.573 mmol) and the resulting mixture was de-gassed (vacuum/argon flush), and PdCl$_2$(dppf)$_2$ (10 mol %, 42 mg) was added. The resulting mixture was allowed to stir for 15 minutes at room temperature and a solution of potassium carbonate (434 mg, 3.144 mmol) was added. The resulting brown reaction was heated to 90° C. and allowed to stir at this temperature for 45 minutes. The reaction mixture was then cooled to room temperature, and diluted with ethyl acetate (80 mL). The organic layer was washed sequentially with aqueous saturated sodium bicarbonate (10 mL) and brine (10 mL), then dried over magnesium sulfate, filtered, and concentrated in vacuo. The resulting residue was purified using column chromatography on silica gel (Biotage 25-S column; gradient: 10 to 50% ethyl acetate in hexanes) to provide compound 59F (140 mg, 83%) as a white solid. M.S. found for $C_{18}H_{16}N_2O_4$: 325.07 (M+H)$^+$.

Step G—Synthesis of Compound 59G

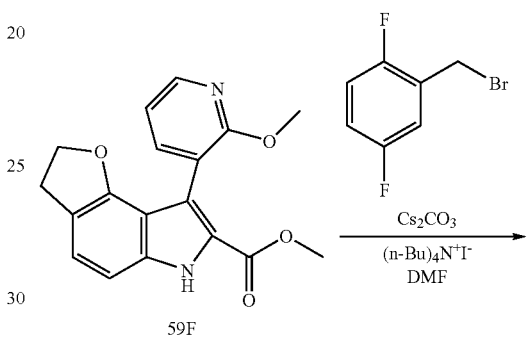

59F

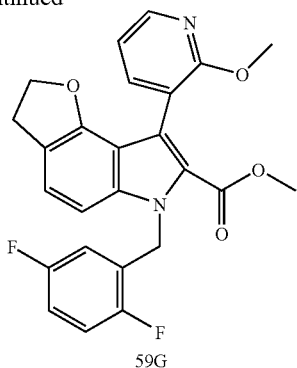

59G

To a solution of compound 59F (130 mg, 0.400 mmol) in 5 mL of dry DMF at 0° C. were added 2,5-difluorobenzyl bromide (99 mg, 0.480 mmol), cesium carbonate (391 mg, 1.200 mmol) and tetrabutylammonium iodide (10 mg, catalytic). The resulting reaction was allowed to stir at 0° C. for 45 minutes, then warmed to room temperature. The mixture was then diluted with ethyl acetate (80 mL), and the resulting solution was sequentially washed with water (10 mL) and brine (10 mL). The organic layer was dried over magnesium sulfate, filtered, and concentrated in vacuo to provide a crude residue which was purified using column chromatography on silica gel (Biotage 25-S column; gradient: 0 to 25% ethyl acetate in hexanes) to provide compound 59G (140 mg, 78%) as a white solid. M.S. found for $C_{25}H_{20}F_2N_2O_4$: 451.12 $(M+H)^+$.

Step H—Synthesis of Compound 59H

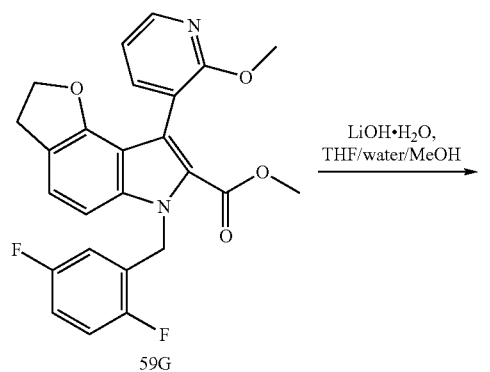

59G

59H

To a solution of compound 59G (140 mg, 0.310 mmol) in 8 mL of a solution of tetrahydrofuran/water/methanol (2:1:1) was added lithium hydroxide monohydrate (65 mg, 1.554 mmol). The reaction was heated to 50° C. for and allowed to stir at this temperature for 5 hours. The mixture was diluted with aqueous 1N HCl solution (40 mL), and then was extracted with dichloromethane (3×25 mL). The combined organic layers were dried (magnesium sulfite), filtered and concentrated in vacuo to provide compound 59H (135 mg, 99%) as a white solid, which was used without further purification.

Step I—Synthesis of Compound 59I

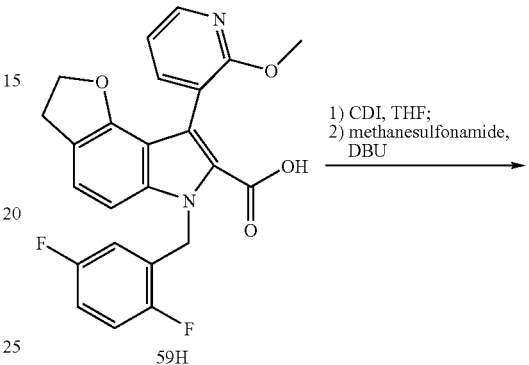

59H

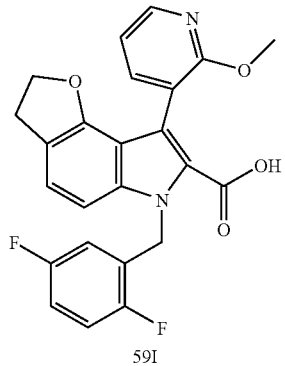

59I

To a solution of compound 59H (150 mg, 0.343 mmol) in tetrahydrofuran (4.0 mL) was added carbonyl diimidazole (69 mg, 0.429 mmol). The resulting mixture was refluxed at 70° C. for 2 h and then cooled to room temperature. Methanesulfonamide (41 mg, 0.429 mmol) and 1,8-diazabicyclo (5.4.0) undec-7-ene (78 mg, 0.514 mmol) were added to the reaction and the resulting reaction mixture was heated to 40° C. and allowed to stir at this temperature for 48 hours. The reaction mixture was diluted with ethyl acetate (60 mL), and sequentially washed with aqueous 1N HCl (10 mL) and brine (10 mL). The organic layer was dried (magnesium sulfate), filtered, and concentrated in vacuo to provide compound 59I (103 mg, 60%), which was used without further purification. $^1$H NMR (400 MHz, d$_6$-DMSO): δ 11.71 (s, 1H), 8.14 & 8.13 (dd, J=2.20 Hz & 5.13 Hz, 1H), 7.79 & 7.77 (dd, J=2.20 Hz & 7.32 Hz, 1H), 7.34-7.26 (m, 1H), 7.20 (d, J=8.79 Hz, 1H), 7.19-7.12 (m, 1H), 7.10-7.07 (m, 2H), 6.58-6.53 (m, 1H), 5.65 (s, 2H), 4.55 (d, J=8.79 Hz, 2H), 3.75 (s, 3H), 3.19-3.14 (m, 2H), 3.06 (s, 3H).

Step J—Synthesis of Compound 59

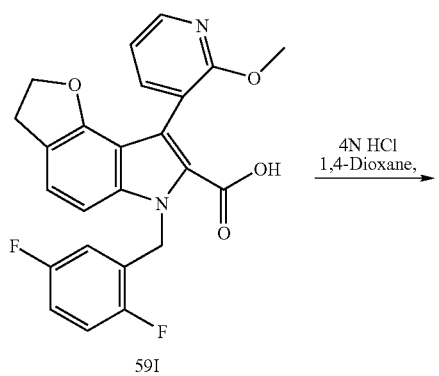

A solution of Compound 59I (100 mg, 0.194 mmol) in 3 mL of HCl (4M in dioxane) and methanol (1 mL) was placed in a sealed tube, heated at 90° C. and allowed to stir at this temperature for 3 hours. The reaction mixture was concentrated in vacuo to provide a yellow solid residue which was purified using reverse phase HPLC (Delta Pak, C18, 5 micrometer, 300A; 300×30 mm I.D.; Flow rate: 30 mL/min; Gradient: 40% acetonitrile in water for 20 min then increase to 80% over 30 min and stay there for 10 min) to provide compound 59 (62 mg, 65%) as a white solid. $^1$H NMR (400 MHz, d$_6$-DMSO): δ 7.78 & 7.76 (dd, J=2.20 Hz & 7.32 Hz, 1H), 7.62 (d, J=5.86 Hz, 1H), 7.55 & 7.53 (dd, J=1.47 Hz & 6.59 Hz, 1H), 7.33-7.27 (m, 2H), 7.23-7.13 (m, 3H), 7.04 (q, J=4.39 Hz & 3.66 Hz, 1H), 6.57 (q, J=6.59 Hz, 1H), 5.66 (s, 2H), 3.25 (s, 3H), 3.20-3.15 (m, 4H). $^{13}$C NMR (125 MHz, d$_6$-DMSO): δ 162.46, 161.32, 161.00, 153.15, 145.25, 140.18, 138.92, 135.30, 128.30, 125.89, 122.76, 122.25, 121.98, 117.41, 117.06, 115.69, 113.19, 112.00, 106.96, 102.46, 72.11, 51.40, 41.06, 28.66. M.S. found for C$_{24}$H$_{19}$F$_2$N$_3$O$_5$S: 500.14 (M+H)$^+$.

Example 11

Preparation of Compound 80

Step A—Synthesis of Compound 80B

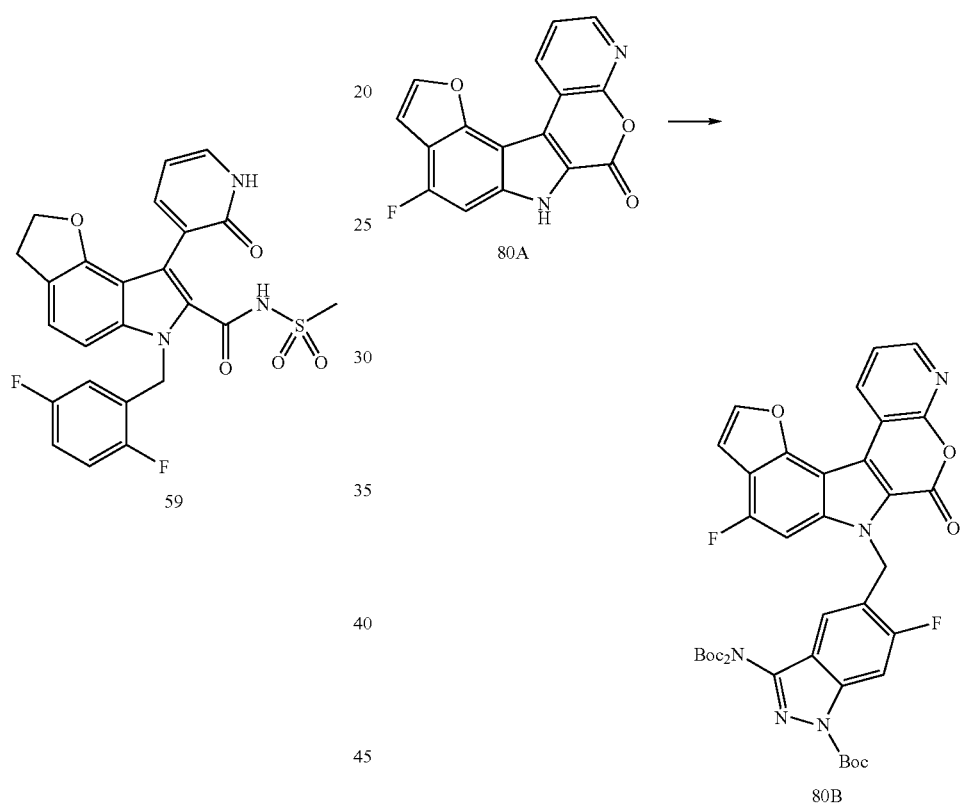

A solution of compound 80A (294.2 mg, 0.99 mmol), Cesium carbonate (488.67 mg, 1.4998 mmol) in DMF (10 mL) was stirred at room temperature for 12 hours, the concentrated in vacuo. The residue obtained was dissolved in EtOAc (200 mL) washed with brine (100 mL), dried (MgSO$_4$), filtered, concentrated in vacuo, and purified using flash column chromatography (SiO$_2$, Acetone/Hexanes) to provide compound 80B (490 mg; Yield=65%)

Step B—Synthesis of Compound 80C

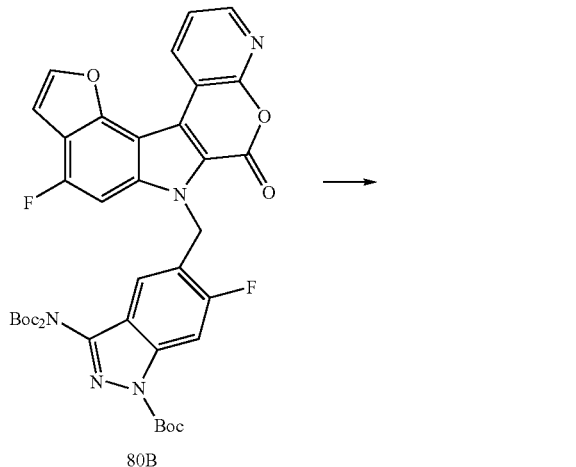

80B

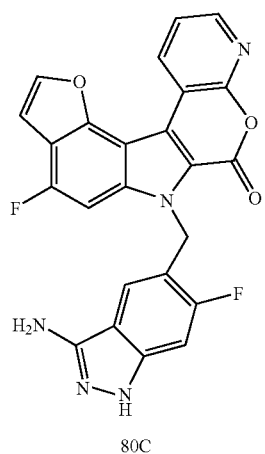

80C

A solution of 80B (490.00 mg, 0.646 mmol) in HCl (4 M in dioxane, 25 mL, Supplier=Aldrich) was stirred at room temperature for 4 h and concentrated in vacuo. The residue obtained was dried under vacuum and used without further purification.

Step C—Synthesis of Compound 80

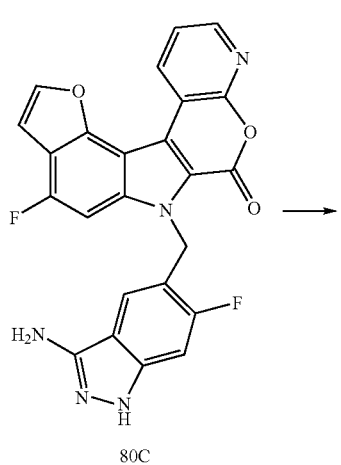

80C

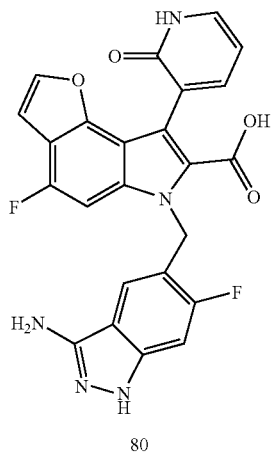

80

To a solution of compound 80C (100 mg, 0.219 mmol), in THF (4 mL) and water (4 mL) was added lithium hydroxide monohydrate (64.2 mg, 1.53 mmol) and the reaction was stirred at room temperature for 12 hours. The reaction mixture was concentrated in vacuo and the resulting residue was purified using HPLC (reverse phase) using following conditions: Column: Waters: Delta Pk, P/No 11805, Wat 011805, 300×30 mm (L/ID) C18, 15 μM, 300 Å, 343K16006 (W): 30 mL/min flow; 10-100% ramp THF, water containing 0.01% TFA; Ramp=0→60 minutes, to provide compound 80 as colorless solid. $^1$H NMR (D6-dmso, 400 MHz), δ 12.48 (s, 1H), 11.74 (b, 2H), 7.90 (d, 1H, J=2.4 Hz), 7.67 (dd, 1H, J=1.8 & 6.7 Hz), 7.42 (d, 1H, J=10.8 Hz), 7.42 (d, 1H, J=2.4 Hz), 7.01 (d, 1H, J=11.0 Hz), 6.33 (t, 1H, J=6.7 Hz), 5.90 (s, 2H), 6.00-4.4 (b, 2H).

Example 12

Preparation of Compound 114

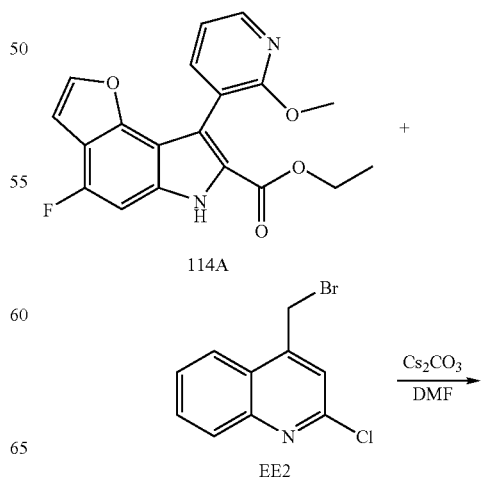

114A

EE2

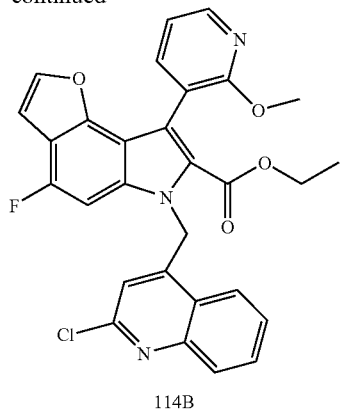

114B

To a suspension of compound 114A (200 mg, 0.564 mmol) and cesium carbonate (600 mg, 1.85 mmol) in DMF (3 mL) was added compound EE2 (520 mg, ~50% purity, ~1 mmol) and the resulting mixture was allowed to stir at room temperature for about 15 hours. The reaction mixture was diluted with ethyl acetate (100 mL), then washed with water (3×40 mL), dried over sodium sulfate, and concentrated in vacuo. The residue obtained was purified using Combi-flash chromatography (12 g silica column) with 0-25% ethyl acetate in hexanes as the eluent to provide compound 114B as a white solid (210 mg, 70%).

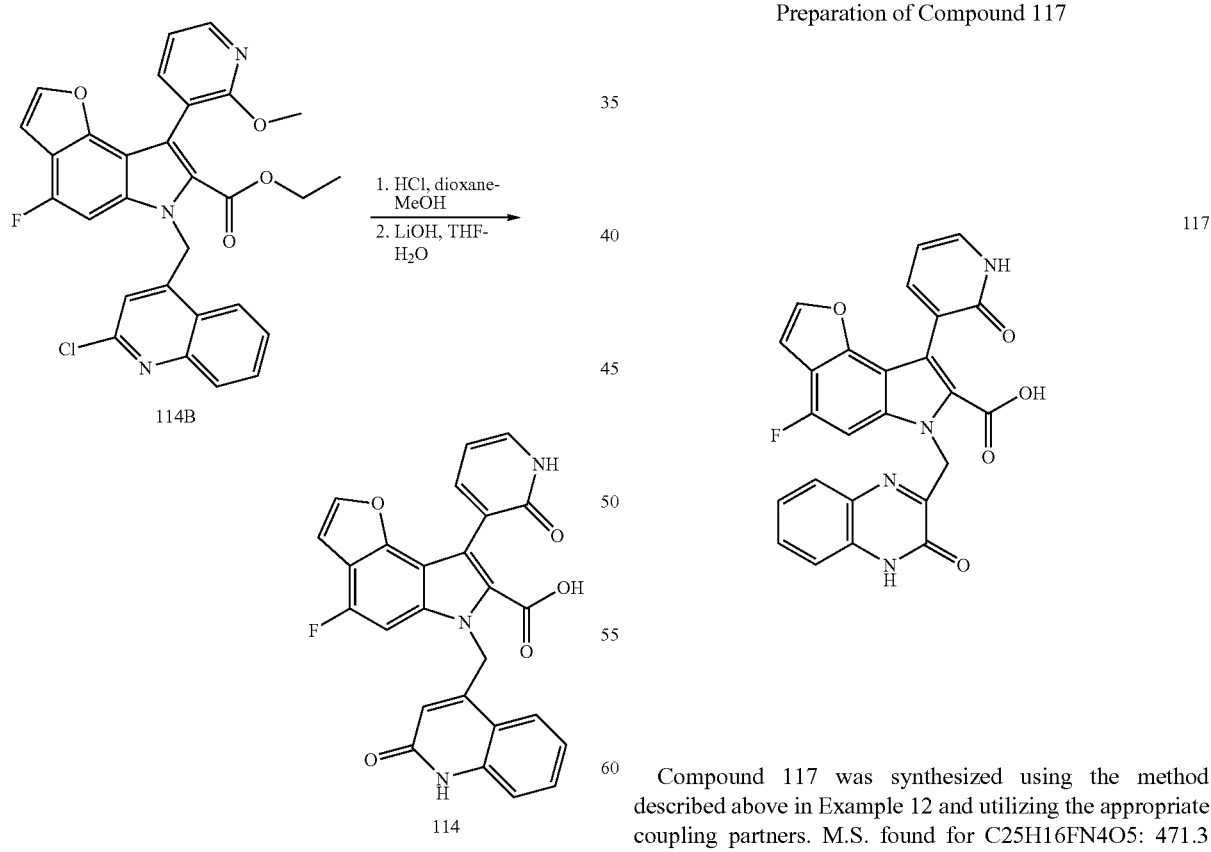

A 15 mL pressure vessel was charged with a solution of compound 114B (210 mg, 0.40 mmol), HCl in dioxane (4M, 5 mL, 20 mmol), and methanol (2 mL) and the resulting reaction was heated to 90° C. and allowed to stir at this temperature for about 15 hours. After cooling to room temperature, the reaction mixture was concentrated in vacuo. The residue obtained was suspended with MeOH (~10 mL) and concentrated again in vacuo to remove excess HCl. The resulting residue was washed with methanol (3×3 mL) and dried under vacuum to provide a white solid (160 mg, 76%), which was diluted with solid THF (8 mL) and aqueous LiOH solution (2.0 mL, 1.0 M, 2.0 mmol). The resulting reaction was heated to reflux and allowed to stir at this temperature for about 7 hours, then cooled to room temperature. The reaction mixture was neutralized using HCl (2.0 mL, 1.0 M, 2.0 mmol) and the resulting suspension was concentrated in vacuo. The resulting residue was washed with water (2×20 mL) and methanol (3 mL), then dried under vacuum to provide compound 114 as a white solid (112 mg, 75%). M.S. found for $C_{26}H_{17}FN_3O_5$: 470.3 $(M+H)^+$; $^1H$ NMR (500 MHz, CD3OD, Na salt): δ 7.85 (1H, dd, J=6.9, 2.2 Hz), 7.64-7.60 (2H, m), 7.44-7.37 (3H, m), 6.97 (1H, d, J=10.4 Hz), 6.91 (1H, d, J=2.2 Hz), 6.51-6.49 (1H, m), 6.34 (2H, s), 5.65 (1H, s).

Example 13

Preparation of Compound 117

117

Compound 117 was synthesized using the method described above in Example 12 and utilizing the appropriate coupling partners. M.S. found for $C_{25}H_{16}FN_4O_5$: 471.3 $(M+H)^+$; $^1H$ NMR (500 MHz, CD3OD, Na salt): δ 7.94 (1H, d, J=1.89 Hz), 7.69 (1H, dd, J=6.94, 1.89 Hz), 7.53-7.40 (4H, m), 7.32 (1H, d, J=8.2 Hz), 7.19 (1H, t, J=7.57 Hz), 7.09 (1H, d, J=1.89 Hz), 6.38 (1H, t, J=6.3 Hz), 5.97 (2H, s).

Example 14

Preparation of Compound 126

Step A—Synthesis of Compound 126B

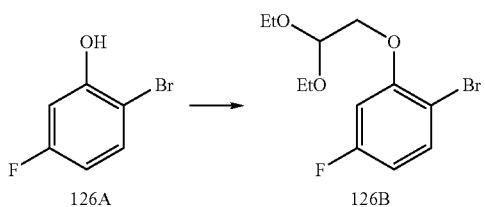 [SMILES: "126B" ; Oc1cc(F)ccc1Br ; CCOC(COc1cc(F)ccc1Br)OCC]

A solution of compound 126A, (228.00 g, 1.19 mmol), Potassium carbonate (247.47 g, 1.79 mol) in DMF (3.00 L) was treated with 2-Bromo-1,1-diethoxyethane (197.54 mL, 1.31 mol) and heated at 135° C. for 7 hours. The reaction mixture was concentrated in vacuo and extracted with EtOAc (3×2 L). The combined organic layers were washed with aqueous NaOH (2M, 4 L). The organic layer was dried (MgSO$_4$), filtered, concentrated in vacuo to provide compound 126B (362.00 g, 98%) which was used without further purification.

Step B—Synthesis of Compound 126C

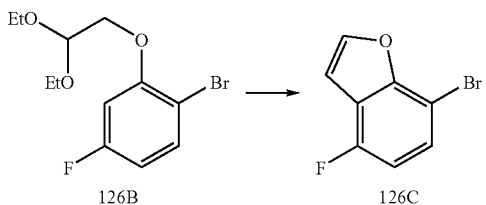 [SMILES: "126C" ; "126B" ; CCOC(COc1cc(F)ccc1Br)OCC ; Fc1ccc(Br)c2occc12]

A solution of compound 126B (352.00 g, 1.15 mol) in toluene (2500 mL, 2.3 mol) was treated with polyphosphoric acid (370.00 g, 3.4 mol) and heated at reflux for 5 hours. The reaction mixture was concentrated in vacuo diluted with water (3 L) and the extracted with EtOAc (4 L). The organic layer was washed with aqueous NaOH (2 L), filtered, concentrated in vacuo and purified by distillation at reduced pressure to provide compound 126C (125.00 g, 50.8%). Bp. 80° C. (1 mm/Hg) as a colorless liquid which solidified at room temperature. $^1$H NMR (400 MHz, CDCl$_3$) δ 7.67 (d, 1H, J=2.2 Hz), 7.39 (dd, 1H J=5.1 & 3.7 Hz), 6.94 (d, 1H, J=2.2 Hz), 6.86 (t, 1H, J=8.8 Hz).

Step C—Synthesis of Compound 126D

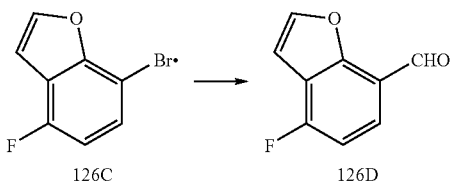

A solution of compound 126C (124.12 g, 577.25 mmol) in ether (2.0 L) was cooled to −78° C. and treated dropwise with a solution of 2.5 M of n-butyllithium in hexane (235.5 mL) and allowed to stir at −78° C. for 15 minutes. To this reaction mixture was added DMF (89.393 mL, 1.15 mol) and allowed to stir at −78° C. for 30 minutes. The reaction mixture was quenched with methanol (23.383 mL, 577.25 mmol) and warmed to room temperature. The reaction mixture was diluted with ether (300 mL) and the organic layer was washed with water (300 mL). The separated organic layer was dried (MgSO$_4$) filtered, concentrated in vacuo to provide compound 126D (89.00 g, 93.9%).

Step D—Synthesis of Compound 126E

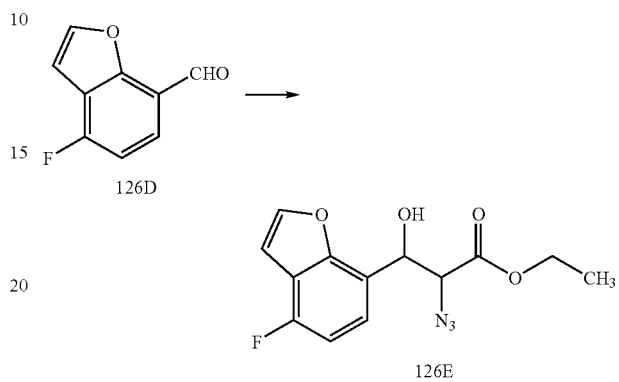

A solution of compound 126D (12.71 g, 77.45 mmol), lithium chloride (6.567 g, 154.9 mmol) and ethyl azidoacetate (20.00 g, 154.9 mmol; added as a 30% solution in CH$_2$Cl$_2$), diazabicyclo[5.4.0]undec-7-ene (23.16 mL, 154.9 mmol) and stirred for 2 hours. The completion of the reaction was followed by TLC (EtOAc/Hexanes 1:4). Upon completion, the reaction mixture was diluted with ethyl acetate (1 L) and washed with water and aqueous HCl (400 mL). The combined organic layers were dried (MgSO$_4$), filtered and concentrated in vacuo and the residue obtained was purified using flash column chromatography SiO$_2$ (EtOAc/Hexanes) to provide compound 126E (18.3 g, 80.6%) as a colorless oil.

Step E—Synthesis of Compound 126F

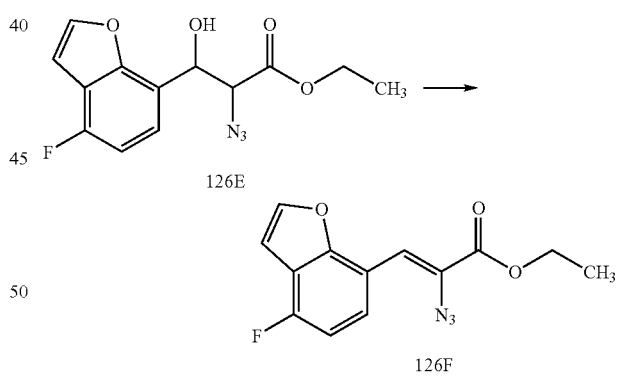

A solution of compound 126E (15.7 g, 53.5 mmol) and methanesulfonyl chloride (8.29 mL, 107 mmol) in methylene chloride (87.7 mL, 1.37 mmol) at −30° C. was treated dropwise with a solution of triethylamine (52.2 mL, 375.0 mmol) in methylene chloride (100 mL). The reaction mixture was allowed to stir at −30° C. for 3 hours, diluted with aqueous saturated sodium bicarbonate and methylene chloride (400 mL). The organic layer was separated and washed with water, aqueous HCl and brine. The organic layer was dried (MgSO$_4$), filtered, concentrated in vacuo, and purified using flash column chromatography (SiO$_2$, 10% EtOAc in (1:1) Hexanes/CH$_2$Cl$_2$) to provide compound 126F (12.6 g, 85.5%).

Step F—Synthesis of Compound 126G

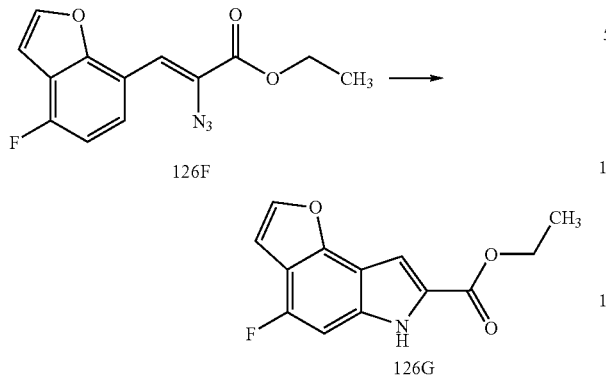

150 mL of xylenes was heated at 165° C. To this boiling solution was added dropwise a solution of compound 126F (11.2 g, 40.7 mmol) in Xylenes (70 mL, 189.4 mmol). The reaction mixture was stirred for additional 20.0 minutes and allowed to cool to room temperature to provide compound 126G as a precipitate (7.00 g, 69.6%), which was filtered, washed with hexanes and dried under vacuum.

Step G—Synthesis of Compound 126H

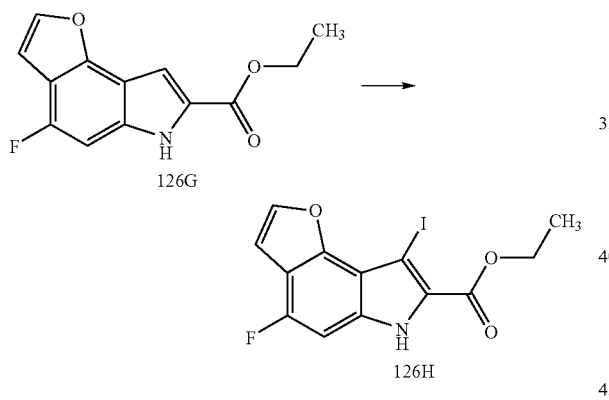

To a solution of compound 126G (15.88 g, 64.23 mmol) in DMF (100 mL) was added N-iodosuccinimide (15.90 g, 70.66 mmol) and allowed to stir at room temperature. for 2 hours. The reaction mixture was diluted with water (1000 mL) and extracted in EtOAc (1000 mL). The organic layer was washed with water (1000 mL), aqueous sodium thiosulfate (5% aqueous soln. 1 L) and dried (MgSO$_4$). The organic layer was dried (MgSO$_4$), filtered, concentrated in vacuo to provide compound 126H (22.30 g, 93.04%) as a solid.

Step H—Synthesis of Compound 126I

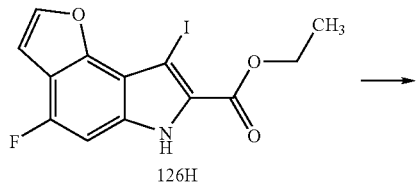

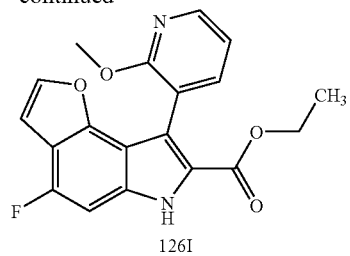

A solution of compound 126H (22.000 g, 58.962 mmol), 2-methoxypyridin-3-ylboronic acid (13.527 g, 88.444 mmol), (PPh$_3$)$_2$PdCl$_2$ (4.13 g, 5.88 mmol) in 1,2-dimethoxyethane (250.0 mL) was degassed for 2 min and allowed to stir at room temperature. for 15 minutes. The orange reaction mixture was treated with a solution of potassium carbonate (30.53 g, 220.9 mmol) in water (250.0 mL) and allowed to stir at 90° C. for 3 hours. The yellow reaction turned orange dark with the disappearance of starting material (TLC). The reaction mixture was diluted with EtOAc (1000 mL) and washed with aqueous NaOH (500 mL, 1M), dried (MgSO$_4$), filtered, concentrated in vacuo, and purified using flash column chromatography SiO$_2$ (THF/Hexanes 0→60%) to provide compound 126I (16.65 g, 79.7%) as pale brown solid.

Step I—Synthesis of Compound 126J

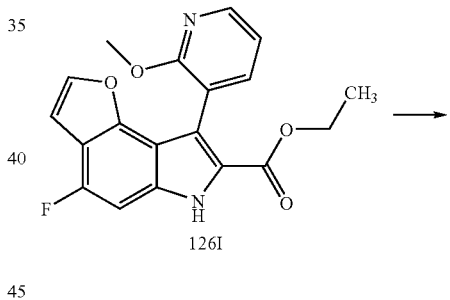

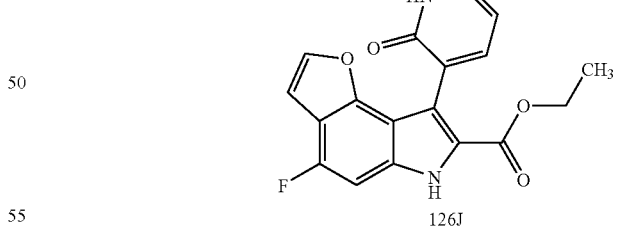

A solution of compound 126I (4.50 g, 12.7 mmol) in methanol (10 mL, 246.9 mmol) was treated with a solution of 4 M HCl in dioxane (100 mL) and heated at 90° C. for 3 hours in a pressure tube. The reaction mixture was concentrated in vacuo and the residue obtained was purified using flash column chromatography (SiO$_2$, THF/Hexanes 0→100%) to provide compound 126J as a colorless solid.

Step J—Synthesis of Compound 126K

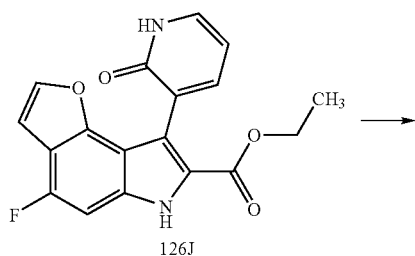

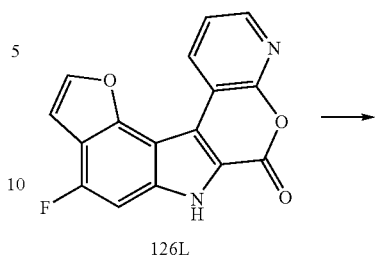

Step L—Synthesis of Compound 126M

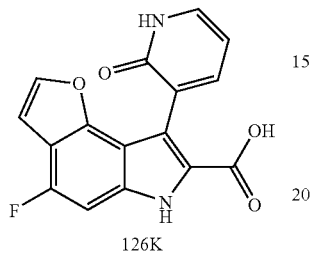

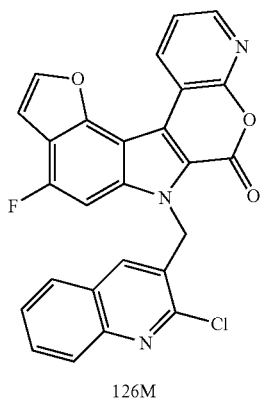

A solution of compound 126J (810.00 mg, 2.38 mmol) in water (25 mL), THF (25 mL) and methanol (25 mL, 780.2 mmol) was treated with lithium hydroxide monohydrate (499.41 mg, 11.901 mmol) and heated at 80° C. for 1 hour. The reaction mixture was then acidified using 1N HCl, filtered and dried in vacuo to provide compound 126K (627.00 mg, 84.4%) as colorless solid.

Step K—Synthesis of Compound 126L

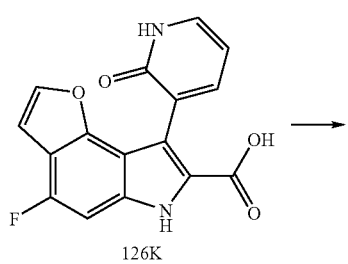

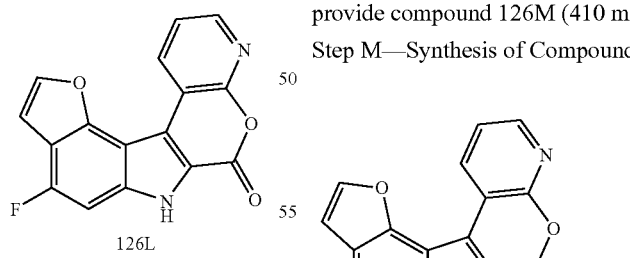

A suspension of compound 126L (300 mg, 1 mmol), cesium carbonate (664.40 mg, 2.0392 mmol) and 2-chloro-3-(chloromethyl)quinoline (432.46 mg, 2.0392 mmol) in DMF (20 mL, 200 mmol) was allowed to stir at room temperature for 2 hours. The reaction mixture was concentrated in vacuo and the residue obtained was stirred with methanol (20 mL). The resulting precipitate was filtered and dried to provide compound 126M (410 mg, 80%)

Step M—Synthesis of Compound 126

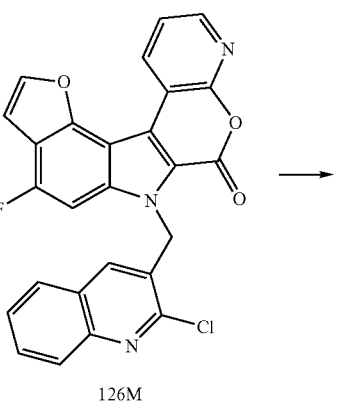

To a suspension of compound 126K (8.00 g, 25.6 mmol) and N-(3-dimethylaminopropyl)-N'-ethylcarbodiimide hydrochloride (9.82 g, 51.2 mmol) in DMF (153.85 mL) was added triethylamine (35.71 mL, 256.2 mmol) and the reaction was stirred overnight at room temperature. The reaction mixture was concentrated in vacuo and the resulting residue was diluted with methanol (100 mL). The resulting precipitate was filtered and dried to provide compound 126L (5.90 g, 78.3%)

231

-continued

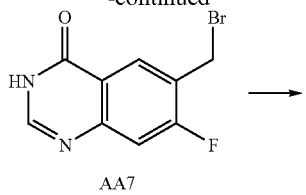

126

A solution of compound 126M (130.00 mg, 0.27668 mmol) in water (10 mL) and THF (10 mL) was treated with lithium hydroxide monohydrate (58.05 mg, 1.38 mmol) and the reaction was allowed to stir at room temperature for 3 hours. The reaction mixture was quenched with aqueous HCl (1M, 3 mL) and mixture was purified by HPLC (reverse phase) using following conditions: Column: Waters: Delta Pk, P/No 11805, Wat 011805, 300×30 mm (L/ID) C18, 15 µM 300 A, 343K16006 (W): 30 mL/min flow; 30-70% ramp acetonitrile, water; 0→40 minutes, to provide compound 126 (47.00 mg, 34.82%) as colorless solid.

Example 15

Preparation of Compound 127

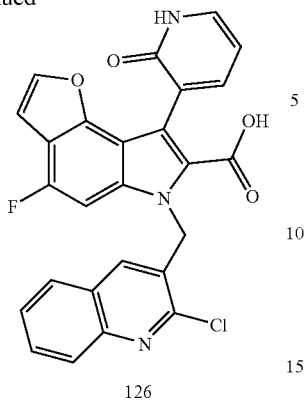

127

Step A—Synthesis of Compound 127B

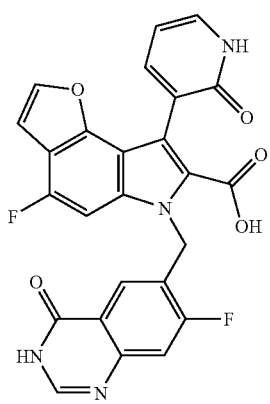

127A

232

-continued

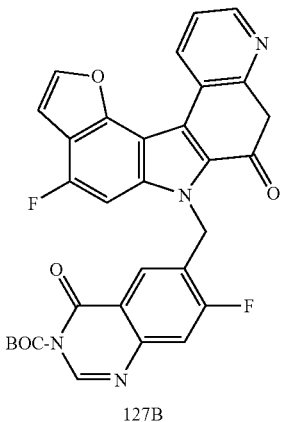

AA7

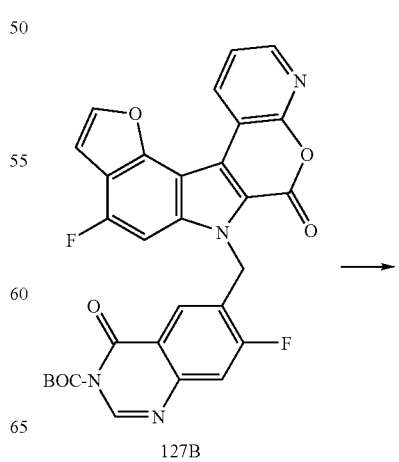

127B

To a solution of compound 127A (130 mg, 0.442) and compound AA7 (225 mg, <0.5 mmol) in DMF (10 mL) was added cesium carbonate (330 mg, 1.01 mmol). The resulting reaction was stirred at room temperature for 18 hours, then diluted with ethyl acetate (100 mL) and water (100 mL). The organic layer was washed with water (2×60 mL), dried (magnesium sulfate), filtered and concentrated in vacuo to provide product 127B (160 mg, 63%), which was further purified using reverse-phase HPLC on a Waters Sunfire $C_{18}$ column (10 µM, 50×250 mm) using 20-100% acetonitrile/water as eluent. MS found for $C_{30}H_{20}F_2N_4O_6$: 470.9 (M+H−100)$^+$.

Step B—Synthesis of Compound 127C

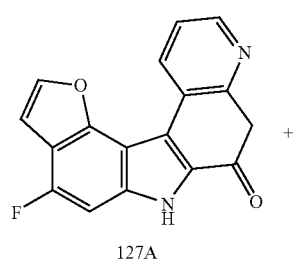

127B

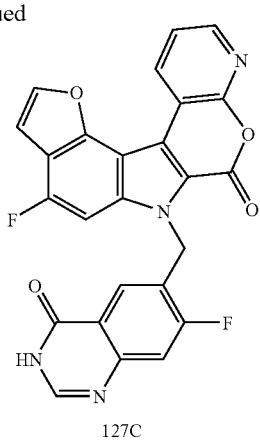

127C

Compound 127B (150 mg, 0.263 mmol) was dissolved in 4 M HCl in 1,4-dioxane (15 mL) and the reaction mixture was stirred for 3 hours, then concentrated in vacuo to provide the crude compound 127C (165 mg, quant.), which was further purified using reverse-phase HPLC as described above. MS found for $C_{25}H_{12}F_2N_4O_4$: 471.0 (M+H)$^+$.

Step C—Synthesis of Compound 127

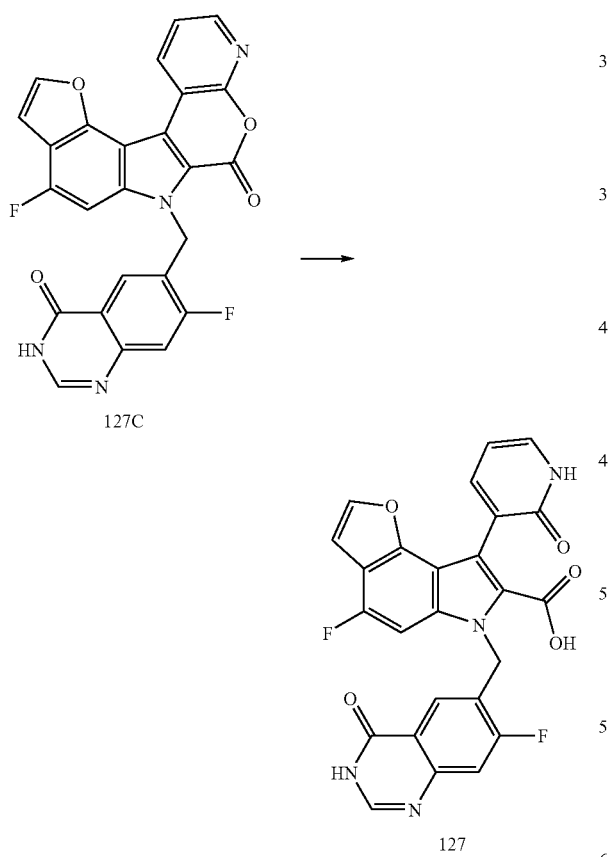

To a solution of the crude product 127C (100 mg, <0.213 mmol, from Step B above) in THF (10 mL) and water (10 mL) was added aqueous LiOH solution (3.0 mL, 3.0 mmol). The reaction was allowed to stir for 30 minutes, then the reaction mixture was acidified using 1 N aqueous HCl solution (3.5 mL), and the acidic solution was extracted with ethyl acetate (3×30 mL). The combined organic extracts were dried over magnesium sulfate, filtered and concentrated in vacuo to provide a residue which was purified using reverse-phase HPLC as described above in Step A to provide compound 127 (26 mg, 25%). $^1$H NMR (500 MHz, d$_6$-DMSO): δ 13.0 (bs, 1H), 12.3 (bs, 1H), 11.8 (bs, 1H), 8.08 (s, 1H), 7.96 (s, 1H), 7.68-7.66 (m, 1H), 7.53 (dd, J=4.0, 11.0 Hz, 2H), 7.42-7.41 (m, 2H), 7.10 (s, 1H), 6.34 (t, J=6.8 Hz, 1H), 6.01 (s, 2H). MS found for $C_{25}H_{14}F_2N_4O_5$: 489.0 (M+H)$^+$.

Example 16

Preparation of Compound 212

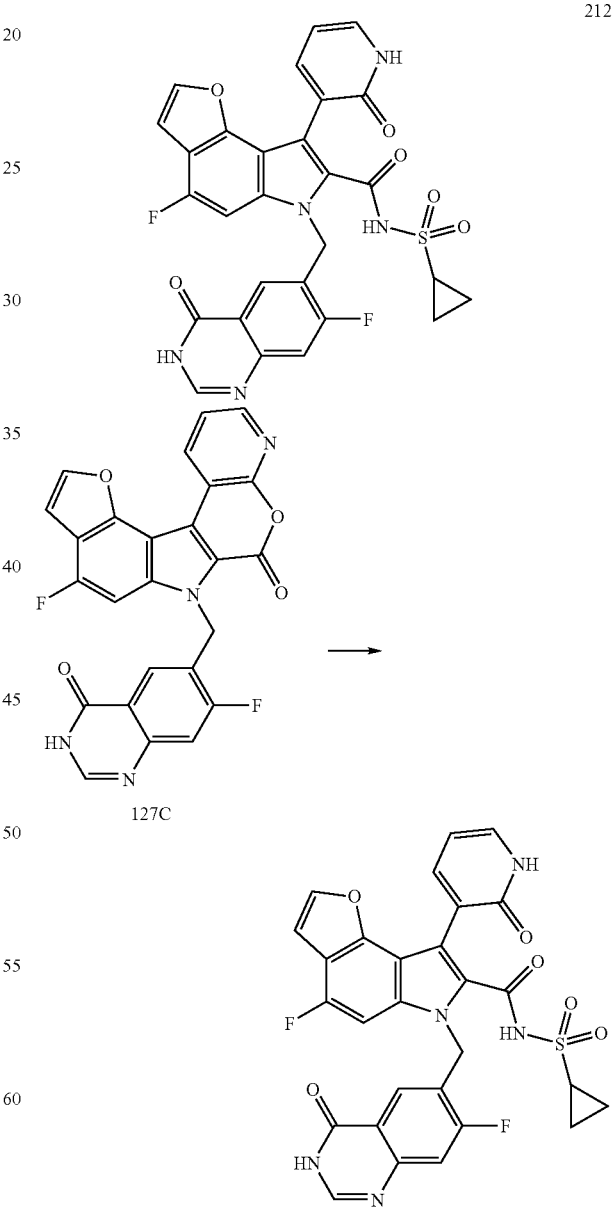

To a solution of compound 127C (15.0 mg, 0.0318 mmol) in THF (10.0 mL) was added sulfonamide cyclopropylsulfonamide (8.0 mg, 0.064 mmol) and NaH (4.0 mg, 0.16 mmol). The resulting reaction was allowed to stir at room temperature for 3 hours, then was diluted with EtOAc (10 mL) and the resulting solution was washed with water (10 mL). The organic phase was dried (MgSO$_4$), filtered, and concentrated in vacuo and the resulting residue was purified using reverse-phase HPLC as described above in Example 14, Step A, to provide compound 212 as a white solid (3.5 mg, 19%). MS found for $C_{28}H_{19}F_2N_5O_6S$: 592.3 (M+H)$^+$.

Example 17

Preparation of Compound 231

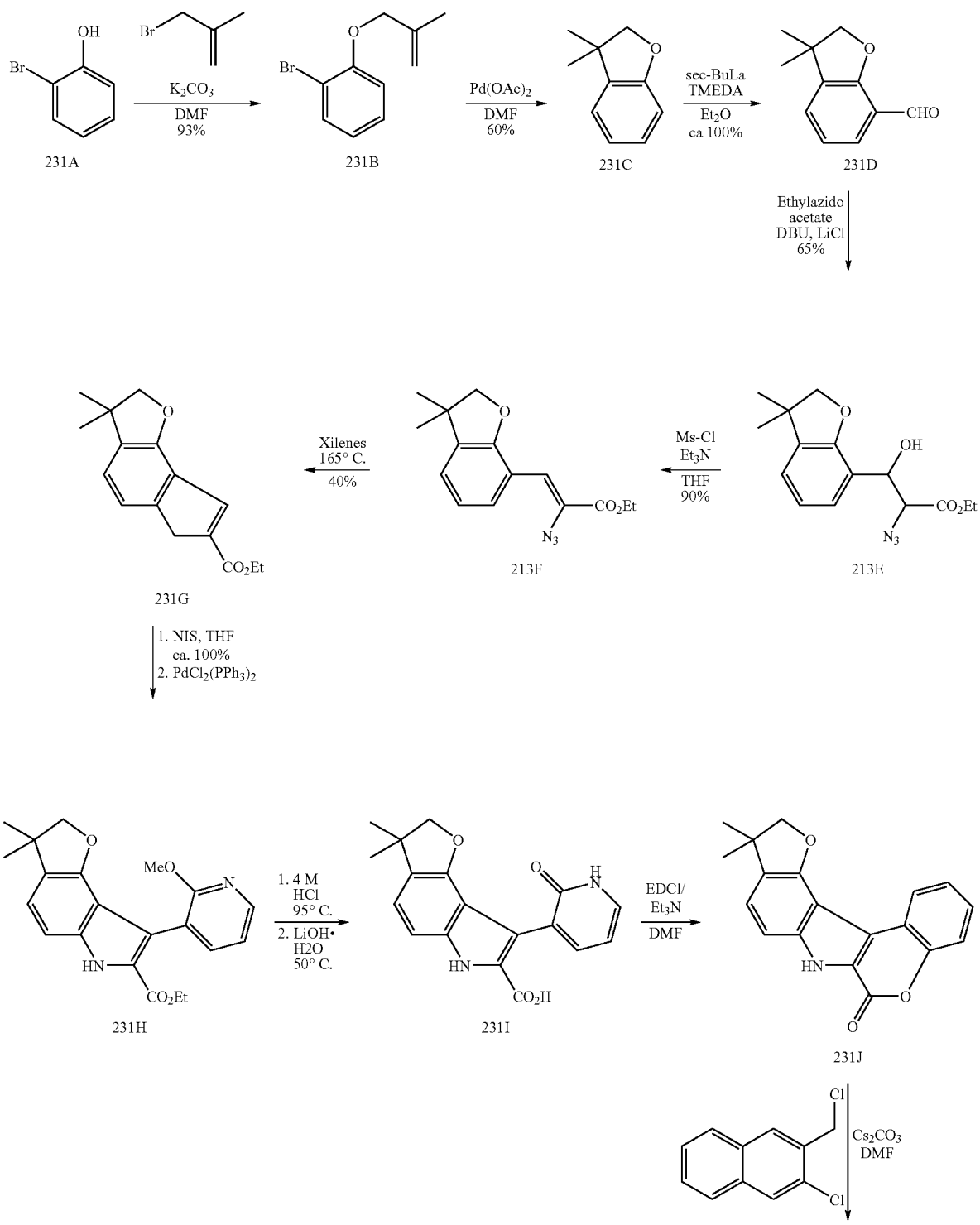

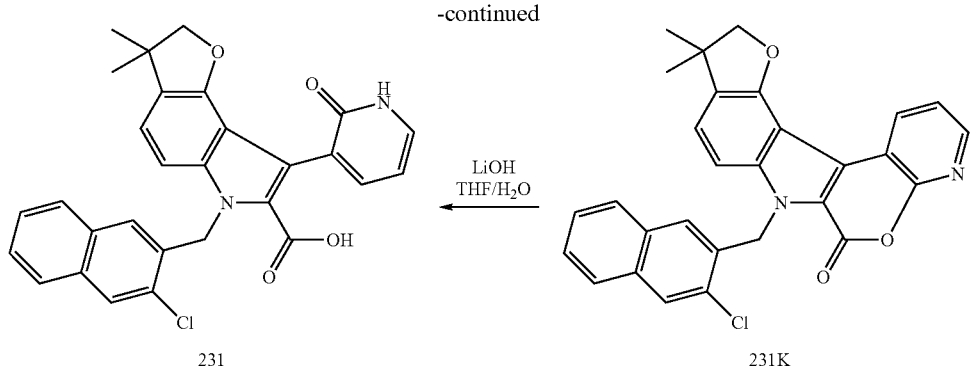

Step A—Synthesis of Compound 231B

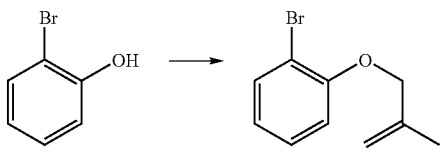

An ice-cooled solution of 2-bromo-phenol (231.2 mmol, 40 g, 26.8 mL, d 1.492) in 460 mL of DMF was treated with 3-bromo-2-methylprop-1-ene (1.1 eq, 24.5 mL, d 1.339) followed by addition of potassium carbonate (2.0 eq, 63.9 g) and tetrabutylammonium iodide (1.0 g). The cooling bath was removed and the reaction mixture was stirred until all starting material had been consumed. After 6 h the mixture was concentrated to one third of its volume in rotavap (high vacuum pump). The mixture was diluted with ethyl acetate (2.0 L) and washed with water (2×200 mL) and brine (200 mL). The organic layer was dried over magnesium sulfate, filtered and concentrated in rotavap to give the crude product as a slightly yellow oil. Compound 231B was purified using bulb to bulb distillation in batches of 10 g each (130° C./1 mmHg) to give the product (49 g, 93%) as a colorless oil. $^1$H-NMR (400 MHz, in dmso-d6): δ 7.57 (1H, dd, J=1.83, 7.93 Hz), 7.32 (1H, ddd, J=1.83, 7.32, 7.93 Hz), 7.10 (1H, dd, J=1.22, 7.93 Hz), 6.88 (1H, ddd, J=1.22, 7.32, 7.93 Hz), 5.12 (1H, s), 4.97 (1H, s), 4.55 (2H, s), 1.79 (3H, s); $^{13}$C-NMR (125 MHz, in dmso-d6): δ 159.2, 140.3, 132.8, 128.7, 121.9, 113.8, 112.2, 110.9, 71.4, 18.9 ppm.

Step B—Synthesis of Compound 231C

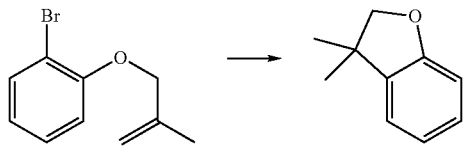

A solution of 1-bromo-2-(2-methyl-allyloxy)-benzene (13.8 g, 60.76 mmol) in 140 mL of DMF (0.1 g/mL) was treated with sodium acetate (2.5 eq, 12.46 g), sodium formate (1.2 eq, 4.95 g) and tetraethylammonium chloride hydrate (1.2 eq, 72.91 mmol [183.72] 13.4 g) and 25 drops of water. The mixture was degassed (vacuum/argon flush) and palladium(II) acetate (5 mol %, 682 mg) was added. The mixture was heated at 90° C. and the flow of the reaction was followed by TLC (10% ethyl acetate in hexanes). After 3 h the mixture was cooled to room temp and diluted with ether (500 mL). The solids were removed by filtration and the filtrate was washed with water (2×80 mL) and brine (80 mL). The organic layer was dried over magnesium sulfate, filtered and concentrated in rotavap. The slightly yellow residue was adsorbed on silica gel and purified on a Biotage 65-M silica gel column The column was eluted with hexanes (200 mL) and a gradient of 0 to 10% ethyl acetate in hexanes. The product 231B (5.3 g, 60%) was obtained as a colorless oil. $^1$H-NMR (400 MHz, in CDCl$_3$): δ 7.13 (1H, m), 7.11 (1H, d, J=7.32 Hz), 6.89 (1H, ddd, J=1.22, 7.32, 7.33 Hz), 6.80 (1H, d, J=7.93 Hz), 4.23 (2H, s), 1.35 (6H, s); $^{13}$C-NMR (125 MHz, in CDCl$_3$): δ 159.1, 136.5, 127.9, 122.2, 120.5, 109.6, 84.4, 41.9, 27.5 ppm.

Step C—Synthesis of Compound 231D

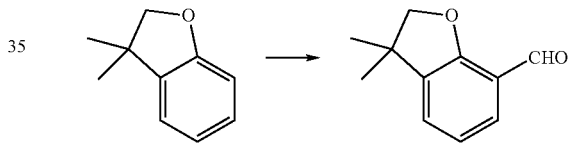

sec-Butyllithium (1.2 eq, 36.43 mL of 1.4 M soln in cyclohexane) was added dropwise to a cooled (−78° C.) solution of TMEDA (1.3 eq, 7.63 mL, d 0.775) in 100 mL of dry ether. After 5 min, a solution of 3,3-dimethyl-2,3-dihydro-benzofuran (6.3 g, 42.51 mmol) in ether (100 mL) was added dropwise. The resulting yellow solution was stirred at −78° C. for 10 min and at 0° C. for 30 min. The slightly yellow solution was cooled again to −78° C. followed by addition of DMF (2.5 eq, 8.19 mL, d 0.948). The mixture was stirred for 10 min and then warmed to 0° C. and stirred for further 30 min. The reaction was quenched by addition of aqueous 1 M HCl (1 mL). The mixture was diluted with 1:1 ether/hexanes (400 mL) and washed with aqueous 1 M HCl (3×80 mL) and brine (80 mL). The organic layer was dried over magnesium sulfate, filtered and concentrated in rotavap to provide compound 231C (ca. 100%, 7.49 g) as a slightly yellow oil, which was used without further purification. $^1$H-NMR (400 MHz, in CDCl$_3$): δ 10.20 (1H, s), 7.59 (1H, dd, J=1.22, 7.32 Hz), 7.31 (1H, dd, J=1.22, 7.32 Hz), 6.97 (1H, dd, J=7.32, 7.32 Hz), 4.40 (2H, s), 1.37 (6H, s); $^{13}$C-NMR (125 MHz, in CDCl$_3$): δ 188.9, 161.3, 139.0, 128.4, 127.6, 120.9, 120.0, 85.9, 41.2, 27.6 ppm. LR-MS (ESI): calcd. for $C_{11}H_{13}O_2$ [M+H]$^+$ 177.09. found 176.99.

Step D—Synthesis of Compound 231E

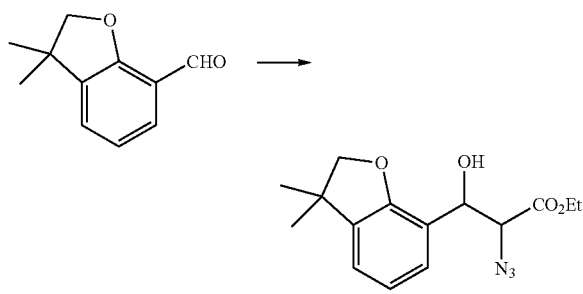

A solution of 3,3-dimethyl-2,3-dihydro-benzofuran-7-carbaldehyde (13.6 g; 77.45 mmol) in 380 mL of dry THF was cooled to 0° C. and treated with lithium chloride (2.0 eq, 6.56 g). The mixture was vigorously stirred for 3 min followed by addition of a solution of ethylazido acetate (2.0 eq, 80.0 mL of a 25% soln in toluene). A solution of DBU (2.0 eq, 23.1 mL, d 1.018) in 38 mL of dry THF was added dropwise. After addition was completed the reaction mixture was stirred for further 4 h at which point TLC (20% ethyl acetate in hexanes) showed almost complete consumption of starting material. The reaction mixture was diluted with ethyl acetate (1.0 L) and washed with aqueous 0.5 M HCl (3×200 mL) and brine (100 mL). The organic layer was dried over magnesium sulfate, filtered and concentrated in rotavap. The residue was purified on a silica gel column (8×18 cm). The column was eluted with 4 L of a gradient of 5 to 20% ethyl acetate in hexanes to provide compound 231E (15.4 g; 65%) as a pale yellow oil. $^1$H-NMR (400 MHz, in CDCl$_3$, reported as diastereomeric mixture) δ 7.19 (0.7H, d, J=7.93 Hz), 7.12 (0.3H, d, J=7.32 Hz), 7.09 (1H, m), 6.93 (0.7H, t, J=7.32 Hz), 6.91 (0.3H, t, J=7.32 Hz), 5.31 (0.7H, dd, J=4.27, 7.32 Hz), 5.07 (0.3H, dd, J=7.32, 7.32 Hz), 4.34-4.20 (5H, m), 3.30 (0.3H, d, J=7.32 Hz), 3.02 (0.7H, d, J=7.32 Hz), 1.34 (6H, s), 1.26 (3H, t, J=7.32 Hz); $^{13}$C-NMR (125 MHz, in CDCl$_3$, major diastereomer): δ 168.7, 155.7, 136.9, 125.7, 122.3, 121.2, 121.1, 85.0, 71.8, 66.1, 62.0, 41.8, 27.4, 14.1 ppm; $^{13}$C-NMR (125 MHz, in CDCl$_3$, minor diastereomer): δ 168.9, 156.2, 137.1, 126.4, 122.6, 121.1, 120.8, 85.0, 72.1, 65.3, 61.9, 41.7, 27.5, 14.0 ppm.

Step E—Synthesis of Compound 231F

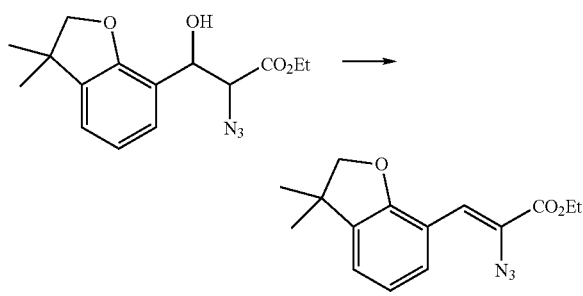

A solution of 2-azido-3-(3,3-dimethyl-2,3-dihydro-benzofuran-7-yl)-3-hydroxy-propionic acid ethyl ester (18.2 g; 59.61 mmol) in 60 mL of dry dichloromethane was cooled to −30° C. and treated with methanesulfonyl chloride (2.0 eq, 9.22 mL, d 1.480). A solution of triethylamine (7.0 eq, 58.1 mL, d 0.726) in 30 mL of dry dichloromethane was added dropwise over 30 min (internal temp was maintained between −40-30° C.). The resulting slurry was stirred for 2 h at which point TLC (20% ethyl acetate in hexanes) showed complete consumption of starting material. The mixture was diluted with ethyl acetate (1.5 L) and washed with aq 0.5 M HCl (2×200 mL) and brine (100 mL). The organic layer was dried over magnesium sulfate, filtered and concentrated in rotavap. The residue was adsorbed on silica gel and purified on a silica gel column (9×17 cm). The column was eluted with 5 L of 2% THF in hexanes containing 200 mL of DCM to provide compound 231F (15.25 g; 90%) as a slightly yellow solid. $^1$H-NMR (400 MHz, in CDCl$_3$): δ 8.04 (1H, d, J=7.93 Hz), 7.18 (1H, s), 7.07 (1H, dd, J=1.22, 7.32 Hz), 6.92 (1H, dd, J=7.32, 7.93 Hz), 4.36 (2H, q, J=7.32 Hz), 4.28 (2H, s), 1.39 (3H, t, J=7.32 Hz), 1.34 (6H, s); $^{13}$C-NMR (125 MHz, in CDCl$_3$): δ 163.6, 158.2, 136.5, 128.2, 125.3, 123.6, 120.7, 118.5, 116.4, 84.7, 62.1, 42.1, 27.5, 14.2 ppm.

Step F—Synthesis of Compound 231G

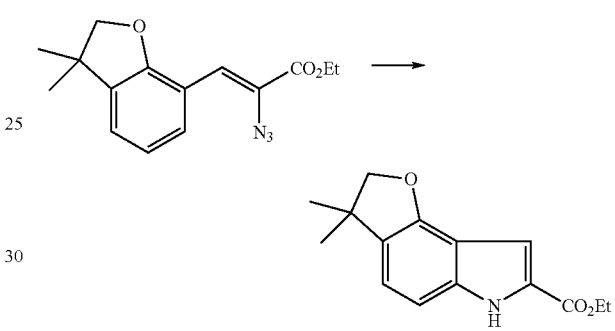

A solution of 2-azido-3-(3,3-dimethyl-2,3-dihydro-benzofuran-7-yl)acrylic acid ethyl ester (15.25 g; 53.07 mmol) in 70 mL of xylenes was added dropwise (over 30 min) to stirring xylenes (30 mL) pre-heated to 165° C. After addition was completed the mixture was stirred for further 10 min and then cooled to room temp. The mixture was kept in freezer (−30° C.) overnight. No crystals were formed and the mixture was concentrated in rotavap. The residue was purified on a Biotage 65-M silica gel column. Elution of the column with 5% THF in hexanes gave the product in fractions containing other impurities. Concentration of those fractions in rotavap provided compound 231G, which precipitated as a white solid (4.0 g; 30%). The mother liquor was concentrated again to give a second batch of product (1.0 g, 7%). $^1$H-NMR (400 MHz, in dmso-d6): δ 11.84 (1H, s), 7.08 (1H, d, J=8.54 Hz), 6.96 (1H, d, J=8.54 Hz), 6.95 (1H, s), 4.32 (2H, s), 4.31 (2H, q, J=7.32 Hz), 1.32 (3H, t, J=7.32 Hz), 1.29 (6H, s); $^{13}$C-NMR (125 MHz, in dmso-d6): δ 161.0, 151.4, 138.9, 127.0, 124.5, 119.2, 113.0, 104.6, 103.4, 84.6, 60.3, 41.5, 27.7, 14.2 ppm. LR-MS (ESI): calcd. for $C_{15}H_{18}NO_3$ [M+H]$^+$ 260.13. found 260.02

Step. G—Synthesis of Compound 231H

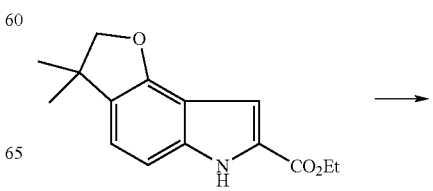

-continued

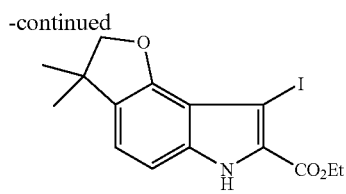

A solution of 3,3-dimethyl-3,6-dihydro-2H-1-oxa-6-aza-indacene-7-carboxylic acid ethyl ester (5.0 g, 19.28 mmol) in THF (200 mL) was cooled to −78° C. and treated with a solution of N-iodosuccinimide (1.1 eq, 4.77 g) in 50 mL of THF. The mixture was stirred for 45 min and then quenched by addition of aqueous saturated sodium bicarbonate (100 mL). The product was taken into ethyl acetate (500 mL) and washed with aq saturated sodium bicarbonate (100 mL) and brine (80 mL). The organic layer was dried over magnesium sulfate, filtered and concentrated in vacuo to provide compound 231H (ca. 100%, 7.42 g) as a dark brown solid which was used without further purification. LR-MS (ESI): calcd. for $C_{15}H_{17}INO_3$ [M+H]$^+$ 386.03. found 385.86

Step H—Synthesis of Compound 231I

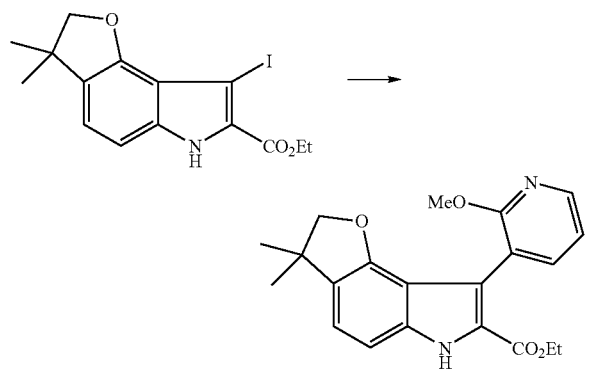

A solution of 8-iodo-3,3-dimethyl-3,6-dihydro-2H-1-oxa-6-aza-indacene-7-carboxylic acid ethyl ester (7.42 g; 19.28 mmol) in 200 mL of 1,2-dimethoxyethane was treated with 2-methoxypyridine-3-boronic acid (2.0 eq, 5.89 g) and bis(triphenylphosphine)palladium(II) chloride (0.1 eq, 1.34 g). The mixture was stirred for 10 min followed by addition of aqueous potassium carbonate (4.0 eq, 38.5 mL of 2 M soln). The mixture was stirred at 90° C. and the flow of the reaction was followed by TLC (30% THF in hexanes). After 2 h the mixture was diluted with ethyl acetate (700 mL) and washed with aqueous saturated sodium bicarbonate (2×100 mL) and brine (100 mL). The organic layer was dried over magnesium sulfate, filtered and concentrated in rotavap. The residue was adsorbed on silica gel and purified on a Biotage 65-M silica gel column. Elution of the column with a gradient of 5 to 20% THF in hexanes/DCM (9:1) gave the product (7.0 g) which contained several impurities. A sample (1.0 g, 2.73 mmol) was dissolved in 10 mL of DMF and purified on a reverse phase prep column (Column: YMC, C18-reverse phase, 120A; 500×50 mm I.D); Flow rate=100 mL/min; Gradient: 20% solvent B for 10 min then increase to 90% over 50 min and stay for 5 min (solvent A: water with 0.01% v/v TFA; solvent B: THF). Three injections were carried out and three fractions were collected from each injection. Fraction A (340 mg) gave 11% of pure product. Fraction B (850 mg) gave 29% of compound 231I with small amount of impurities; Fraction C (520 mg) gave 18% of C7-methoxypyridyl (regioisomeric) product. $^1$H-NMR (400 MHz, in dmso-d6): ᵟ 11.86 (1H, s), 8.11 (1H, dd, J=1.83, 4.88 Hz), 7.64 (1H, dd, J=1.83, 7.32 Hz), 7.08 (1H, d, J=7.93 Hz), 6.99 (1H, d, J=7.93 Hz), 6.98 (1H, dd, J=4.88, 7.32 Hz), 4.15 (2H, s), 4.11 (2H, q, J=7.32 Hz), 3.74 (3H, s), 1.25 (6H, s), 1.05 (3H, t, J=7.32 Hz); $^{13}$C-NMR (125 MHz, in dmso-d6): ᵟ 161.1, 161.0, 152.0, 145.0, 140.3, 137.7, 125.1, 123.7, 119.2, 118.0, 115.9, 114.4, 113.4, 104.4, 84.5, 59.9, 52.7, 41.0, 27.6, 13.7 ppm. LR-MS (ESI): calcd. for $C_{21}H_{23}N_2O_4$ [M+H]$^+$ 367.17. found 367.05.

Step I—Synthesis of Compound 231J

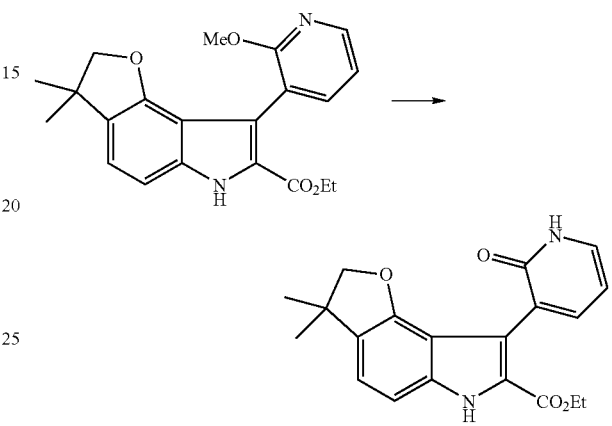

The 8-(2-methoxy-pyridin-3-yl)-3,3-dimethyl-3,6-dihydro-2H-1-oxa-6-aza-indacene-7-carboxylic acid ethyl ester (840 mg, 2.292 mmol) was dissolved in 4 M HCl solution in dioxane (20 mL) and methanol (5 mL). The homogeneous solution was heated in a sealed tube (95° C.) until all starting material had been consumed. After 3 h, the mixture was concentrated to dryness in rotavap to provide compound 231J (ca 100%, 807 mg) as a slightly yellow solid which was dried under high vacuum and used without further purification.

Step J—Synthesis of Compound 231K

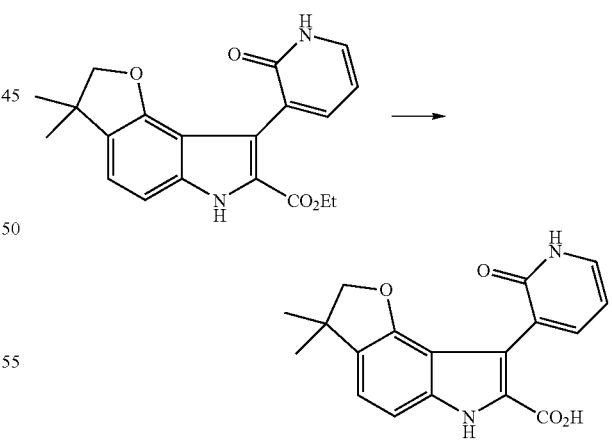

The 3,3-dimethyl-8-(2-oxo-1,2-dihydro-pyridin-3-yl)-3,6-dihydro-2H-1-oxa-6-aza-indacene-7-carboxylic acid ethyl ester (2.292 mmol) was dissolved in 20 mL of 2:1 THF/MeOH and water was added (2 mL). The resulting solution was treated with lithium hydroxide monohydrate (5.0 eq, 480 mg) and heated to 50° C. for 3 hours. TLC (50% THF in dichloromethane) showed complete consumption of the starting material. The mixture was treated with 15 mL of aq 1 M HCl and the volatiles were removed in rotavap to give a tick slurry which was diluted with aq 1 M HCl (15 mL). The solids were recovered by filtration (whatman #1) to provide compound 231K (480 mg, 67%) as a pale green solid. The product contains impurities but no further purification was carried out.

Step K—Synthesis of Compound 231L

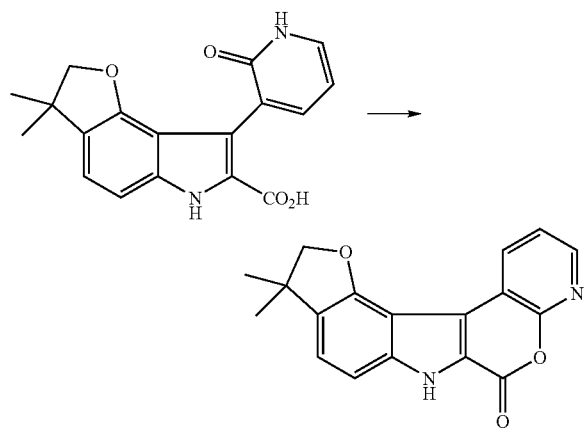

The 3,3-dimethyl-8-(2-oxo-1,2-dihydro-pyridin-3-yl)-3,6-dihydro-2H-1-oxa-6-aza-indacene-7-carboxylic acid (480 mg, 1.480 mmol) was suspended in 15 mL of dry DMF and treated with EDCI (2.0 eq, 567 mg) and triethylamine (10 eq, 2.08 mL, d 0.720). The mixture was stirred overnight at room temp. All the volatiles were removed in rotavap (high vacuum pump) and the residue was treated with 2:1 ethyl acetate/THF (60 mL) and washed with aqueous 1 M HCl (3×10 mL) and brine (10 mL). The organic layer was set aside overnight and a white precipitate was formed. It was recovered by filtration (50 mg; discard) and the filtrate was concentrated to one third of its volume and set aside for 2 hours. A precipitate was formed and was recovered by filtration (145 mg) to provide compound 231L as a white solid. The filtrate was concentrated to almost dryness and set aside for 1 hour. A second crop of product was formed and was recovered by filtration (170 mg) to give a combined yield of 73%. $^1$H-NMR (400 MHz, in dmso-d6): δ 12.83 (1H, s), 9.21 (1H, dd, J=1.83, 7.93 Hz), 8.39 (1H, dd, J=1.83, 4.88 Hz), 7.55 (1H, dd, J=4.88, 7.93 Hz), 7.40 (1H, d, J=8.54 Hz), 7.16 (1H, d, J=8.54 Hz), 4.56 (2H, s), 1.39 (6H, s); LR-MS (ESI): calcd. for $C_{18}H_{15}N_2O_3$ [M+H]$^+$ 307.11. found 306.95.

Step L—Synthesis of Compound 231M

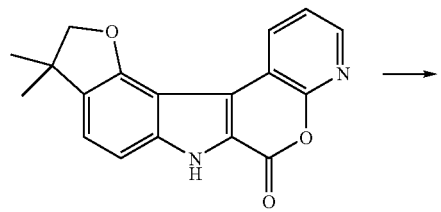

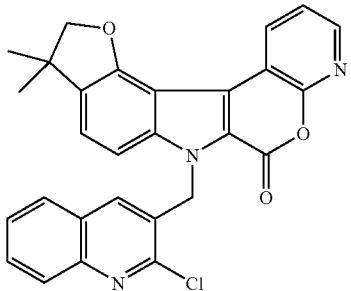

The lactone (145 mg; 0.473 mmol) was suspended in 2.5 mL of DMF and treated with 2-chloro-3-chloromethyl-quinoline (1.20 eq, 120 mg) and cessium carbonate (2.0 eq, 308 g). The reaction mixture was stirred at room for 6 hours. TLC (40% THF in hexanes) showed complete consumption of the starting material. The slurry was filtered using filter paper (whatman #1) and the solids were washed with dichloromethane (20 mL), water (2×20 mL) and ether (2×20 mL) to provide compound 231M (ca. 100%, 227 mg) as a white solid which was used without further purification. $^1$H-NMR (400 MHz, in dmso-d6): δ 9.35 (1H, dd, J=1.83, 7.93 Hz), 8.44 (1H, dd, J=1.83, 4.88 Hz), 7.96 (1H, m), 7.76 (2H, m), 7.60 (1H, dd, J=4.88, 7.93 Hz), 7.53 (1H, d, J=7.32 Hz), 7.44 (1H, d, J=8.54 Hz), 7.25 (1H, d, J=8.54 Hz), 6.08 (2H, s), 4.63 (2H, s), 1.40 (6H, s); LR-MS (ESI): calcd. for $C_{28}H_{21}ClN_3O_3$ [M+H]$^+$ 482.13. found 481.99.

Step M—Synthesis of Compound 231

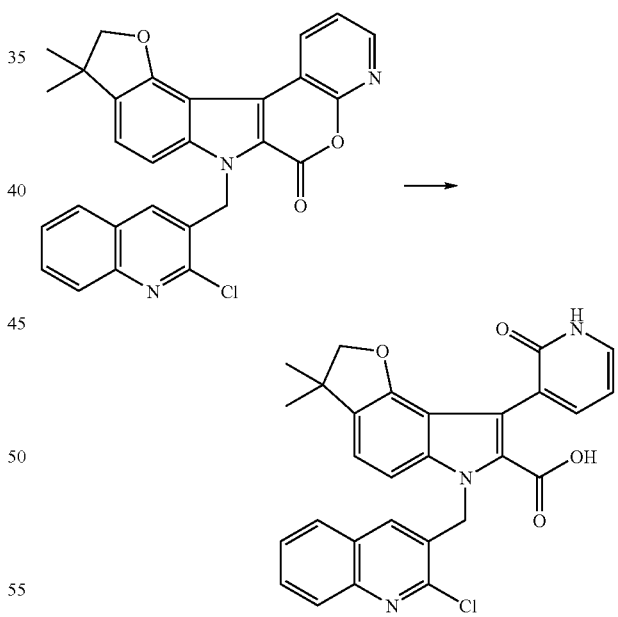

The lactone (40 mg; 0.100 mmol) was suspended in 5 mL of a 2:1 mixture of THF/water and treated with lithium hydroxide monohydrate (5.0 eq, 99 mg). The mixture was stirred at room temp. TLC (40% THF in hexanes) showed complete consumption of the starting material after 1 hour. The reaction was quenched by addition of aqueous 1 M HCl (3 mL) and the THF was removed in rotavap. The product precipitated as a white solid and the mixture was dissolved in DMF (10 mL) and purified on prep-HPLC (reverse C-18) to give the product (60 mg, 25%) as a white solid. NMR showed some impurities from chloroquinoline and the compound was treated with 10 mL of ether. The mixture was filtered to provide compound 231 (35 mg) as a white solid. $^1$H-NMR (400 MHz, in dmso-d6): δ 12.90 (1H, broad s), 11.68 (1H, broad s), 7.98 (1H, d, J=8.54 Hz), 7.82 (1H, d, J=7.93 Hz), 7.78 (1H, dd, J=7.32, 7.32 Hz), 7.58 (2H, m), 7.37 (1H, d, J=4.88 Hz), 7.32 (1H, s), 7.13 (1H, d, J=8.54 Hz), 7.03 (1H, d, J=8.54 Hz), 6.31 (1H, dd, J=6.71, 6.71 Hz), 5.90 (2H, s), 4.27 (2H, s), 1.29 (6H, s); LR-MS (ESI): calcd. for $C_{28}H_{23}ClN_3O_4$ [M+H]$^+$ 500.14. found 499.95.

Example 18

Preparation of Compounds 87 and 228

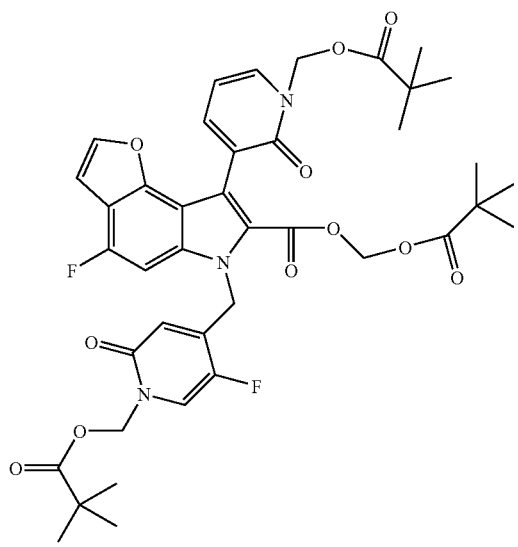 [SMILES: CC(C)(C)C(=O)OCOC(=O)c1c(-c2cccn(COC(=O)C(C)(C)C)c2=O)c2c3occc3c(F)cc2n1Cc1cc(=O)n(COC(=O)C(C)(C)C)cc1F]

Step A—Synthesis of Compound 228B

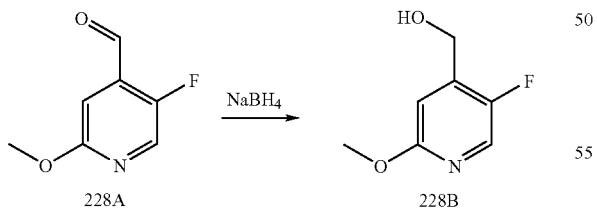

To a solution of 5-Fluoro-2-methoxy-pyridine-4-carbaldehyde (0.3 g, 1.94 mmol) in ethanol (5 mL) was added sodium borohydride (0.037 mg, 0.97 mmol) and the reaction was allowed to stir at room temperature for 1 hour. The reaction mixture was concentrated in vacuo. The reaction mixture was extracted with EtOAc (50 mL), washed with brine, dried (Na$_2$SO$_4$), filtered, and concentrated in vacuo to provide compound 228B and used as it is in the next step.

Step B—Synthesis of Compound 228C

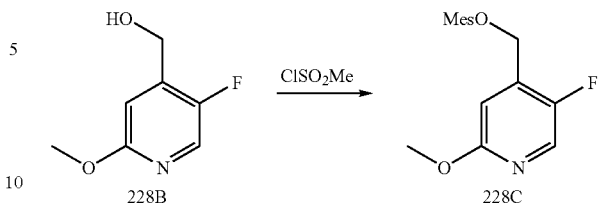

To a solution of (5-Fluoro-2-methoxy-pyridin-4-yl)-methanol in 5 ml of the THF and 1.0 ml TEA was dropped solution of the 0.45 ml methanesulfonyl chloride in 5 ml THF and the reaction was allowed to stir at room temperature for 1 hour. The reaction mixture was concentrated in vacuo. The reaction mixture was extracted with EtOAc (50 mL), washed with brine, dried (Na$_2$SO$_4$), filtered, and concentrated in vacuo to provide compound 228C and used as it is in the next step.

Step C—Synthesis of Compound 228D

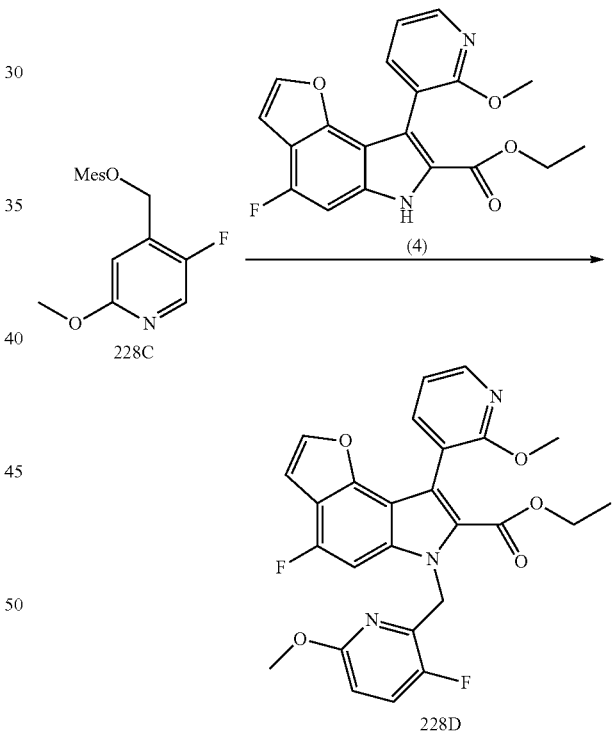

To a solution of compound (4) (0.687 g, 1.94 mmol) in DMF (10 mL) was added cesium carbonate (0.632 g, 1.94 mmol) and compound (3) and the resulting reaction was allowed to stir at room temperature for 24 hour. The reaction mixture was diluted with EtOAc and washed with water, brine. The combined organic layers were dried (Na$_2$SO$_4$), filtered, and concentrated in vacuo to provide compound 228D 0.80 g and used as it is in the next step.

Step D—Synthesis of Compound 228E

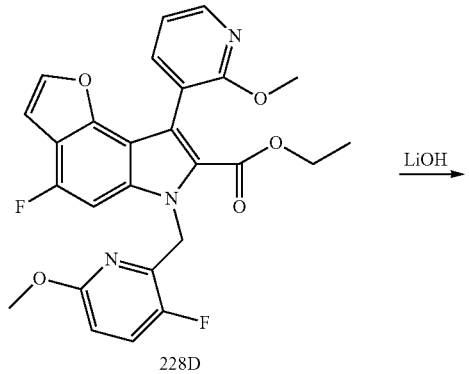

228D

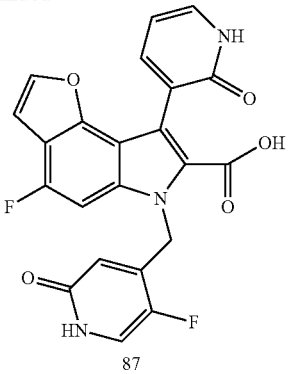

87

Compound 228E (450 mg, 0.97 mmol) was dissolved in 5 ml Dioxane and 5 ml 4N HCl in a pressure tube and the resulting reaction mixture was heated to 90° C. and allowed to remain at this temperature for 4 hour. The reaction mixture was cooled to room temperature, then concentrated in vacuo to provide a crude product which was purified using preparative HPLC to provide compound 87 (150 mg, 37%).

M.S. found: 438.2 (M+H)+; $^1$H NMR (500 MHz, DMSO): δ 7.97 (d, J=2.2 Hz, 1H), 7.73 (m, 1H), 7.69 (dd, J=2.2 Hz, J=6.9 Hz, 1H), 7.54 (d, J=11.0 Hz, 1H), 7.43 (m, 1H), 7.11 (d, J=2.2 Hz, 1H), 6.34 (t, J=6.6 Hz, 1H), 5.85 (s, 2H), 5.27 (s, 1H).

Step F—Synthesis of Compound 228

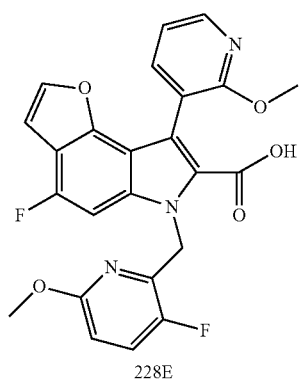

228E

To a solution of compound 228D water/THF (15 ml each) was added lithium hydroxide (0.288 g 12 mmol) and the resulting reaction was allowed to stir at 65° C. overnight. The reaction mixture was diluted with aqueous HCl and extracted into ethyl acetate. The combined organic layers were dried (Na$_2$SO$_4$), filtered, concentrated in vacuo to provide 0.755 g of the product 228E.

Step E—Synthesis of Compound 87

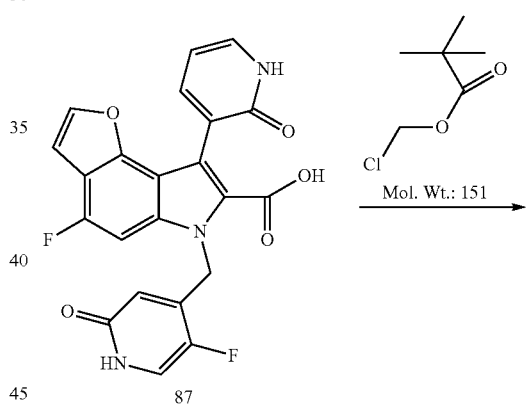

87

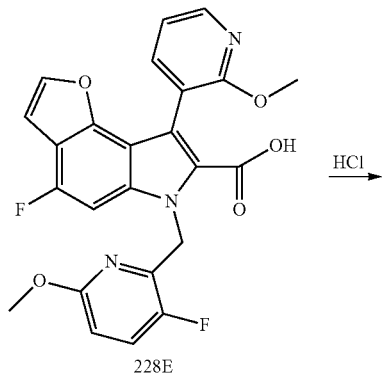

228E

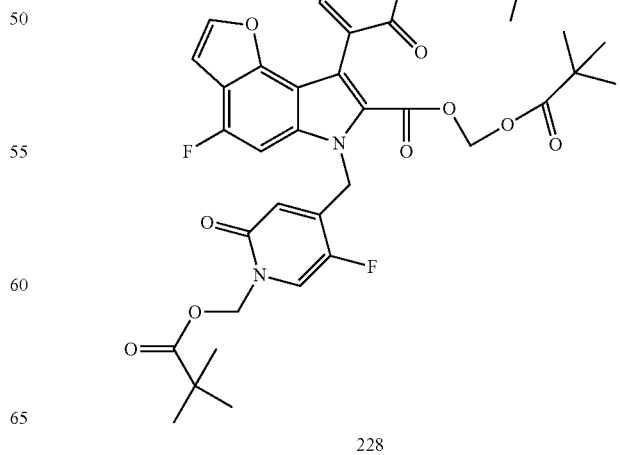

228

To a solution of compound 87 (0.06 g, 0.14 mmol) in DMF (5 mL) was added cesium carbonate (0.091 g, 0.28 mmol) and 2,2-Dimethyl-propionic acid chloromethyl ester (0.042 g, 0.28 mmol) and the resulting reaction was allowed to stir at 40° C. for 24 hour. The reaction mixture was diluted with EtOAc and washed with water, then brine. The combined organic layers were dried ($Na_2SO_4$), filtered, and concentrated in vacuo to provide compound 228 (0.003 g). M.S. found: 780.4 $(M+H)^+$; $^1H$ NMR (500 MHz, $CDCl_3$): δ 7.69 (dd, J=2.2 Hz, J=6.9 Hz, 1H), 7.63 (dd, J=2.2 Hz, J=6.9 Hz, 1H), 7.56-7.52 (m, 2H), 6.91 (d, J=2.2 Hz, 1H), 6.83 (d, J=9.8 Hz, 1H), 6.37 (t, J=6.9 Hz, 1H), 6.01 (m, 2H), 5.81-5.77 (m, 4H), 5.75 (s, 2H), 5.70 (m, 1H), 1.26-1.22 (m, 18H), 1.16 (s, 9H).

Example 19

Preparation of Intermediate Compound AA7

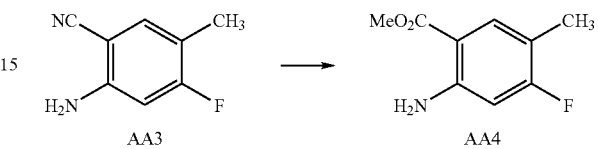

Step A—Synthesis of Compound AA2

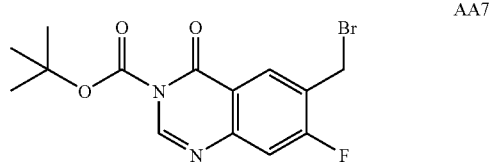 [SMILES: CC(C)(C)OC(=O)n1cnc2cc(F)c(CBr)cc2c1=O]

A mixture of compound AA1 (6.00 g, 47.9 mmol) and anhydrous potassium carbonate (6.70 g, 48.5 mmol) in anhydrous dichloromethane (130 mL) was cooled to −15° C. in a salt-ice bath and then added dropwise to a solution of bromine (7.70 g, 48.2 mmol) in anhydrous dichloromethane (80 mL). After addition was complete, the reaction was allowed to stir at −15° C. for 1 hour. Ice water (100 mL) was added to the reaction mixture and the aqueous layer was extracted with dichloromethane (2×100 mL). The combined organic layers were dried over $MgSO_4$ and concentrated in vacuo to provide compound AA2 (11.0 g, quant.), which was used without further purification.

Step B—Synthesis of Compound AA3

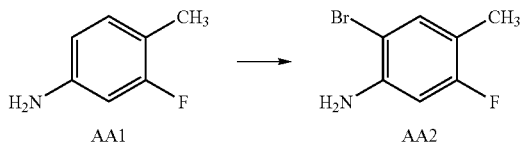

Compound AA2 was dissolved in DMF (150 mL) and to this solution was added copper (I) cyanide (11.0 g, 123 mmol). The mixture was heated to 160° C. and allowed to stir at this temperature for 20 hours. After being cooled to room temperature, with water (200 mL), iron (III) chloride (42.0 g, 155 mmol) and concentrated hydrochloric acid (20 mL) were added to the reaction mixture and the resulting reaction was stirred for 45 minutes. The reaction mixture was then basified to pH>10 using commercial ammonium hydroxide solution. The basic solution was then extracted with ethyl acetate (4×400 mL). The combined organic extracts were washed with water, dried over magnesium sulfate, filtered and concentrated in vacuo. The residue obtained was purified using flash chromatography to provide compound AA3 (5.82 g, 81%). $^1H$ NMR (400 MHz, $d_6$-DMSO): δ 7.34 (d, J=8.4 Hz, 1H), 6.52 (d, J=12.4 Hz, 1H), 6.10 (s, 2H), 2.08 (s, 3H).

Step C—Synthesis of Compound AA4

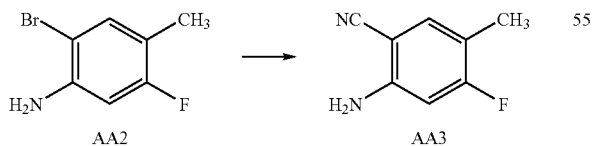

To the solution of AA3 (2.0 g, 13.3 mmol) in anhydrous methanol (15 mL) at room temperature was added concentrated sulfuric acid (4.0 mL). The reaction mixture was heated to 70° C. and stirred for four days. After cooled to room temperature, it was poured into with ice water. The mixture was then diluted with ethyl acetate (200 mL) and was made basic (pH>10) with commercial ammonium hydroxide solution. The layers were separated. The aqueous layer was extracted with ethyl acetate (2×100 mL). The combined organic solution was dried over $MgSO_4$ and concentrated in vacuo to provide the crude product which, was purified using flash chromatography to provide compound AA4 (1.0 g, 41%) and some recovered AA3. $^1H$ NMR (400 MHz, $d_6$-DMSO): δ 7.61 (d, J=8.8 Hz, 1H), 6.69 (s, 2H), 6.51 (d, J=12.0 Hz, 1H), 3.77 (s, 3H), 2.06 (s, 3H).

Step D—Synthesis of Compound AA5

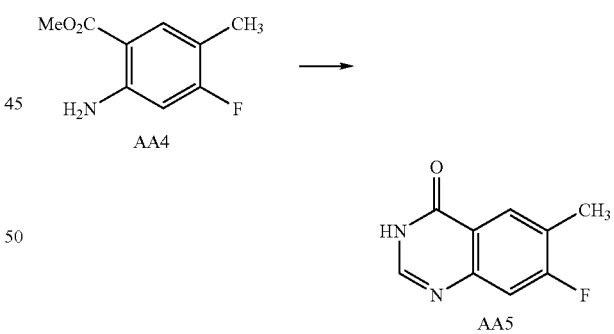

The solution of compound AA4 (500 mg, 2.73 mmol) in formamide (6.0 mL) was heated to 150° C. in an oil bath and stirred for 18 hours. After cooled to room temperature, ethyl acetate (100 mL) and water (100 mL) were added and the layers were separated. The organic solution was washed with water (2×60 mL), dried over $MgSO_4$ and concentrated in vacuo to provide the crude product AA5 (0.50 g, quant.) which, was used without further purification. MS found for $C_9H_7FN_2O$: 179.0 $(M+H)^+$.

Step E—Synthesis of Compound AA6

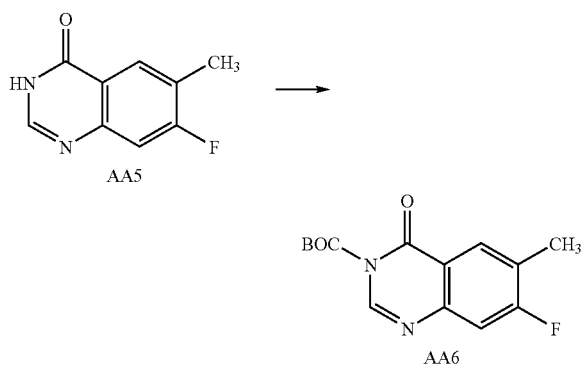

To the solution of AA5 (from Step 4) in anhydrous THF (20 mL) at room temperature was added di-tert-butyl dicarbonate (1.84 g, 8.43 mmol), 4-dimethylaminopyridine (350 mg, 2.86 mmol) and triethyl amine (0.40 mL, 2.87 mmol). The reaction mixture was stirred for 18 hours. Ethyl acetate (100 mL) and water (100 mL) were added and the layers were separated. The aqueous layer was extracted with ethyl acetate (2×50 mL). The combined organic solution was dried over $MgSO_4$ and concentrated in vacuo to provide the crude product which, was purified using flash chromatography to provide compound AA6 (285 mg, 36%). MS found for $C_{14}H_{15}FN_2O_3$: 179.0 $(M+H-100)^+$.

Step F—Synthesis of Compound AA7

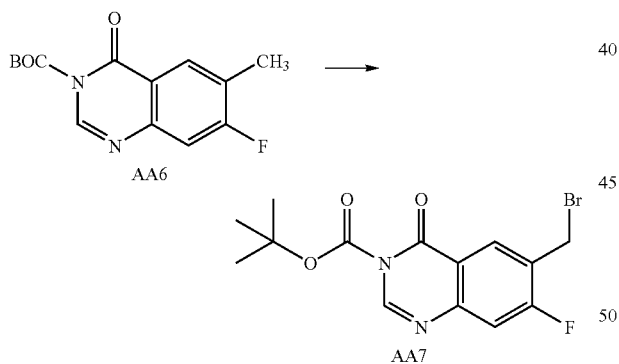

The mixture of AA6 (282 mg, 1.01 mmol), NBS (253 mg, 1.42 mmol) and AIBN (58 mg, 0.353 mmol) in anhydrous carbon tetrachloride (60 mL) was heated to 90° C. in an oil bath and stirred for 4 hours. After cooled to room temperature and concentrated in vacuo, the residue was dissolved in ethyl acetate (100 mL) and water (100 mL). The layers were separated. The organic solution was washed with water (100 mL), dried over $MgSO_4$ and concentrated in vacuo to provide the crude product AA7 (453 mg, quant.) which, was used without further purification.

Example 20

Preparation of Intermediate Compound BB2

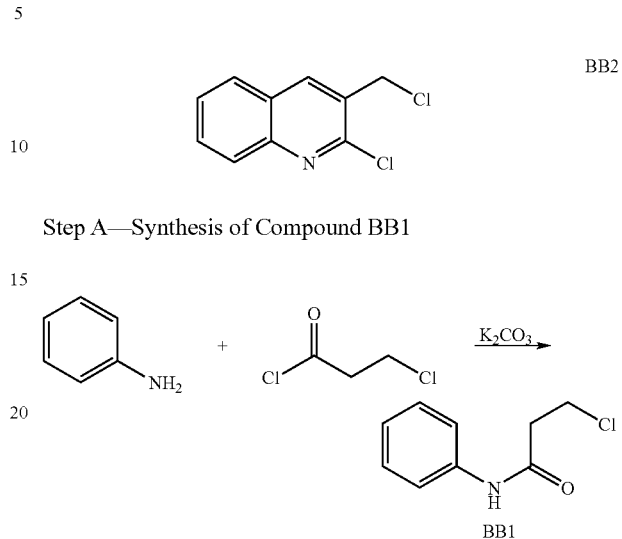

Step A—Synthesis of Compound BB1

A mixture of aniline (65.04 mL, 713.8 mmol), potassium carbonate (54.4 g, 394 mmol) and water (300 mL) were added to a 2000 mL flask. The resulting reaction was kept at room temperature using a room temperature water bath and stirred with a mechanic stirrer. 3-Chloro-propionyl chloride (75.18 mL, 787.6 mmol) was added dropwise via additional funnel and the resulting suspension was allowed to stir at room temperature for 3 hours. The reaction mixture was filtered and the collected solid was washed sequentially with water (300 mL), aq. HCl (1M, 2×300 mL), and water (300 mL), then dried to provide compound BB1, which was used without purification (114.5 g, 87%).

Step B—Synthesis of Compound BB2

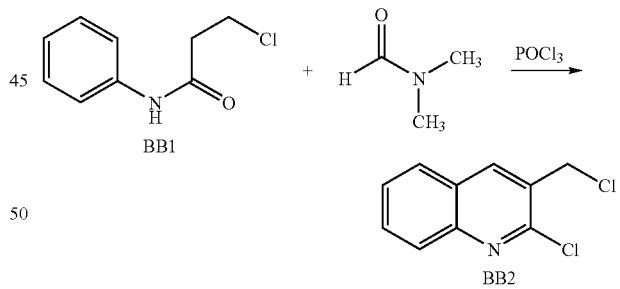

N,N-Dimethylformamide (53.7 mL, 694 mmol) was charged into a three necked flask and cooled to 0° C. and treated with phosphoryl chloride (177.7 mL, 1906 mmol) dropwise. The reaction was stirred at that temperature for 10 min and treated with 3-Chloro-N-phenylpropanamide BB1 (50.00 g, 272.3 mmol) and stirred at room temperature. for 30 min. The reaction mixture was heated at 80° C. for 3 h and slowly poured into ice. The solid separating out was filtered and washed extensively with water (2×1000 mL), aq. saturated sodium bicarbonate (500 mL), and taken in EtOAc (1 L), The solution was dried ($MgSO_4$) filtered concentrated in vacuo and the residue obtained was recrystallized from boiling hexanes to provide compound BB2 (20 g).

Example 21

Preparation of Intermediate Compound CC5

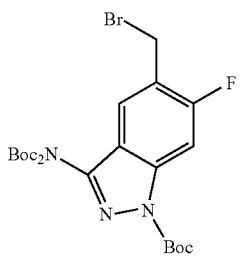

Step A—Synthesis of Compound CC1

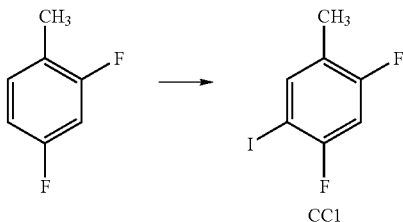

A solution of 2,4-difluorotoluene (4.72 g, 36.8 mmol) in trifluoroacetic acid (12.29 mL, 159.5 mmol) was cooled to 0° C., then N-Iodosuccinimide (9.59 g, 42.6 mmol) was added and the resulting reaction was allowed to stir at room temperature for about 15 hours. The reaction mixture was then concentrated in vacuo and the residue obtained was dissolved in hexanes (100 mL), washed with aqueous sodium thiosulfate (100 mL), brine (100 mL), then dried (MgSO₄), filtered and concentrated in vacuo. The resulting residue was purified using bulb-to-bulb distillation to provide compound CC1 (7.2 g, 77%) as a colorless oil.

Step B—Synthesis of Compound CC2

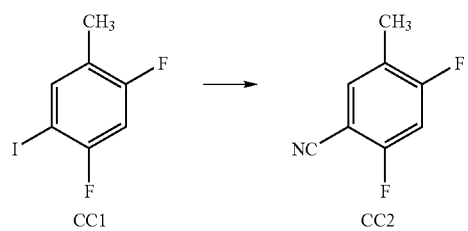

A solution of compound CC1 (7.11 g, 28.0 mmol), zinc cyanide (1.97 g, 16.8 mmol) and tetrakis(triphenylphosphine) palladium(0) (3.23 g, 2.80 mmol) in DMF (30 mL) was heated to 90° C. and allowed to stir at this temperature for 1.5 hours. The reaction mixture was concentrated in vacuo and the residue obtained was taken up in water (400 mL) and extracted with ether (400 mL). The organic extract was washed with aqueous ammonium hydroxide solution (1N). The organic layer was dried (MgSO₄) filtered, concentrated in vacuo to provide a residue that was purified using flash column chromatography (SiO₂, EtOAc/Hexanes) to provide a mixture that contained product and triphenylphosphine. This mixture was further purified using sublimation at 1 mm/Hg at 45° C. to provide compound CC2 (1.8 g; Yield=42%).

Step C—Synthesis of Compound CC3

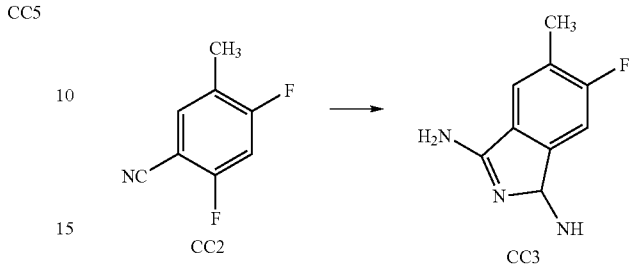

A solution of compound CC2 (1.400 g, 9.154 mmol) and hydrazine (0.700 mL, 22.3 mmol) in isopropyl alcohol (50 mL, 653.1 mmol), was heated to reflux and allowed to stir at this temperature for 24 hours. The reaction mixture was cooled to room temperature, concentrated in vacuo and the residue obtained was purified using flash column chromatography (SiO₂, Acetone/Hexanes 0→50%) to provide compound CC3 (330 mg, 22%).

Step D—Synthesis of Compound CC4

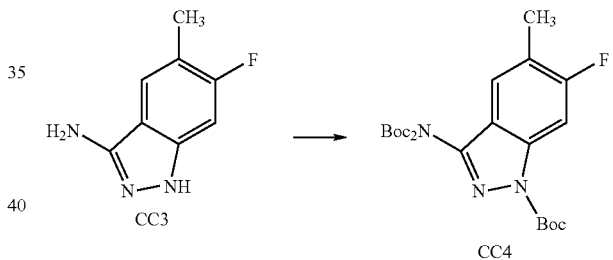

A solution of compound CC3 (330.00 mg, 1.998 mmol), di-tert-butyldicarbonate (2.6163 g, 11.98 mmol) and 4-dimethylaminopyridine (48.817 mg, 0.39959 mmol) in acetonitrile (15 mL, 287.2 mmol) was heated to reflux and allowed to stir at this temperature for 2 hours. The reaction mixture was cooled to room temperature, concentrated in vacuo, and the resulting residue was purified using flash column chromatography (SiO₂, EtOAc/Hexanes 0-20%) to provide compound CC4 (640.00 mg, 68%) as a colorless oil.

Step E—Synthesis of Compound CC5

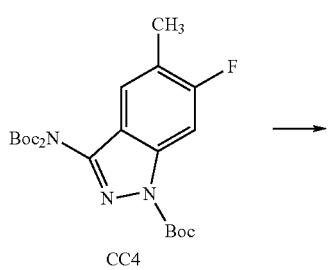

-continued

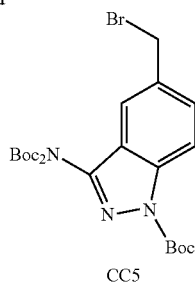

CC5

A solution of compound CC4 (630.00 mg, 1.3533 mmol), N-bromosuccinimide (337.22 mg, 1.8947 mmol) and benzoyl peroxide (65.563 mg, 0.27067 mmol) in carbon tetrachloride (20 mL) was heated to reflux and allowed to stir at this temperature for 3 hours. The reaction mixture was cooled to room temperature, concentrated in vacuo and the residue obtained was dissolved in EtOAc (300 mL). The resulting solution was washed with aqueous sodium thiosulfate (100 mL), brine (100 mL), dried (MgSO$_4$), filtered, and concentrated in vacuo. The residue obtained was purified using flash column chromatography (SiO$_2$, EtOAc/Hexanes) to provide compound CC5 as a colorless oil.

Example 22

Preparation of Intermediate Compounds DD5 and DD6

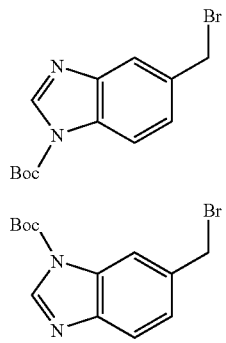

DD5

DD6

Step A—Synthesis of Compound DD2

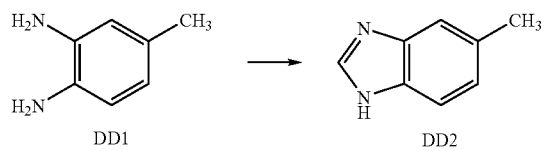

DD1     DD2

A solution of compound DD1 (3 g, 24.5 mmol) in trimethyl orthoformate (15 mL) was treated with 2 drops conc. HCl and heated to 80° C. for 2 hours. The reaction mixture was cooled to room temperature and concentrated in vacuo to provide compound DD2 (3.65 g), which was used without further purification. M.S. found for C$_8$H$_8$N$_2$: 133.2 (M+H)$^+$.

Step B—Synthesis of Compounds DD3 and DD4

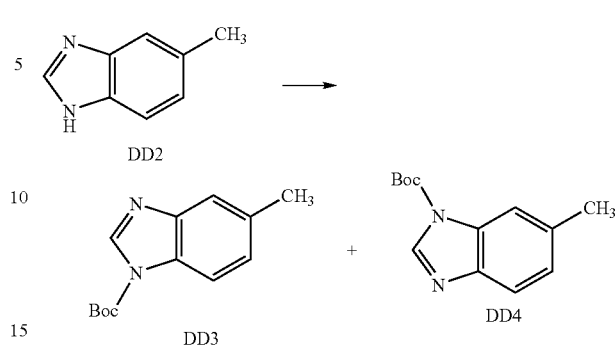

DD2

DD3     DD4

To a solution of compound DD2 (24.5 mmol) in CH$_3$CN (65 mL) was added di-tertbutyl dicarbonate (5.89 g, 27.0 mmol), triethylamine (3.76 mL, 27.0 mmol) and 4-dimethylamino pyridine (300 mg, 2.45 mmol) and the resulting reaction was heated to 80° C. and allowed to stir at this temperature for 1.5 hours. The reaction mixture was cooled to room temperature, concentrated in vacuo, and the residue obtained was purified using flash column chromatography (silica gel, EtOAc/Hexanes 5-20%) to provide a mixture of isomeric compounds DD3 and DD4 (5.38 g, 94.3% yield over steps A and B).

Step C—Synthesis of Compounds DD5 and DD6

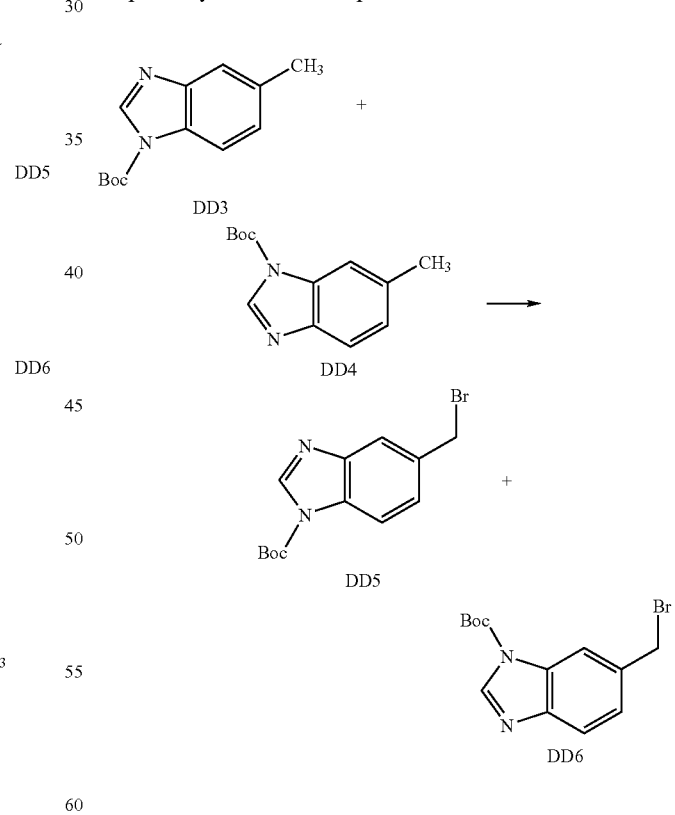

DD3

DD4

DD5

DD6

To a solution of compounds DD3 and DD4 (2 g, 8.61 mmol) in carbon tetrachloride (40 mL) was added N-bromosuccinimide (1.6 g, 9.04 mmol) and dibenzoyl peroxide (41.7 mg, 0.1722 mmol) and the resulting reaction was heated to 90° C. and allowed to stir at this temperature for 12 hours. The reaction was cooled to room temperature, solids were filtered off and the filtrate was washed with water, dried over sodium sulfate and concentrated in vacuo to provide compounds DD5 and DD6 (2.58 g) which was used without further purification. M.S. found for $C_{13}H_{15}BrN_2O_2$: 334.7 $(M+Na)^+$.

Example 23

Preparation of Intermediate Compound EE2

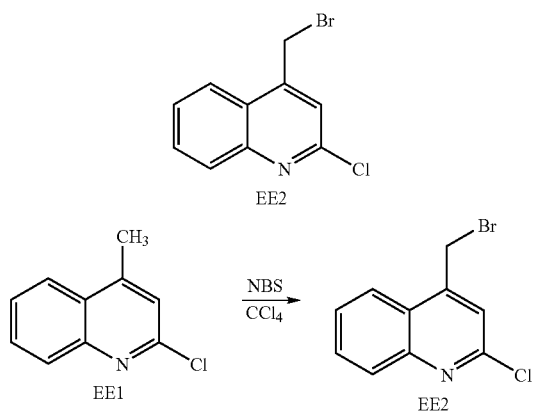

A mixture of compound EE1 (1.5 g, 8.44 mmol), NBS (1.8 g, 10.11 mmol) in carbon tetrachloride (50 mL) was heated to reflux, then benzoyl peroxide (0.21 g, 0.866 mmol) was added. The resulting suspension was allowed to stir at reflux for 19 hours, then cooled to room temperature and filtered. The filtrate was washed with saturated sodium carbonate, dried over sodium sulfate and concentrated in vacuo to provide a mixture (1.7 g) which contains about 50% of compound EE2, and was used without further purification.

Example 24

HCV NS5B Polymerase Inhibition Assay

An in vitro transcribed heteropolymeric RNA known as D-RNA or DCoH has been shown to be an efficient template for HCV NS5B polymerase (S.-E. Behrens et al., EMBO J. 15: 12-22 (1996); WO 96/37619). A chemically synthesized 75-mer version, designated DCoH75, whose sequence matches the 3'-end of D-RNA, and DCoH75ddC, where the 3'-terminal cytidine of DCoH75 is replaced by dideoxycytidine, were used for assaying the NS5B enzyme activity as described in Ferrari et al., *12th International Symposium on HCV and Related Viruses*, P-306 (2005). The sequence of the template RNA was: 5'-UGU GCC GGU CUU UCU GAA CGG GAU AUA AAC CUG GCC AGC UUC AUC GAA CAA GUU GCC GUG UCU AUG ACA UAG AUC-3'. A soluble C-terminal 21-amino acid truncated NS5B enzyme form (NS5BΔCT21, from HCV-Con 1 isolate, genotype 1b, Genbank accession number AJ238799) was produced and purified from *Escherichia coli* as C-terminal polyhistidine-tagged fusion protein as described in Ferrari et al., *J. Virol.* 73:1649-1654 (1999). A typical assay contained 20 mM Hepes pH 7.3, 10 mM $MgCl_2$, 60 mM NaCl, 100 µg/ml BSA, 20 units/ml RNasin, 7.5 mM DTT, 0.1 µM ATP/GTP/UTP, 0.026 µM CTP, 0.25 mM GAU, 0.03 µM RNA template, 20 µCi/ml $[^{33}P]$-CTP, 2% DMSO, and 30 or 150 nM NS5B enzyme. Reactions were incubated at 22° C. for 2 hours, then stopped by adding 150 mM EDTA, washed in DE81 filter plate in 0.5M di-basic sodium phosphate buffer, pH 7.0, and counted using Packard TopCount after the addition of scintillation cocktail. Polynucleotide synthesis was monitored by the incorporation of radiolabeled CTP. The effect of the Compounds of Formula (I) on the polymerase activity was evaluated by adding various concentrations of a Compound of Formula (I), typically in 10 serial 2-fold dilutions, to the assay mixture. The starting concentrations ranged from 200 µM to 1 µM. An $IC_{50}$ value for the inhibitor, defined as the compound concentration that provides 50% inhibition of polymerase activity, was determined by fitting the cpm data to the Hill equation $Y=100/(1+10^{((LogIC50-X)*HillSlope)})$, where X is the logarithm of compound concentration, and Y is the % inhibition. Ferrari et al., *12th International Symposium on HCV and Related Viruses*, P-306 (2005) described in detail this assay procedure. It should be noted that such an assay as described is exemplary and not intended to limit the scope of the invention. The skilled practitioner can appreciate that modifications including but not limited to RNA template, primer, nucleotides, NS5B polymerase form, buffer composition, can be made to develop similar assays that yield the same result for the efficacy of the compounds and compositions described in the invention.

NS5B polymerase inhibition data for selected Compounds of Formula (I) is provided below in Table 2, wherein the compound numbers correspond to the compound numbering set forth in the above specification. The data is designated as follows: "A" for $IC_{50}$ values less than 25 nanomolar (nM), "B" for $IC_{50}$ values between 25 to and 100 nM and "C" for $IC_{50}$ values greater than 100 nM.

Example 25

Cell-Based HCV Replicon Assay

To measure cell-based anti-HCV activity of the a Compound of Formula (I), replicon cells were seeded at 5000 cells/well in 96-well collagen I-coated Nunc plates in the presence of the Compound of Formula (I). Various concentrations of a Compound of Formula (I), typically in 10 serial 2-fold dilutions, were added to the assay mixture, with the starting concentration ranging from 250 µM to 1 µM. The final concentration of DMSO was 0.5%, fetal bovine serum was 5%, in the assay media. Cells were harvested on day 3 by the addition of 1× cell lysis buffer (Ambion cat #8721). The replicon RNA level was measured using real time PCR (Taqman assay). The amplicon was located in 5B. The PCR primers were: 5B.2F, ATGGACAGGCGCCCTGA; 5B.2R, TTGATGGGCAGCTTGGTTTC; the probe sequence was FAM-labeled CACGCCATGCGCTGCGG. GAPDH RNA was used as endogenous control and was amplified in the same reaction as NS5B (multiplex PCR) using primers and VIC-labeled probe recommended by the manufacturer (PE Applied Biosystem). The real-time RT-PCR reactions were run on ABI PRISM 7900HT Sequence Detection System using the following program: 48° C. for 30 min, 95° C. for 10 min, 40 cycles of 95° C. for 15 sec, 60° C. for 1 min. The ΔCT values ($CT_{5B}$-$CT_{GAPDH}$) were plotted against the concentration of test compound and fitted to the sigmoid dose-response model using XLfit4 (MDL). $EC_{50}$ was defined as the concentration of inhibitor necessary to achieve ΔCT=1 over the projected baseline; $EC_{90}$ the concentration necessary to achieve ΔCT=3.2 over the baseline. Alternatively, to quantitate the absolute amount of replicon RNA, a standard curve was established by including serially diluted T7 transcripts of replicon RNA in the Taqman assay. All Taqman reagents were from PE Applied Biosystems. Such an assay procedure was described in detail in e.g. Malcolm et al., *Antimicrobial Agents and Chemotherapy* 50: 1013-1020 (2006).

HCV Replicon assay data for selected Compounds of Formula (I) is provided below in Table 1, wherein the compound numbers correspond to the compound numbering set forth in the above specification. The data is designated as follows: "A" for $EC_{50}$ values less than 0.5 micromolar (μM), "B" for $EC_{50}$ values between 0.5 and 1.5 μM and "C" for $EC_{50}$ values greater than 1.5 μM.

TABLE 1

| # | IC50 | EC50 | LR-MS (M + H) | $^1$H NMR DATA |
|---|---|---|---|---|
| 1 | A | A | 403.4 | See Example 4 for Experimental Details and Data |
| 2 | A | B | 421.4 | 1H NMR (400 MHz, D6-dmso), δ 11.75 (s, 1H), 7.85 (d, 1H, J = 2.2 Hz), 7.66 (dd, 1H, J = 2.2 & 6.6 Hz), 7.55 & 7.47 (AB, 2H, J = 8.8 Hz), 7.40 (d, 1H, J = 5.9 Hz), 7.28 (dt, 1H, J = 2.2 & 10.9 Hz), 6.96 (d, 1H, J = 2.2 Hz), 6.95 (dt, 1H, J = 2.9 & 5.9 Hz), 6.68 (q, 1H), 6.33 (t, 1H), 5.91 (s, 2H). |
| 3 | B | A | 421.4 | 1H NMR (400 MHz, D6-dmso), δ 12.8 (s, 1H), 11.74 (s, 1H), 7.85 (d, 1H, J = 1.5 Hz), 7.68 (dd, 1H, J = 2.2 & 6.6 Hz), 7.56 & 7.47 (AB, 2H, J = 8.8 Hz), 7.40 (d, 1H, J = 5.2 Hz), 7.30 (dt, 1H, J = 4.4 & 5.0 Hz), 7.16-7.11 (m, 1H), 6.97 (d, 1H, J = 2.2 Hz), 6.36-6.31 (m, 2H), 5.93 (s, 2H). |
| 4 | A | A | 480.5 | See Example 5 for Experimental Details and Data |
| 5 | B | A | 498.5 | 1H NMR (400 MHz, D6-dmso), δ 12.8 (s, 1H), 12.9 (s, 1H), 7.96 (d, 1H, J = 6.6 Hz), 7.84 (d, 1H, J = 2.2 Hz), 7.66 (bt, 1H), 7.59 & 7.51 (AB, 2H, J = 8.8 Hz), 7.28 (dt, 1H, J = 2.2 & 8.8 Hz), 6.98 (d, 1H, J = 2.2 Hz), 6.98-6.87 (m, 2H), 6.61 (t, 1H, J = 6.6 Hz), 5.77 (s, 3H), 3.25 (s, 3H). |
| 6 | A | A | 498.5 | 1H NMR (400 MHz, D6-dmso), δ 12.6 (s, 1H), 12.7 (s, 1H), 7.99 (d, 1H, J = 6.6 Hz), 7.85 (s, 1H), 7.69-7.65 (m, 1H), 7.60 & 7.49 (AB, 2H, J = 8.8 Hz), 7.33-7.24 (m, 1H), 7.18-7.13 (m, 1H), 6.99 (s, 1H), 6.63-6.53 (m, 2H), 5.78 (s, 2H), 3.24 (s, 3H) |
| 7 | A | C | 413.5 | $^1$H NMR (500 MHz, CDCl$_3$) δ 7.59-7.10 (m, 11H), 5.98 (m, 2H), 2.07 (s, 3H), 1.90 (s, 3H). |
| 8 | C | C | 441.5 | 1H NMR (500 MHz, CDCl3) δ 9.96 (s, 1H), 7.46-7.10 (m, 11H), 5.98 (ABq, JAB = 16.7 Hz, 2H), 4.03 (m, 2H), 2.30 (s, 3H), 1.46 (s, 3H), 0.84 (t, J = 7.3 Hz, 3H). C28H25FN2O2; |
| 9 | A | C | 498.5 | See Example 3 for Experimental Details and Data |
| 10 | B | C | 590.6 | 1H NMR (400 MHz, D6-dmso), δ 12.9 (s, 1H), 12.8 (s, 1H), 7.95 (s, 1H), 7.79 (m, 2H), 7.66 (d, 2H), 7.61 & 7.52 (AB, 2H, J = 8.8 Hz), 7.15 (t, 1H, J = 9.5 Hz), 7.02 (d, 2H, J = 8.8 Hz), 6.81 (t, 1H, J = 8.8 Hz), 6.64-6.58 (m, 2H), 6.41 (s, 1H), 5.65 (s, 2H), 3.81 (s, 3H). |
| 11 | B | C | 653.7 | 1H NMR (400 MHz, D6-dmso), δ 10.22 (s, 1H), 7.82-7.77 (m, 4H), 7.62 & 7.53 (AB, 2H, J = 8.8 Hz), 7.49-7.40 (m, 4H), 7.15 (dt, 1H, J = 2.2 & 8.8 Hz), 6.82 (dt, 1H, J = 3.0 Hz & 8.8 Hz), 6.66 (t, 2H), 6.42 (d, 1H, J = 1.5 Hz), 5.64 (s, 2H), 3.00 (s, 3H). |
| 12 | A | B | 498.53 | See Example 1 for Experimental Details and Data |
| 13 | C | C | 418.4 | 1H NMR (400 MHz, D6-dmso), δ above 12 (s, 1H), 11.89 (s, 1H), 9.18 (s, 1H), 8.04 (d, 1H, J = 9.2 Hz), 7.95 (bs, 2H), 7.90 (d, 1H, J = 5.6 Hz), 7.74 (d, 1H, J = 9.2 Hz), 7.57 (dd, 1H, J = 2.0 & 5.2 Hz), 7.52-7.50 (m, 1H), 6.66 (dd, 1H, J = 1.6 & 5.2 Hz), 6.36 (t, 1H, J = 6.4 Hz), 6.31 (s, 1H), 5.99 (bd, 2H). |
| 14 | A | B | 418.4 | 1H NMR (500 MHz, d6-DMSO): δ 11.7 (s, 1H), 9.33 (s, 1H), 8.08 (d, J = 8.8 Hz, 1H), 7.98-7.87 (m, 2H), 7.71 (d, J = 8.8 Hz, 1H), 7.60 (d, J = 6.3 Hz, 1H), 7.39 (d, J = 5.7 Hz, 1H), 6.65 (t, J = 6.3 Hz, 1H), 6.31 (s, 2H), 5.99 (s, 2H), 4.46 (s, 1H), 3.60 (s, 1H) |
| 16 | C | C | 438.4 | See Example 2 for Experimental Details and Data |
| 17 | A | C | 438.4 | 1H NMR (400 MHz, D6-DMSO) d, 9.15 (s, 1H), 8.01 & 7.98 ((d, J = 9.52 Hz, 1H), 7.79 & 7.77 (d, J = 8.79 Hz, 1H), 7.59 & 7.57 (d, J = 6.59 Hz, 1H), 7.497 & 7.48 (d, J = 5.86 Hz, 1H), 7.29 (t, J = 9.52 Hz, 1H), 6.96 (t, J = 9.50 Hz, 1H), 6.70 (q, J = 8.79 & 15.38 Hz, 1H), 6.34 (t, J = 7.32 Hz, 1H), 5.98 (q, J = 16.11 & 46.87 Hz, 2H). |
| 24 | C | C | 449.4 | 1H NMR (400 MHz, D6-dmso), δ 13.2 (s, 1H), 11.92 (s, 1H), 7.75 (d, 1H, J = 6.6 Hz), 7.57 & 7.44 (AB, 2H, J = 8.8 Hz), 7.50 (d, 1H, J = 6.6 Hz), 7.47 (s, 1H), 7.30 (dt, 1H, J = 4.4 & 4.3 Hz), 7.15-7.09 (m, 1H), 6.35 (t, 1H, J = 6.6 Hz), 6.16-6.13 (m, 1H), 6.00 (s, 2H), 2.77 (q, 2H, J = 7.3 Hz), 1.18 (t, 3H, J = 7.3 Hz). |
| 33 | B | C | 437.4 | $^1$H NMR (400 MHz, D$_6$-dmso), δ 11.75 (s, 1H), 7.79 & 7.60 (AB, 2H, J = 8.8 Hz), 7.59 (t, 1H, J = 3.7 Hz), 7.50-7.46 (m, 3H), 7.31 (dt, 1H, J = 4.4 Hz), 7.17-7.12 (m, 1H), 6.33 (t, 1H, J = 6.6 Hz), 6.02 & 5.93 (AB, 2H, J = 18.3 Hz). |

TABLE 1-continued

| # | IC50 | EC50 | LR-MS (M + H) | $^1$H NMR DATA |
|---|---|---|---|---|
| 34 | B | B | 419.5 | $^1$H NMR (400 MHz, D$_6$-dmso), δ above 12 (s, 1H), 11.76 (s, 1H), 7.77 (d, 1H, J = 8.8 Hz), 7.59-7.57 (m, 2H), 7.48 & 7.45 (AB, 2H, J = 5.2 Hz), 7.49-7.44 (bs, 1H), 7.30-7.20 (m, 2H), 7.02 (dt, 1H, J = 1.6 & 7.6 Hz), 6.58 (dt, 1H, J = 1.6 & 7.6 Hz), 6.33 (t, 1H, J = 6.8 Hz), 6.07 & 5.94 (AB, 2H, J = 16.0 Hz) |
| 37 | A | C | 461.3 | 1H NMR (400 MHz, d6-DMSO): δ, 11.8 (bs, 1H), 7.62 (dd, J = 6.8, 2.0 Hz, 1H), 7.47 (d, J = 9.2 Hz, 1H), 7.43-7.41 (m, 2H), 7.30 (td, J = 9.2, 4.4 Hz, 1H), 7.19-7.14 (m, 1H), 6.52-6.48 (m, 1H), 6.32 (t, J = 6.6 Hz, 1H), 5.88 (s, 2H). |
| 39 | B | C | 403.4 | 1H-NMR (400 MHz, in dmso-d6): δ 11.80 (1H, broad s), 7.94 (1H, s), 7.58 (2H, m), 7.48 (1H, d, J = 9.52 Hz), 7.45 (1H, m), 7.24 (2H, m), 7.01 (1H, t, J = 7.32 Hz), 6.57 (2H, s), 6.34 (1H, dd, J = 5.86, 6.59 Hz), 5.97 (2H, s) |
| 40 | B | C | 421.4 | 1H-NMR (400 MHz, in dmso-d6): δ 11.81 (1H, broad s), 7.95 (1H, s), 7.60 (2H, d, J = 8.78 Hz), 7.5 (1H, d, J = 9.5 Hz), 7.46 (1H, d, J = 6.59 Hz), 7.30 (1H, ddd, J = 4.39, 8.78, 9.52 Hz), 7.13 (1H, m), 6.57 (1H, s), 6.32 (1H, m), 5.95 (2H, s) |
| 41 | A | A | 399.4 | $^1$H NMR (400 MHz, D$_6$-dmso), δ 12.8 (s, 1H), 11.72 (s, 1H), 7.84 (s, 1H), 7.70 (d, 1H, J = 5.9 Hz), 7.49 & 7.19 (AB, 2H, J = 8.8 Hz), 7.40 (d, 1H, J = 4.4 Hz), 7.19 (d, 1H, J = 6.6 Hz), 7.07 (t, 1H, J = 6.6 Hz), 6.96 (s, 1H), 6.92 (t, 1H, J = 6.0 Hz), 6.34 (t, 1H, J = 5.9 Hz), 6.03 (d, 1H, J = 7.3 Hz), 5.86 (s, 2H), 2.42 (s, 3H). |
| 43 | C | C | 431.4 | 1H NMR (400 MHz, D6-dmso), δ 13.04 (s, 1H), 11.92 (s, 1H), 7.75 (dd, 1H, J = 2.1 & 4.7 Hz), 7.55 & 7.41 (AB, 2H, J = 8.8 Hz), 7.50 (dd, 1H, J = 1.7 & 4.7 Hz), 7.46 (s, 1H), 7.29-7.19 (m, 2H), 6.97 (dt, 1H, J = 1.7 & 7.7 Hz), 6.36-6.33 (m, 2H), 6.0 (s, 2H), 2.76 (q, 2H, J = 7.7 Hz), 1.18 (t, 3H, J = 7.7 Hz). |
| 45 | A | A | 437.8 | 1H NMR (400 MHz, D6-dmso), δ 13.04 (s, 1H), 11.75 (s, 1H), 8.16 (s, 1H), 7.67 (dd, 1H, J = 2.1 & 4.7 Hz), 7.60 & 7.47 (AB, 2H, J = 9.0 Hz), 7.40 (d, 1H, J = 6.4 Hz), 7.27 (q, 1H, J = 7.7 Hz), 7.23 (q, 1H, J = 10.3 Hz), 7.03 (t, 1H, J = 7.2 Hz), 6.59 (t, 1H, J = 7.7 Hz), 6.32 (t, 1H, J = 6.8 Hz), 5.97 (s, 2H). |
| 46 | A | A | 455.8 | 1H NMR (400 MHz, D6-dmso), δ 13.11 (s, 1H), 11.76 (s, 1H), 8.18 (s, 1H), 7.69 (dd, 1H, J = 2.2 & 4.4 Hz), 7.63 & 7.49 (AB, 2H, J = 8.8 Hz), 7.41 (d, 1H, J = 5.5 Hz), 7.30 (dt, 1H, J = 4.4 & 4.3 Hz), 7.17-7.11 (m, 1H), 6.38-6.33 (m, 1H), 6.32 (t, 1H, J = 6.6 Hz), 5.95 (s, 2H). |
| 47 | C | C | 435.4 | 1H NMR (400 MHz, D6-dmso), δ above 12 (s, 1H), 11.94 (s, 1H), 7.77 (dd, 1H, J = 2.0 & 8.5 Hz), 7.54 & 7.47 (AB, 2H, J = 8.8 Hz), 7.54-7.44 (m, 2H), 7.33-7.27 (m, 1H), 7.17-7.08 (m, 1H), 6.35 (t, 1H, J = 6.8 Hz), 6.15-6.10 (m, 1H), 5.96 (s, 2H), 2.28 (s, 3H). |
| 48 | C | C | 431.4 | 1H NMR (400 MHz, D6-dmso), δ above 12 (s, 1H), 11.93 (s, 1H), 7.77 (dd, 1H, J = 2.0 & 6.8 Hz), 7.51-7.39 (m, 4H), 7.11 (t, 1H, J = 8.0 Hz), 6.84 (t, 1H, J = 7.6 Hz), 6.35 (t, 1H, J = 6.8 Hz), 6.13 (t, 1H, J = 7.2 Hz), 6.00 (s, 2H), 2.27 (s, 3H), 2.36 (d, 3H, J = 1.2 Hz). |
| 49 | A | C | 514.5 | See Example 6 for Experimental Details and Data |
| 50 | A | A | 497.5 | 1H NMR (400 MHz, d6-DMSO): δ, 9.31 (s, 1H), 8.09 (d, J = 8.8 Hz, 1H), 7.94 (dd, J = 6.8, 4.0 Hz, 1H), 7.81 (d, J = 9.2 Hz, 1H), 7.66 (d, J = 4.8 Hz, 1H), 7.34-7.29 (m, 2H), 7.26-7.21 (m, 1H), 7.08 (t, J = 7.4 Hz, 1H), 6.84 (t, J = 7.8 Hz, 1H), 6.59 (t, J = 6.6 Hz, 1H), 5.88 (s, 2H), 3.57 (s, 3H), 3.60 (s, 1H). |
| 51 | A | A | 493.6 | See Example 7 for Experimental Details and Data |
| 52 | A | C | 514.5 | See Example 8 for Experimental Details and Data |
| 53 | A | C | 480.5 | 1H-NMR (400 MHz, in dmso-d6): δ 12.77 (1H, broad s), 12.69 (1H, broad s), 7.97 (1H, s), 7.88 (1H, d, J = 6.84 Hz), 7.75 (1H, m), 7.64 (1H, d, J = 8.79 Hz), 7.54 (1H, d, J = 8.79 Hz), 7.29 (1H, m), 7.22 (1H, m), 7.05 (1H, dd, J = 7.32, 7.32 Hz), 6.82 (1H, dd, J = 7.32, 7.81 Hz), 6.65 (1H, dd, J = 6.35, 6.84 Hz), 6.47 (1H, s), 5.83 (2H, s), 3.23 (3H, s) |
| 56 | A | C | 520.5 | See Example 9 for Experimental Details and Data |
| 57 | A | A | 512.5 | 1H NMR (400 MHz, D6-dmso), δ above 12 (s, 1H), 8.00 (d, 1H, J = 7.2 Hz), 7.84 (dd, 1H, J = 2.0 & 7.2 Hz), 7.69 (t, 1H, J = 6.4 Hz), 7.61 & 7.53 (AB, 2H, J = 9.2 Hz), 7.30 (dt, 1H, J = 4.0 & 8.8 Hz), 7.18-7.13 (m, 1H), 6.99 (dd, 1H, J = 1.2 & 2.4 Hz), 6.64 (t, 1H, J = 7.6 Hz), 6.57-6.53 (m, 1H), 5.79 (s, 2H), 3.35 (q, 2H, J = 8.0 Hz), 1.04 (d, 3H, J = 7.6 Hz) |

TABLE 1-continued

| # | IC50 | EC50 | LR-MS (M + H) | ¹H NMR DATA |
|---|---|---|---|---|
| 58 | A | C | 498.5 | 1H-NMR (400 MHz, in dmso-d6): δ 12.92 (1H, broad s), 11.67 (1H, broad s), 7.98 (1H, d, J = 2.20 Hz), 7.91 (1H, dd, J = 2.20, 7.32), 7.75 (1H, m), 7.65 (1H, d, J = 9.52 Hz), 7.54 (1H, d, J = 9.52 Hz), 7.30 (1H, ddd, J = 4.39, 9.52, 9.52), 7.15 (1H, m), 6.65 (1H, t, J = 6.59 Hz), 6.57 (1H, ddd, J = 2.92, 5.86, 8.79 Hz), 6.38 (1H, d, J = 1.47 Hz), 5.80 (2H, s) 3.25 (3H, s) |
| 59 | A | A | 500.5 | See Example 10 for Experimental Details and Data |
| 60 | A | A | 490.6 | 1H NMR (400 MHz, D6-dmso), δ 12.70 (s, 1H), 12.59 (d, 1H, J = 5.4 Hz), 7.99 (dd, 1H, J = 1.9 & 4.9 Hz), 7.85 (t, 1H, J = 1.5 Hz), 7.66 (t, 1H, J = 4.9 Hz), 7.54 & 7.35 (AB, 2H, J = 8.8 Hz), 7.00 (bs, 1H), 6.98 (d, 1H, J = 2.5 Hz), 6.76 (d, 1H, J = 7.8 Hz), 6.62 (t, 1H, J = 6.4 Hz), 6.14 (d, 1H, J = 7.8 Hz), 5.66 (s, 2H), 3.10 (s, 3H), 2.31 (s, 3H), 2.18 (s, 3H). |
| 61 | A | A | 476.5 | 1H NMR (400 MHz, D6-dmso), δ 12.69 (s, 1H), 12.60 (s, 1H), 8.00 (dd, 1H, J = 1.5 & 5.4 Hz), 7.85 (d, 1H, J = 2.5 Hz), 7.66 (t, 1H, J = 5.9 Hz), 7.55 & 7.36 (AB, 2H, J = 8.8 Hz), 7.19 (d, 1H, J = 7.3 Hz), 7.10 (t, 1H, J = 7.3 Hz), 6.98 (d, 1H, J = 2.0 Hz), 6.95 (t, 1H, J = 7.8 Hz), 6.62 (t, 1H, J = 6.8 Hz), 6.22 (d, 1H, J = 7.8 Hz). 5.71 (s, 2H), 3.09 (s, 3H), 2.37 (s, 3H). |
| 62 | A | A | 524.5 | 1H NMR (400 MHz, D6-dmso), δ above 12 (2H), 7.98 (dd, 1H, J = 2.0 & 7.2 Hz), 7.84 (d, 1H, J = 2.0 Hz), 7.69 (t, 1H, J = 5.2 Hz), 7.61 & 7.52 (AB, 2H, J = 8.4 Hz), 7.30 (dt, 1H, J = 5.2 & 9.6 Hz), 7.19-7.13 (m, 1H), 6.99 (d, 1H, J = 2.0 Hz), 6.63 (t, 1H, J = 6.4 Hz), 6.60-6.56 (m, 1H), 5.80 (s, 2H), 2.96-2.89 (m, 1H), 0.96 (d, 4H, J = 6.4 Hz). |
| 63 | A | A | 526.5 | 1H NMR (400 MHz, D6-dmso), δ above 12 (2H), 8.00 (td, 1H, J = 1.6 & 6.8 Hz), 7.84 (m, 1H), 7.71 (t, 1H, J = 6.8 Hz), 7.62 & 7.54 (AB, 2H, J = 8.8 Hz), 7.30 (dt, 1H, J = 4.4 & 8.8 Hz), 7.18-7.13 (m, 1H), 6.99-6.98 (m, 1H), 6.64 (t, 1H, J = 7.2 Hz), 6.54-6.49 (m, 1H), 5.80 (s, 2H), 3.63-3.55 (m, 1H), 1.14 (d, 6H, J = 7.2 Hz) |
| 64 | A | A | 508.5 | 1H NMR (400 MHz, D6-dmso), δ above 12 (2H), 7.98 (dd, 1H, J = 2.0 & 6.8 Hz), 7.83-7.26 (m, 1H), 7.71 (t, 1H, J = 5.6 Hz), 7.60 & 7.53 (AB, 2H, J = 8.8 Hz), 7.29 (q, 1H, J = 9.2 Hz), 7.21 (t, 1H, J = 8.8 Hz), 7.05 (t, 1H, J = 7.6 Hz), 6.99-6.98 (m, 1H), 6.75 (t, 1H, J = 8.0 Hz), 6.65 (t, 1H, J = 6.8 Hz), 5.83 (s, 2H), 3.62-3.55 (m, 1H), 1.14 (d, 6H, J = 6.8 Hz) |
| 65 | A | A | 506.5 | 1H NMR (400 MHz, D6-dmso), δ above 12 (2H), 7.96 (td, 1H, J = 1.2 & 9.0 Hz), 7.83-7.82 (m, 1H), 7.69 (t, 1H, J = 7.12 Hz), 7.59 & 7.52 (AB, 2H, J = 8.8 Hz), 7.30 (q, 1H, J = 6.0 Hz), 7.22 (t, 1H, J = 8.8 Hz), 7.06 (t, 1H, J = 7.6 Hz), 6.98-6.97 (m, 1H), 6.83 (t, 1H, J = 8.0 Hz), 6.63 (t, 1H, J = 7.2 Hz), 5.83 (s, 2H), 2.93-2.87 (m, 1H), 0.95 (d, 4H, J = 6.4 Hz) |
| 66 | A | A | 494.5 | 1H NMR (400 MHz, D6-dmso), δ above 12 (2H), 7.97 (dd, 1H, J = 1.6 & 6.8 Hz), 7.84-7.83 (m, 1H), 7.66 (t, 1H, J = 6.4 Hz), 7.58 & 7.48 (AB, 2H, J = 8.8 Hz), 7.16 (t, 1H, J = 8.5 Hz), 6.98-6.97 (m, 1H), 6.92 (t, 1H, J = 7.6 Hz), 6.61 (t, 1H, J = 6.8 Hz), 6.57 (t, 1H, J = 7.2 Hz), 5.79 (s, 2H), 3.22 (s, 3H), 2.23 (s, 3H). |
| 67 | A | A | 496.9 | 1H NMR (400 MHz, D6-dmso), δ above 12 (2H), 8.02 (dd, 1H, J = 1.2 & 5.2 Hz), 7.86-7.85 (m, 1H), 7.68 (t, 1H, J = 6.4 Hz), 7.57 (d, 1H, J = 8.8 Hz), 7.51 & 7.33 (AB, 2H, J = 8.8 Hz), 7.30 (t, 1H, J = 7.6 Hz), 7.15 (t, 1H, J = 7.2 Hz), 7.00-6.99 (m, 1H), 6.64 (t, 1H, J = 6.8 Hz), 6.40 (d, 1H, J = 8.0 Hz), 5.79 (s, 2H), 3.17 (s, 3H). |
| 68 | A | A | 494.5 | 1H NMR (400 MHz, D6-dmso), δ above 12 (2H), 7.97 (dd, 1H, J = 2.0 & 7.2 Hz), 7.84-7.83 (m, 1H), 7.70 (t, 1H, J = 6.8 Hz), 7.60 & 7.53 (AB, 2H, J = 8.8 Hz), 7.30 (q, 1H, J = 7.6 Hz), 7.21 (t, 1H, J = 8.4 Hz), 7.05 (t, 1H, J = 7.6 Hz), 6.99-6.97 (m, 1H), 6.78 (t, 1H, J = 6.8 Hz), 6.64 (t, 1H, J = 6.8 Hz), 5.82 (s, 2H), 3.34 (q, 2H, J = 8.0 Hz), 1.01 (t, 3H, J = 7.2 Hz) |
| 69 | C | A | 526.5 | 1H NMR (400 MHz, D6-dmso), δ 12.20 (s, 1H), 11.95 (s, 1H), 7.82 (s, 1H), 7.73 (dd, 1H, J = 2.2 & 4.7 Hz), 7.62 & 7.46 (AB, 2H, J = 9.0 Hz), 7.52 (dd, 1H, J = 1.7 & 4.3 Hz), 7.31 (dt, 1H, J = 4.3 & 9.3 Hz), 7.16-7.10 (m, 1H), 6.36 (t, 1H, J = 6.8 Hz), 6.27-6.22 (m, 1H), 5.93 (s, 2H), 3.32 (s, 3H), 2.77 (q, 2H, J = 7.7 Hz), 1.19 (t, 3H, J = 7.7 Hz). |
| 70 | C | C | 508.5 | 1H NMR (400 MHz, D6-dmso), δ 12.18 (s, 1H), 11.94 (s, 1H), 7.81 (s, 1H), 7.72 (dd, 1H, J = 1.7 & 5.1 Hz), 7.59 & 7.44 (AB, 2H, J = 9.0 Hz), 7.52 (d, 1H, J = 2.2 Hz), 7.27-7.19 (m, 2H), 6.99 (t, 1H, J = 7.7 Hz), 6.46 (t, 1H, J = 7.7 Hz), |

TABLE 1-continued

| # | IC50 | EC50 | LR-MS (M + H) | 1H NMR DATA |
|---|---|---|---|---|
| | | | | 6.35 (t, 1H, J = 6.8 Hz), 5.95 (s, 2H), 3.32 (s, 3H), 2.76 (q, 2H, J = 7.2 Hz), 1.18 (t, 3H, J = 7.7 Hz). |
| 74 | A | A | 532.9 | 1H NMR (400 MHz, D6-dmso), δ 12.71 (s, 1H), 12.59 (d, 1H, J = 5.5 Hz), 8.18 (s, 1H), 8.00 (dd, 1H, J = 1.8 & 6.8 Hz), 7.67-7.63 (m, 1H), 7.65 & 7.53 (AB, 2H, J = 8.5 Hz), 7.30 (dt, 1H, J = 4.2 & 8.9 Hz), 7.18-7.13 (m, 1H), 6.61-6.56 (m, 2H), 5.80 (s, 2H), 3.24 (s, 3H). |
| 76 | B | C | 417.4 | 1H NMR (400 MHz, D6-dmso), δ 12.95 (s, 1H), 11.76 (s, 1H), 7.69 (dd, 1H, J = 1.8 & 6.9 Hz), 7.42 & 7.36 (AB, 2H, J = 8.7 Hz), 7.43-7.40 (m, 1H), 7.29-7.18 (m, 2H), 7.02 (t, 1H, J = 7.3 Hz), 6.58 (t, 1H, J = 6.9 Hz), 6.56 (s, 1H), 6.34 (t, 1H, J = 6.9 Hz), 5.92 (s, 2H), 2.34 (s, 3H). |
| 77 | A | A | 419.4 | 1H NMR (400 MHz, D6-dmso, δ above 12 (1H), 11.76 (s, 1H), 7.95 (d, 1H, J = 2.0 Hz), 7.89 (bs, 2H), 7.87 (bs, 1H), 7.64 (dd, 1H, J = 2.4 & 6.8 Hz), 7.43 (d, 1H, J = 10.8 Hz), 7.43-7.41 (m, 1H), 7.09 (d, 1H, J = 2.4 Hz), 6.62 (dd, 1H, J = 1.6 Hz), 6.33 (t, 1H, J = 6.8 Hz), 6.28 (s, 1H), 5.88 (s, 2H). |
| 78 | B | A | 420.4 | Compound 78; 1H NMR (500 MHz, DMSO): 7.95 (bs, 1H), 7.68 (m, 1H), 7.44 (m, 2H), 7.31 (m, 1H), 7.09 (bs, 1H), 6.33 (t, 1H, J = 6.6 Hz), 5.95 (m, 1H), 5.72 (s, 2H), 5.64 (bs, 1H) |
| 79 | A | A | 421.4 | 1H NMR (400 MHz, D6-dmso, δ above 12 (1H), 11.74 (s, 1H), 7.92 (d, 1H, J = 2.0 Hz), 7.65 (dd, 1H, J = 2.0 & 6.8 Hz), 7.44 (d, 1H, J = 10.8 Hz), 7.41-7.37 (m, 1H), 7.28 (q, 1H, J = 6.0 Hz), 7.21 (t, 1H, J = 8.4 Hz), 7.07 (d, 1H, J = 2.4 Hz), 7.04 (dt, 1H, J = 7.6 & 1.2 Hz), 6.58 (t, 1H, J = 8.8 Hz), 6.31 (t, 1H, J = 6.4 Hz), 5.93 (s, 2H) |
| 80 | A | A | | See Example 11 for Experimental Details and Data |
| 81 | A | A | 432.4 | 1H NMR (400 MHz, dmso) δ 3.965 (q, 2H, J = 5.5 Hz), 5.885 (s, 2H), 6.326 (t, 1H, J = 6.7 Hz), 6.972 (d, 1H, J = 6.1 Hz), 7.0595 (d, 1H, J = 2.4 Hz), 7.280 (s, 1H), 7.30-7.39 (m, 3H), 7.413 (d, 1H, J = 7.3 Hz), 7.644 (dd, 1H, J = 6.7, 1.8 Hz), 7.922 (d, 1H, J = 2.4 Hz), 8.203 (br s, 3H) |
| 82 | A | A | 432.4 | 1H NMR (400 MHz, dmso) δ 3.941 (q, 2H, J = 5.5 Hz). 5.883 (s, 2H), 6.316 (t, 1H, J = 6.7 Hz), 7.056 (d, 1H, J = 1.8 Hz), 7.12 (d, 2H, J = 7.9 Hz), 7.369 (d, 2H, J = 7.9 Hz), 7.409 (dd, 1H, J = 6.1, 1.8 Hz), 7.443 (d, 1H, J = 11 Hz), 7.637 (dd, 1H, J = 6.7, 1.8 Hz), 7.915 (d, 1H, J = 1.8 Hz), 8.166 (br s, 3H) |
| 83 | A | A | 434.4 | 1H NMR (500 MHz, CD3OD): δ 7.81 (dd, 1H, J = 2.2 Hz), 7.62 (d, 1H, J = 2 Hz), 7.42 (m, 1H, 7.24 (bs, 1H), 6.98 (d, 1H, J = 10.7), 6.90 (d, 1H, J = 2.2 Hz), 6.48 (t, 1H, J = 6.3 Hz), 5.91 (s, 2H), 5.50 (bs, 1H), 2.29 (s, 3H) |
| 84 | A | A | 435.4 | 1H NMR (400 MHz, D6-dmso, δ above 12 (1H), 11.74 (s, 1H), 7.92 (d, 1H, J = 2.0 Hz), 7.65 (dd, 1H, J = 2.0 & 6.8 Hz), 7.42 (d, 1H, J = 10.8 Hz), 7.39-7.38 (m, 1H), 7.14 (t, 1H, J = 7.6 Hz), 7.06 (d, 1H, J = 2.0 Hz), 6.91 (t, 1H, J = 7.6 Hz), 6.36 (t, 1H, J = 7.6 Hz), 6.31 (t, 1H, J = 6.4 Hz), 5.91 (s, 2H), 2.23 (d, 3H, J = 1.2 Hz) |
| 85 | A | C | 435.4 | 1H NMR (400 MHz, D6-dmso, δ above 12.97 (s, H), 11.75 (s, 1H), 7.70 (dd, 1H, J = 1.8 & 6.8 Hz), 7.44 & 7.38 (AB, 2H, J = 8.7 Hz), 7.45-7.36 (m, 1H), 7.29 (dt, 1H, J = 4.6 & 9.1 Hz), 7.15-7.10 (m, 1H), 6.57 (d, 1H, J = 0.9 Hz), 6.34 (t, 1H, J = 6.8 Hz), 6.35-6.30 (m, 1H), 5.89 (s, 2H), 2.34 (s, 3H). |
| 87 | A | A | 438.4 | 1H NMR (500 MHz, DMSO): δ 7.97 (d, J = 2.2 Hz, 1H), 7.73 (m, 1H), 7.69 (dd, J = 2.2 Hz, J = 6.9 Hz, 1H), 7.54 (d, J = 11.0 Hz, 1H), 7.43 (m, 1H), 7.11 (d, J = 2.2 Hz, 1H), 6.34 (t, J = 6.6 Hz, 1H), 5.85 (s, 2H), 5.27 (s, 1H). DATA |
| 88 | B | B | 438.4 | 1H-NMR (400 MHz, in dmso-d6): δ 12.92 (1H, broad s), 9.74 (1H, s), 7.89 (1H, s), 7.49 (1H, d, J = 10.90 Hz), 7.25 (2H, m), 7.04 (3H, m), 6.94 (2H, m), 6.56 (1H, dd, J = 7.266, 7.266), 5.97 (2H, s) |
| 89 | A | A | 439.4 | 1H NMR (400 MHz, D6-dmso), δ above 12 (1H), 11.75 (s, 1H), 7.93 (d, 1H, J = 2.0 Hz), 7.66 (dd, 1H, J = 2.4 & 7.5 Hz), 7.48 (d, 1H, J = 10.8 Hz), 7.41-7.39 (m, 1H), 7.30 (dt, 1H, J = 4.8 & 8.2 Hz), 7.17-7.12 (m, 1H), 7.08 (d, 1H, J = 2.0 Hz), 6.37-6.33 (m, 1H), 6.31 (t, 1H, J = 6.8 Hz), 5.90 (s, 2H) |
| 91 | A | A | 443.4 | 1H NMR (400 MHz, dmso) δ 6.058 (s, 2H), 6.328 (t, 1H, J = 6.6 Hz), 7.063 (d, 1H, 2.2 Hz), 7.388 (dd, 1H, J = 8.7, 1.46 Hz), 7.41-7.45 (m, 1H), 7.479 (s, 1H), 7.502 (d, 1H, J = 10.3 Hz), 7.642 (dd, 1H, J = 7.3, 2.2 Hz), 7.796 (d, 1H, 8 Hz), 7.927 (d, 1H, J = 2.2 Hz), 9.456 (s, 1H) |

TABLE 1-continued

| # | IC50 | EC50 | LR-MS (M + H) | ¹H NMR DATA |
|---|---|---|---|---|
| 92 | A | A | 446.4 | 1H NMR (400 MHz, dmso) δ 5.901 (s, 2H), 6.313 (t, 1H, J = 6.6 Hz), 7.05-7.07 (m, 1H), 7.09 (d, 1H, J = 8 Hz), 7.3-7.375 (m, 2H), 7.398 (d, 1H, J = 6.6 Hz), 7.45 (d, 1H, J = 10.3 Hz), 7.646 (d, 1H, J = 6.6 Hz), 7.712 (m, 2H), 7.9-7.96 (m, 2H) |
| 93 | A | A | 446.4 | 1H NMR (400 MHz, dmso) δ 5.911 (s, 2H), 6.313 (t, 1H, J = 6.6 Hz), 7.05-7.07 (m, 1H), 7.101 (d, 2H, J = 7.3 Hz), 7.306 (s, 1H), 7.402 (d, 1H, J = 6.6 Hz), 7.437 (d, 1H, J = 11 Hz), 7.660 (dd, 1H, J = 6.6, 1.5 Hz), 7.50 (d, 2H, J = 7.3 Hz), 7.879 (s, 1H), 7.9-7.94 (m, 1H) |
| 94 | A | A | 446.4 | 1H NMR (400 MHz, D6-dmso), δ above 12 (1H), 11.75 (s, 1H), 7.86 (bs, 1H), 7.84-7.83 (m, 1H), 7.81-7.77 (m, 1H), 7.66 (td, 1H, J = 1.2 & 5.2 Hz), 7.55 (dd, 1H, J = 1.2 & 8.4 Hz), 7.46 (d, 1H, J = 8.8 Hz), 7.41 (d, 1H, J = 5.6 Hz), 7.32-7.28 (m, 3H), 6.97-6.96 (m, 1H), 6.34 (t, 1H, J = 6.8 Hz), 5.95 (s, 2H). |
| 95 | A | A | 450.4 | 1H NMR (400 MHz, D6-dmso), δ 11.79 (s, 2H), 8.38 (b, 3H), 7.93 (d, 1H, J = 2.0 Hz), 7.65 (dd, 1H, J = 2.0 & 4.8 Hz), 7.46-7.39 (m, 3H), 7.15 (d, 1H, J = 8.0 Hz), 7.07 (d, 1H, J = 2.0 Hz), 6.62 (t, 1H, J = 7.6 Hz), 6.32 (t, 1H, J = 6.8 Hz), 5.93 (s, 2H), 3.98-3.94 (m, 2H). |
| 96 | A | A | 452.4 | 1H NMR (500 MHz, DMSO): 7.99 (m, 1H), 7.98 (m, 1H), 7.69 (m, 1H), 7.53 (m, 1H), 7.44 (s, 1H), 7.11 (m, 1H), 6.34 (m, 1H), 5.84 (s, 2H), 5.21 (m, 1H), 3.33 (s, 3H) |
| 97 | A | A | 452.4 | 1H-NMR (400 MHz, in dmso-d6): δ 12.94 (1H, broad s), 11.73 (1H, broad s), 7.94 (1H, Broad s), 7.90 (1H, dd, J = 0.55, 2.20 Hz), 7.62 (1H, dd, J = 2.2, 6.6 Hz), 7.54 (1H, s), 7.52 (1H, dd, J = 1.1, 1.65 Hz), 7.40 (1H, m), 7.37 (1H, d, 1.1 Hz), 7.31 (1H, Broad s), 7.06 (1H, d, J = 2.2 Hz), 6.31 (1H, dd, J = 6.6, 7.14), 5.0 (1H, s) |
| 98 | B | B | 453.4 | 1H-NMR (400 MHz, in dmso-d6): δ 13.09 (1H, broad s), 11.73 (1H, broad s), 8.06 (2H, m), 7.90 (1H, s), 7.74 (2H, m), 7.60 (1H, d, J = 6.04 Hz), 7.40 (1H, d, J = 4.94 Hz), 7.06 (1H, s), 6.30 (1H, dd, J = 6.04, 6.59 Hz), 6.09 (2H, s) |
| 99 | A | B | 454.5 | 1H-NMR (400 MHz, in dmso-d6): δ 12.87 (1H, broad s), 11.64 (1H, broad s), 7.94 (1H, s), 7.50 (1H, d, J = 1.65 Hz), 7.43 (1H, dd, J = 1.65, 6.59 Hz), 7.33 (1H, d, J = 2.2.0 Hz), 7.31 (2H, s), 7.00 (1H, d, J = 9.89 Hz), 6.24 (1H, t, J = 6.59 Hz), 5.65 (2H, s), 4.60 (2H, t, J = 8.79 Hz), 3.18 (2H, t, J = 8.79 Hz) |
| 100 | A | A | 458.4 | 1H NMR (400 MHz, D6-dmso), δ 12.96 (s, 1H), 11.74 (s, 2H), 7.90 (d, 1H, J = 2.0 Hz), 7.64 (dd, 1H, J = 1.2 & 5.6 Hz), 7.51 (s, 1H), 7.45 (d, 1H, J = 10.8 Hz), 7.40 (d, 1H, J = 6.8 Hz), 7.17 (d, 1H, J = 8.4 Hz), 7.05-7.03 (m, 2H), 6.32 (t, 1H, J = 6.4 Hz), 5.88 (s, 2H), 3.35 (s, 2H). |
| 101 | A | A | 458.4 | 1H NMR (400 MHz, D6-dmso), δ 13.02 (s, 1H), 12.45 (s, 1H), 12.36 (s, 1H), 11.75 (s, 1H), 8.42 (s, 2H), 7.92 (d, 1H, J = 2.0 Hz), 7.63 (dd, 1H, J = 2.0 & 6.8 Hz), 7.48 (d, 1H, J = 10.8 Hz), 7.41 (d, 1H, J = 6.0 Hz), 7.27 (d, 1H, J = 8.4 Hz), 7.08-7.05 (m, 3H), 6.32 (t, 1H, J = 6.4 Hz), 5.93 (s, 2H). |
| 102 | A | A | 459.4 | 1H NMR (400 MHz, D6-dmso), δ 12.89 (s, 1H), 11.74 (s, 1H), 7.91 (dd, 1H, J = 2.0 & 0.4 Hz), 7.65 (dd, 1H, J = 2.0 & 6.8 Hz), 7.55 (bs, 1H), 7.46 (d, 1H, J = 10.8 Hz), 7.40 (d, 1H, J = 6.8 Hz), 7.37 (d, 1H, J = 8.8 Hz), 7.24 (dd, 1H, J = 1.2 & 8.8 Hz), 7.06 (d, 1H, J = 2.4 Hz), 6.33 (s, 2H), 6.32 (t, 1H, J = 6.8 Hz), 5.93 (s, 2H). |
| 103 | A | A | 459.4 | 1H NMR (400 MHz, d6-DMSO): δ 11.76 (br s, 1H), 10.54 (s, 1H), 10.48 (S, 1H), 7.90 (d, 1H, J = 2.0 Hz), 7.62 (dd, J = 2.0, 6.8 Hz, 1H), 7.48 (d, J = 6.8 Hz, 1H), 7.40 (dd, J = 1.6, 6.4 Hz, 1H), 7.05 (d, J = 2.0 Hz, 1H), 6.83-6.77 (m, 2H), 6.69 (s, 1H), 6.31 (t, J = 6.8 Hz, 1H), 5.82 (s, 2H); LCMS found for C24H15FN4O5: 459.3 (M + H)+. |
| 104 | A | C | 460.4 | 1H NMR (400 MHz, D6-dmso), δ 13.01 (s, 1H), 11.76 (s, 1H), 8.17 (dd, 1H, J = 2.8 & 9.2 Hz), 7.85 (d, 1H, J = 2.0 Hz), 7.68 (dd, 1H, J = 2.4 & 6.8 Hz), 7.53 & 7.38 (AB, 2H, J = 8.8 Hz), 7.43-7.41 (m, 1H), 7.35 (d, 1H, J = 2.8 Hz), 7.28 (d, 1H, J = 9.2 Hz), 6.96 (d, 1H, J = 2.0 Hz), 6.35 (t, 1H, J = 6.8 Hz), 5.86 (s, 2H), 4.01 (s, 3H) |
| 105 | A | A | 461.4 | 1H NMR (400 MHz, dmso) δ 6.058 (s, 2H), 6.335 (t, 1H, J = 6.6 Hz), 6.946 (d, 1H, J = 5.9 Hz), 7.079 (d, 1H, J = 2.2 Hz), 7.425 (dd, 1H, J = 6.6, 2.2 Hz), 7.507 (d, 1H, J = 11 Hz), 7.652 (dd, 1H, J = 6.6, 2.2 Hz), 7.791 (d, 1H, J = 9.5 Hz), 7.944 (d, 1H, J = 2.2 Hz), 9.370 (s, 1H) |
| 106 | A | A | 499.3 | 1H NMR (500 MHz, CDCl3): 8.06 (d, 1H, J = 6.9 Hz), 7.54 (m, 1H), 7.49 (d, 1H, J = 2.2 Hz), 7.29 (m, 1H), 7.14 (d, 1H, J = 10.08 Hz), 7.06 (dd, 1H, J = 3.7 Hz), 6.91 (d, |

TABLE 1-continued

| # | IC50 | EC50 | LR-MS (M + H) | $^1$H NMR DATA |
|---|---|---|---|---|
| | | | | 1H, J = 2.2 Hz), 6.73 (t, 1H, J = 6.6 Hz), 5.96 (bs, 2H), 1.90 (m, 1H), 0.85 (m, 4H) |
| 107 | A | A | 464.4 | 1H NMR (400 MHz, D6-dmso), δ above 12.91 (s, H), 11.74 (s, 1H), 7.92 (d, 1H, J = 2.4 Hz), 7.87 (s, 1H), 7.82-7.78 (m, 1H), 7.64 (dd, 1H, J = 2.1 & 6.8 Hz), 7.47 (d, 1H, J = 10.8 Hz), 7.40 (d, 1H, J = 7.6 Hz), 7.31-7.27 (m, 3H), 7.07 (d, 1H, J = 2.4 Hz), 6.32 (t, 1H, J = 6.8 Hz), 5.92 (s, 2H). |
| 108 | A | B | 465.4 | 1H NMR (400 MHz, D6-dmso), δ above 12.94 (s, H), 11.74 (s, 1H), 7.93 (d, 1H, J = 2.0 Hz), 7.89-7.85 (m, 1H), 7.63 (dd, 1H, J = 2.4 & 4.4 Hz), 7.49 (d, 1H, J = 10.8 Hz), 7.42-7.32 (m, 3H), 7.08 (d, 1H, J = 2.0 Hz), 6.32 (t, 1H, J = 6.4 Hz), 5.93 (s, 2H). |
| 109 | A | A | 465.4 | 1H-NMR (400 MHz, in dmso-d6): δ 12.96 (1H, broad s), 11.76 (1H, broad s), 8.60 (1H, d, J = 1.1 Hz), 8.12 (1H, s), 7.94 (1H, d, J = 2.2 Hz), 7.64 (1H, dd, J = 2.20, 6.59 Hz), 7.59 (1H, s), 7.57 (1H, s), 7.41 (1H, d, J = 5.5 Hz), 7.09 (1H, d, J = 2.2 Hz), 6.32 (1H, dd, J = 6.59, 6.59 Hz), 5.88 (2H, s) |
| 111 | A | A | 466.4 | 1H NMR (400 MHz, D6-dmso), δ 13.00 (s, 1H), 11.74 (s, 1H), 8.23-8.19 (m, 1H), 7.94 (d, 1H, J = 2.0 Hz), 7.64 (dd, 1H, J = 2.0 & 6.8 Hz), 7.58-7.57 (m, 1H), 7.56, 7.53 (AB, 2H, J = 3.6 Hz), 7.41 (d, 1H, J = 7.2 Hz), 7.08 (d, 1H, J = 2.0 Hz), 6.31 (t, 1H, J = 6.8 Hz), 5.95 (s, 2H). |
| 113 | A | A | 467.4 | 1H-NMR (400 MHz, in dmso-d6): δ 12.90 (1H, broad s), 11.66 (1H, broad s), 8.59 (1H, d, J = 1.65 Hz), 8.12 (1H, s), 7.59 (1H, s), 7.55 (1H, dd, J = 1.65, 9.34 Hz), 7.45 (1H, dd, J = 2.2, 6.59 Hz), 7.02 (1H, d, J = 0.89, Hz), 6.25 (1H, dd, J = 6.59, 6.59 Hz), 5.74 (2H, s), 4.63 (2H, t, J = 8.79 Hz), 3.20 (2H, t, J = 8.79 Hz) |
| 114 | A | A | | See Example 12 for Experimental Details and Data |
| 115 | A | A | 470.4 | 1H NMR (400 MHz, dmso) δ 5.686 (s, 2H), 6.338 (t, 1H, J = 6.7 Hz), 6.854 (d, 2H, J = 1.8 Hz), 7.025-7.09 (m, 2H), 7.296 (d, 1H, J = 7.9 Hz), 7.38-7.46 (m, 4H), 7.694 (dd, 1H, J = 6.7, 1.8 Hz), 7.926 (d, 1H, J = 2.4 Hz) |
| 116 | A | A | 470.9 | 1H NMR (400 MHz, D6-dmso), δ above 12.93 (s, H), 11.77 (s, 1H), 7.96 (d, 1H, J = 8.8 Hz), 7.88 (d, 1H, J = 2.0 Hz), 7.77-7.74 (m, 3H), 7.55, 7.48 (AB, 2H, J = 8.4 Hz), 7.56-7.49 (m, 1H), 7.43 (dd, 1H, J = 2.0 & 4.8 Hz), 7.18 (s, 1H), 6.99 (d, 1H, J = 2.0 Hz), 6.36 (t, 1H, J = 6.4 Hz), 6.05 (s, 2H). |
| 117 | A | A | | See Example 13 for Experimental Details and Data |
| 119 | A | A | 473.8 | 1H NMR (400 MHz, D6-dmso), δ 13.06 (s, 1H), 11.76 (s, 1H), 8.20 (s, 1H), 7.66 (dd, 1H, J = 2.0 & 6.8 Hz), 7.61 (d, 1H, J = 11.6 Hz), 7.40 (d, 1H, J = 6.4 Hz), 7.29 (dt, 1H, J = 4.4 & 9.2 Hz), 7.17-7.10 (m, 1H), 6.40-6.35 (m, 1H), 6.30 (t, 1H, J = 6.8 Hz), 5.91 (s, 2H). |
| 120 | A | A | 477.9 | 1H NMR (400 MHz, dmso) δ 6.044 (s, 2H), 6.349 (t, 1H, J = 6.6 Hz), 6.535 (s, 1H), 7.091 (d, 1H, J = 2.2 Hz), 7.406 (d, 1H, J = 11 Hz), 7.435 (dd, 1H, J = 6.6, 1.5 Hz), 7.665-7.695 (m, 1H), 7.966 (d, 1H, 1 = 2.2 Hz), 8.049 (s, 1H), 9.305 (s, 1H) |
| 121 | A | A | 478.4 | 1H NMR (400 MHz, D6-dmso), δ above 12 (2H), 11.41 (s, 1H), 8.26 (b, 1H), 7.80 (s, 1H), 7.70-7.65 (m, 1H), 7.54-7.46 (m, 1H), 7.27 (t, 1H, J = 8.0 Hz), 7.21-7.14 (m, 1H), 7.12-7.05 (m, 1H), 6.96 (s, 1H), 6.19 (b, 1H), 6.04 (b, 2H), 2.64 (d, 3H, J = 4.4 Hz). |
| 126 | A | A | 488.9 | 1H NMR (400 MHz, D6-dmso), δ above 12.90 (s, H), 11.77 (s, 1H), 7.96-7.94 (m, 2H), 7.79-7.71 (m, 3H), 7.56-7.51 (m, 2H), 7.42 (d, 1H, J = 6.0 Hz), 7.17 (s, 1H), 7.09 (d, 1H, J = 2.8 Hz), 6.34 (t, 1H, J = 6.4 Hz), 6.01 (s, 2H). |
| 127 | A | A | 489.4 | See Example 14 for Experimental Details and Data |
| 128 | C | A | 489.9 | 1H NMR (400 MHz, D6-dmso), δ 12.94 (s, 1H), 7.96 (d, 1H, J = 8.8 Hz), 7.93-7.92 (m, 1H), 7.81 (d, 1H, J = 7.2 Hz), 7.76 (tt, 1H, J = 6.8 & 1.2 Hz), 7.65 (tt, 1H, J = 7.6 & 1.2 Hz), 7.61 (d, 1H, J = 11.2 Hz), 7.55-7.51 (m, 1H), 7.45 (q, 1H, J = 7.2 Hz), 7.31-7.26 (m, 2H), 7.21 (s, 1H), 7.10-7.09 (m, 1H), 6.06 (s, 2H). |
| 130 | B | A | 492.5 | 1H NMR (400 MHz, D6-dmso), δ 11.74 (s, 1H), 7.95 (dd, 1H, J = 0.4 & 2.5 Hz), 7.89 (b, 1H), 7.82-7.78 (m, 1H), 7.68 (dd, 1H, J = 1.6 & 6.8 Hz), 7.52 (d, 1H, J = 10.8 Hz), 7.40 (d, 1H, J = 6.4 Hz), 7.33-7.27 (m, 3H), 7.09 (dd, 1H, J = 0.4 & 1.6 Hz), 6.30 (t, 1H, J = 6.4 Hz), 5.89 (s, 2H), 4.02 (q, 2H, J = 6.8 Hz), 0.98 (t, 2H, J = 6.8 Hz). |
| 131 | A | A | 493.9 | 1H NMR (400 MHz, d6-DMSO): ? 11.75 (br s, 1H), 10.71 (s, 1H), 10.40 (S, 1H), 7.94 (s, 1H), 7.64 (d, J = 2.0 Hz, |

TABLE 1-continued

| # | IC50 | EC50 | LR-MS (M + H) | ¹H NMR DATA |
|---|---|---|---|---|
| | | | | 1H), 7.42 (s, 1H), 7.28 (d, J = 11.2 Hz, 1H), 7.08 (s, 1H), 7.01 (s, 1H), 6.34 (s, 1H), 5.87 (s, 3H); LCMS found for C24H14ClFN4O5: 493.3 (M + H)+. |
| 132 | B | B | 494.5 | 1H NMR (400 MHz, D6-dmso), δ above 12.80 (s, H), 12.62 (d, 1H), 7.97 (dd, 1H, J = 2.0 & 4.8 Hz), 7.69 (dt, 1H, J = 16 & 6.0 Hz), 7.46, 7.40 (AB, 2H, J = 8.4 Hz), 7.31-7.26 (m, 1H), 7.20 (t, 1H, J = 9.2 Hz), 7.04 (t, 1H, J = 8.0 Hz), 6.80 (t, 1H, J = 8.0 Hz), 6.62 (t, 1H, J = 6.8 Hz), 6.59 (d, 1H, J = 0.8 Hz), 5.78 (s, 2H), 3.22 (s, 3H), 2.33 (s, 3H). |
| 133 | A | A | 496.5 | 1H NMR (400 MHz, D6-dmso), δ above 12 (2H), 7.97 (dd, 1H, J = 2.4 & 4.8 Hz), 7.88 (d, 1H, J = 6.8 Hz), 7.79 (b, 1H), 7.72 (b, 1H), 7.44 (d, 1H, J = 10.4 Hz), 7.12 (d, 1H, J = 2.4 Hz), 6.66 (t, 1H, J = 6.8 Hz), 6.61 (dd, 1H, J = 6.4 & 1.6 Hz), 6.37 (s, 1H), 5.72 (s, 2H), 3.27 (s, 3H). |
| 134 | A | A | 498.5 | 1H NMR (400 MHz, D6-dmso), δ above 12 (2H), 7.97 (m, 1H), 7.92 (d, 1H, J = 2.0 Hz), 7.66 (b, 1H), 7.51 (d, 1H, J = 10.4 Hz), 7.30 (dd, 1H, J = 7.2 & 14.4 Hz), 7.21 (t, 1H, J = 8.0 Hz), 7.09 (d, 1H, J = 2.4 Hz), 7.07 (dt, 1H, J = 1.2 & 7.2 Hz), 6.83 (t, 1H, J = 8.4 Hz), 6.60 (b, 1H), 5.79 (s, 2H), 3.19 (s, 3H). |
| 135 | A | A | 499.3 | 1H NMR (500 MHz, DMSO): δ 7.93 (bs, 1H), 7.80 (m, 1H), 7.66 (m, 1H), 7.41 (m, 2H), 7.08 (m, 1H), 6.34 (m, 1H), 5.76 (bs, 2H), 5.03 (m, 1H). M.S. found: 498.3 (M)+. |
| 136 | A | A | 502.9 | 1H NMR (500 MHz, DMSO): 7.93 (d, 1H, J = 2.2 Hz), 7.60-7.80 (m, 3H), 7.52 (d, 1H, J = 10 Hz), 7.42 (m, 1H), 7.09 (d, 1H, J = 2.2 Hz), 6.34 (t, 1H, J = 6.9 Hz, 6.3 Hz), 5.99 (bs, 2H) |
| 138 | A | A | 502.6 | 1H NMR (400 MHz, D6-dmso), δ above 12 (2H), 7.99 (b, 1H), 7.83 (d, 1H, J = 2.0 Hz), 7.69 (b, 1H), 7.55 (d, 1H, J = 8.0 Hz), 7.37 (d, 1H, J = 8.8 Hz), 7.20 (d, 1H, J = 8.4 Hz), 7.11 (t, 1H, J = 7.6 Hz), 6.98-6.94 (m, 2H), 6.64 (b, 1H), 6.22 (d, 1H, J = 7.6 Hz), 5.74 (s, 2H), 2.85-2.70 (m, 1H), 2.38 (s, 3H), 0.90-0.83 (m, 4H). |
| 139 | A | A | 502.9 | 1H NMR (500 MHz, DMSO): δ 7.98 (d, 1H, J = 2.2 Hz), 7.76 (bs, 1H), 7.75 (dd, 1H, J = 1.89 Hz, 2.2 Hz), 7.68 (d, 1H, J = 8.5 Hz), 7.57 (d, 1H, J = 10.7 Hz), 7.45 (m, 1H), 7.40 (dd, 1H, J = 1.57 Hz), 7.12 (m, 2H), 6.36 (t, 1H, J = 6.3 Hz), 6.01 (bs, 2H), 2.50 (s, 3H, hidden in DMSO). M.S. found: 502.3 (M + H)+. |
| 140 | A | A | 502.9 | 1H NMR (500 MHz, CD3OD): 7.95-7.80 (m, 2H), 7.66 (m, 1H), 7.57 (m, 1H), 7.51 (s, 1H), 7.45 (m, 1H), 7.40 (s, 1H), 6.96 (d, J = 10.4 Hz, 1H), 6.91 (m, 1H), 6.53 (m, 1H), 6.15 (s, 2H), 2.43 (s, 3H). |
| 141 | A | C | 504.5 | 1H NMR (400 MHz, D6-dmso), δ above 12.92 (s, H), 11.47 (s, 1H), 8.36 (d, 1H, J = 4.0 Hz), 7.93 (d, 1H, J = 2.4 Hz), 7.75-7.71 (m, 1H), 7.40 (dd, 1H, J = 2.0 & 6.8 Hz), 7.47 (d, 1H, J = 10.8 Hz), 7.41 (d, 1H, J = 5.2 Hz), 7.31-7.23 (m, 2H), 7.08 (d, 1H, J = 2.4 Hz), 6.32 (t, 1H, J = 6.4 Hz), 5.93 (s, 2H), 2.72-2.66 (m, 1H), 0.63-0.58 (m, 2H), 0.49-0.45 (m, 2H). |
| 143 | A | A | 506.9 | 1H NMR (500 MHz, CD3OD): δ 7.88 (dd, J = 2.2 Hz, J = 6.9 Hz, 1H), 7.64 (d, J = 2.2 Hz, 1H), 7.45-7.41 (m, 2H), 6.94-6.90 (m, 2H), 6.50 (t, J = 6.6 Hz, 1H), 6.05 (s, 2H), 3.97 (s, 3H), 2.34 (s, 3H). |
| 145 | A | B | 511.4 | 1H NMR (400 MHz, dmso) δ 6.011 (s, 2H), 6.322 (t, 1H, J = 6.7 Hz), 7.055 (d, 1H, J = 1.8 Hz), 7.212 (dd, 1H, J = 8.5, 1.2 Hz), 7.351 (s, 1H), 7.407 (dd, 1H, J = 6.1, 1.8 Hz), 7.508 (d, 1H, J = 11 Hz), 7.642 (d, 1H, J = 1.8 Hz), 7.659 (d, 1H, J = 1.8 Hz), 7.91 (d, 1H, J = 1.8 Hz) |
| 146 | A | A | 512.5 | 1H NMR (400 MHz, D6-dmso), δ above 12 (2H), 7.95 (dd, 1H, J = 6.4 & 1.2 Hz), 7.91 (d, 1H, J = 2.0 Hz), 7.66 (t, 1H, J = 5.2 Hz), 7.49 (d, 1H, J = 10.8 Hz), 7.17 (t, 1H, J = 8.0 Hz), 7.08 (d, 1H, J = 2.0 Hz), 6.94 (t, 1H, J = 7.6 Hz), 6.64-6.55 (m, 2H), 5.76 (s, 2H), 3.19 (s, 3H), 2.22 (m, 3H). |
| 147 | A | C | 512.5 | 1H NMR (400 MHz, D6-dmso), δ above 12.79 (s, 1H), 12.61 (s, 1H), 8.00 (td, 1H, J = 2.0 & 7.2 Hz), 7.67 (t, 1H, J = 6.0 Hz), 7.50 7.39 (m, 2H), 7.32-7.26 (m, 1H), 7.17-7.12 (m, 1H), 6.62 (t, 1H, J = 6.8 Hz), 6.59-6.53 (m, 2H), 5.75 (s, 2H), 3.24 (d, 3H, J = 1.2 Hz), 2.34 (s, 3H). |
| 148 | A | A | 514.5 | 1H-NMR (400 MHz, in dmso-d6): δ 12.96 (1H, broad s), 11.76 (1H, broad s), 7.76 (1H, d, J = 5.86 Hz), 7.59 (1H, m), 7.28 (1H, ddd, J = 3.66, 8.79, 8.79 Hz), 7.20 (1H, d, J = 8.79), 7.16 (1H, m), 7.03 (1H, d, J = 8.79), 6.59 (1H, m), 6.54 (1H, dd, J = 6.59, 6.59 Hz), 5.64 (2H, s), 4.66 (1H, |

TABLE 1-continued

| # | IC50 | EC50 | LR-MS (M + H) | ¹H NMR DATA |
|---|---|---|---|---|
| | | | | dd, J = 8.79, 9.52 Hz), 4.04 (1H, dd, J = 7.32, 8.79 Hz), 3.51 (1H, m), 3.23 (3H, s), 1.23 (3H, d, J = 5.86 Hz) |
| 149 | A | A | 514.9 | 1H NMR (400 MHz, D6-dmso), δ 12.73 (s, 1H), 12.59 (s, 1H), 8.17 (s, 1H), 7.97 (d, 1H, J = 8.0 Hz), 7.66 & 7.51 (AB, 2H, J = 9.0 Hz), 7.67-7.36 (bm, 1H), 7.30 (q, 1H, J = 7.3 Hz), 7.21 (t, 1H, J = 8.5 Hz), 7.05 (t, 1H, J = 7.3 Hz), 6.82 (t, 1H, J = 7.7 Hz), 6.59 (t, 1H, J = 6.8 Hz), 5.83 (s, 2H), 3.22 (s, 3H). |
| 150 | A | A | 516.5 | 1H NMR (400 MHz, D6-dmso), δ above 12 (2H), 7.98 (d, 1H, J = 6.4 Hz), 7.93 (d, 1H, J = 2.4 Hz), 7.66 (t, 1H, J = 5.2 Hz), 7.52 (d, 1H, J = 10.8 Hz), 7.30 (dt, 1H, J = 4.0 & 8.8 Hz), 7.19-7.13 (m, 1H), 7.10 (d, 1H, J = 2.4 Hz), 6.62-6.57 (m, 2H), 5.76 (s, 2H), 3.22 (m, 2H). |
| 151 | A | B | 516.5 | 1H NMR (400 MHz, D6-dmso), δ 12.71 (s, 1H), 12.54 (s, 1H), 7.99 (dd, 1H, J = 6.8 & 2.1 Hz), 7.89 (d, 1H, J = 2.1 Hz), 7.66 (s, 1H), 7.42 (d, 1H, J = 12.8 Hz), 7.30 (dt, 1H, J = 4.7 & 9.4 Hz), 7.18-7.12 (m, 1H), 6.96 (d, 1H, J = 1.7 Hz), 6.60 (t, 1H, J = 6.8 Hz), 6.55-6.5 1 (m, 1H), 5.79 (s, 2H), 3.27 (s, 3H). |
| 152 | A | A | 516.6 | 1H NMR (400 MHz, D6-dmso), δ above 12 (2H), 7.98 (d, 1H, J = 6.4 Hz), 7.83 (s, 1H), 7.69 (b, 1H), 7.54 (t, 1H, J = 10.0 Hz), 7.36 (d, 1H, J = 9.6 Hz), 7.00 (bs, 1H), 6.97 (bs, 1H), 6.77 (d, 1H, J = 9.2 Hz), 6.64 (t, 1H, J = 11.2 Hz), 6.14 (d, 1H, J = 8.8 H.z), 5.69 (s, 2H), 2.83-2.76 (m, 1H), 2.33 (s, 3H), 2.18 (s, 3H), 0.89 (bm, 4H). |
| 153 | A | A | 518.9 | 1H NMR (500 MHz, DMSO): δ 7.98 (d, J = 2.0 Hz, 1H), 7.74 (dd, J = 1.9 Hz, J = 6.8 Hz, 1H), 7.71 (d, J = 9.0 Hz, 1H), 7.55 (d, J = 10.8 Hz, 1H), 7.45 (m, 1H), 7.39 (d, J = 2.4 Hz, 1H), 7.19 (dd, J = 2.4 Hz, J = 9.0 Hz, 1H), 7.13 (s, 1H), 7.11 (d, J = 2.0 Hz, 1H), 6.37 (t, J = 6.5 Hz, 1H), 6.0 (s, 2H), 3.91 (s, 3H). |
| 154 | A | A | 518.9 | 1H NMR (500 MHz, DMSO): δ 7.99 (d, J = 2.2 Hz, 1H), 7.87 (d, J = 9.2 Hz, 1H), 7.74 (dd, J = 2.1 Hz, J = 6.8 Hz, 1H), 7.55 (d, J = 10.9 Hz, 1H), 7.45 (m, 1H), 7.38 (dd, J = 2.8 Hz, J = 9.2 Hz, 1H), 7.21 (m, 1H), 7.13 (d, J = 2.2 Hz, 1H), 7.11 (m, 1H), 6.37 (t, J = 6.6 Hz, 1H), 6.02 (s, 2H), 3.77 (s, 3H). |
| 155 | A | A | 520.6 | 1H NMR (400 MHz, D6-dmso), δ above 12 (2H), 7.95 (d, 1H, J = 5.6 Hz), 7.82 (bd, 1H, J = 2.0 Hz), 7.69 (b, 1H), 7.58, 7.50 (AB, 2H, J = 8.8 Hz), 7.16 (t, 1H, J = 7.6 Hz), 6.97 (d, 1H, J = 2.4 Hz), 6.94 (t, 1H, J = 6.4 Hz), 6.68-6.57 (m, 2H), 5.81 (s, 2H), 2.95-2.88 (m, 1H), 2.22 (s, 3H), 0.97 (s, 2H), 0.93 (s, 2H). |
| 156 | A | B | 520.9 | 1H NMR (500 MHz, DMSO): 7.98 (d, J = 2.2 Hz, 1H), 7.72 (dd, J = 2.1 Hz, J = 6.8 Hz, 1H), 7.49 (d, J = 10.9 Hz, 1H), 7.45 (m, 1H), 7.11 (d, J = 2.2 Hz, 1H), 7.03 (m, 1H), 6.36 (t, J = 6.7 Hz, 1H), 5.97 (s, 2H), 5.12 (m, 1H), 1.49 (s, 3H), 1.47 (s, 3H). |
| 158 | A | B | 522.6 | 1H NMR (400 MHz, D6-dmso), δ above 12 (2H), 7.97 (dt, 1H, J = 2.0 & 6.8 Hz), 7.83 (bd, 1H), 7.73-7.69 (m, 1H), 7.59, 7.52 (AB, 2H, J = 8.8 Hz), 7.16 (t, 1H, J = 8.0 Hz), 6.98 (t, 1H, J = 2.4 Hz), 6.92 (t, 1H, J = 8.0 Hz), 6.64 (t, 1H, J = 6.8 Hz), 6.53 (t, 1H, J = 8.0 Hz), 5.81 (s, 2H), 3.60-2.54 (m, 1H), 2.22 (s, 3H), 1.12 (d, 6H, J = 6.8 Hz). |
| 159 | A | A | 523.3 | 1H NMR (400 MHz, D6-dmso), δ 12.98 (s, 1H), 11.77 (s, 1H), 8.24 (d, 1H, J = 2.4 Hz), 7.95 (d, 1H, J = 8.5 Hz), 7.77 (t, 1H, J = 7.3 Hz), 7.73-7.66 (m, 3H), 7.53 (t, 1H, J = 7.9 Hz), 7.42 (d, 1H, J = 6.1 Hz), 7.17 (s, 1H), 6.33 (t, 1H, J = 6.7 Hz), 6.02 (s, 2H). |
| 161 | A | A | 523.5 | 1H NMR (400 MHz, D6-dmso), δ above 12 (2H), 7.98 (dt, 1H, J = 2.4 & 7.2 Hz), 7.86 (s, 1H), 7.82-7.80 (m, 2H), 7.68 (t, 1H, J = 6.0 Hz), 7.59, 7.52 (AB, 2H, J = 3.2 Hz), 7.53-7.51 (m, 1H), 7.33 (s, 1H), 7.30 (t, 1H, J = 9.2 Hz), 6.98-6.96 (m, 1H), 6.63 (t, 1H, J = 7.2 Hz), 5.81 (s, 2H), 3.25 (s, 3H). |
| 162 | A | A | 524.5 | 1H NMR (400 MHz, D6-dmso), δ above 12 (2H), 7.95 (d, 1H, J = 6.4 Hz), 7.92 (d, 1H, J = 2.0 Hz) 7.69 (s, 1H), 7.53 (d, 1H, J = 10.8 Hz), 7.31 (dd, 1H, J = 1.5 & 1.4 Hz), 7.21 (t, 1H, J = 8.0 Hz), 7.10-7.06 (m, 2H), 6.84 (t, 1H, J = 8.4 Hz), 6.62 (s, 1H), 5.81 (s, 2H), 2.91-2.85 (m, 1H), 0.95 (s, 2H), 0.93 (s, 2H). |
| 163 | A | A | 526.5 | 1H NMR (400 MHz, D6-dmso), δ above 12 (2H), 7.97 (dd, 1H, J = 1.6 & 6.8 Hz), 7.91 (d, 1H, J = 2.4 Hz) 7.71 (t, 1H, J = 6.4 Hz), 7.55 (d, 1H, J = 10.8 Hz), 7.30 (dd, 1H, J = 6.0 & 8.4 Hz), 7.21 (t, 1H, J = 8.4 Hz), 7.08 (d, 1H, J = 2.0 Hz), 7.06 (t, 1H, J = 7.6 Hz), 6.77 (t, 1H, J = 7.2 Hz), |

TABLE 1-continued

| # | IC50 | EC50 | LR-MS (M + H) | ¹H NMR DATA |
|---|---|---|---|---|
| | | | | 6.63 (t, 1H, J = 6.8 Hz), 5.81 (s, 2H), 3.56 (h, 1H, J = 6.8 Hz), 1.10 (d, 6H, J = 6.8 Hz). |
| 164 | A | A | 526.5 | 1H-NMR (400 MHz, in dmso-d6): δ 12.61 (1H, broad s), 12.53 (1H, broad s), 7.74 (1H, dd, J = 2.20, 6.59 Hz), 7.62 (1H, ddd, J = 2.2, 6.59, 6.59 Hz), 7.29 (1H, ddd, J = 4.39, 8.79, 8.79 Hz), 7.21 (1H, d, J = 8.79 Hz), 7.15 (1H, m), 7.03 (1H, d, J = 8.79 Hz), 6.55 (2H, m), 5.66 (2H, s), 4.52 (2H, t, J = 8.79 Hz), 3.15 (2H, t, 8.79 Hz), 2.90 (1H, dt, J = 5.86, 12.45 Hz), 0.94 (4H, d, J = 5.86 Hz) |
| 164 | A | A | 526.5 | 1H-NMR (400 MHz, in dmso-d6): δ 12.61 (1H, broad s), 12.53 (1H, broad s), 7.74 (1H, dd, J = 2.20, 6.59 Hz), 7.62 (1H, ddd, J = 2.2, 6.59, 6.59 Hz), 7.29 (1H, ddd, J = 4.39, 8.79, 8.79 Hz), 7.21 (1H, d, J = 8.79 Hz), 7.15 (1H, m), 7.03 (1H, d, J = 8.79 Hz), 6.55 (2H, m), 5.66 (2H, s), 4.52 (2H, t, J = 8.79 Hz), 3.15 (2H, t, 8.79 Hz), 2.90 (1H, dt, J = 5.86, 12.45 Hz), 0.94 (4H, d, J = 5.86 Hz) |
| 165 | A | A | 529.5 | 1H-NMR (400 MHz, in dmso-d6): δ 12.67 (2H, m), (7.93 (1H, dd, J = 2.2., 7.14 Hz), 7.91 (1H, d, J = 2.20 Hz), 7.87 (1H, s), 7.65 (1H, ddd, J = 1.10, 5.49 Hz), 7.59 (1H, d, J = 10.99 Hz), 7.50 (1H, s), 7.49 (1H, d, J = 11.54 Hz), 7.34 (1H, s), 7.09 (1H, d, J = 2.20 Hz), 6.60 (1H, t, J = 6.59 Hz), 5.66 (2H, s), 3.23 (3H, s) |
| 167 | A | A | 531.6 | 1H-NMR (400 MHz, in dmso-d6): δ 12.61 (1H, broad s), 12.53 (1H, broad s), 7.87 (1H, s), 7.68 (1H, dd, J = 2.20, 7.14 Hz), 7.58 (1H, d, J = 6.04 Hz), 7.49 (1H, d, J = 1.65 Hz), 7.42 (1H, s), 7.33 (1H, s), 7.05 (1H, d, J = 10.44 Hz), 6.51 (1H, dd, J = 6.59, 7.14 Hz), 5.52 (2H, s), 4.61 (2H, t, J = 8.79 Hz), 3.26 (3H, s), 3.19 (2H, t, J = 8.79 Hz) |
| 168 | A | A | 535.0 | 1H NMR (500 MHz, DMSO): 7.84 (t, 1H, J = 2.2 Hz), 7.68 (bs, 1H), 7.61 (d, 1H, J = 8.2 Hz), 7.57 (m, 1H), 7.38 (d, 1H, J = 8.8 Hz), 7.29 (m, 1H), 7.17 (m, 1H), 7.11 (bs, 1H), 6.99 (m, 1H), 6.20 (m, 1H), 6.10 (bs, 2H), 2.60 (s, 3H) |
| 169 | A | A | 535.5 | 1H NMR (400 MHz, D6-dmso), δ 12.73 (s, 1H), 12.62 (s, 1H), 12.42 (s, 2H), 8.42 (s, 1H), 7.95 (s, 1H), 7.92 (d, 1H, J = 7.9 Hz), 7.69-7.66 (m, 1H), 7.54 (d, 1H, J = 11.0 Hz), 7.27 (d, 1H, J = 7.9 Hz), 7.14 (s, 1H), 7.09-7.07 (m, 2H), 6.59 (t, 1H, J = 6.7 Hz), 5.77 (s, 2H), 3.26 (s, 3H). |
| 170 | A | A | 536.5 | 1H NMR (400 MHz, D6-dmso), δ 12.63 (s, 2H), 7.95 (dd, 1H, J = 2.0 & 6.8 Hz), 7.91 (d, 1H, J = 2.4 Hz), 7.65 (t, 1H, J = 4.4 Hz), 7.58 (bs, 1H), 7.54 (d, 1H, J = 10.8 Hz), 7.38 (d, 1H, J = 8.4 Hz), 7.30 (dd, 1H, J = 2.0 & 8.4 Hz), 7.09 (d, 1H, J = 2.0 Hz), 6.60 (t, 1H, J = 7.6 Hz), 6.31 (s, 2H), 5.79 (s, 2H), 3.22 (s, 3H). |
| 171 | A | A | 538.5 | 1H NMR (400 MHz, D6-dmso), δ above 12 (2H), 7.94 (dd, 1H, J = 1.2 & 6.4 Hz), 7.91 (d, 1H, J = 2.0 Hz) 7.69 (t, 1H, J = 6.0 Hz), 7.52 (d, 1H, J = 10.8 Hz), 7.17 (t, 1H, J = 8.8 Hz), 7.08 (d, 1H, J = 2.4 Hz), 6.96 (t, 1H, J = 7.6 Hz), 6.62 (q, 2H, J = 6.8 Hz), 5.79 (s, 2H), 2.89 (h, 1H, J = 1.3 Hz), 2.21 (s, 3H), 0.95 (s, 2H), 0.94 (s, 2H). |
| 173 | A | A | 540.6 | |
| 174 | A | A | 541.5 | 1H NMR (500 MHz, DMSO): 7.96 (d, J = 2.2 Hz, 1H), 7.73 (m, 2H), 7.59 (d, J = 10.9 Hz, 1H), 7.13 (d, J = 2.2 Hz, 1H), 6.66 (m, 1H), 5.72 (s, 2H), 5.53 (s, 1H), 2.94 (m, 1H), 1.02-0.96 (m, 4H). |
| 175 | A | A | 541.5 | 1H NMR (400 MHz, D6-dmso), δ 12.72 (s, 1H), 12.68 (s, 1H), 7.96 (dd, 1H, J = 2.2 & 7.1 Hz), 7.92 (d, 1H, J = 2.2 Hz), 7.88 (d, 1H, J = 2.2 Hz), 7.84-7.80 (m, 1H), 7.69-7.64 (m, 1H), 7.58-7.50 (m, 3H), 7.36-7.27 (m, 2H), 7.09 (d, 1H, J = 2.2 Hz), 6.62 (t, 1H, J = 7.1 Hz), 5.79 (s, 2H), 3.21 (s, 3H). |
| 176 | A | A | 542.5 | 1H-NMR (400 MHz, in dmso-d6): δ 12.74 (1H, broad s), 12.73 (1H, broad s), 8.61 (1H, d, J = 1.65 Hz), 8.11 (1H, s), 8.00 (1H, dd, J = 2.2, 7.14 Hz), 7.94 (1H, d, J = 2.2 Hz), 7.77 (1H, dd, J = 2.2, 9.3 Hz), 7.70 (1H, ddd, J = 2.2, 6.59, 6.04 Hz), 7.60 (1H, s), 7.57 (1H, s), 7.11 (1H, d, J = 2.2 Hz), 6.64 (1H, dd, J = 6.59, 7.14 Hz), 5.76 (2H, s), 3.23 (3H, s) |
| 177 | A | A | 542.5 | 1H NMR (400 MHz, D6-dmso), δ above 12 (2H), 7.97 (dd, 1H, J = 2.0 & 7.2 Hz), 7.92 (d, 1H, J = 2.4 Hz) 7.69 (t, 1H, J = 6.8 Hz), 7.54 (d, 1H, J = 10.8 Hz), 7.29 (dt, 1H, J = 4.8 & 9.2 Hz), 7.18-7.14 (m, 1H), 7.09 (d, 1H, J = 2.0 Hz), 6.63-6.59 (m, 2H), 5.78 (s, 2H), 2.93-2.86 (m, 1H), 0.95 (d, 4H, J = 6.4 Hz) |
| 178 | A | A | 542.5 | 1H NMR (400 MHz, D6-dmso), d, 12.71 (s, 1H), 12.60 (s, 1H), 7.97 (dd, 1H, J = 1.7 & 6.8 Hz), 7.89 (d, 1H, J = 2.1 Hz), 7.68 (bs, 1H), 7.43 (d, 1H, J = 12.8 Hz), 7.31 (dt, 1H, |

TABLE 1-continued

| # | IC50 | EC50 | LR-MS (M + H) | ¹H NMR DATA |
|---|---|---|---|---|
| | | | | J = 9.3 & 4.3 Hz), 7.19-7.13 (d, 1H, J = 2.2 Hz), 6.97 (d, 1H, J = 2.2 Hz), 6.61 (t, 1H, J = 6.4 Hz), 6.56-6.51 (m, 1H), 5.81 (s, 2H), 2.97-2.91 (m, 1H), 0.99 (d, 2H, J = 3.0 Hz), 0.97 (s, 2H). |
| 179 | A | A | 543.5 | 1H NMR (400 MHz, D6-dmso), d, 12.67 (s, 2H), 8.25-8.21 (m, 1H), 7.98-7.97 (m, 1H), 7.94 (d, 1H, J = 2.4 Hz), 7.74 (dd, 1H, J = 3.0 & 6.1 Hz), 7.68-7.66 (m, 1H), 7.61 (d, 1H, J = 10.3 Hz), 7.55 (t, 1H, J = 9.2 Hz), 7.11 (d, 1H, J = 2.4 Hz), 6.62-6.59 (m, 1H), 5.86 (s, 2H), 3.22 (s, 3H). |
| 180 | A | A | 548.0 | |
| 181 | A | A | 552.5 | |
| 182 | A | A | 555.0 | 1H NMR (400 MHz, dmso) δ 3.17 (s, 3H), 5.885 (s, 2H), 6.653 (t, 1H, J = 6.6), 6.747 (s, 1H), 7.111 (d, 1H, J = 2.2 Hz), 7.411 (d, 1H, J = 10.3 Hz), 7.68-7.74 (br s, 1H), 7.959 (d, 1H, J = 2.2 Hz), 7.985 (s, 1H), 7.995-8.03 (m, 1H), 9.09 (br s, 1H) |
| 183 | A | A | 555.6 | 1H-NMR (400 MHz, in dmso-d6): δ 12.65 (1H, broad s), 11.60 (1H, broad s), 7.91 (2H, m), 7.86 (1H, broad s), 7.67 (1H, ddd, J = 2.2, 6.04, 6.6 Hz), 7.62 (1H, d, J = 10.99 Hz), 7.50 (1H, s), 7.46 (1H, s), 7.34 (1H, broad s), 7.09 (1H, d, J = 2.2 Hz), 6.60 (1H, dd, J = 6.59, 6.59 Hz), 5.68 (2H, s), 3.02 (1H, m), 1.1 (4H, d, J = 7.7 Hz) |
| 184 | A | A | 557.6 | 1H NMR (400 MHz, D6-dmso), δ above 12 (s, 1H), 12.36 (bd, 1H, J = 6.4 Hz), 7.96 (d, 1H, J = 2.1 Hz), 7.91 (dd, 1H, J = 2.2 Hz), 7.80 (dd, 1H, J = 1.5 & 8.1 Hz), 7.67 (t, 1H, J = 7.7 Hz), 7.59 (d, 1H, J = 10.4 Hz), 7.60-7.55 (m, 1H), 7.46 (t, 1H, J = 8.1 Hz), 7.28-7.23 (m, 1H), 7.19 (d, 1H, J = 8.1 Hz), 7.17-7.11 (m, 1H), 7.12 (d, 1H, J = 2.2 Hz), 7.03 (t, 1H, J = 7.3 Hz), 6.97 (t, 1H, J = 7.3 Hz), 6.50 (t, 1H, J = 6.6 Hz), 5.98 (s, 2H). |
| 185 | A | A | 557.6 | 1H-NMR (400 MHz, in dmso-d6): δ 12.60 (2H, broad m), 7.87 (1H, s), 7.68 (1H, dd, J = 1.65, 6.59 Hz), 7.60 (1H, m), 7.48 (1H, s), 7.40 (1H, s), 7.35 (1H, s), 7.09 (1H, d, J = 9.89 Hz), 6.53 (1H, t, J = 6.59 Hz), 5.54 (2H, s), 4.61 (2H, t, J = 8.79 Hz), 3.19 (2H, t, J = 8.79 Hz), 2.99 (1H, m), 0.98 (4H, m) |
| 186 | A | A | 557.6 | 1H-NMR (400 MHz, in dmso-d6): δ 12.74 (1H, d, J = 5.49 Hz), 12.54 (1H, s), 7.93 (1H, dd, J = 1.65, 7.14 Hz), 7.91 (1H, d, J = 2.20 Hz), 7.87 (1H, s), 7.69 (1H, ddd, J = 1.65, 6.04, 6.59 Hz), 7.64 (1H, d, J = 10.44 Hz), 7.49 (1H, d, J = 1.10 Hz), 7.41 (1H, d, J = 1.10 Hz), 7.35 (1H, s), 7.09 (1H, d, J = 2.20 Hz), 6.62 (1H, t, J = 6.59 Hz), 5.67 (2H, s), 3.67 (2H, s), 1.15 (6H, d, J = 6.59 Hz) |
| 187 | A | A | 558.5 | |
| 188 | A | A | 559.6 | 1H-NMR (400 MHz, in dmso-d6): δ 12.67 (1H, broad s), 12.54 (1H, broad s), 7.88 (1H, s), 7.70 (1H, dd, J = 2.20, 7.14 Hz), 7.62 (1H, m), 7.48 (1H, d, J = 1.10 Hz), 7.35 (1H, s), 7.11 (1H, d, J = 9.89 Hz), 6.54 (1H, dd, J = 6.59, 7.14 Hz), 5.53 (2H, s), 4.61 (2H, t, J = 8.79 Hz), 3.64 (1H, h, J = 7.12 Hz), 3.19 (2H, t, j = 8.79 Hz), 1.13 (6H, d, J = 7.12 Hz) |
| 190 | A | A | 562.6 | 1H NMR (400 MHz, D6-dmso), δ 12.67 (d, 1H, J = 5.5 Hz), 12.59 (s, 1H), 8.00 (dd, 1H, J = 1.9 & 7.3 Hz), 7.91 (d, 1H, J = 2.4 Hz), 7.70-7.65 (m, 1H), 7.61-7.58 (m, 2H), 7.38 (d, 1H, J = 8.5 Hz), 7.29 (dd, 1H, J = 1.2 & 8.5 Hz), 7.09 (d, 1H, J = 2.4 Hz), 6.61 (t, 1H, J = 6.7 Hz), 6.32 (s, 2H), 5.81 (s, 2H), 2.99-2.95 (m, 1H), 0.93-0.89 (m, 4H). |
| 192 | A | A | 564.6 | 1H NMR (400 MHz, D6-dmso, δ above 12 (2H), 7.97 (d, 1H, J = 8.0 Hz), 7.93-7.89 (m, 1H), 7.84 (d, 1H, J = 2.0 Hz), 7.72 (t, 1H, J = 6.0 Hz), 7.61, 7.54 (AB, 2H, J = 8.8 Hz), 7.58 (dd, 1H, J = 2.0 & 7.2 Hz), 7.39 (dd, 1H, J = 8.8 & 9.6 Hz), 6.99 (d, 1H, J = 2.0 Hz), 6.65 (t, 1H, J = 4.4 Hz), 5.86 (s, 2H), 3.73 (s, 3H), 2.93-2.86 (m, 1H), 0.96-0.92 (m, 4H). |
| 193 | A | B | 566.0 | 1H NMR (400 MHz, D6-dmso), δ above 12 (2H), 8.32 (d, 1H, J = 8.4 Hz), 8.10 (d, 1H, J = 8.0 Hz), 8.03 (dd, 1H, J = 0.8 & 8.4 Hz), 7.96 (d, 1H, J = 2.0 Hz), 7.91 (ddd, 1H, J = 1.6, 7.2 & 6.8 Hz), 7.79 (ddd, 1H, J = 1.6, 7.2 & 6.8 Hz), 7.71 (t, 1H, J = 8.0 Hz), 7.47 (d, 1H, J = 10.8 Hz), 7.12 (d, 1H, J = 2.0 Hz), 6.66 (t, 1H, J = 5.2 Hz), 6.34 (s, 1H), 6.28 (s, 2H), 3.11 (s, 3H). |
| 194 | A | A | 566.0 | 1H NMR (400 MHz, D6-dmso), δ 12.69 (s, 2H), 8.06 (dd, 1H, J = 1.8 & 6.7 Hz), 7.97-7.95 (m, 2H), 7.81-7.74 (m, 2H), 7.71 (t, 1H, J = 4.9 Hz), 7.56 (dt, 1H, J = 4.2 & 1.2 Hz), 7.54 (s, 1H), 7.38 (s, 1H,), 7.11 (d, 1H, J = 1.8 Hz), 6.67 (t, 1H, J = 6.7 Hz), 5.87 (s, 2H), 3.12 (s, 3H). |

TABLE 1-continued

| # | IC50 | EC50 | LR-MS (M + H) | ¹H NMR DATA |
|---|---|---|---|---|
| 195 | A | A | 567.5 | 1H NMR (400 MHz, D6-dmso), δ 12.75 (d, 1H, J = 5.5 Hz), 12.71 (s, 1H), 7.95 (dd, 1H, J = 1.8 & 6.7 Hz), 7.92 (d, 1H, J = 1.8 Hz), 7.88 (s, 1H) 7.70 (t, 1H, J = 4.9 Hz) 7.57 (d, 1H, J = 11.0 Hz), 7.53 (t, 1H, J = 6.1 Hz), 7.40 (s, 1H), 7.29 (t, 1H, J = 8.5 Hz) 7.09 d, 1H, J = 1.8 Hz), 6.63 (t, 1H, J = 6.7 Hz), 5.82 (s, 2H), 2.92-2.83 (m, 1H), 0.95 (s, 2H), 0.93 (s, 2H). |
| 196 | A | A | 568.0 | 1H-NMR (400 MHz, in dmso-d6): δ 12.92 (1H, broad s), 11.67 (1H, broad s), 7.96 (1H, d, J = 8.06 Hz), 7.83 (1H, d, J = 7.32 Hz), 7.82 (1H, d, J = 7.32), 7.77 (1H, m), 7.63 (1H, ddd, J = 2.2, 6.6, 6.6 Hz), 7.57 (1H, dd, J = 7.32, 7.32 Hz), 7.38 (1H, s), 7.01 (1H, d, J = 9.52 Hz), 6.59 (1H, dd, J = 6.59, 6.59 Hz), 5.73 (2H, s), 4.66 (2H, t, J = 8.79 Hz), 3.21 (2H, t, J = 8.79 Hz), 3.09 (3H, s) |
| 197 | A | A | 568.5 | 1H-NMR (400 MHz, in dmso-d6): δ 12.75 (2H, broad s); 8.62 (1H, d, J = 1.95 Hz), 8.11 (1H, s), 7.98 (1H, dd, J = 1.95, 6.84 Hz) 7.93 (1H, d, J = 1.95 Hz), 7.80 (1H, dd, J = 1.95, 9.77 Hz), 7.72 (1H, d, J = 5.37 Hz), 7.62 (1H, s), 7.60 (1H, s), 7.19 (1H, d, J = 2.44 Hz), 6.64 (1H, t, J = 6.35, 6.84 Hz), 5.79 (2H, s), 2.88 (1H, q, J = 6.35 Hz), 0.95 (4H, d, J = 6.35 Hz); LR-MS (ESI) |
| 197 | A | A | 568.5 | 1H-NMR (400 MHz, in dmso-d6): δ 12.75 (2H, broad s); 8.62 (1H, d, J = 1.95 Hz), 8.11 (1H, s), 7.98 (1H, dd, J = 1.95, 6.84 Hz) 7.93 (1H, d, J = 1.95 Hz), 7.80 (1H, dd, J = 1.95, 9.77 Hz), 7.72 (1H, d, J = 5.37 Hz), 7.62 (1H, s), 7.60 (1H, s), 7.19 (1H, d, J = 2.44 Hz), 6.64 (1H, t, J = 6.35, 6.84 Hz), 5.79 (2H, s), 2.88 (1H, q, J = 6.35 Hz), 0.95 (4H, d, J = 6.35 Hz); LR-MS (ESI): calcd. for C26H20F2NO6S+ [M + H]+ 568.11, found 567.97 |
| 198 | A | A | 569.5 | 1H NMR (400 MHz, D6-dmso), δ 12.71 (s, 2H), 8.25-8.21 (m, 1H), 7.97 (dd, 1H, J = 1.8 & 7.3 Hz), 7.93 (d, 1H, J = 2.4 Hz), 7.75-7.69 (m, 2H), 7.62 (d, 1H, J = 10.4 Hz), 7.55 (t, 1H, J = 9.8 Hz), 7.10 (d, 1H, J = 2.4 Hz), 6.63 (t, 1H, J = 6.7 Hz), 5.88 (s, 2H), 2.91-2.84 (m, 1H), 0.94 (d, 4H, J = 6.7 Hz). |
| 199 | A | A | 569.6 | 1H NMR (400 MHz, D6-dmso), δ above 12 (2H), 7.98 (d, 1H, J = 7.2 Hz), 7.93-7.92 (m, 1H), 7.89 (b, 1H), 7.84-7.81 (m, 1H), 7.72 (t, 1H, J = 5.2 Hz), 7.60 (d, 1H, J = 11.0 Hz), 7.50 (d, 1H, J = 6.8 Hz), 7.38 (b, 1H), 7.29 (t, 1H, J = 9.6 Hz), 7.10-7.09 (m, 1H), 6.64 (t, 1H, J = 6.8 Hz), 5.82 (s, 2H), 3.53 (h, 1H, J = 7.2 Hz), 1.07 (d, 6H, J = 6.8 Hz). |
| 200 | A | A | 570.5 | 1H-NMR (400 MHz, in dmso-d6): δ 12.67 (1H, broad s), 8.60 (1H, s), (8.12 (1H, s), 7.76 (2H, m), 7.63 (1H, m), 7.60 (1H, s), 7.06 (1H, d, J = 9.77 Hz), 6.56 (1H, dd, J = 6.35, 6.84 Hz), 5.64 (2H, s), 4.62 (2H, t, J = 8.79 Hz), 3.20 (2H, t, J = 8.79 Hz), 2.87 (1H, m), 0.92 (4H, d, J = 5.86 Hz) |
| 201 | A | A | 574.0 | 1H NMR (400 MHz, D6-dmso), d, 12.74 (s, 1H), 12.70 (d, 1H, J = 5.5 Hz) 8.05 (dd, 1H, J = 1.8 & 6.7 Hz), 7.96 (d, 1H, J = 8.0 Hz), 7.87 (d, 1H, J = 2.5 Hz), 7.79-7.75 (m, 2H),, 7.71 (dt, 1H, J = 1.8 & 6.1 Hz), 7.58 (t, 2H, J = 9.2 Hz), 7.53 (t, 1H, J = 9.2 Hz), 7.38 (s, 1H), 7.00 (d, 1H, J = 2.4 Hz), 6.68 (t, 1H, J = 6.7 Hz), 5.92 (s, 2H), 2.79-2.74 (m, 1H), 0.83-0.79 (m, 2H), 0.76-0.71 (m, 2H). |
| 202 | A | A | 575.6 | 1H NMR (400 MHz, dmso) δ 5.656 (s, 2H), 6.546 (t, 1H, J = 7.3 Hz), 6.60-6.69 (m, 2H), 6.729 (d, 1H, J = 7.3 Hz), 6.979 (t, 1H, J = 7.3 Hz), 7.066 (d, 1H, J = 2.2 Hz), 6.95-7.00 (m, 1H), 7.22-7.3 (m, 2H), 7.445 (d, 1H, J = 11 Hz), 7.480 (dd, 1H, J = 8, 1.5 Hz), 7.70-7.756 (m, 1H), 7.87-7.91 (m, 2H). |
| 204 | A | A | 577.0 | 1H NMR (400 MHz, D6-dmso), δ 12.70 (d, 1H, J = 4.9 Hz), 12.45 (d, 1H) 8.04 (dd, 1H, J = 1.8 & 6.7 Hz), 7.96 (d, 1H, J = 9.2 Hz), 7.87 (d, 1H, J = 2.4 Hz), 7.79-7.75 (m, 2H), 7.70 (t, 1H, J = 6.7 Hz), 7.59-7.52 (m, 3H), 7.34 (s, 1H), 7.00 (d, 1H, J = 2.4 Hz), 6.66 (t, 1H, J = 6.7 Hz), 5.92 (s, 2H), 2.52 (s, 6H). |
| 205 | A | A | 581.0 | 1H NMR (400 MHz, dmso) δ 0.82-0.92 (m, 4H), 2.78-2.86 (m, 1H), 5.907 (s, 2H), 6.664 (t, 1H, J = 6.6 Hz), 6.714 (s, 1H), 7.109 (d, 1H, J = 2.2 Hz), 7.445 (d, 1H, J = 11 Hz), 7.731 (br s, 1H), 7.953 (d, 1H, J = 2.2 Hz), 7.97-8.03 (m, 2H), 9.087 (br s, 1H). |
| 206 | A | B | 581.6 | 1H NMR (400 MHz, D6-dmso), d, 12.75 (s, 1H), 12.70 (d, 1H, J = 4.9 Hz) 8.38 (d, 1H, J = 4.3 Hz), 7.96 (dd, 1H, J = 2.4 & 7.3 Hz), 7.93 (d, 1H, J = 2.4 Hz), 7.78-7.43 (m, 1H), 7.69 (dt, 1H, J = 1.8 & 6.1 Hz), 7.55 (d, 1H, J = 10.4 Hz), 7.51 (d, 1H, J = 7.3 Hz), 7.29 (t, 1H, J = 9.1 Hz), 7.10 (d, 1H, J = 1.8 Hz), 6.63 (t, 1H, J = 6.1 Hz), |

TABLE 1-continued

| # | IC50 | EC50 | LR-MS (M + H) | ¹H NMR DATA |
|---|---|---|---|---|
| | | | | 5.80 (s, 2H), 3.23 (s, 3H), 2.75-2.69 (m, 1H), 0.65-0.60 (m, 2H), 0.51-0.46 (m, 2H). |
| 207 | A | A | 584.6 | 1H NMR (400 MHz, d6-DMSO): ? 12.71 (s, 1H), 12.67 (s, 1H), 7.94 (dd, J = 2.0, 6.8 Hz, 1H), 7.91 (d, J = 2.0 Hz, 1H), 7.70 (m, 1H), 7.54 (d, J = 10.8 Hz, 1H), 7.26 (m, 1H), 7.13 (dd, J = 8.4, 10.0 Hz, 1H), 7.09 (d, J = 2.0 Hz, 1H), 6.91 (dd, J = 2.0, 7.2 Hz, 1H), 6.62 (t, J = 6.8 Hz, 1H), 5.80 (s, 2H), 4.37 (t, J = 6.0 Hz, 1H), 3.26 (d, J = 6.4 Hz, 2H), 2.86 (m, 1H), 0.95-0.92 (M, 4H) |
| 208 | A | A | 588.5 | 1H NMR (400 MHz, dmso) δ 3.253 (s, 3H), 5.857 (s, 2H), 6.597 (t, 1H, J = 6.6 Hz), 7.076 (d, 1H, J = 2.2 Hz), 7.242 (dd, 1H, J = 8.8, 1.5 Hz), 7.456 (s, 1H), 7.558 (d, 1H, J = 11 Hz), 7.653 (d, 2H, J = 8 Hz), 7.912 (d, 1H, J = 2.2 Hz), 7.959 (dd, 1H, J = 7.3, 2.2 Hz) |
| 209 | A | A | 591.1 | 1H NMR (400 MHz, d6-DMSO): d, 9.34 (s, 1H), 8.09 (d, J = 9.2 Hz, 1H), 8.02-8.01 (m, 1H), 7.98 (d, J = 8.8 Hz, 1H), 7.85-7.77 (m, 3H), 7.72-7.70 (m, 1H), 7.57 (t, J = 7.0 Hz, 1H), 7.40 (s, 1H), 6.64 (t, J = 6.0 Hz, 1H), 6.00 (s, 2H), 2.79-2.76 (m, 1H), 0.81-0.74 (m, 4H). |
| 210 | A | B | 592.0 | 1H NMR (400 MHz, D6-dmso, δ above 12 (2H), 8.34 (d, 1H, J = 8.8 Hz), 8.08 (d, 1H, J = 8.0 Hz), 8.02 (d, 1H, J = 8.4 Hz), 7.96 (d, 1H, J = 2.4 Hz), 7.91 (t, 1H, J = 7.2 Hz), 7.79 (t, 1H, J = 8.0 Hz), 7.72 (t, 1H, J = 4.0 Hz), 7.52 (d, 1H, J = 10.4 Hz), 7.11 (d, 1H, J = 2.0 Hz), 6.66 (t, 1H, J = 6.4 Hz), 6.32 (s, 1H), 6.30 (s, 2H), 2.74-2.69 (m, 1H), 0.85 (b, 2H), 0.75 (b, 2H). |
| 211 | A | A | 592.0 | |
| 212 | A | A | | See Example 15 for Experimental Details and Data |
| 213 | A | A | 594.0 | 1H NMR (500 MHz, DMSO): δ 8.07 (dd, 1H, J = 1.89 Hz), 7.98 (m, 2H), 7.80 (m, 2H), 7.74 (m, 1H), 7.65 (d, 1H, J = 10.7 Hz), 7.58 (t, 1H, J = 8.19 Hz), 7.14 (d, 1H, J = 2.2 Hz), 6.69 (t, 1H, J = 6.3 Hz), 5.93 (s, 2H), 3.16 (t, 2H, J = 7.5 Hz), 1.23 (p, 2H), 0.60 (t, 3H). M.S. found: 593.3 (M)+. |
| 215 | A | A | 595.0 | 1H NMR (400 MHz, D6-dmso, δ, 12.70 (d, 1H, J = 5.5 Hz), 12.38 (d, 1H) 8.03 (dd, 1H, J = 1.8 & 7.3 Hz), 7.97-7.95 (m, 2H), 7.79-7.74 (m, 2H), 7.70 (dt, 1H, J = 1.2 & 6.1 Hz), 7.61 (d, 1H, J. = 11.0 Hz) 7.56 (dt, 1H, J = 7.3 & 1.2H), 7.33 (s, 1H), 7.11 (d, 1H, J = 1.8 Hz), 6.65 (t, 1H, J = 6.7 Hz), 5.89 (s, 2H), 2.48 (s, 6H). |
| 216 | A | A | 596.1 | 1H-NMR (400 MHz, in dmso-d6): δ 12.96 (1H, broad s), 11.76 (1H, broad s), 7.95 (1H, d, J = 8.79 Hz), 7.74 (2H, m), 7.58 H1H, dd, J = 4.39, 7.32 Hz), 7.50 (1H, dd, J = 7.32, 8.06 Hz), 7.35 (1H, s), 7.26 (1H, d, J = 10.25 Hz), 6.63 (2H, s), 6.02 (2H, s), 5.01 (2H, t, J = 8.79 Hz), 3.40 (2H, t, J = 8.79 Hz), 1.21 (6H, d, J = 6.6 Hz) |
| 218 | A | C | 599.4 | 1H NMR (400 MHz, D6-dmso), δ above 12 (2H), 7.95 (d, 1H, J = 6.0 Hz), 7.92 (dd, 1H, J = 1.2 & 2.4 Hz), 7.79 (d, 1H, J = 10.4 Hz), 7.70-7.66 (b, 1H), 7.57 (d, 1H, J = 7.6 Hz), 7.49 (d, 1H, J = 8.0 Hz), 7.14 (dt, 1H, J = 0.8 & 7.6 Hz), 7.10 (dd, 1H, J = 0.8 & 2.0 Hz), 6.84 (s, 1H), 6.60 (t, 1H, J = 7.6 Hz), 5.99 (s, 2H), 3.15 (s, 3H). |
| 219 | C | A | 603.0 | 1H NMR (400 MHz, cdcl3) δ 1.232 (s, 9H), 5.940 (s, 2H), 6.094 (s, 2H), 6.705-6.752 (m, 1H), 6.819 (d, 1H, J = 9.5 Hz), 6.911 (d, 1H, J = 2.2 Hz), 7.382 (s, 1H), 7.418-7.437 (m, 1H), 7.494 (d, 1H, J = 2.2 Hz), 7.565 (d, 1H, J = 7.3 Hz), 7.65-7.71 (m, 1H), 7.871 (dd, 1H, J = 6.6, 1.5 Hz), 8.02 (d, 1H, J = 8 Hz), 8.06-8.11 (m, 1H) |
| 221 | A | C | 607.6 | 1H NMR (400 MHz, D6-dmso, δ 12.76 (d, 1H, J = 5.6 Hz) 12.74 (s, 1H), 8.39 (d, 1H, J = 4.0 Hz), 7.95 (dd, 1H, J = 2.0 & 6.8 Hz), 7.92 (d, 1H, J = 2.4 Hz), 7.78-7.43 (m, 1H), 7.71 (dt, 1H, J = 1.6 & 6.0 Hz), 7.57 (d, 1H, J = 10.8 Hz), 7.53 (dd, 1H, J = 2.0 & 7.2 Hz), 7.28 (dd, 1H, J = 1.2 & 8.8 Hz), 7.09 (d, 1H, J = 2.4 Hz), 6.64 (t, 1H, J = 6.4 Hz), 5.80 (s, 2H), 2.92-2.86 (m, 1H), 2.72 (m, 1H), 0.95 (s, 2H), 0.94 (m, 2H), 0.65-0.61 (m, 2H), 0.50-0.47 (m, 2H). |
| 222 | A | A | 614.6 | 1H NMR (400 MHz, dmso) δ 0.93-0.97 (m, 4H), 2.47-2.495 (m, 1H), 5.88 (s, 2H), 6.615 (t, 1H, J = 6.6 Hz), 7.077 (d, 1H, J = 2.2 Hz), 7.248 (dd, 1H, J = 8.8, 1.5 Hz), 7.471 (s, 1H), 7.607 (d, 1H, J = 11H), 7.635-7.715 (m, 2H), 7.904 (d, 1H, J = 2.2 Hz), 7.948 (dd, 1H, J = 7.3, 2.2 Hz) |
| 223 | A | A | 643.1 | 1H NMR (400 MHz, dmso) δ 4.09-4.14 (m, 2H), 5.703 (s, 2H), 6.28-6.35 (m, 1H), 6.538 (d, 1H, J = 8.8 Hz), 6.66-6.74 (m, 1H), 7.06-7.13 (m, 2H), 7.26-7.34 (m, 2H), 7.48 (d, 1H, J = 11 Hz), 7.52-7.58 (m, 1H), 7.64-7.72 (m, 2H), 7.72-7.8 (m, 2H), 7.91-8.04 (m, 2H) |

TABLE 1-continued

| # | IC50 | EC50 | LR-MS (M + H) | ¹H NMR DATA |
|---|---|---|---|---|
| 225 | A | B | 671.7 | 1H NMR (400 MHz, D6-dmso), δ, 12.76 (s, 2H) 12.13 (s, 1H), 7.96-7.92 (m, 3H), 7.71 (bs, 1H), 7.66 (d, 1H, J = 6.8 Hz), 7.60 (d, 1H, J = 10.8 Hz), 7.38 (t, 1H, J = 8.0 Hz), 7.10 (s, 1H), 6.38 (t, 1H, J = 7.6 Hz), 5.84 (s, 2H), 3.09-3.01 (m, 1H), 2.90-2.83 (m, 1H), 1.16-1.05 (m, 4H), 1.00-0.90 (m, 4H) |
| 226 | C | A | 680.7 | 1H NMR (500 MHz, CDCl3): δ 8.02 (s, 1H), 7.72 (dd, J = 7.25 Hz, J = 2.21 Hz, 1H), 7.63 (dd, J = 7.25 Hz, J = 2.21 Hz, 1H), 7.52 (d, J = 2.20 Hz, 1H), 6.905 (d, J = 2.20 Hz, 1H), 6.85 (d, J = 9.8 Hz 1H), 6.37 (t, J = 6.9 Hz 1H), 6.01 (s, 2H), 5.99 (s, 1H), 5.84 (s, 2H), 5.79 (s, 2H), 3.79 (s, 3H), 1.244 (s, 9H), 1.135 (s, 9H). |
| 227 | C | A | 740.8 | 1H NMR (500 MHz, CDCl3) δ 8.50 (s, 1H), 7.96 (m, 2H), 7.73 (m, 1H), 7.53 (d, J = 8.0 Hz, 1H), 7.11 (s, 1H), 6.67 (m, 1H), 6.53 (s, 1H), 5.91 (s, 1H), 5.77 (s, 2H), 1.16 (m, 18H), 0.98 (m, 4H) |
| 228 | C | A | 780.8 | M.S. found: 780.4 (M + H)+; 1H NMR (500 MHz, CDCl3): δ 7.69 (dd, J = 2.2 Hz, J = 6.9 Hz, 1H), 7.63 (dd, J = 2.2 Hz, J = 6.9 Hz, 1H), 7.56- m, 2H), d, J = 2.2 Hz, 1H), 6.83 (d, J = 9.8 Hz, 1H), 6.37 (t, J = 6.9 Hz, 1H), 6.01 (m, 2H), 5.81-5.77 (m, 4H), 5.75 (s, 2H), 5.70 (m, 1H), 1.26-1.22 (m, 18H), 1.16 (s, 9H). |
| 231 | A | A | | See Example 16 for Experimental Details and Data |

Uses of the Compounds of Formula (I)

The Compounds of Formula (I) are useful in human and veterinary medicine for treating or preventing a viral infection or a virus-related disorder in a patient. In accordance with the invention, the Compounds of Formula (I) can be administered to a patient in need of treatment or prevention of a viral infection or a virus-related disorder.

Accordingly, in one embodiment, the invention provides methods for treating a viral infection in a patient comprising administering to the patient an effective amount of at least one Compound of Formula (I) or a pharmaceutically acceptable salt, solvate, ester or prodrug thereof. In another embodiment, the invention provides methods for treating a virus-related disorder in a patient comprising administering to the patient an effective amount of at least one Compound of Formula (I) or a pharmaceutically acceptable salt, solvate, ester or prodrug thereof.

Treatment or Prevention of a Viral Infection

The Compounds of Formula (I) can be used to treat or prevent a viral infection. In one embodiment, the Compounds of Formula (I) can be inhibitors of viral replication. In a specific embodiment, the Compounds of Formula (I) can be inhibitors of HCV replication. Accordingly, the Compounds of Formula (I) are useful for treating viral diseases and disorders related to the activity of a virus, such as HCV polymerase.

Examples of viral infections that can be treated or prevented using the present methods, include but are not limited to, hepatitis A infection, hepatitis B infection and hepatitis C infection.

In one embodiment, the viral infection is hepatitis C infection.

In one embodiment, the hepatitis C infection is acute hepatitis C. In another embodiment, the hepatitis C infection is chronic hepatitis C.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., *Pathology*, 30(2):192-195 (1998). The nomenclature set forth in Simmonds et al., *J Gen Virol*, 74(Pt11):2391-2399 (1993) is widely used and classifies isolates into six major genotypes, 1 through 6, with two or more related subtypes, e.g., 1a, 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3 (see Lamballerie et al, *J Gen Virol*, 78(Pt1):45-51 (1997)). The major genotypes have been defined as having sequence similarities of between 55 and 72% (mean 64.5%), and subtypes within types as having 75%-86% similarity (mean 80%) when sequenced in the NS-5 region (see Simmonds et al., *J Gen Virol*, 75(Pt 5):1053-1061 (1994)).

Treatment or Prevention of a Virus-Related Disorder

The Compounds of Formula (I) can be used to treat or prevent a virus-related disorder. Accordingly, the Compounds of Formula (I) are useful for treating disorders related to the activity of a virus, such as liver inflammation or cirrhosis. Virus-related disorders include, but are not limited to, RNA-dependent polymerase-related disorders and disorders related to HCV infection.

Treatment or Prevention of a RNA-Dependent Polymerase-Related Disorder

The Compounds of Formula (I) are useful for treating or preventing a RNA dependent polymerase (RdRp) related disorder in a patient. Such disorders include viral infections wherein the infective virus contain a RdRp enzyme.

Accordingly, in one embodiment, the present invention provides a method for treating a RNA dependent polymerase-related disorder in a patient, comprising administering to the patient an effective amount of at least one Compound of Formula (I) or a pharmaceutically acceptable salt, solvate, ester or prodrug thereof.

Treatment or Prevention of a Disorder Related to HCV Infection

The Compounds of Formula (I) can also be useful for treating or preventing a disorder related to an HCV infection. Examples of such disorders include, but are not limited to, cirrhosis, portal hypertension, ascites, bone pain, varices, jaundice, hepatic encephalopathy, thyroiditis, porphyria cutanea tarda, cryoglobulinemia, glomerulonephritis, sicca syndrome, thrombocytopenia, lichen planus and diabetes mellitus.

Accordingly, in one embodiment, the invention provides methods for treating an HCV-related disorder in a patient, wherein the method comprises administering to the patient a therapeutically effective amount of at least one Compound of Formula (I), or a pharmaceutically acceptable salt, solvate, ester or prodrug thereof.

Combination Therapy

In another embodiment, the present methods for treating or preventing a viral infection can further comprise the administration of one or more additional therapeutic agents which are not Compounds of Formula (I).

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one Compound of Formula (I), or a pharmaceutically acceptable salt, solvate, ester or prodrug thereof, and (ii) at least one other antiviral agent that is other than a Compound of Formula (I), wherein the amounts administered are together effective to treat or prevent a viral infection.

When administering a combination therapy of the invention to a patient, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Compound of Formula (I) and an additional therapeutic agent may be present in fixed amounts (dosage amounts) in a single dosage unit (e.g., a capsule, a tablet and the like). A commercial example of such single dosage unit containing fixed amounts of two different active compounds is VYTORIN® (available from Merck Schering-Plough Pharmaceuticals, Kenilworth, N.J.).

In one embodiment, the at least one Compound of Formula (I) is administered during at time when the additional antiviral agent(s) exert their prophylactic or therapeutic effect, or vice versa.

In another embodiment, the at least one Compound of Formula (I) and the additional antiviral agent(s) are administered in doses commonly employed when such agents are used as monotherapy for treating a viral infection.

In another embodiment, the at least one Compound of Formula (I) and the additional antiviral agent(s) are administered in doses lower than the doses commonly employed when such agents are used as monotherapy for treating a viral infection. In still another embodiment, the at least one Compound of Formula (I) and the additional antiviral agent(s) act synergistically and are administered in doses lower than the doses commonly employed when such agents are used as monotherapy for treating a viral infection.

In one embodiment, the at least one Compound of Formula (I) and the additional antiviral agent(s) are present in the same composition. In one embodiment, this composition is suitable for oral administration. In another embodiment, this composition is suitable for intravenous administration.

Viral infections and virus-related disorders that can be treated or prevented using the combination therapy methods of the present invention include, but are not limited to, those listed above.

In one embodiment, the viral infection is HCV infection.

The at least one Compound of Formula (I) and the additional antiviral agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of at least one Compound of Formula (I) and the additional antiviral agent(s) may inhibit the resistance of a viral infection to these agents.

Non-limiting examples of other therapeutic agents useful in the present compositions and methods include an HCV polymerase inhibitor, an interferon, a viral replication inhibitor, an antisense agent, a therapeutic vaccine, a viral protease inhibitor, a virion production inhibitor, an antibody therapy (monoclonal or polyclonal), and any agent useful for treating an RNA-dependent polymerase-related disorder.

In one embodiment, the other antiviral agent is a viral protease inhibitor.

In another embodiment, the other antiviral agent is an HCV protease inhibitor.

In another embodiment, the other antiviral agent is an interferon.

In still another embodiment, the other antiviral agent is a viral replication inhibitor.

In another embodiment, the other antiviral agent is an antisense agent.

In another embodiment, the other antiviral agent is a therapeutic vaccine.

In a further embodiment, the other antiviral agent is an virion production inhibitor.

In another embodiment, the other antiviral agent is antibody therapy.

In another embodiment, the other antiviral agents comprise a protease inhibitor and a polymerase inhibitor.

In still another embodiment, the other antiviral agents comprise a protease inhibitor and an immunosuppressive agent.

In yet another embodiment, the other antiviral agents comprise a polymerase inhibitor and an immunosuppressive agent.

In a further embodiment, the other antiviral agents comprise a protease inhibitor, a polymerase inhibitor and an immunosuppressive agent.

In another embodiment the other agent is ribavirin.

HCV polymerase inhibitors useful in the present methods and compositions include, but are not limited to VP-19744 (Wyeth/ViroPharma), HCV-796 (Wyeth/ViroPharma), NM-283 (Idenix/Novartis), R-1626 (Roche), MK-0608 (Merck), A848837 (Abbott), GSK-71185 (Glaxo SmithKline), XTL-2125 (XTL Biopharmaceuticals), and those disclosed in Ni et al., *Current Opinion in Drug Discovery and Development*, 7(4):446 (2004); Tan et al., *Nature Reviews*, 1:867 (2002); and Beaulieu et al., *Current Opinion in Investigational Drugs*, 5:838 (2004).

Interferons useful in the present methods and compositions include, but are not limited to, interferon alfa-2a, interferon alfa-2b, interferon alfacon-1 and PEG-interferon alpha conjugates. "PEG-interferon alpha conjugates" are interferon alpha molecules covalently attached to a PEG molecule. Illustrative PEG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™), interferon alpha-2c (Berofor Alpha™, Boehringer Ingelheim, Ingelheim, Germany), interferon alpha fusion polypeptides, or consensus interferon as defined by determination of a consensus sequence of naturally occurring interferon alphas (Infergen™, Amgen, Thousand Oaks, Calif.).

Antibody therapy agents useful in the present methods and compositions include, but are not limited to, antibodies specific to IL-10 (such as those disclosed in US Patent Publication No. US2005/0101770, humanized 12G8, a humanized monoclonal antibody against human IL-10, plasmids containing the nucleic acids encoding the humanized 12G8 light and heavy chains were deposited with the American Type Culture Collection (ATCC) as deposit numbers PTA-5923 and PTA-5922, respectively), and the like). Viral protease inhibitors useful in the present methods and compositions include, but are not limited to, NS3 serine protease inhibitors (including, but not limited to, those disclosed in U.S. Pat. Nos. 7,012,066, 6,914,122, 6,911,428, 6,846,802, 6,838,475, 6,800,434, 5,017,380, 4,933,443, 4,812,561 and 4,634,697; and U.S. Patent Publication Nos. US20020160962, US20050176648 and US20050249702), HCV protease inhibitors (e.g., SCH503034 (Schering-Plough), VX-950 (Vertex), GS-9132 (Gilead/Achillion), ITMN-191 (Inter-Mune/Roche)), amprenavir, atazanavir, fosemprenavir, indinavir, lopinavir, ritonavir, nelfinavir, saquinavir, tipranavir and TMC114.

Viral replication inhibitors useful in the present methods and compositions include, but are not limited to, NS3 helicase inhibitors, NS5A inhibitors, ribavirin, viramidine, A-831 (Arrow Therapeutics); an antisense agent or a therapeutic vaccine.

In one embodiment, viral replication inhibitors useful in the present methods and compositions include, but are not limited to, NS3 helicase inhibitors or NS5A inhibitors.

Examples of protease inhibitors useful in the present methods include, but are not limited to, an HCV protease inhibitor and a NS-3 serine protease inhibitor.

Examples of HCV protease inhibitors useful in the present methods include, but are not limited to, those disclosed in Landro et al., *Biochemistry*, 36(31):9340-9348 (1997); Ingallinella et al., *Biochemistry*, 37(25):8906-8914 (1998); Llinàs-Brunet et al., *Bioorg Med Chem Lett*, 8(13):1713-1718 (1998); Martin et al., *Biochemistry*, 37(33):11459-11468 (1998); Dimasi et al., *J Virol*, 71(10):7461-7469 (1997); Martin et al., *Protein Eng*, 10(5):607-614 (1997); Elzouki et al., *J Hepat*, 27(1):42-48 (1997); *BioWorld Today*, 9(217):4 (Nov. 10, 1998); and
International Publication Nos. WO 98/14181; WO 98/17679, WO 98/17679, WO 98/22496 and WO 99/07734.

Further examples of protease inhibitors useful in the present methods include, but are not limited to, Additional examples of other therapeutic agents useful in the present methods include, but are not limited to, Levovirin™ (ICN Pharmaceuticals, Costa Mesa, Calif.), VP 50406™ (Viropharma, Incorporated, Exton, Pa.), ISIS 14803™ (ISIS Pharmaceuticals, Carlsbad, Calif.), Heptazyme™ (Ribozyme Pharmaceuticals, Boulder, Colo.), VX-950™ (Vertex Pharmaceuticals, Cambridge, Mass.), Thymosin™ (SciClone Pharmaceuticals, San Mateo, Calif.), Maxamine™ (Maxim Pharmaceuticals, San Diego, Calif.), NKB-122 (JenKen Bioscience Inc., North Carolina), mycophenolate mofetil (Hoffman-LaRoche, Nutley, N.J.).

The doses and dosage regimen of the other agents used in the combination therapies of the present invention for the treatment or prevention of a viral infection can be determined by the attending clinician, taking into consideration the approved doses and dosage regimen in the package insert; the age, sex and general health of the patient; and the type and severity of the viral infection or related disease or disorder. When administered in combination, the Compound of Formula (I)(s) and the other agent(s) for treating diseases or conditions listed above can be administered simultaneously (i.e., in the same composition or in separate compositions one right after the other) or sequentially. This is particularly useful when the components of the combination are given on different dosing schedules, e.g., one component is administered once daily and another every six hours, or when the preferred pharmaceutical compositions are different, e.g. one is a tablet and one is a capsule. A kit comprising the separate dosage forms is therefore advantageous.

Generally, a total daily dosage of the at least one Compound of Formula (I) and the additional antiviral agent(s), when administered as combination therapy, can range from about 0.1 to about 2000 mg per day, although variations will necessarily occur depending on the target of the therapy, the patient and the route of administration. In one embodiment, the dosage is from about 10 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In a further embodiment, the dosage is from about 1 to about 20 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

In one embodiment, when the other therapeutic agent is INTRON-A interferon alpha 2b (commercially available from Schering-Plough Corp.), this agent is administered by subcutaneous injection at 3MIU (12 mcg)/0.5 mL/TIW is for 24 weeks or 48 weeks for first time treatment.

In another embodiment, when the other therapeutic agent is PEG-INTRON interferon alpha 2b pegylated (commercially available from Schering-Plough Corp.), this agent is administered by subcutaneous injection at 1.5 mcg/kg/week, within a range of 40 to 150 mcg/week, for at least 24 weeks.

In another embodiment, when the other therapeutic agent is ROFERON A inteferon alpha 2a (commercially available from Hoffmann-La Roche), this agent is administered by subcutaneous or intramuscular injection at 3MIU (11.1 mcg/mL)/TIW for at least 48 to 52 weeks, or alternatively 6MIU/TIW for 12 weeks followed by 3MIU/TIW for 36 weeks.

In still another embodiment, when the other therapeutic agent is PEGASUS interferon alpha 2a pegylated (commercially available from Hoffmann-La Roche), this agent is administered by subcutaneous injection at 180 mcg/1 mL or 180 mcg/0.5 mL, once a week for at least 24 weeks.

In yet another embodiment, when the other therapeutic agent is INFERGEN interferon alphacon-1 (commercially available from Amgen), this agent is administered by subcutaneous injection at 9 mcg/TIW is 24 weeks for first time treatment and up to 15 mcg/TIW for 24 weeks for non-responsive or relapse treatment.

In a further embodiment, when the other therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

Compositions and Administration

Due to their activity, the Compounds of Formula (I) are useful in veterinary and human medicine. As described above, the Compounds of Formula (I) are useful for treating or preventing a viral infection or a virus-related disorder in a patient in need thereof.

When administered to a patient, the IDs can be administered as a component of a composition that comprises a pharmaceutically acceptable carrier or vehicle. The present invention provides pharmaceutical compositions comprising an effective amount of at least one Compound of Formula (I) and a pharmaceutically acceptable carrier. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

The Compounds of Formula (I) of the present invention may also be deliverable transdermally. The transdermal compositions can take the form of creams, lotions, aerosols and/or emulsions and can be included in a transdermal patch of the matrix or reservoir type as are conventional in the art for this purpose.

Additionally, the compositions of the present invention may be formulated in sustained release form to provide the rate controlled release of any one or more of the components or active ingredients to optimize the therapeutic effects, i.e. anti-inflammatory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Compounds of Formula (I) are administered orally.

In another embodiment, the one or more Compounds of Formula (I) are administered intravenously.

In another embodiment, the one or more Compounds of Formula (I) are administered topically.

In still another embodiment, the one or more Compounds of Formula (I) are administered sublingually.

In one embodiment, a pharmaceutical preparation comprising at least one Compound of Formula (I) is in unit dosage form. In such form, the preparation is subdivided into unit doses containing appropriate quantities of the active component, e.g., an effective amount to achieve the desired purpose.

Compositions can be prepared according to conventional mixing, granulating or coating methods, respectively, and the present compositions can contain, in one embodiment, from about 0.1% to about 99% of the Compound of Formula (I)(s) by weight or volume. In various embodiments, the present compositions can contain, in one embodiment, from about 1% to about 70% or from about 5% to about 60% of the Compound of Formula (I)(s) by weight or volume.

The quantity of Compound of Formula (I) in a unit dose of preparation may be varied or adjusted from about 0.1 mg to about 2000 mg. In various embodiment, the quantity is from about 1 mg to about 2000 mg, 100 mg to about 200 mg, 500 mg to about 2000 mg, 100 mg to about 1000 mg, and 1 mg to about 500 mg.

For convenience, the total daily dosage may be divided and administered in portions during the day if desired. In one embodiment, the daily dosage is administered in one portion.

In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Compounds of Formula (I) will be regulated according to the judgment of the attending clinician considering such factors as age, condition and size of the patient as well as severity of the symptoms being treated. Generally, a total daily dosage of the Compounds of Formula (I) range from about 0.1 to about 2000 mg per day, although variations will necessarily occur depending on the target of the therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one Compound of Formula (I) or a pharmaceutically acceptable salt, solvate, ester or prodrug thereof; (ii) one or more additional therapeutic agents that are not a Compound of Formula (I); and (iii) a pharmaceutically acceptable carrier, wherein the amounts in the composition are together effective to treat a viral infection or a virus-related disorder.

Kits

In one aspect, the present invention provides a kit comprising a therapeutically effective amount of at least one Compound of Formula (I), or a pharmaceutically acceptable salt, solvate, ester or prodrug of said compound and a pharmaceutically acceptable carrier, vehicle or diluent.

In another aspect the present invention provides a kit comprising an amount of at least one Compound of Formula (I), or a pharmaceutically acceptable salt, solvate, ester or prodrug of said compound and an amount of at least one additional therapeutic agent listed above, wherein the amounts of the two or more ingredients result in a desired therapeutic effect.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:
1. A compound having the formula:

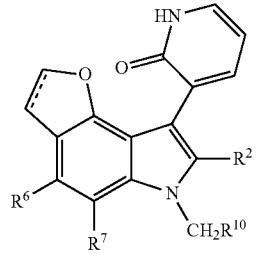

(Ia)

or a pharmaceutically acceptable salt or ester thereof, wherein the dotted line indicates an optional and additional bond, and wherein:

$R^2$ is —C(O)OR$^9$ or —C(O)NHSO$_2$R$^{11}$;

$R^6$ and $R^7$ are each independently selected from H, alkyl, F, Cl, —CF$_3$, —OH, —O-alkyl, —OCF$_3$, —NH$_2$ and —NHSO$_2$-alkyl;

each occurrence of $R^8$ is independently H, alkyl, alkenyl, alkynyl, —[C(R$^{12}$)$_2$]$_q$-aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, haloalkyl or hydroxyalkyl;

each occurrence of $R^{11}$ is independently alkyl, aryl, cycloalkyl, cycloalkenyl, heterocycloalkyl, heterocycloalkenyl, heteroaryl, haloalkyl, hydroxy or hydroxyalkyl, wherein a cycloalkyl, cycloalkenyl, heterocycloalkyl, heterocycloalkenyl, aryl or heteroaryl group can be optionally substituted with up to 4 substituents, which are each independently selected from —H, alkyl, alkenyl, alkynyl, aryl, —[C(R$^{12}$)$_2$]$_q$-cycloalkyl, —[C(R$^{12}$)$^2$]$_q$-cycloalkenyl, —[C(R$^{12}$)$^2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$^2$]$_q$-haloalkyl, —[C(R$^{12}$)$^2$]$_q$-hydroxyalkyl, halo, —OH, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$alkyl, —[C(R$^{12}$)$_2$]$_q$—NHSO$_2$cycloalkyl, —[C(R$^{12}$)$_2$]$_q$—NHSO$_2$aryl, —[C(R$^{12}$)$_2$]$_q$—SO$_2$N(R$^9$)$_2$ and —SO$_2$N(R$^9$)C(O)N(R$^9$)$_2$;

$R^9$ is H or alkyl; and $R^{10}$ is:

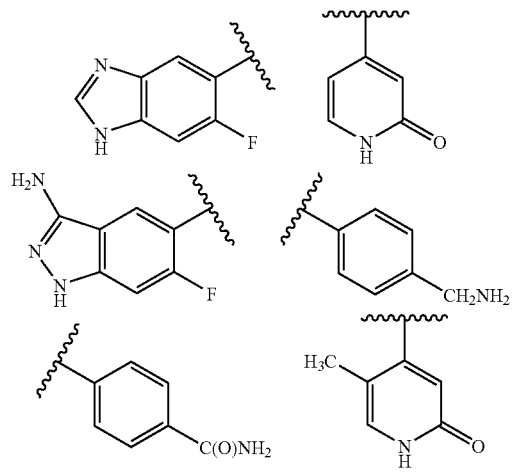

-continued
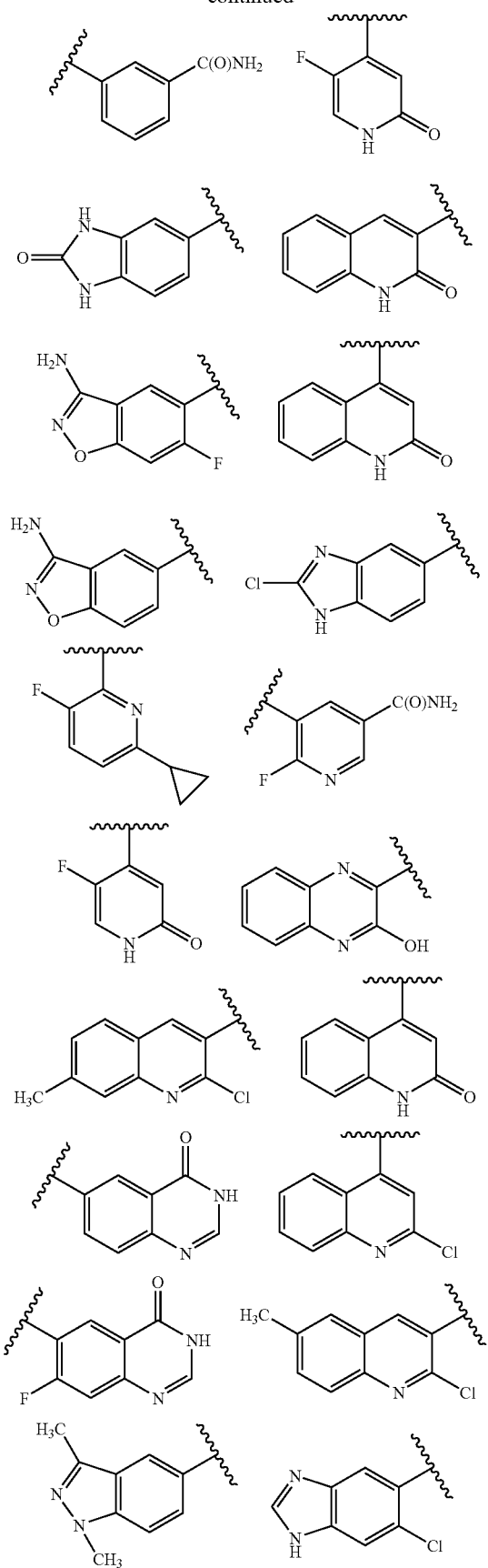
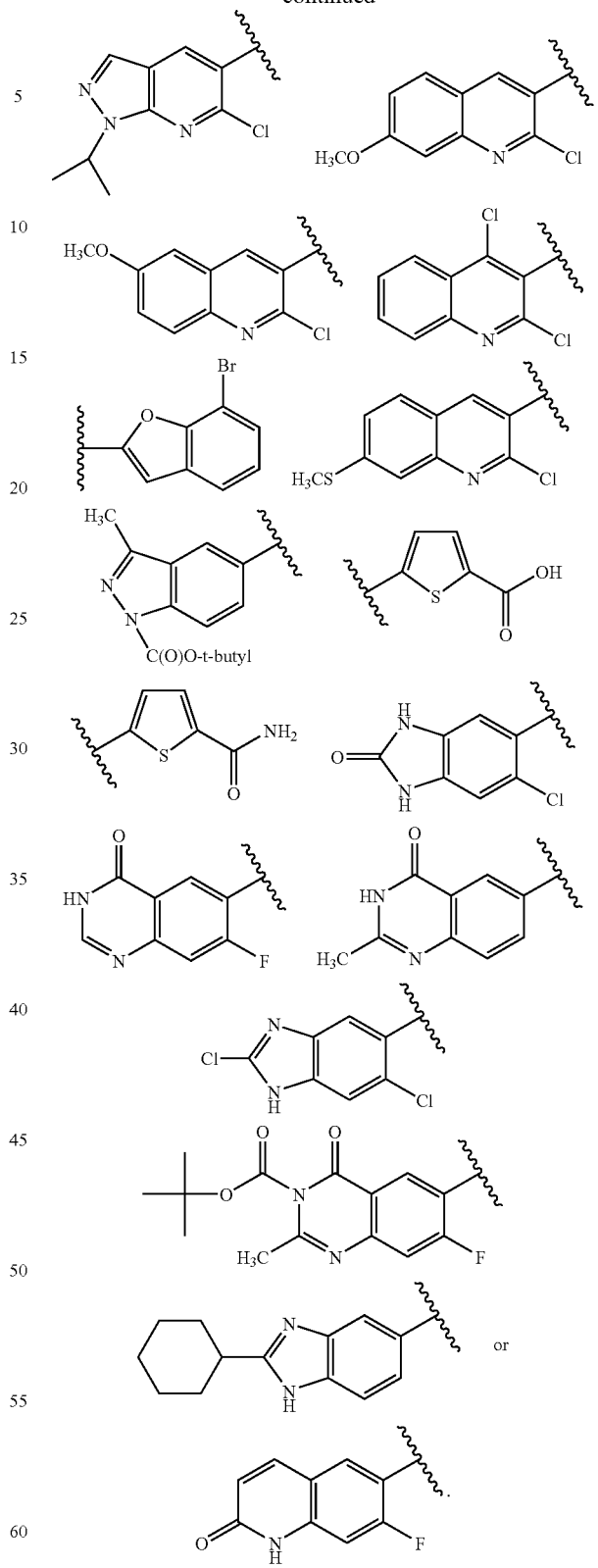
each occurrence of $R^{12}$ is independently H, halo, —$N(R^9)_2$, —$OR^9$, alkyl, cycloalkyl, cycloalkenyl, heterocycloalkyl or heterocycloalkenyl, wherein a cycloalkyl, cycloalkenyl, heterocycloalkyl or heterocycloalkenyl group can be optionally substituted with up to 4 substituents, which are each independently selected from alkyl, halo, haloalkyl, hydroxyalkyl, —OH, —CN, —C(O)alkyl, —C(O)Oalkyl, —C(O)NHalkyl, —C(O)N(alkyl)$_2$, —O-alkyl, —NH$_2$, —NH(alkyl), —N(alkyl)$_2$, —NHC(O)alkyl, —NHSO$_2$alkyl, —SO$_2$alkyl or —SO$_2$NH-alkyl, or two R$^{12}$ groups, together with the carbon atoms to which they are attached, join to form a cycloalkyl, heterocycloalkyl or C=O group.

2. The compound of claim 1, wherein R$^2$ is —C(O)OH, —C(O)Oalkyl, —C(O)NH$_2$, —C(O)NH-alkyl, —C(O)NH-cycloalkyl, —C(O)NHSO$_2$R$^{11}$, heteroaryl,

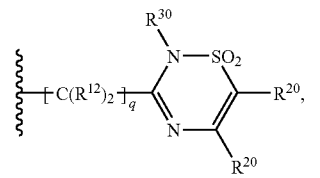

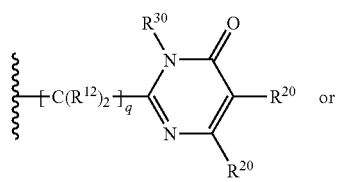 or

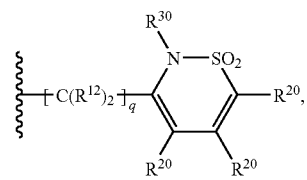

wherein the heteroaryl, arylthiazin-yl- or arylthiadiazol-yl-group can be optionally substituted with up to 3 substituents, which are the same or different, and are selected from alkyl, aryl, heteroaryl, halo, haloalkyl, hydroxyalkyl, —OH, —CN, —C(O)R$^8$, —C(O)OR$^9$, —C(O)N(R$^9$)$_2$, —[C(R$^{12}$)$_2$]$_q$—OR$^9$, —[C(R$^{12}$)$_2$]$_q$—N(R$^9$)$_2$, —NHC(O)R$^8$, —NHSO$_2$R$^{11}$, —S(O)$_p$R$^{11}$ or —SO$_2$N(R$^9$)$_2$; such that if Z is thiophene-yl, R$^2$ is other than —C(O)O-alkyl; wherein each occurrence of R$^8$ is independently H, alkyl, alkenyl, alkynyl, —[C(R$^{12}$)$_2$]$_q$-aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$^2$]$_q$-heterocycloalkenyl, —[C(R$^{12}$)$^2$]$_q$-heteroaryl, haloalkyl or hydroxyalkyl;

each occurrence of R$^{11}$ is independently alkyl, aryl, cycloalkyl, cycloalkenyl, heterocycloalkyl, heterocycloalkenyl, heteroaryl, haloalkyl, hydroxy or hydroxyalkyl, wherein a cycloalkyl, cycloalkenyl, heterocycloalkyl, heterocycloalkenyl, aryl or heteroaryl group can be optionally substituted with up to 4 substituents, which are each independently selected from —H, alkyl, alkenyl, alkynyl, aryl, —[C(R$^{12}$)$_2$]$_q$-cycloalkyl, —[C(R$^{12}$)$^2$]$_q$-cycloalkenyl, —[C(R$^{12}$)$^2$]$_q$-heterocycloalkyl, —[C(R$^{12}$)$^2$]$_q$-heterocycloalkenyl, —[C(R$^{12}$)$^2$]$_q$-heteroaryl, —[C(R$^{12}$)$^2$]$_q$-haloalkyl, —[C(R$^{12}$)$^2$]$_q$-hydroxyalkyl, halo, —OH, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$^2$]$_q$—NHSO$_2$alkyl, —[C(R$^{12}$)$^2$]$_q$—NHSO$_2$cycloalkyl, —[C(R$^{12}$)$^2$]$_q$—NHSO$_2$aryl, —[C(R$^{12}$)$^2$]$_q$—SO$_2$N(R$^9$)$_2$ and —SO$_2$N(R$^9$)C(O)N(R$^9$)$_2$;

each occurrence of R$^{12}$ is independently H, halo, —N(R$^9$)$_2$, —OR$^9$, alkyl, cycloalkyl, cycloalkenyl, heterocycloalkyl or heterocycloalkenyl, wherein a cycloalkyl, cycloalkenyl, heterocycloalkyl or heterocycloalkenyl group can be optionally substituted with up to 4 substituents, which are each independently selected from alkyl, halo, haloalkyl, hydroxyalkyl, —OH, —CN, —C(O)alkyl, —C(O)Oalkyl, —C(O)NHalkyl, —C(O)N(alkyl)$_2$, —O-alkyl, —NH$_2$, —NH(alkyl), —N(alkyl)$_2$, —NHC(O)alkyl, —NHSO$_2$alkyl, —SO$_2$alkyl or —SO$_2$NH-alkyl, or two R$^{12}$ groups, together with the carbon atoms to which they are attached, join to form a cycloalkyl, heterocycloalkyl or C=O group;

or a pharmaceutically acceptable salt or ester thereof.

3. The compound of claim 2, wherein R$^2$ is —C(O)NHSO$_2$-alkyl, —C(O)NHSO$_2$-aryl, —C(O)NHSO$_2$-cycloalkyl or —C(O)NHSO$_2$-alkylene-cycloalkyl.

4. The compound of claim 3, wherein R$^2$ is —C(O)NHSO$_2$-methyl, —C(O)NHSO$_2$-ethyl, —C(O)NHSO$_2$-isopropyl, —C(O)NHSO$_2$-t-butyl, —C(O)NHSO$_2$-phenyl or —C(O)NHSO$_2$-cyclopropyl.

5. The compound of claim 2, wherein R$^2$ is —C(O)OH.

6. A compound having the structure:

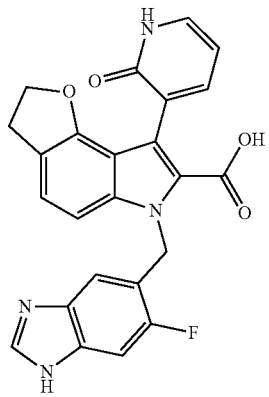

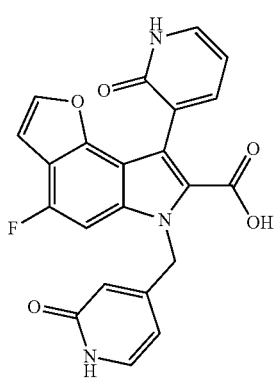

297
-continued
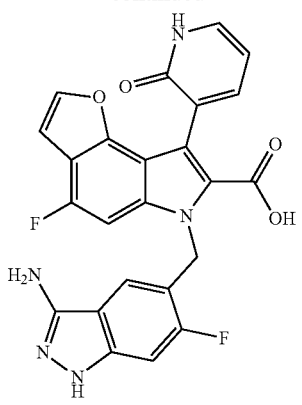
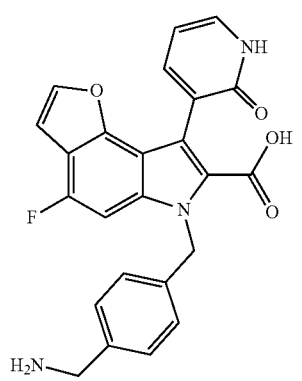
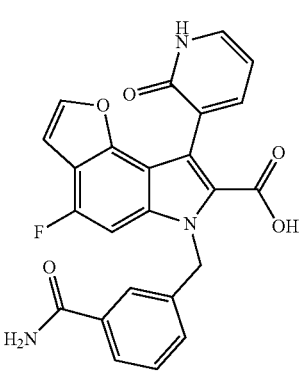
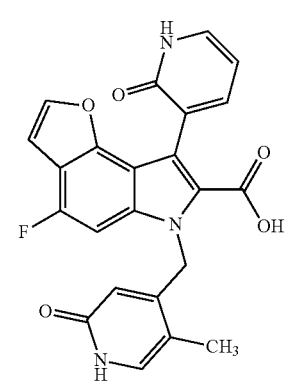
298
-continued
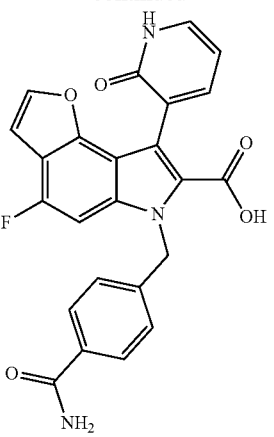
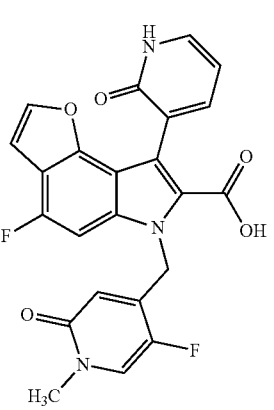
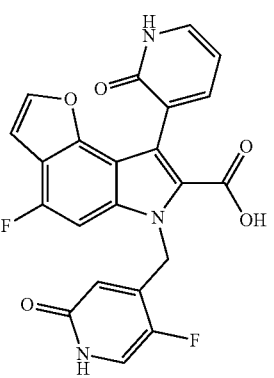
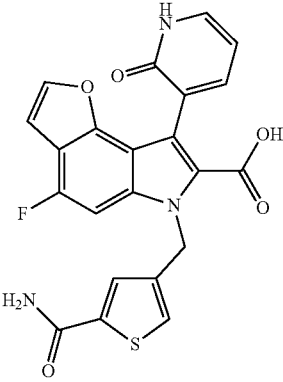

-continued
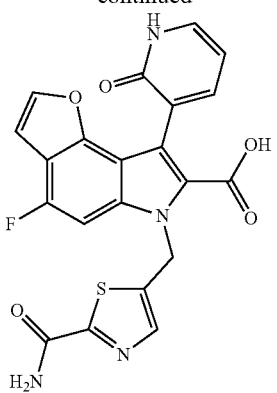
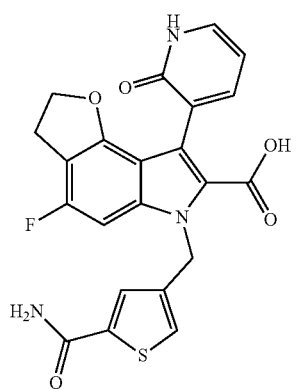
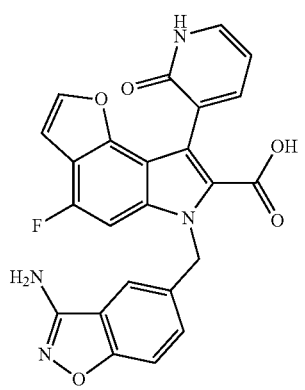
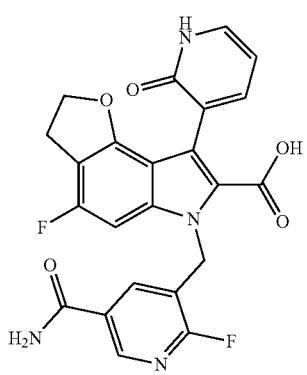
-continued
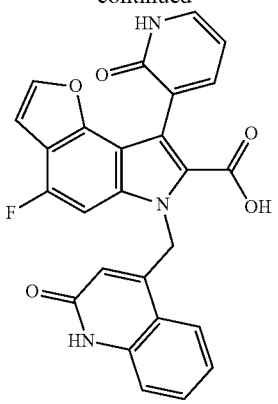
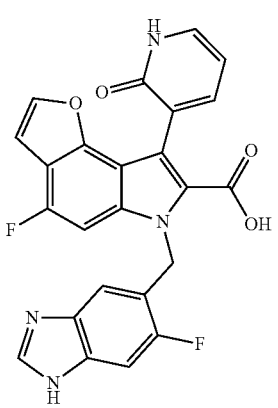
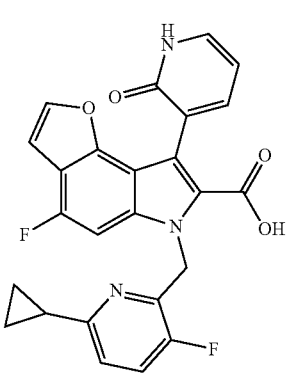
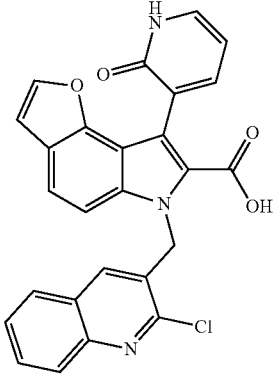

301
-continued
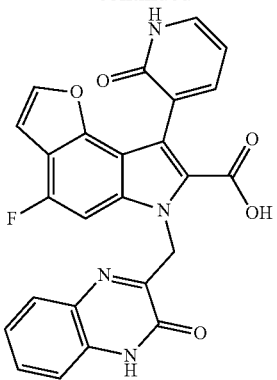
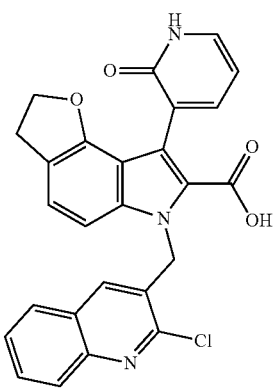
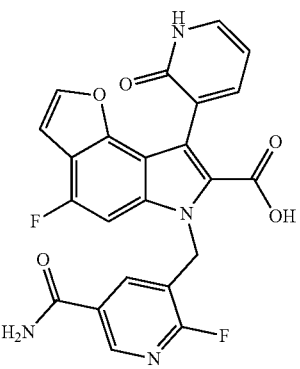
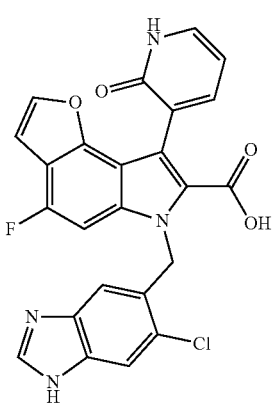
302
-continued
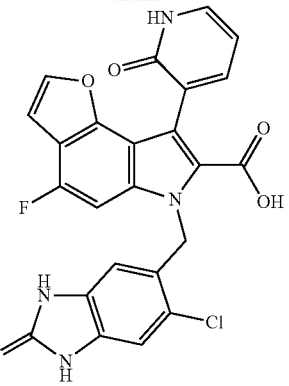
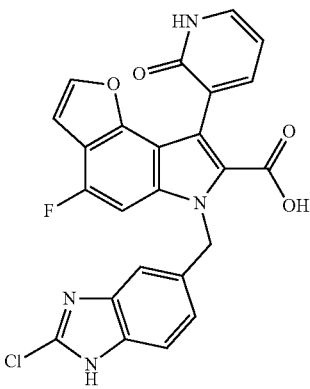
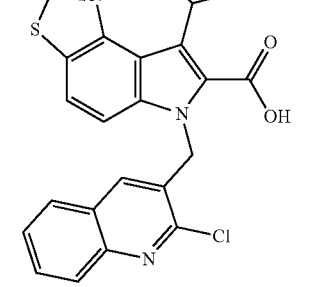
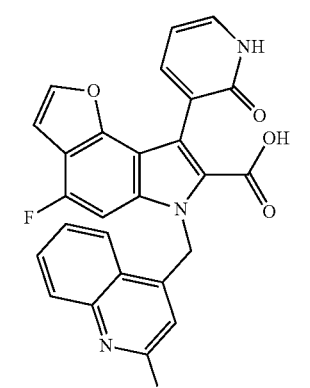

-continued
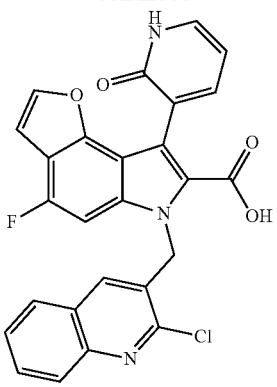
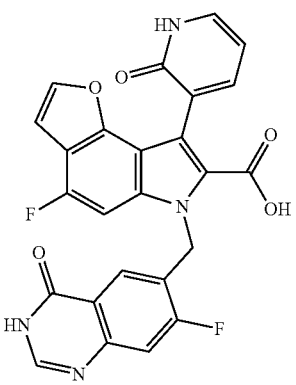
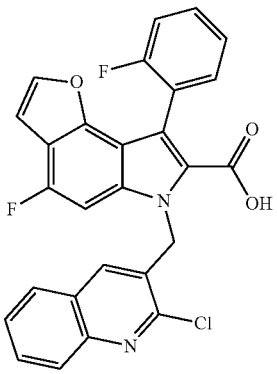
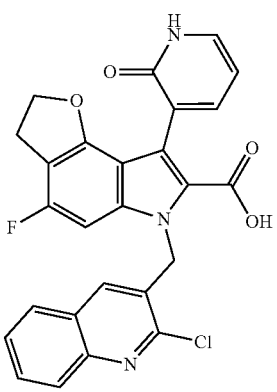
-continued
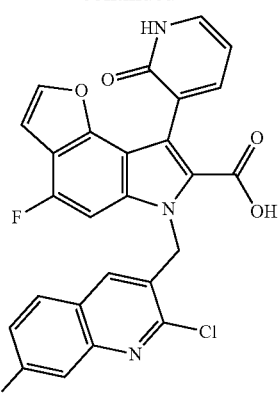
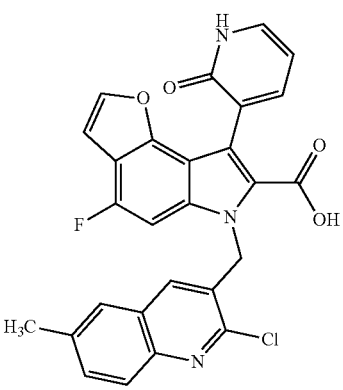
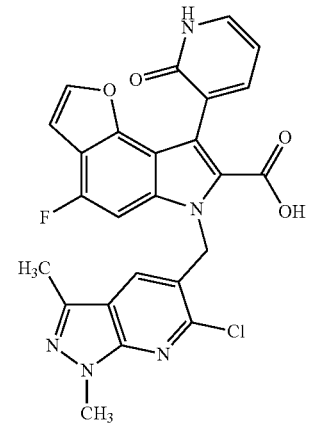
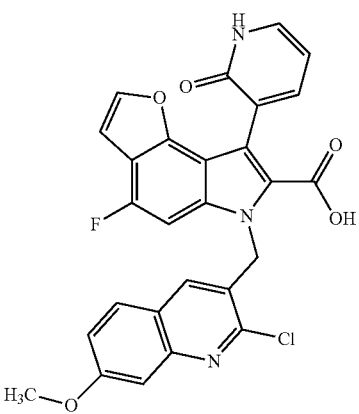

305
-continued
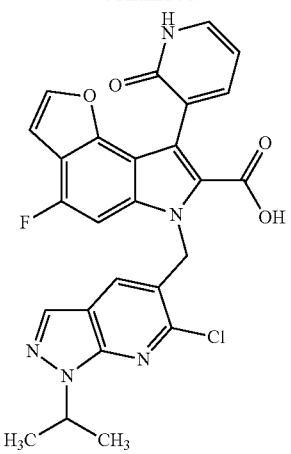
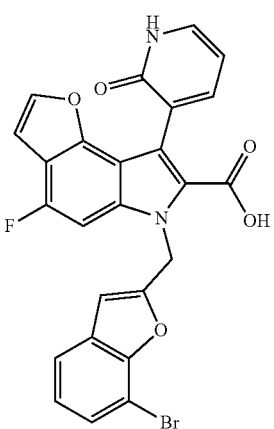
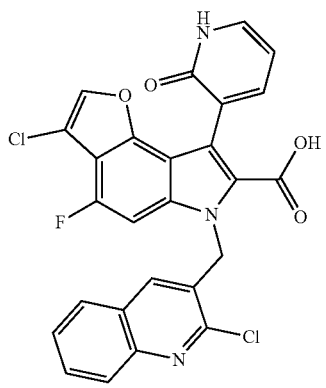
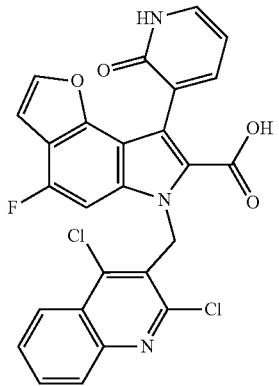
306
-continued
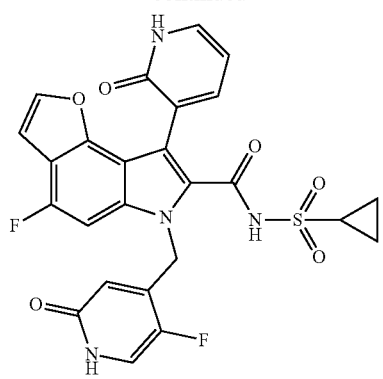
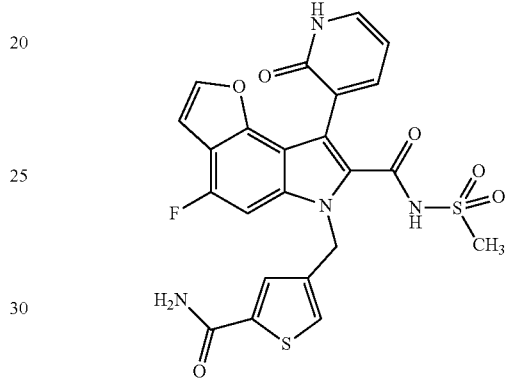
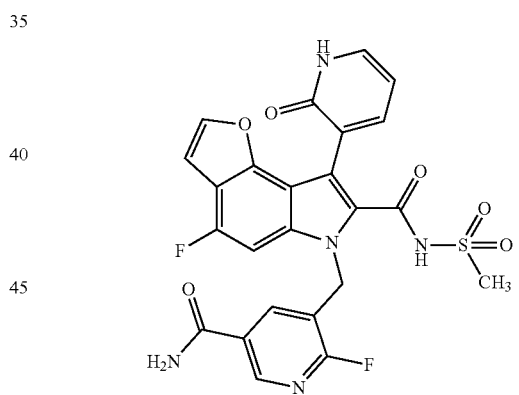
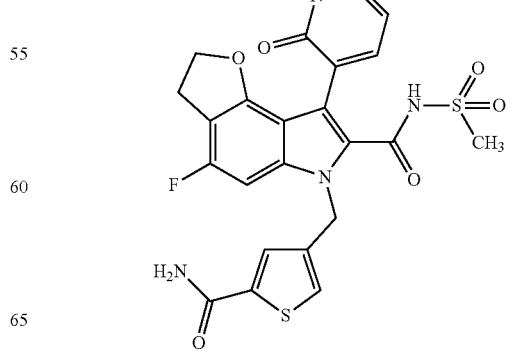

307
-continued
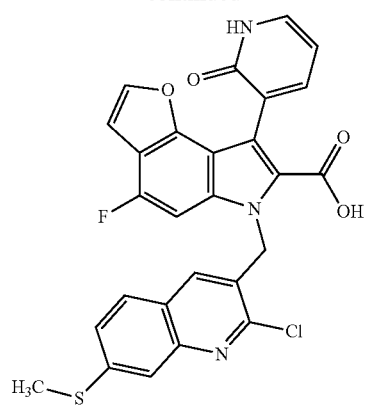
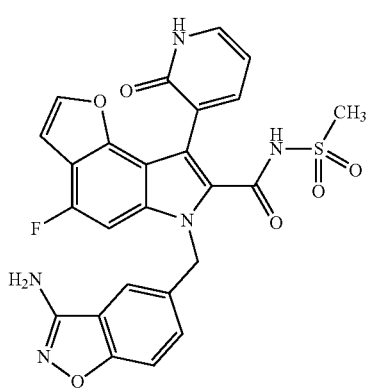
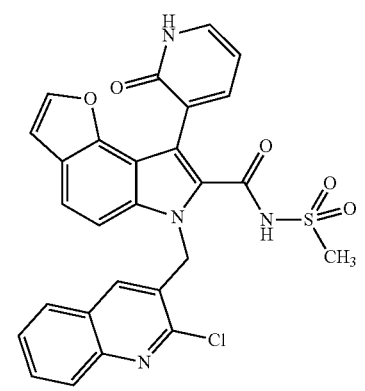
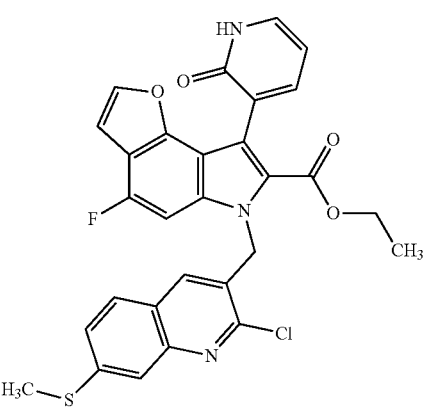
308
-continued
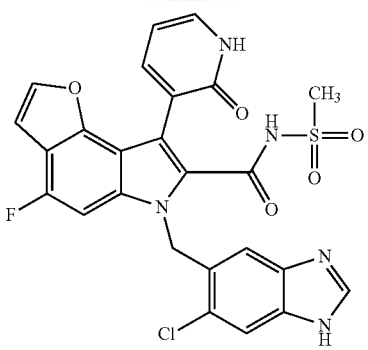
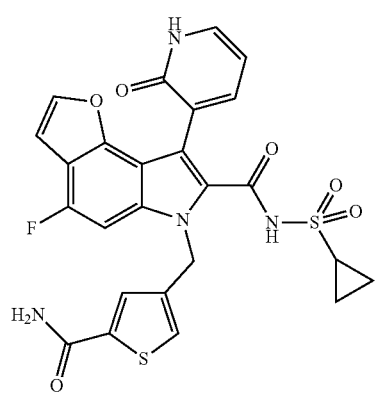
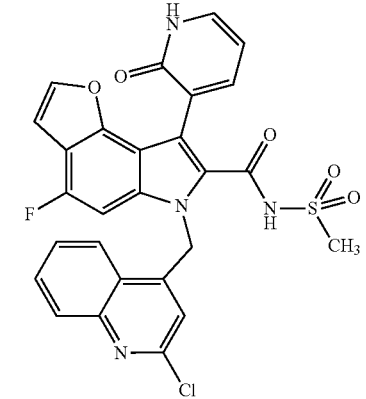
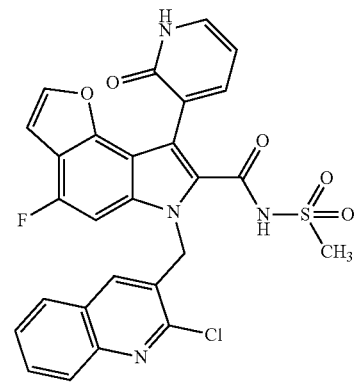

309 -continued
310 -continued
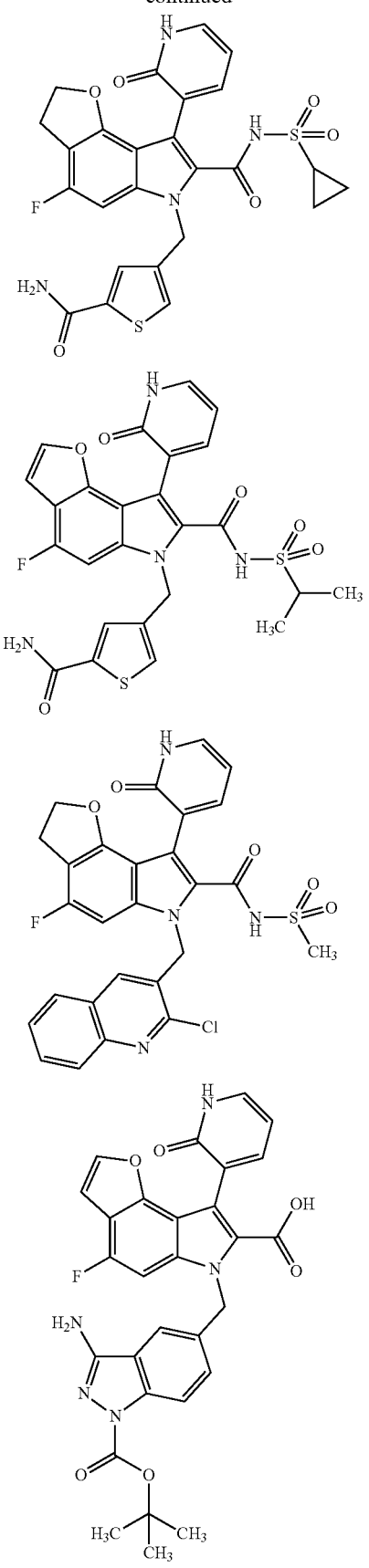

311
-continued
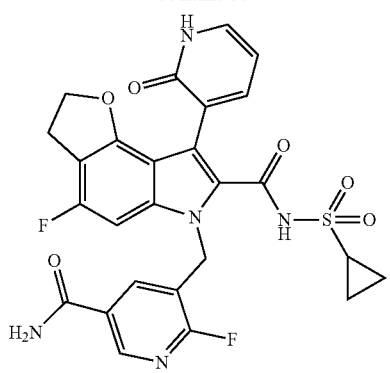
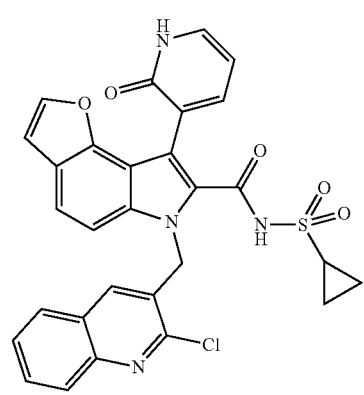
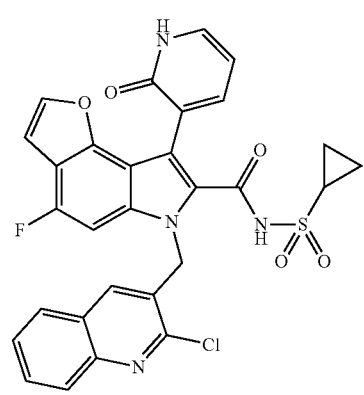
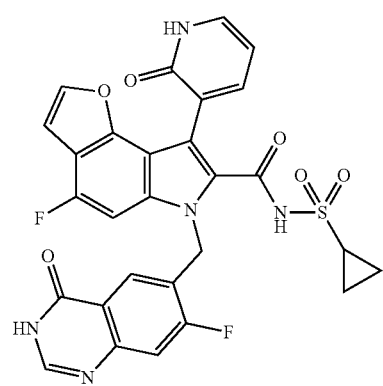
312
-continued
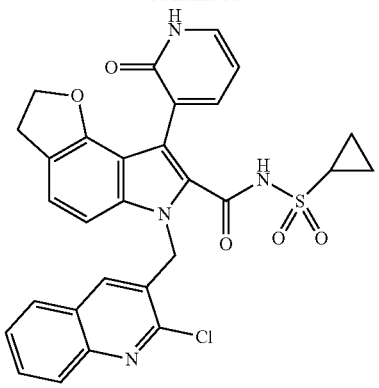
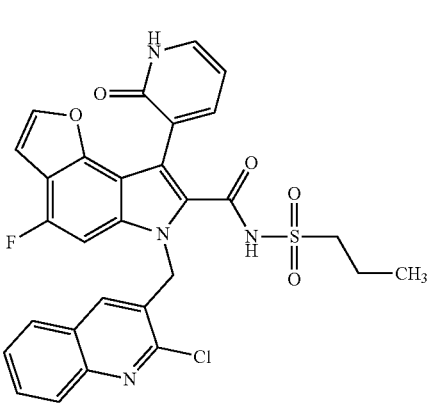
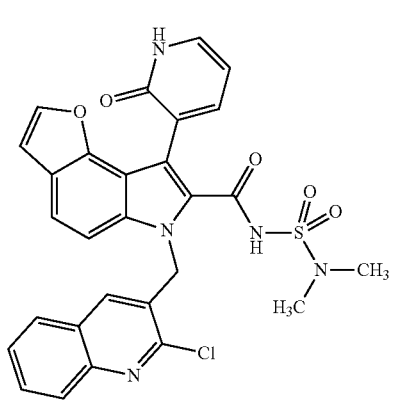
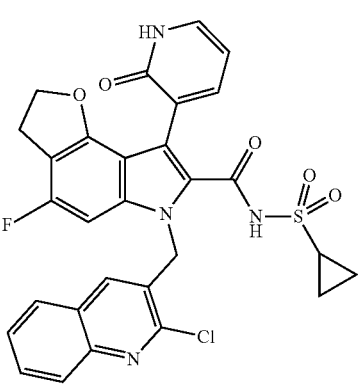

313
-continued

314
-continued

315
-continued
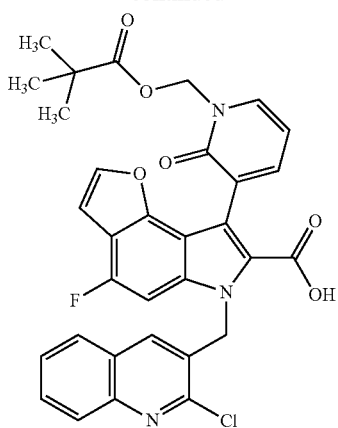
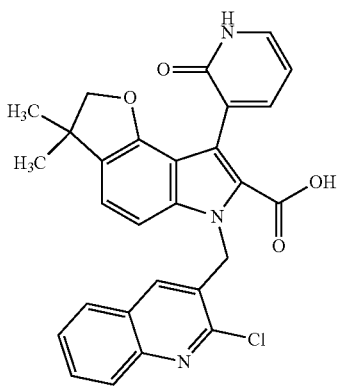
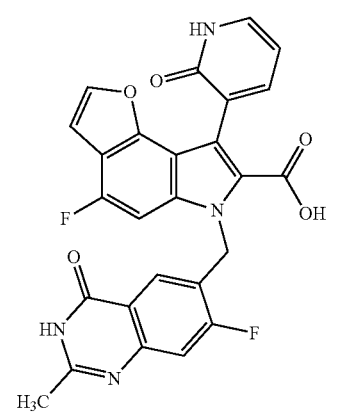
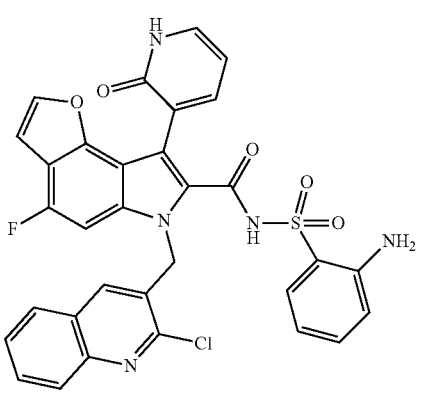
316
-continued
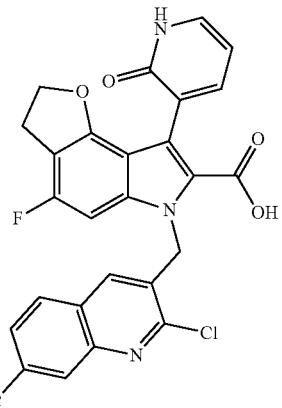
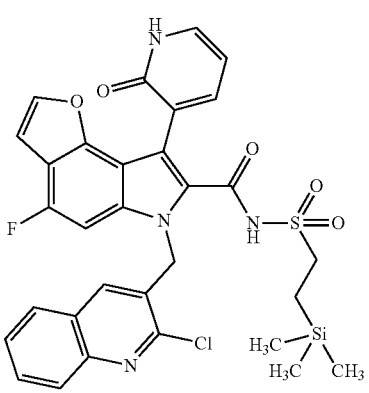
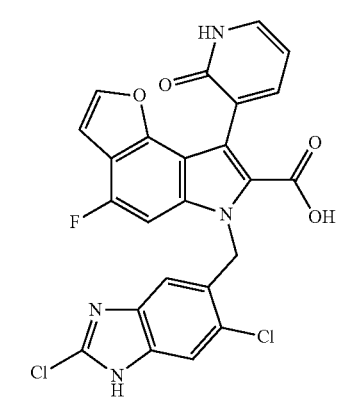

-continued

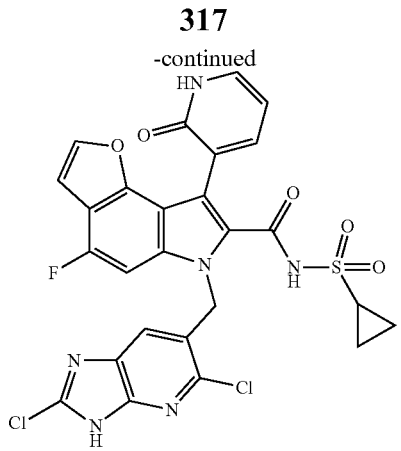

or a pharmaceutically acceptable salt or ester thereof.

7. A pharmaceutical composition comprising at least one compound of claim 1 or a pharmaceutically acceptable salt thereof, and at least one pharmaceutically acceptable carrier.

8. The pharmaceutical composition of claim 7, further comprising at least one additional antiviral agent, wherein the additional agent is not a compound of claim 1.

9. The composition of claim 8, wherein the additional antiviral agent is selected from: an HCV polymerase inhibitor; an interferon; a RNA replication inhibitor; an antisense agent; a therapeutic vaccine; a protease inhibitor and an antibody therapy (monoclonal or polyclonal).

10. A method for treating hepatitis V virus (HCV) infection in a patient, the method comprising administering to the patient an effective amount of at least one compound of claim 1 or a pharmaceutically acceptable salt thereof.

11. The method of claim 10, further comprising administering to the patient at least one additional antiviral agent, wherein the additional agent is not a compound of claim 1, and wherein the amounts administered are together effective to treat hepatitis V virus (HCV) infection.

12. The method of claim 11, wherein the additional antiviral agent is selected from: an HCV polymerase inhibitor; an interferon; a RNA replication inhibitor; an antisense agent; a therapeutic vaccine; a protease inhibitor and an antibody therapy (monoclonal or polyclonal).

13. A compound having the structure:

-continued

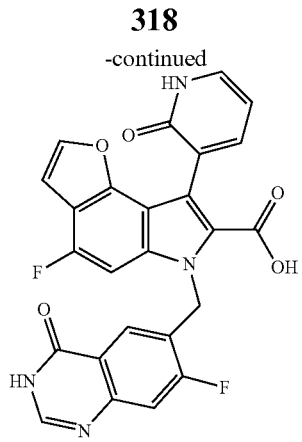

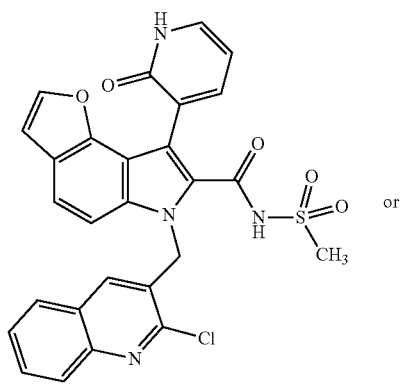

or

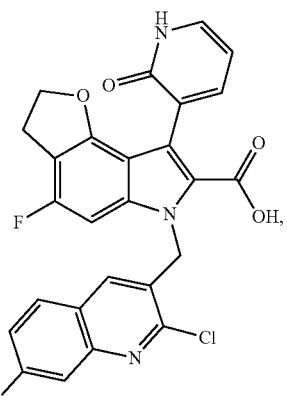

or a pharmaceutically acceptable salt or ester thereof.

* * * * *

UNITED STATES PATENT AND TRADEMARK OFFICE
CERTIFICATE OF CORRECTION

PATENT NO. : 8,557,848 B2  Page 1 of 1
APPLICATION NO. : 12/519715
DATED : October 15, 2013
INVENTOR(S) : Chen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1014 days.

Signed and Sealed this
Fifteenth Day of September, 2015

Michelle K. Lee
*Director of the United States Patent and Trademark Office*